US012703680B2

(12) United States Patent
Sebahar et al.

(10) Patent No.: US 12,703,680 B2
(45) Date of Patent: Aug. 11, 2026

(54) TRPV4 RECEPTOR LIGANDS

(71) Applicant: UNIVERSITY OF UTAH RESEARCH FOUNDATION, Salt Lake City, UT (US)

(72) Inventors: Paul Richard Sebahar, Salt Lake City, UT (US); Ryan Looper, Salt Lake City, UT (US); David Krizaj, Salt Lake City, UT (US); Christopher A. Reilly, Salt lake City, UT (US); Seth Wilson Grant, Woodland Hills, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 701 days.

(21) Appl. No.: 17/778,584

(22) PCT Filed: Nov. 20, 2020

(86) PCT No.: PCT/US2020/061587
§ 371 (c)(1),
(2) Date: May 20, 2022

(87) PCT Pub. No.: WO2021/102314
PCT Pub. Date: May 27, 2021

(65) Prior Publication Data

US 2023/0026696 A1 Jan. 26, 2023

Related U.S. Application Data

(60) Provisional application No. 62/938,693, filed on Nov. 21, 2019.

(51) Int. Cl.

| | |
|---|---|
| ***C07D 205/04*** | (2006.01) |
| ***A61P 27/02*** | (2006.01) |
| ***C07D 401/12*** | (2006.01) |
| ***C07D 403/12*** | (2006.01) |
| ***C07D 405/12*** | (2006.01) |
| ***C07D 413/06*** | (2006.01) |
| ***C07D 417/12*** | (2006.01) |

(52) U.S. Cl.
CPC ............ *C07D 205/04* (2013.01); *A61P 27/02* (2018.01); *C07D 401/12* (2013.01); *C07D 403/12* (2013.01); *C07D 405/12* (2013.01); *C07D 413/06* (2013.01); *C07D 417/12* (2013.01)

(58) Field of Classification Search
CPC .. C07D 205/04; C07D 401/12; C07D 403/12; C07D 405/12; C07D 413/06; C07D 417/12; A61P 27/02; A61K 31/4155; A61K 31/427; A61K 31/4427; A61K 31/661; A61K 31/337; C07F 9/568; A01K 2207/30; A01K 2217/00; A01K 2227/10; A01K 2227/105; A01K 2267/0375
See application file for complete search history.

(56) References Cited

U.S. PATENT DOCUMENTS

| | | | |
|---|---|---|---|
| 2004/0220389 | A1 | 11/2004 | Buchwald et al. |
| 2013/0109668 | A1 | 5/2013 | Ceccarelli et al. |
| 2013/0172273 | A1 | 7/2013 | Aizpurua Iparraguirre et al. |
| 2014/0378430 | A1 | 12/2014 | Mccarthy et al. |
| 2017/0334902 | A1 | 11/2017 | Andrez et al. |
| 2018/0250273 | A1 | 9/2018 | Blumstein et al. |
| 2019/0125728 | A1 | 5/2019 | Ikeda et al. |

FOREIGN PATENT DOCUMENTS

| | | | |
|---|---|---|---|
| CN | 108840812 | A | 11/2018 |
| DE | 1921743 | A1 | 2/1970 |
| EP | 0337549 | A1 | 10/1989 |
| EP | 2407478 | A1 | 1/2012 |
| WO | 2000005204 | A1 | 2/2000 |
| WO | 2001064632 | A1 | 9/2001 |
| WO | 2006048473 | A1 | 5/2006 |
| WO | 2007129119 | A1 | 11/2007 |
| WO | 2008139287 | A1 | 11/2008 |
| WO | 2010130424 | A1 | 11/2010 |
| WO | 2009154132 | A1 | 12/2011 |
| WO | 2012007562 | A1 | 1/2012 |
| WO | 2013102242 | A1 | 7/2013 |
| WO | 2015002755 | A2 | 1/2015 |
| WO | 2015046193 | A1 | 4/2015 |
| WO | 2017011776 | A1 | 1/2017 |
| WO | 2017037221 | A1 | 3/2017 |
| WO | 2017112768 | A1 | 6/2017 |
| WO | 2017202704 | A1 | 11/2017 |
| WO | 2017207387 | A1 | 12/2017 |
| WO | 2017214505 | A1 | 12/2017 |
| WO | 2018050686 | A1 | 3/2018 |

(Continued)

OTHER PUBLICATIONS

Joseph E. Pero, et al., Journal of Medicinal Chemistry 2018 61 (24), 11209-11220 DOI: 10.1021/acs.jmedchem.8b01344 (Year: 2018).*
Brnardic et al., J. Med. Chem. 2018, 61, 9738-9755 DOI: 10.1021/acs.jmedchem.8b01317 (Year: 2018).*
Skerratt et al., Med. Chem. Commun., 2013, 4, 244; doi.org/10.1039/C2MD20259J (Year: 2013).*
Aizpurua, J. M., et al. “Chirality-driven folding of short-lactam pseudopeptides.” The Journal of Organic Chemistry 78.2 (2013): 224-237.
Beasley, B. O., et al. “Pictet-Spengler reactions of oxetan-3-ones and related heterocycles.” Tetrahedron Letters 55.2 (2014): 541-543.
Burkhard, J. A., et al. “Synthesis of azaspirocycles and their evaluation in drug discovery.” Angewandte Chemie International Edition 49.20 (2010): 3524-3527.

(Continued)

*Primary Examiner* — James H Alstrum-Acevedo
*Assistant Examiner* — Chantal Adlam
(74) *Attorney, Agent, or Firm* — Michael Best & Friedrich LLP

(57) ABSTRACT

Described are receptor ligands of transient receptor potential cation channel subfamily V member 4 (TRPV4), pharmaceutical compositions including the compounds, and methods of using the compounds and compositions for treating ocular disorders.

21 Claims, 2 Drawing Sheets

(56) References Cited

FOREIGN PATENT DOCUMENTS

| | | | |
|---|---|---|---|
| WO | 2018055524 | A1 | 3/2018 |
| WO | 2018085288 | A1 | 5/2018 |
| WO | 2018106818 | A1 | 6/2018 |
| WO | 2018106820 | A1 | 6/2018 |
| WO | 2018175746 | A1 | 9/2018 |
| WO | 2018235966 | A1 | 12/2018 |
| WO | 2019055966 | A2 | 3/2019 |

OTHER PUBLICATIONS

C.T.F.A. Cosmetic Ingredient Handbook, 1992, pp. 587-592.

Chakka, N., et al. "Applications of parallel synthetic lead hopping and pharmacophore-based virtual screening in the discovery of efficient glycine receptor potentiators." European Journal of Medicinal Chemistry 137 (2017): 63-75.

Couty, F. et al. "Ring Expansion of 2-(1-Hydroxyalkyl) azetidines to 4-(2-Chloroethyl) oxazolidinones." (2011): 794-801.

Deering-Rice, C. E., et al. "Drofenine: a 2-APB analog with improved selectivity for human TRPV3." Pharmacology research & perspectives 2.5 (2014): e00062.

Deering-Rice, C. E., et al. "Transient receptor potential vanilloid-1 (TRPV1) is a mediator of lung toxicity for coal fly ash particulate material." Molecular pharmacology 81.3 (2012): 411-419.

Duréault, A., et al. "Synthesis of highly functionalized homochiral azetidines and azetidine-2-carboxylic esters." Tetrahedron 49.20 (1993): 4201-4210.

Duvall, J. R., et al. "Novel diversity-oriented synthesis-derived respiratory syncytial virus inhibitors identified via a high throughput replicon-based screen." Antiviral research 131 (2016): 19-25.

Gelatt, K. N., et al. "Changes in intraocular pressure associated with topical dorzolamide and oral methazolamide in glaucomatous dogs." Veterinary Ophthalmology 4.1 (2001): 61-67.

Hamza, D., et al. "Synthesis of novel 2, 6-diazaspiro [3.3] heptanes." Synlett 2007.16 (2007): 2584-2586.

Huang, L.-Z., et al. "Asymmetric Rh (II)/Pd (0) Relay Catalysis: Synthesis of α-Quaternary Chiral β-Lactams through Enantioselective C—H Insertion/Diastereoselective Allylation of Diazoamides." ACS Catalysis 8.8 (2018): 7340-7345.

International Preliminary Report on Patentability for Application No. PCT/US2020/061587 dated Nov. 12, 2021 (7 pages).

International Search Report and Written Opinion for Application No. PCT/US2020/061587, dated Feb. 22, 2021 (16 pages).

IUPAC 1974 Recommendations for Section E, Fundamental Stereochemistry, in Pure Appl. Chem., 1976, 45: 13-30.

Ivachtchenko, A. V., et al. "Design, synthesis and biological evaluation of novel 5-oxo-2-thioxoimidazolidine derivatives as potent androgen receptor antagonists." European Journal of Medicinal Chemistry 99 (2015): 51-66.

Jo, A. O., et al. "Differential vol. regulation and calcium signaling in two ciliary body cell types is subserved by TRPV4 channels." Proceedings of the National Academy of Sciences 113.14 (2016): 3885-3890.

Jo, A. O., et al. "TRPV4 and AQP4 channels synergistically regulate cell vol. and calcium homeostasis in retinal Müller glia." Journal of Neuroscience 35.39 (2015): 13525-13537.

Jones, R., et al. "Structures and photochemistry of dibenzobarrelene monoamides." Acta Crystallographica Section B: Structural Science 52.6 (1996): 1007-1013.

Komáromy, A. M. et al. "Looking into the future: Gene and cell therapies for glaucoma." Veterinary Ophthalmology 24 (2021): 16-33.

Križaj, D. "What is glaucoma?." Webvision: The Organization of the Retina and Visual System [Internet] 1733-1771 (2019).

Leszczynska, G., et al. "mt-IRNA components: Synthesis of (2-thio) uridines modified with blocked glycine/taurine moieties at C-5, 1." Nucleosides, Nucleotides and Nucleic Acids 32.11 (2013): 599-616.

Lowe, J. T., et al. "Synthesis and profiling of a diverse collection of azetidine-based scaffolds for the development of CNS-focused lead-like libraries." The Journal of organic chemistry 77.17 (2012): 7187-7211.

Matsumoto, H., et al. "Retinal Detachment-Induced Muller Glial Cell Swelling Activates TRPV4 Ion Channels and Triggers Photoreceptor Death at Body Temperature." The Journal of Neuroscience 38.41 (2018): 8745.

McCutcheon's vol. 1, Emulsifiers & Detergents, 1994, North American Edition, pp. 236-239.

Miller, R. A., et al. "A practical process for the preparation of azetidine-3-carboxylic acid." Synthetic communications 33.19 (2003): 3347-3353.

Modern Pharmaceutics, Chapters 9 and 10, Banker & Rhodes, eds. (1979) 329-427.

Molnár, T., et al. "Store-Operated Calcium Entry in Muller Glia Is Controlled by Synergistic Activation of TRPC and Orai Channels." The Journal of Neuroscience 36.11 (2016): 3184.

Palomo, C., et al. "Functionalization of N-[(Silyl) methyl]-β-lactam Carbanions with Carbon Electrophiles." The Journal of Organic Chemistry 71.17 (2006): 6368-6373.

Palomo, C., et al. "Synthesis of β-lactam scaffolds for ditopic peptidomimetics." Organic Letters 9.1 (2007): 101-104.

Pubchem CID 11076939 Create Date: Oct. 26, 2006. 7 pages.

Reddy, L. R., et al. "Asymmetric synthesis 1-substituted 2, 6-diazaspiro [3.3] heptanes through addition of 3-azetidinecarboxylate anions to Davis-Ellman imines." Organic letters 21.10 (2019): 3481-3484.

Remington's Pharmaceutical Sciences, 15th Ed. 1975, pp. 335-337.

Ryskamp, D. A., et al. "Swelling and eicosanoid metabolites differentially gate TRPV4 channels in retinal neurons and glia." Journal of Neuroscience 34.47 (2014): 15689-15700.

Ryskamp, D. A., et al. "The polymodal ion channel transient receptor potential vanilloid 4 modulates calcium flux, spiking rate, and apoptosis of mouse retinal ganglion cells." Journal of Neuroscience 31.19 (2011): 7089-7101.

Ryskamp, D. A., et al. "TRPV4 regulates calcium homeostasis, cytoskeletal remodeling, conventional outflow and intraocular pressure in the mammalian eye." Scientific reports 6 (2016): 30583.

Scardillo, A., et al. "Effects of topical 0.5% levobunolol alone or in association with 2% dorzolamide compared with a fixed combination of 0.5% timolol and 2% dorzolamide on intraocular pressure and heart rate in dogs without glaucoma." Vet Ther 11.3 (2010): E1-E6.

Shapiro, D., et al. "Activation of transient receptor potential ankyrin-1 (TRPA1) in lung cells by wood smoke particulate material." Chemical research in toxicology 26.5 (2013): 750-758.

Shindo, M., et al. "Cycloaddition of lithium ynolate to imines: Synthesis of 3, 4-disubstituted β-lactams." Heterocycles 49.1 (1998): 113-116.

Sivaprakasham, M., et al. "A straightforward synthesis of 3-substituted azetidinic amino acids." Arkivoc 2007 (2007).

Van Berkom, L. W. A. Combinatorial exploration of cyano-and nitroalkenes. Diss. [SI: sn], 2005 (145 pages).

Wang, Z., et al. "Copper-catalyzed intramolecular C (sp3)—H and C (sp2)—H amidation by oxidative cyclization." Angewandte Chemie-International Edition 53.13 (2014): 3496-3499.

Wu, X., et al. "Copper-catalyzed site-selective intramolecular amidation of unactivated C ($sp_3$)—H bonds." Angewandte Chemie (International ed. in English) 53.14 (2014): 3706-3710.

Wu, X., et al. "Nickel-Catalyzed Site-Selective Amidation of Unactivated C (sp3)—H Bonds." Chemistry—A European Journal 20.31 (2014): 9530-9533.

Xiong, H.-Y., et al. "Pd-catalyzed directed chlorination of unactivated C (sp3)—H bonds at room temperature." European Journal of Organic Chemistry 2016.21 (2016): 3625-3630.

Xu, Z., et al. "Synthesis of spirocyclic β-keto-lactams: copper catalyzed process." Chemical Communications 47.17 (2011): 4923-4925.

Yang, S.-W., et al. "Bioavailable pyrrolo-benzo-1, 4-diazines as Nav1. 7 sodium channel blockers for the treatment of pain." Bioorganic & Medicinal Chemistry Letters 24.21 (2014): 4958-4962.

(56) References Cited

OTHER PUBLICATIONS

Yerande, S. G., et al. "Application of cyclic ketones in MCR: Ugi/amide coupling based synthesis of fused tetrazolo [1, 5-a][1, 4] benzodiazepines." Tetrahedron Letters 55.21 (2014): 3263-3266.
Zheng, T., et al. "Diverse ring opening of thietanes and other cyclic sulfides: an electrophilic aryne activation approach." Chemical Communications 54.11 (2018): 1303-1306.
European Patent Office Extended European Search Report for Application No. 20890028.2, dated Nov. 22, 2023 (9 pages).
Chinese Patent Office Second Office Action for Application No. 202080080479.8 dated Nov. 24, 2023 (9 pages including English translation).
Burkhard et al., "Synthesis and Structural Analysis of a New Class of Azaspiro[3.3]heptanes as Building Blocks for Medicinal Chemistry" Organic Letters, vol. 12, Edition No. 9, 1944-1947, Scheme 1.
Guerot, Carine et al., "Synthesis of Novel Angular Spirocyclic Azetidines" Organic Letters, vol. 13, Edition No. 4, pp. 780-783, Scheme 2.
Sarah E. Skerratt et. al., "Identification of false positives in "HTS hits to lead": The application of Bayesian models in HTS triage to rapidly deliver a series of selective TRPV4 antagonists" Med. Chem. Commun., Oct. 23, 2012 , p. 244-251 FIG.1 and Table 1.
Chinese Patent Office First Office Action for Application No. 202080080479.8 dated May 30, 2023 (17 pages including English translation).
Registry(STN)[online], Dec. 4, 2011 [search date: Jun. 7, 2024], CAS 1348423-41-5, Ethyl 1-benzoyl-3-[[(5-chloro-2-pyrazinyl)oxy]methyl]-3-azetidinecarboxylate (1 page).
Registry(STN)[online], Nov. 16, 1984 [search date: Jun. 7, 2024], CAS 47187-68-8, 1-(Phenylmethyl)-3-[[(phenylmethyl)amino]methyl]-3-azetidinemethanol (1 page).
Stanković, S., et al. "Application of 3-Bromo-3-ethylazetidines and 3-Ethylideneazetidines for the Synthesis of Functionalized Azetidines." Synlett 25.01 (2014): 75-80.
Japanese Patent Office. Notification of Reason for Rejection for Application No. 297522, dated Jul. 9, 2024 (12 pages with translation).
Australian Patent Office Examination Report No. 1 for Application No. 2020388645 dated Dec. 1, 2025 (4 pages).
European Patent Office Action for Application No. 20890028.2, dated Nov. 18, 2025 (5 pages).
Canadian Patent Office Action for Application No. 3,157,279 dated Jan. 21, 2026 (10 pages).

* cited by examiner

TRPV4 RECEPTOR LIGANDS

CROSS-REFERENCE TO RELATED APPLICATIONS

This application is a U.S. national stage entry of International Patent Application No. PCT/US2020/061587, filed on Nov. 20, 2020, which claims priority to U.S. Provisional Patent Application No. 62/938,693, filed on Nov. 21, 2019, the entire contents of each of which are fully incorporated herein by reference.

FEDERALLY SPONSORED RESEARCH

This invention was made with government support under grant EY027920 awarded by the National Institutes of Health. The government has certain rights in this invention.

TECHNICAL FIELD

The present disclosure relates to compounds, compositions, and methods for treating TRPV4-related diseases and/or disorders, such as glaucoma and related diseases.

BACKGROUND

Transient receptor potential cation channel subfamily V member 4 (TRPV4) is a member of the OSM9-like transient receptor potential channel (OTRPC) subfamily that in humans is encoded by the TRPV4 gene. TRPV4 protein is a $Ca^{2+}$-permeable, nonselective cation channel that is thought to be involved in the regulation of systemic osmotic pressure. TRPV4 also functions as a ciliary mechanosensory channel. Mutations in the TRPV4 gene have been associated with disorders including brachyolmia type 3, congenital distal spinal muscular atrophy, scapuloperoneal spinal muscular atrophy and subtype 2C of Charcot-Marie-Tooth disease.

Defects in cilia formation or maintenance underlie a wide range of human diseases, including retinitis pigmentosa, renal cysts, polydactyly, and developmental delays, which are collectively called ciliopathies. OCRL, an inositol polyphosphate 5-phosphatase implicated in Oculocerebrorenal syndrome of Lowe (Lowe syndrome), a rare X-linked recessive disorder that presents in males with bilateral cataracts and glaucoma, as well as renal failure, muscular hypotonia, and mental retardation, regulates cilia biogenesis. OCRL substrates include phosphatidylinositol-4,5-bisphophatase [PI(4,5)$P_2$] and phosphatidylinositol-3,4,5-triphosphate [PI (3,4,5)$P_3$]. Decreased 5-phosphatase activity is demonstrated in fibroblasts from Lowe patients, as well as a two- to threefold elevated ratio of PI(4,5)$P_2$:PI(4)P.

Mechanosensation of pressure underlies a number of important human diseases including the development of hypertension and glaucoma. In the kidney epithelium, ciliary proteins polycystins (PC1/2) have been shown to be important for flow-dependent calcium flux. In the lining of the ventricles of the brain, cerebrospinal fluid is regulated by cilia. Similar to the kidney, the eye is an enclosed organ with sensitive homeostatic regulation of fluid production and egress. Defective sensation of pressure may result in imbalance of aqueous humor, resulting in elevated intraocular pressure. Low levels of eye pressure result in structural changes of the retina and poor vision, while elevated eye pressure may damage the optical nerve. Glaucoma is an optic neuropathy associated with elevated intraocular pressure and is a leading cause of irreversible blindness in the world.

Trabecular meshwork (TM) cells are responsible for the drainage of the majority of aqueous fluid. Dysfunction of the trabecular outflow leads to elevated intraocular pressure, which in susceptible individuals, results in the death of retinal ganglion cells that leads to irreversible vision loss. Trabecular meshwork cells of the eye have primary cilia that are responsive to pressure changes.

Consistent with the central role of increased pressure in the pathology of glaucoma, the only proven treatment is lowering of pressure. There exists a need to develop treatments for lowering eye pressure.

A distinctive feature of glaucoma is the optic neuropathy in the posterior eye (retina) that reflects inflammatory activation of retinal glial cells and degeneration and loss of retinal ganglion cells (RGCs). The primary risk factor for developing the disease in an increase in intraocular pressure (IOP), with IOP-dependence contributing ~30-70% of glaucoma cases. While ‘glaucoma’ is a late-stage designation of the injured retina, RGCs are remarkably sensitive to acute changes in pressure which result in immediate changes in excitability, loss of spatiotemporal contrast sensitivity and reduced visual acuity. Functional dysfunction correlates with the retraction, thinning and reduced complexity of RGC dendrites, loss of synapses and changes in axonal transport. Pressure-induced changes in cell firing and dendritic injury are compounded by the obstruction of (anterograde/retrograde) transport of neurotrophic factors and organelles which, if it persists, can contribute to gross structural remodeling at the optic nerve head. A plausible multi-compartmental regulator of pressure-induced damage could be the calcium ion, which drives the remodeling of dendrites, somata and axons through Ca2+-dependent proteases, caspases, MAP kinases, ER stress, autophagy and apoptosis.

Currently accepted treatments of glaucoma are largely limited to IOP lowering. Because IOP lowering may also reduce the progression of vision loss in patients with ‘normal’ IOP (8-15 mm Hg) levels, glaucoma can be viewed as a disease that involves pathological cellular mechanotransduction that increases the susceptibility of RGCs to mechanical stress at any IOP level (Križaj, 2019). Unfortunately, the most commonly used IOP lowering agent latanoprost (a prostaglandin F2$\alpha$ analog) targets the secondary uveoscleral mechanism of aqueous humor drainage and does not lower IOP more than 20% in a significant fraction (25-50%) of patients whereas up to 6% of POAG patients are unresponsive or do not tolerate any IOP medications. An attractive strategy, therefore, would be to target both IOP-generating mechanism in the anterior eye and the pressure sensitivity of retinal ganglion cells and glia.

The present invention is based on the finding that the pressure sensitivity of retinal ganglion cells, Muller glia and microglia is mediated in part by TRPV4 (transient receptor potential vanilloid isoform 4), a calcium-permeable channel that is activated by a range of mechanical stressors (strain, pressure, compression, shear), moderate temperature and polyunsaturated fatty acids. Excessive activation of the channel induces selective death of RGCs (Ryskamp et al., Journal of Neuroscience 2011) and reactive gliosis (Ryskamp et al., Journal of Neuroscience 2014) whereas inhibition or genetic ablation of the channel are neuroprotective (Ryskamp et al., Scientific Reports 2016). It is believed that TRPV4 antagonists are useful for providing neuroprotective effects in ocular hypertension by suppressing the pressure sensitivity of both glia (reducing neuroinflammation) and RGCs (suppressing neurodegeneration). They are also believed to counter pressure-dependent calcium overloads that may damage RGC dendrites and axons in glaucoma. Because these compounds also decrease IOP (Ryskamp et al., Scientific Reports 2016), this invention offers a treatment strategy that combines IOP lowering with neuroprotection. Moreover, the efficacy of TRPV4 antagonists in reducing glial and neuronal swelling and cytokine release in the retina (Jo et al., Journal of Neuroscience 2015; Matsumoto et al., Journal of Neuroscience 2018) offers a neuroprotective strategy to treat excessive swelling and/or edema in diseases such as diabetic retinopathy and macular degeneration.

Ryskamp D A, Jo A O, Frye A, Macaulay N, Vazquez-Chona F, Thoreson W B and Križaj D (2014) Swelling and eicosanoid metabolites differentially gate TRPV4 channels in retinal neurons and glia. Journal of Neuroscience 34(47):15689-15700. PMID: 25411497; PMC4236400

Jo A O*, Ryskamp D A*, Phuong T T T, Verkman A, Yarishkin O, MacAulay N and Križaj D (2015) Synergistic signaling of TRPV4 and AQP4 channels is required for cell volume and calcium homeostasis regulation in retinal Müller glia. Journal of Neuroscience, 35(39):13525-13537. PMID: 26424896. PMC4588615

Ryskamp D A, Frye A M, Phuong T T T, Yarishkin O, Jo A O, Xu Y, Lakk M, Redmon S, Iuso A, Hageman G, Ambati B, Prestwich G D, Torrejon K Y and Križaj D (2016) TRPV4 regulates calcium homeostasis, cytoskeletal remodeling, conventional outflow and intraocular pressure in the mammalian eye. Scientific Reports 6:30583. PMID: 27510430. PMC4980693

Matsumoto H, Sugio S, Križaj D, Ishizaki Y and Shibasaki K (2018) Retinal detachment-induced Müller glial cell swelling activates TRPV4 ion channels and triggers rod photoreceptor death. Journal of Neuroscience 38(41):8745-8758. PMID:30143574. PMC6181316

Križaj D (2019) What is glaucoma? Webvision: The Organization of the Retina and Visual System. Eds. H Kolb, E Fernandez, R Nelson. University of Utah Health Sciences, Salt Lake City. PMID31241881

SUMMARY

In one aspect, disclosed are compounds of formula (I):

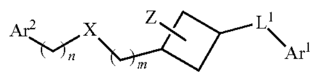

(I)

or a pharmaceutically acceptable salt thereof, wherein:

$L^1$ is —C(O)—, —$S(O_2)$—, —S(O)—, or $C_1$-$C_4$alkylene;

X is O or $NR^1$;

m is 0, 1, 2, 3, or 4;

n is 0, 1, 2, 3, or 4;

$Ar^1$ and $Ar^2$ are each independently selected from a 5-10 membered aryl or heteroaryl;

Z is $CHR^2R^3$, $COR^4$, or $NHR^5$;

$R^1$ is selected from hydrogen and $C_1$-$C_4$alkyl;

$R^2$, $R^3$, $R^4$, and $R^5$ are each independently selected from the group consisting of hydrogen, hydroxy, $C_1$-$C_6$alkyl, hydroxy-$C_1$-$C_6$alkyl, $C_1$-$C_6$alkoxy, $C_1$-$C_6$alkoxy-$C_1$-$C_6$alkyl, phosphate, $C_1$-$C_6$alkyl phosphate, $C_4$-$C_8$heterocyclyl, $NR^6R^7$, —$OC(O)R^8$, —$C(O)R^9$, —$S(O)_2R^{10}$, and —$OS(O)_2R^{11}$;

$R^6$, $R^7$, $R^8$, $R^9$, $R^{10}$, and $R^{11}$ are each independently selected from the group consisting of hydrogen, $C_1$-$C_6$alkyl, $C_1$-$C_6$heteroalkyl, $C_1$-$C_6$alkoxy, $C_4$-$C_8$cycloalkyl, $C_4$-$C_8$heterocyclyl, $C_5$-$C_8$aryl, $C_5$-$C_8$heteroaryl, $C_1$-$C_6$alkoxy-$C_1$-$C_6$alkyl, $C_5$-$C_8$aryl-$C_1$-$C_6$alkyl, $C_5$-$C_8$heteroaryl-$C_1$-$C_6$alkyl, $C_5$-$C_8$heterocyclyl-$C_1$-$C_6$alkyl, amino-$C_1$-$C_6$alkyl, hydroxy-$C_1$-$C_6$alkyl, hydroxy-$C_3$-$C_8$cycloalkyl, cyano-$C_1$-$C_6$alkyl, hydroxysulfonyl-$C_1$-$C_6$alkyl, phosphate-$C_1$-$C_6$alkyl, alkylphosphate-$C_1$-$C_6$alkyl, —$COR^{12}$, and —$CR^{13}R^{14}C(O)R^{15}$;

$R^{12}$ is selected from the group consisting of $C_1$-$C_6$alkyl, $C_1$-$C_6$heteroalkyl, $C_1$-$C_6$alkoxy, amino-$C_1$-$C_6$alkyl, $C_4$-$C_8$heterocyclyl, hydroxy-$C_1$-$C_6$alkyl, amino-$C_4$-$C_8$heterocyclyl, phosphate-$C_1$-$C_6$alkyl, and $C_1$-$C_6$alkyl phosphate;

$R^{13}$ and $R^{14}$ are each independently selected from the group consisting of hydrogen, $C_1$-$C_6$alkyl and, $C_1$-$C_6$heteroalkyl, or optionally taken together with the atoms to which they are attached to form a ring; and $R^{15}$ is hydroxy, $C_1$-$C_6$alkoxy or amino;

wherein at least one of m and n is not zero, and each aryl, heteroaryl, cycloalkyl, or heterocycle is independently unsubstituted or substituted with one or more substituents independently selected from cyano, halo, $C_1$-$C_6$alkyl, $C_1$-$C_6$alkoxy, amino-$C_1$-$C_6$alkyl, haloalkyl, sulfonyl, —C(O)—$C_1$-$C_6$alkoxy, and —C(O)—$NH_2$.

Also disclosed are pharmaceutical compositions comprising the compounds, and methods of using the compounds and compositions for treatment of disorders, such as ocular hypertension or glaucoma, or other associated TRPV4 related medical disorders and/or diseases.

DETAILED DESCRIPTION

Figure 1:
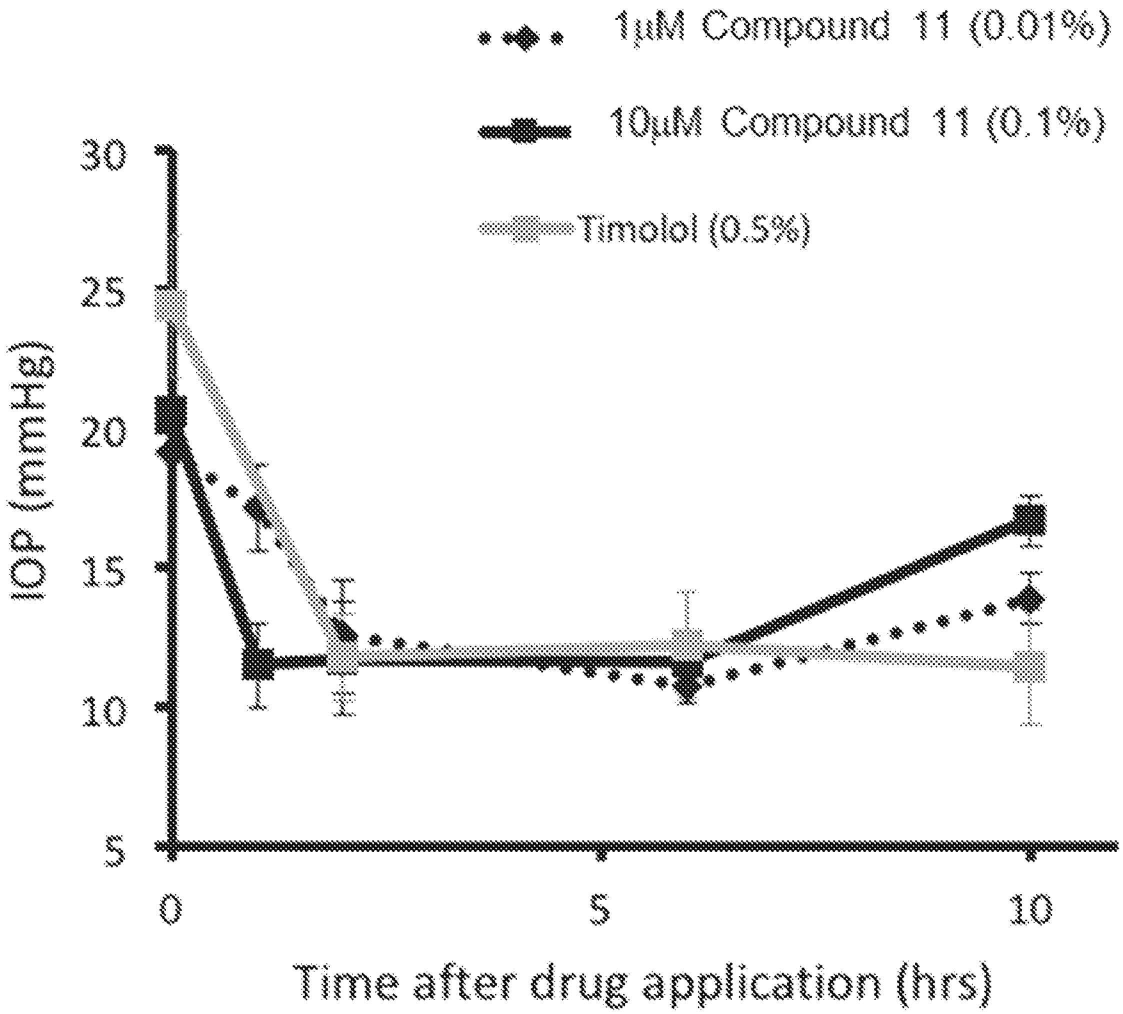
FIG. 1 is a graph showing the effect that two concentrations of topical compound 11 (0.01% and 0.1%), 0.5% timolol, and control PBS had on IOP in the microbead (MB) mouse model of ocular hypertension (N=3 separate experiments, with 7-10 mice per experimental cohort). Error bars=±S.E.M. Ocular hypertension in the mouse model of primary open angle glaucoma (POAG) was induced with intracameral injection of polystyrene microbeads. Antagonist stock solutions (10 mM) were prepared in DMSO, the final concentrations were made in PBS diluted to <0.0001% DMSO.
Figure 2:
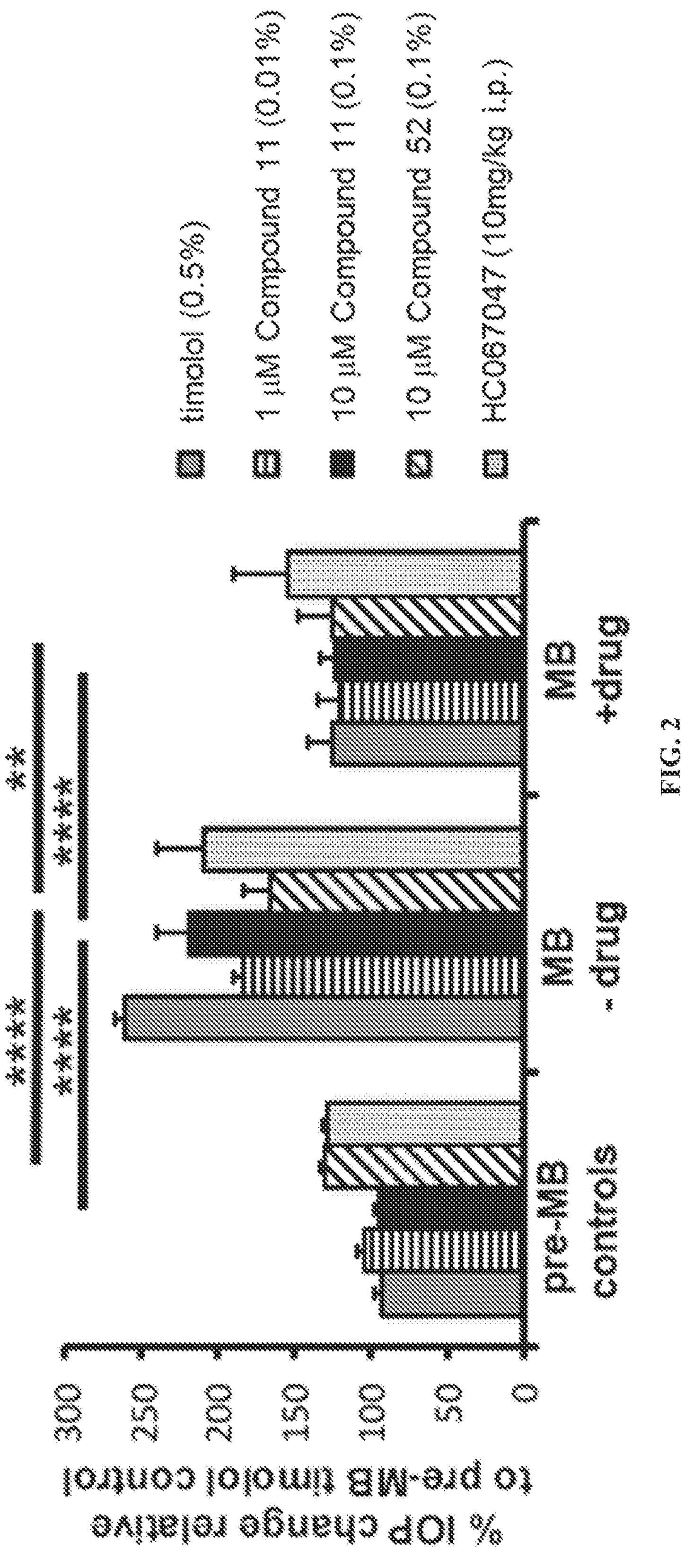
FIG. 2 is a bar chart showing the cumulative data for pre-IOP elevation cohorts of mouse eyes (N≥3 separate experiments, with 7-10 mice per experimental cohort). Left panel: the IOP data are plotted as % of the control value of the timolol-treated eye cohort. Middle panel: MB injection elevated IOP in all experimental cohorts. Right panel: topical application of timolol, Compound 11 and Compound 52 and intraperitoneal injection of HC067047 significantly lowered IOP levels in MB-treated eyes (P<0.01; **P<0.001; two-way ANOVA followed by Holm-Šidak tests).

Disclosed herein are receptor ligands (e.g., antagonists) of transient receptor potential cation channel subfamily V member 4 (TRPV4). The compounds can have the structure of formula (I). Compounds of formula (I) may exhibit selectivity for TRPV4 over other TRPV receptors (e.g., TRPV3). Compounds of formula (I) may be used to treat or prevent diseases and disorders associated with TRPV4 by modulating TRPV4 activity. For example, compounds of formula (I) be used to treat or prevent ocular diseases and disorders, such as glaucoma.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry,* $5^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* $3^{rd}$ Edition, Cambridge University Press, Cambridge, 1987; the entire contents of each of which are incorporated herein by reference.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, isopropyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkoxyalkyl," as used herein, refers to an alkoxy group, as defined herein, appended to the parent molecular moiety through an alkyl group, as defined herein.

The term "alkylamino," as used herein, means at least one alkyl group, as defined herein, is appended to the parent molecular moiety through an amino group, as defined herein.

The term "alkylphosphate," as used herein, means an ester of phosphoric acid $H_3PO_4$, in which any or all of the hydrogens can be replaced by an alkyl group, as defined herein, such that the alkyl phosphate may be mono-substituted, $R^1H_2PO_4$, di-substituted, $R^1R^2H_2PO_4$ or tri-substituted, $R^1R^2R^3H_2PO_4$, wherein $R^1$, $R^2$, and $R^3$ may be the same or different alkyl groups.

The term "alkylphosphate alkyl," as used herein, refers to an alkylphosphate group, as defined herein, appended to the parent molecular moiety through an alkyl group, as defined herein.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "amino," as used herein, means $—NR_xR_y$, wherein $R_x$ and $R_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be $—NR_x—$, wherein $R_x$ may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "aminoheterocyclyl," as used herein, means at least one amino group, as defined herein, is appended to the parent molecular moiety through an heterocycle group, as defined herein.

The term "aryl," as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl and tetrahydroquinolinyl.

The term "arylalkyl," as used herein, means at least one aryl group, as defined herein, is appended to the parent molecular moiety through an alkylene group, as defined herein.

The term "cyano," as used herein, means at least one —CN group.

The term "cyanoalkyl," as used herein, means at least one —CN group, is appended to the parent molecular moiety through an alkylene group, as defined herein.

The term "cycloalkyl," as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl. "Cycloalkyl"

also includes carbocyclic ring systems in which a cycloalkyl group is appended to the parent molecular moiety and is fused to an aryl group as defined herein (e.g., a phenyl group), a heteroaryl group as defined herein, or a heterocycle as defined herein. Representative examples of such cycloalkyl groups include, but are not limited to, 2,3-dihydro-1H-indenyl (e.g., 2,3-dihydro-1H-inden-1-yl and 2,3-dihydro-1H-inden-2-yl), 6,7-dihydro-5H-cyclopenta[b]pyridinyl (e.g., 6,7-dihydro-5H-cyclopenta[b]pyridin-6-yl), and 5,6,7,8-tetrahydroquinolinyl (e.g., 5,6,7,8-tetrahydroquinolin-5-yl).

The term "fluoroalkyl," as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "halogen" or "halo," as used herein, means $C_1$, Br, I, or F.

The term "haloalkyl," as used herein, means an alkyl group, as defined herein, in which one, two, three, four, five, six, seven or eight hydrogen atoms are replaced by a halogen.

The term "heteroalkyl," as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl," as used herein, refers to an aromatic monocyclic ring or an aromatic bicyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, benzimidazolyl, benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl, quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl, naphthyridinyl, pyridoimidazolyl, thiazolo[5,4-b]pyridin-2-yl, thiazolo[5,4-d]pyrimidin-2-yl.

The term "heteroarylalkyl," as used herein, means at least one heteroaryl group, as defined herein, is appended to the parent molecular moiety through an alkylene group, as defined herein.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0]hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.13,7]decane), and oxa-adamantane (2-oxatricyclo[3.3.1.13,7]decane). The monocyclic, bicyclic, and tricyclic heterocycles are connected to the parent molecular moiety through any carbon atom or any nitrogen atom contained within the rings, and can be unsubstituted or substituted.

The term "heterocyclylalkyl," as used herein, means at least one heterocycle, as defined herein, is appended to the parent molecular moiety through an alkylene group, as defined herein.

The term "hydroxyl" or "hydroxy," as used herein, means an —OH group.

The term "hydroxyalkyl," as used herein, means at least one —OH group, is appended to the parent molecular moiety through an alkylene group, as defined herein.

The term "hydroxycycloalkyl," as used herein, means at least one —OH group, is appended to the parent molecular moiety through an cycloalkyl group, as defined herein.

Hydroxysulfonyl

The term "hydroxysulfonyl-alkyl," as used herein, means at least one hydroxysulfonyl group, as defined herein, is appended to the parent molecular moiety through an alkylene group, as defined herein.

The term "phosphate alkyl," as used herein, means at least one phosphate group is appended to the parent molecular moiety through an alkylene group, as defined herein.

The term "sulfonyl," as used herein, means an $—SO_2—$ group.

In some instances, the number of carbon atoms in a hydrocarbyl substituent (e.g., alkyl or cycloalkyl) is indicated by the prefix "$C_x$-$C_y$—", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituents" refers to a group "substituted" on an aryl, heteroaryl, phenyl or pyridinyl group at any atom of that group. Any atom can be substituted.

The term "substituted" refers to a group that may be further substituted with one or more non-hydrogen substituent groups. Substituent groups include, but are not limited to, halogen, ═O (oxo), ═S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl. For example, if a group is described as being "optionally substituted" (such as an alkyl, alkenyl, alkynyl, aryl, heteroaryl, cycloalkyl, heteroalkyl, heterocycle or other group such as an R group), it may have 0, 1, 2, 3, 4 or 5 substituents independently selected from halogen, ═O (oxo), ═S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

The term "---" designates a single bond (—) or a double bond (═).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOUNDS

In one aspect, disclosed are compounds of formula (I):

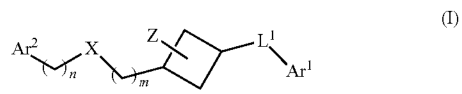

(I)

or a pharmaceutically acceptable salt thereof, wherein:

$L^1$ is —C(O)—, $—S(O_2)—$, —S(O)—, or $C_1$-$C_4$alkylene;

X is O or $NR^1$;

m is 0, 1, 2, 3, or 4;

n is 0, 1, 2, 3, or 4;

$Ar^1$ and $Ar^2$ are each independently selected from a 5-10 membered aryl or heteroaryl;

Z is $CHR^2R^3$, $COR^4$, or $NHR^5$;

$R^1$ is selected from hydrogen and $C_1$-$C_4$alkyl;

$R^2$, $R^3$, $R^4$, and $R^5$ are each independently selected from the group consisting of hydrogen, hydroxy, $C_1$-$C_6$alkyl, hydroxy-$C_1$-$C_6$alkyl, $C_1$-$C_6$alkoxy, $C_1$-$C_6$alkoxy-$C_1$-$C_6$alkyl, phosphate, $C_1$-$C_6$alkyl phosphate, $C_4$-$C_8$heterocyclyl, $NR^6R^7$, $—OC(O)R^8$, $—C(O)R^9$, $—S(O)_2R^{10}$, and $—OS(O)_2R^{11}$;

$R^6$, $R^7$, $R^8$, $R^9$, $R^{10}$, and $R^{11}$ are each independently selected from the group consisting of hydrogen, $C_1$-$C_6$alkyl, $C_1$-$C_6$heteroalkyl, $C_1$-$C_6$alkoxy, $C_4$-$C_8$cycloalkyl, $C_4$-$C_8$heterocyclyl, $C_5$-$C_8$aryl, $C_5$-$C_8$heteroaryl, $C_1$-$C_6$alkoxy-$C_1$-$C_6$alkyl, $C_5$-$C_8$aryl-$C_1$-$C_6$alkyl, $C_5$-$C_8$heteroaryl-$C_1$-$C_6$alkyl, $C_5$-$C_8$heterocyclyl-$C_1$-$C_6$alkyl, amino-$C_1$-$C_6$alkyl, hydroxy-$C_1$-$C_6$alkyl, hydroxy-$C_3$-$C_8$cycloalkyl, cyano-$C_1$-$C_6$alkyl, hydroxysulfonyl-$C_1$-$C_6$alkyl, phosphate-$C_1$-$C_6$alkyl, alkylphosphate-$C_1$-$C_6$alkyl, $—COR^{12}$, and $—CR^{13}R^{14}C(O)R^{15}$;

$R^{12}$ is selected from the group consisting of $C_1$-$C_6$alkyl, $C_1$-$C_6$heteroalkyl, $C_1$-$C_6$alkoxy, amino-$C_1$-$C_6$alkyl, $C_4$-$C_8$heterocyclyl, hydroxy-$C_1$-$C_6$alkyl, amino-$C_4$-$C_8$heterocyclyl, phosphate-$C_1$-$C_6$alkyl, and $C_1$-$C_6$alkyl phosphate;

$R^{13}$ and $R^{14}$ are each independently selected from the group consisting of hydrogen, $C_1$-$C_6$alkyl and, $C_1$-$C_6$heteroalkyl, or optionally taken together with the atoms to which they are attached to form a ring; and $R^{15}$ is hydroxy, $C_1$-$C_6$alkoxy or amino;

wherein at least one of m and n is not zero, and each aryl, heteroaryl, cycloalkyl, or heterocycle is independently unsubstituted or substituted with one or more substituents independently selected from cyano, halo, $C_1$-$C_6$alkyl, $C_1$-$C_6$alkoxy, amino-$C_1$-$C_6$alkyl, haloalkyl, sulfonyl, —C(O)—$C_1$-$C_6$alkoxy, and —C(O)—$NH_2$.

In some embodiments, $L^1$ is $—S(O_2)—$.

In some embodiments, $Ar^1$ is selected from a 5-membered aryl, a 5-membered heteroaryl, a 6-membered aryl, or a 6-membered heteroaryl. Each aryl or heteroaryl may be unsubstituted or substituted with one or two substituents independently selected from cyano, halo, $C_1$-$C_6$alkyl, $C_1$-$C_6$alkoxy, haloalkyl, sulfonyl, and —C(O)—$C_1$-$C_6$alkoxy. In some embodiments, the halo is fluoro or chloro. In some embodiments, the haloalkyl is trifluoromethyl.

In some embodiments, $Ar^1$ is

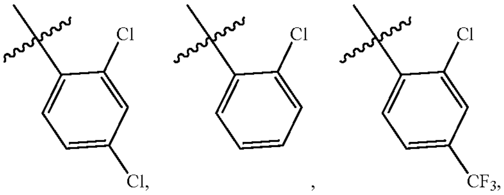
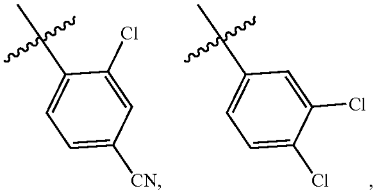
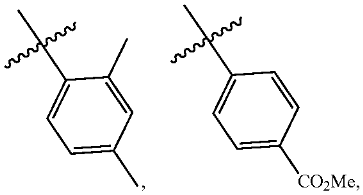
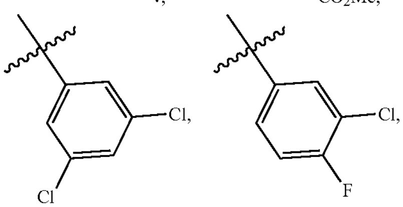
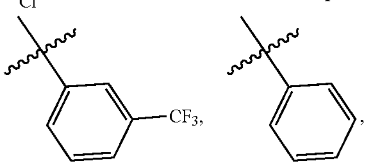
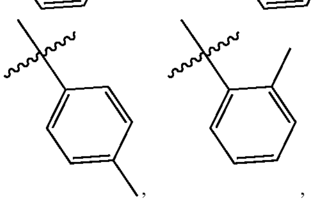
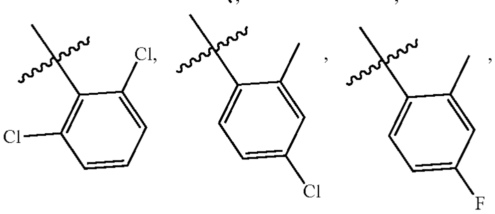
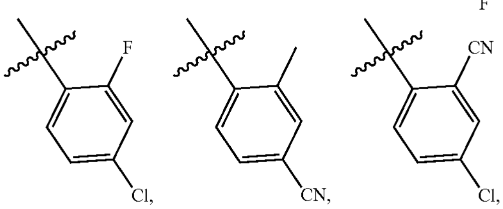
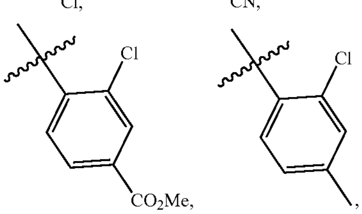

-continued

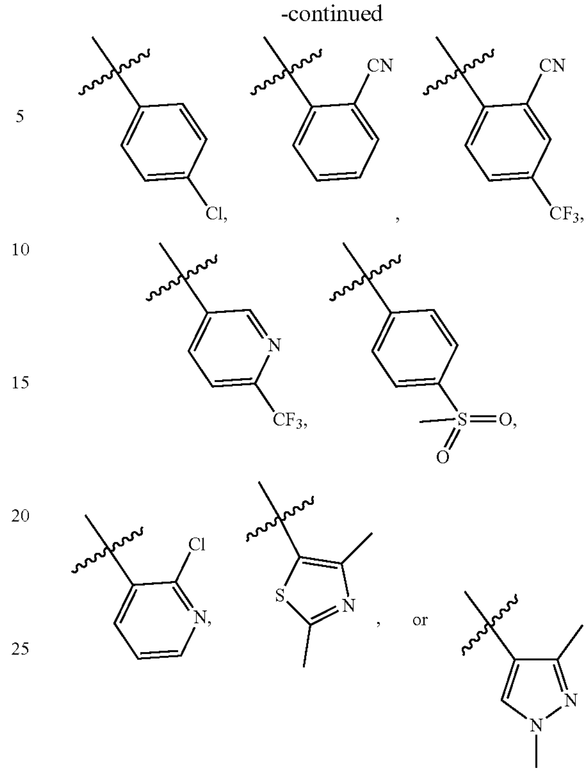

In exemplary embodiments, $Ar^1$ is

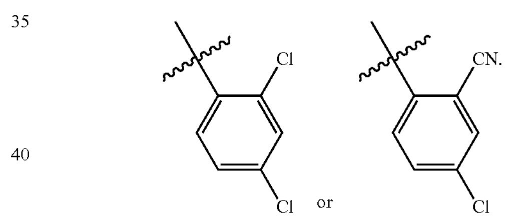

In some embodiments, $Ar^2$ is selected from a 5-membered aryl, a 5-membered heteroaryl, a 6-membered aryl, or a 6-membered heteroaryl. Each aryl or heteroaryl may be unsubstituted or substituted with one or two substituents independently selected from cyano, halo, $C_1$-$C_6$alkyl, $C_1$-$C_6$alkoxy, —C(O)—$C_1$-$C_6$alkoxy, and —C(O)—$NH_2$. In some embodiments, the halo is fluoro or chloro.

In some embodiments, $Ar^2$ is

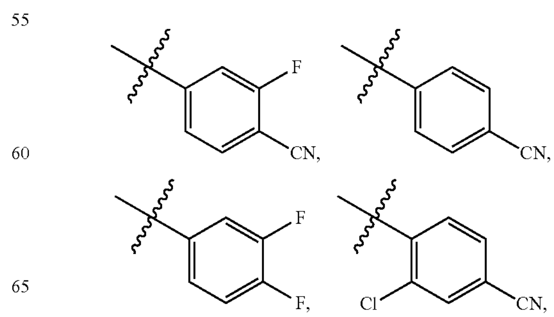

-continued

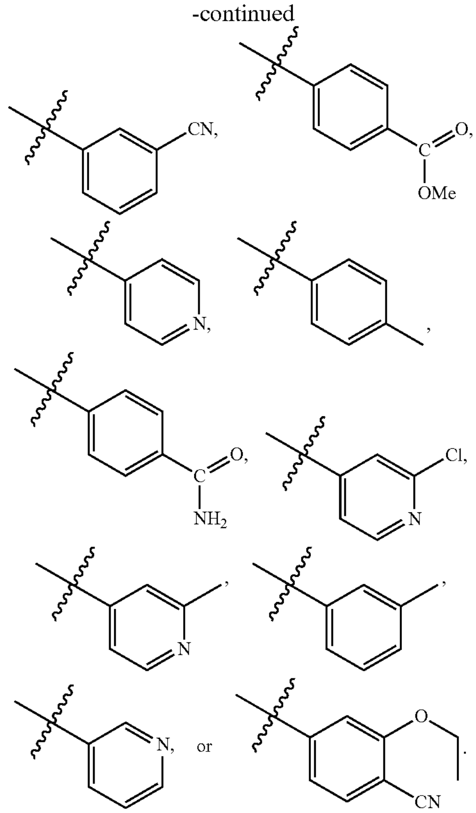

In exemplary embodiments, $Ar^2$ is

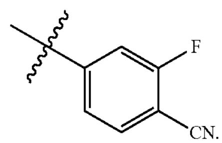 [SMILES: *c1ccc(C#N)c(F)c1]

In some embodiments, Z is $CHR^2R^3$, $COR^4$, or $NHR^5$;

$R^2$ and $R^3$ are each independently selected from the group consisting of hydrogen, hydroxy, $C_1$-$C_6$alkoxy, $C_4$-$C_8$heterocyclyl, phosphate, $NR^6R^7$, —OC(O)$R^8$, and $S(O)_2R^{10}$; $R^4$ is selected from the group consisting of hydroxy, $C_1$-$C_6$alkoxy, and $NR^6R^7$;

$R^5$ is selected from the group consisting of hydrogen, $C_1$-$C_6$alkyl, —C(O)$R^9$, and —$S(O)_2R^{10}$;

$R^6$ and $R^7$ are each independently selected from the group consisting of hydrogen, $C_1$-$C_6$alkyl, $C_1$-$C_6$heteroalkyl, $C_4$-$C_8$heterocyclyl, $C_1$-$C_6$alkoxy-$C_1$-$C_6$alkyl, $C_5$-$C_8$heteroaryl-$C_1$-$C_6$alkyl, $C_5$-$C_8$heterocyclyl-$C_1$-$C_6$alkyl, amino-$C_1$-$C_6$alkyl, hydroxy-$C_1$-$C_6$alkyl, hydroxy-$C_3$-$C_8$cycloalkyl, cyano-$C_1$-$C_6$alkyl, hydroxysulfonyl-$C_1$-$C_6$alkyl, alkylphosphate-$C_1$-$C_6$alkyl, —$COR^{12}$, and —$CHR^{13}C(O)R^{14}$;

$R^8$ is $C_5$-$C_8$aryl or $C_5$-$C_8$heteroaryl;

$R^9$ is selected from the group consisting of $C_1$-$C_6$alkyl, $C_1$-$C_6$heteroalkyl, amino-$C_1$-$C_6$alkyl, hydroxy-$C_1$-$C_6$alkyl, or —$COR^{12}$;

$R^{10}$ is amino-$C_1$-$C_6$alkyl;

$R^{12}$ is selected from the group consisting of $C_1$-$C_6$alkyl, $C_1$-$C_6$heteroalkyl, $C_1$-$C_6$alkoxy, amino-$C_1$-$C_6$alkyl, $C_4$-$C_8$heterocyclyl, amino-$C_4$-$C_8$heterocyclyl, phosphate-$C_1$-$C_6$alkyl, and $C_1$-$C_6$alkyl phosphate;

$R^{13}$ and $R^{14}$ are each independently selected from the group consisting of hydrogen and $C_1$-$C_6$alkyl; and $R^{15}$ is selected from the group consisting of hydroxy, $C_1$-$C_6$alkoxy and amino.

In exemplary embodiments, Z is —$CH_2OH$, —C(O)OH, $NH_2$, —NHC(O)$CH_2$, —$CH_2NH_2$, —$CH_2NHCH_3$, —$CH_2NH(CH_2)_2OH$, —$CH_2NH(CH_2)_3OH$, —$CH_2NH(C_5H_9O)$, —$CH_2NH(CH_2)_2OCH_3$, —$CH_2NHCH_2(C_4H_7O)$, —$CH_2NHCH_2CH_3$, —$CH_2NHCH_2CH(OH)CH_3$, —$CH_2NH(C_3H_5O)$, or —$CH_2NHCH_2(C_3H_5O)$.

In some embodiments, X is O and n is 0. In some embodiments, m is 1. In some embodiments, X is O, m is 1, and n is 0.

In some embodiments, X is $NR^1$. In some embodiments $R^1$ is hydrogen.

In some embodiments, X is $NR^1$ and m is 0. In certain embodiments, X is $NR^1$, m is 0, and n is 1.

In some embodiments, X is $NR^1$ and n is 0. In certain embodiments, X is $NR^1$, m is 1, and n is 0.

A compound selected from the group consisting of:

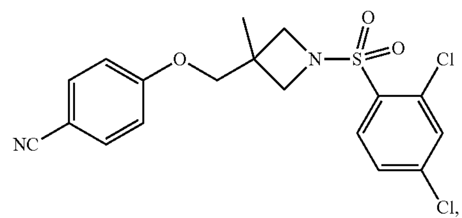

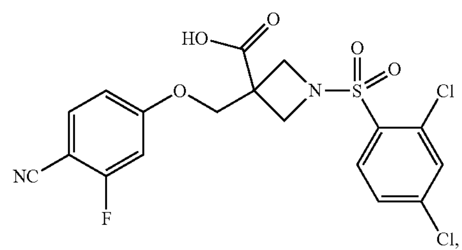

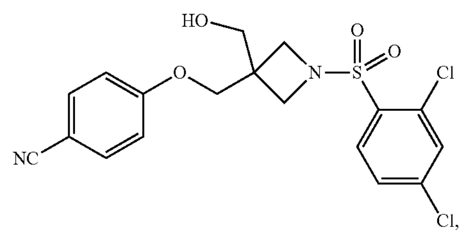

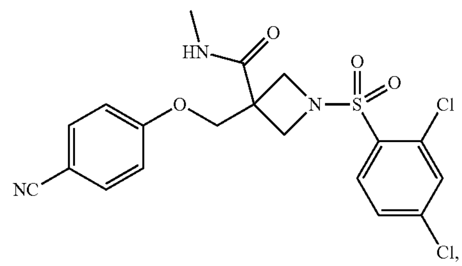

-continued
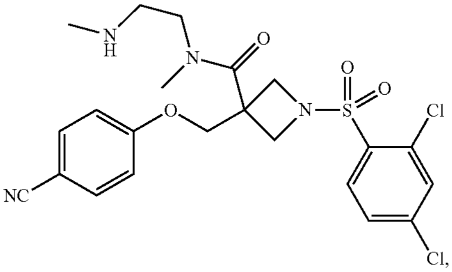
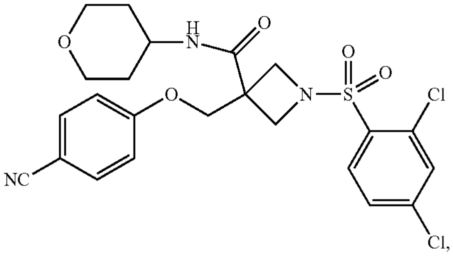
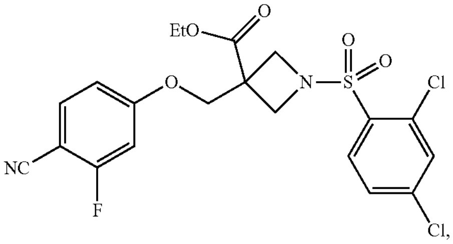
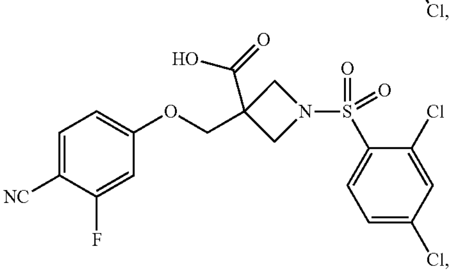
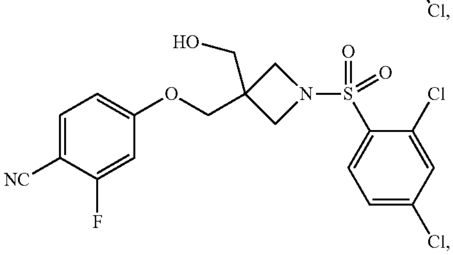
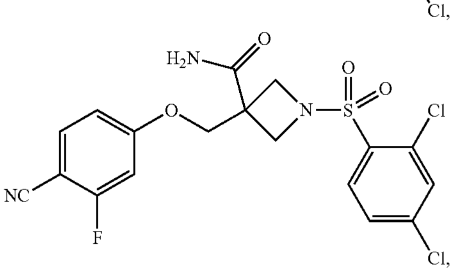
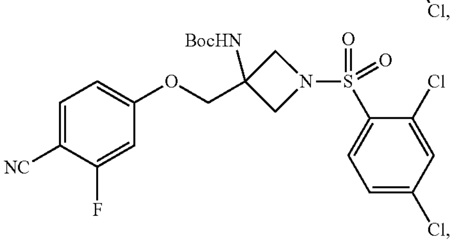
-continued
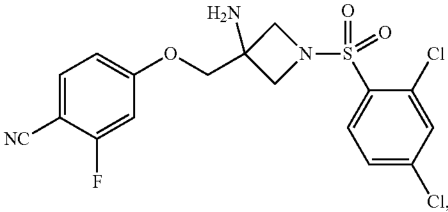
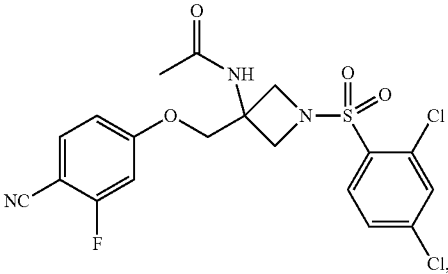
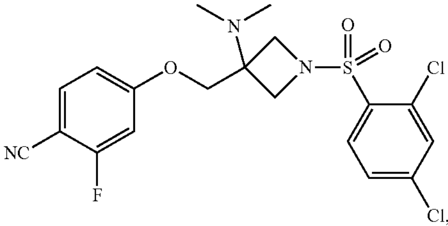
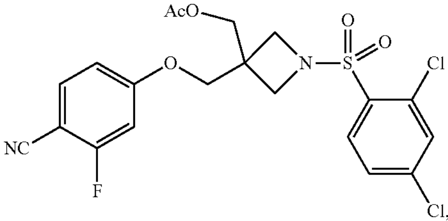
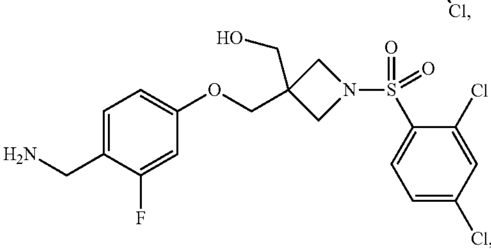
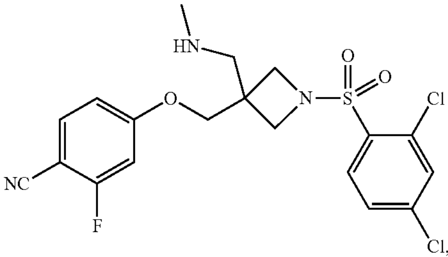
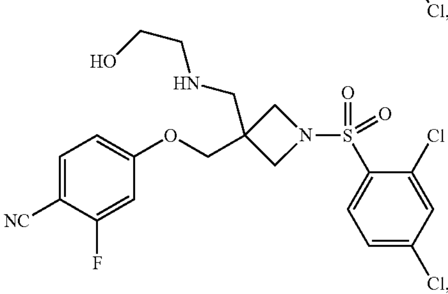

-continued
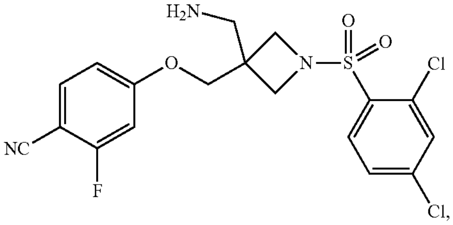
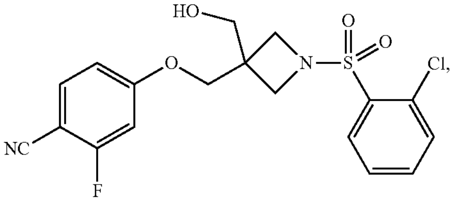
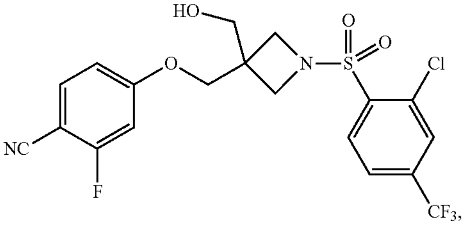
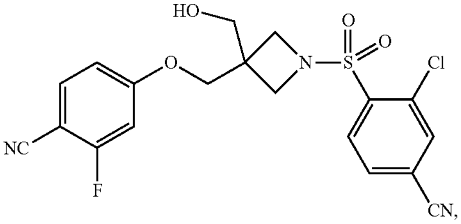
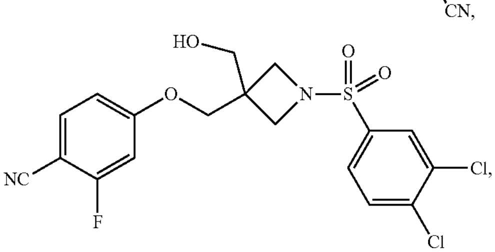
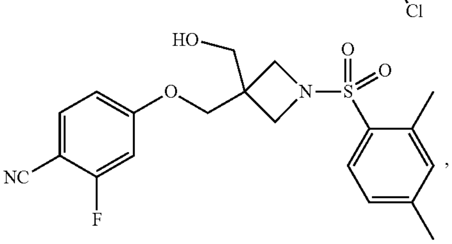
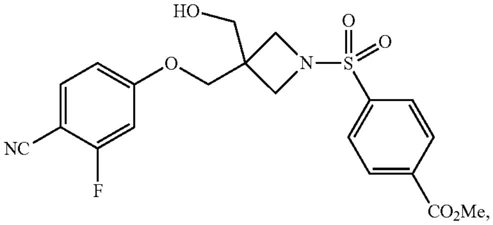
-continued
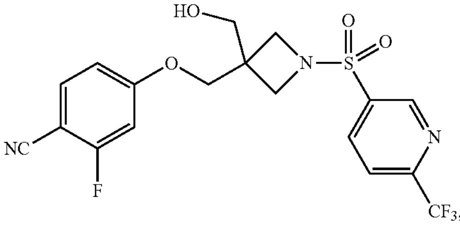
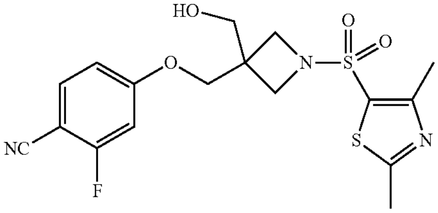
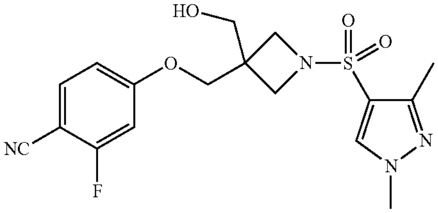
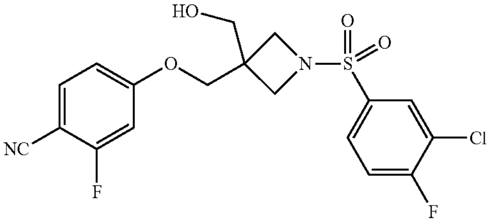
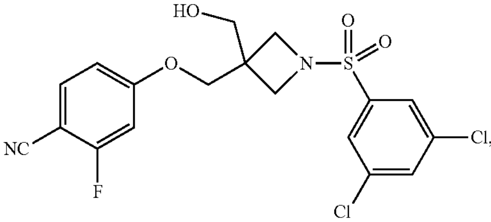
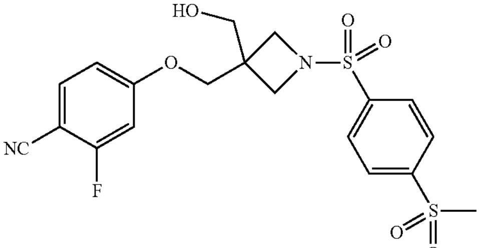
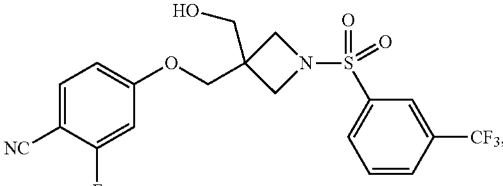

-continued
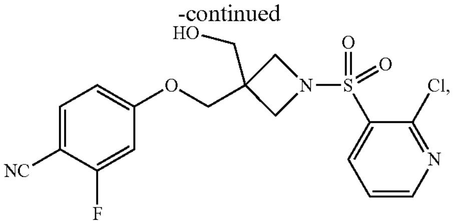
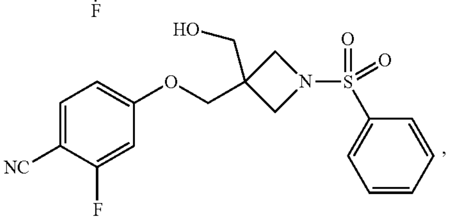
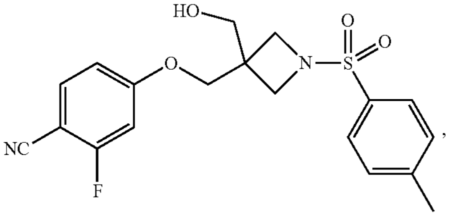
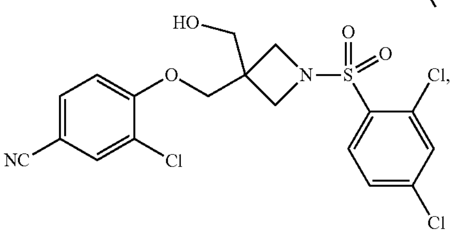
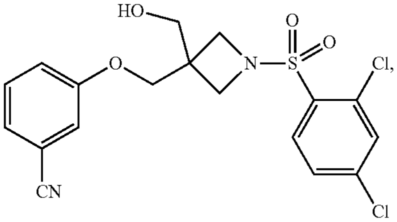
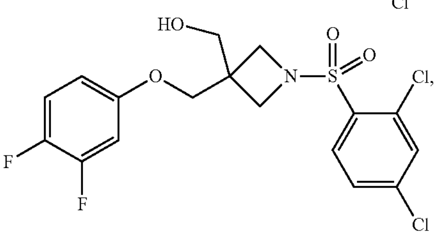
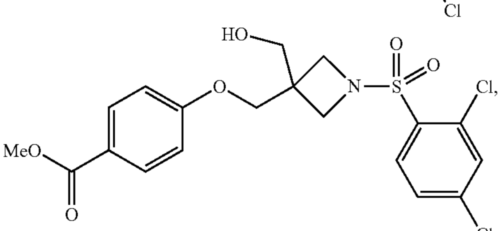
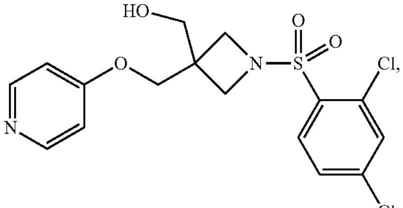
-continued
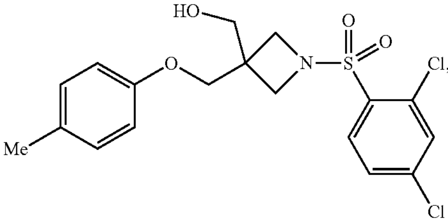
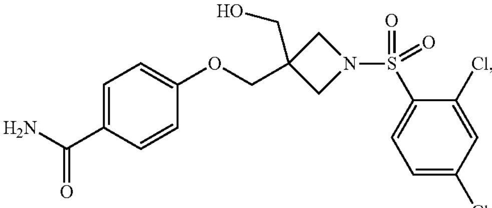
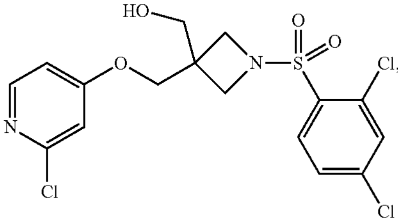
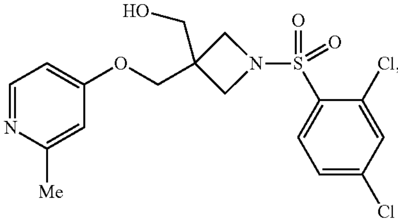
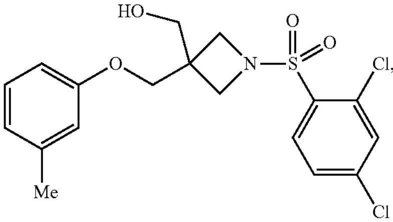
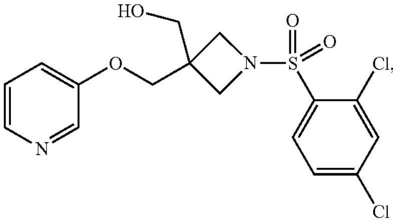
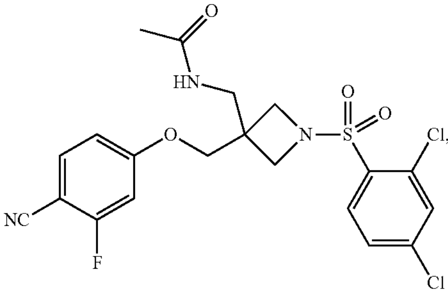

-continued
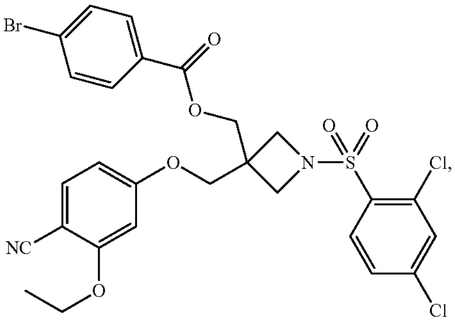
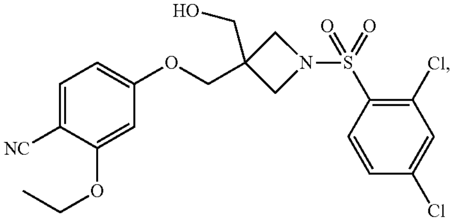
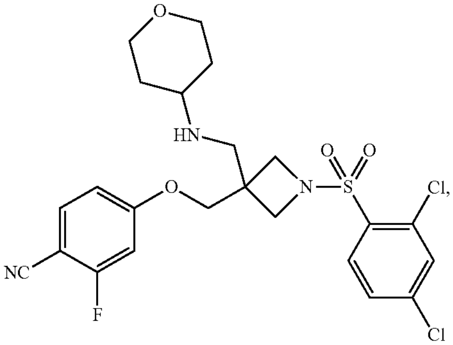
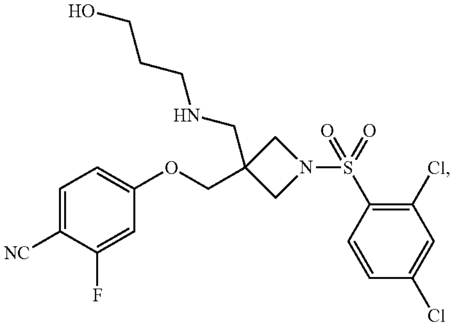
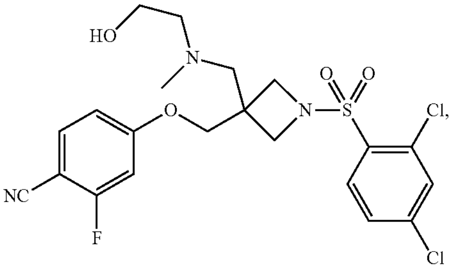
-continued
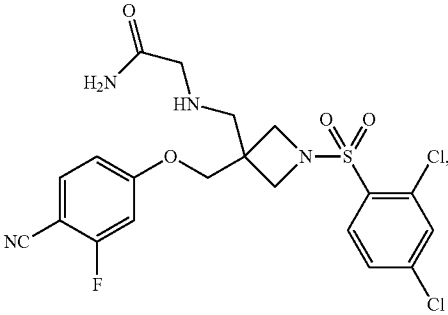
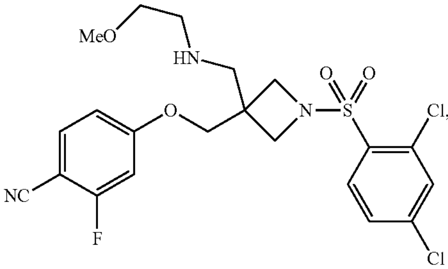
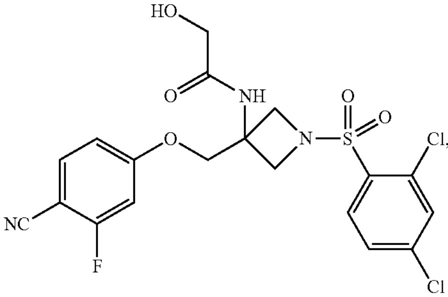
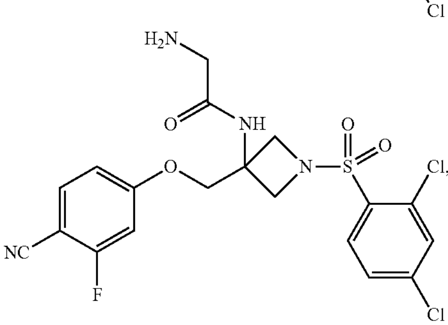
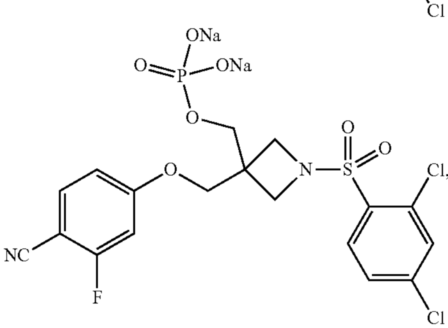
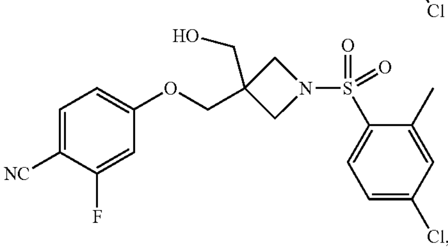

-continued
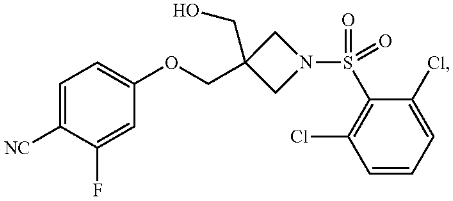
,
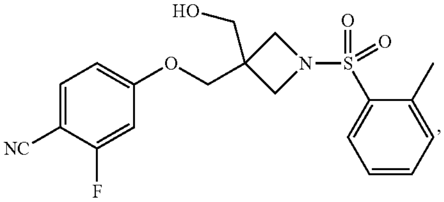
,
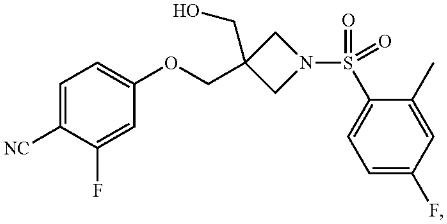
,
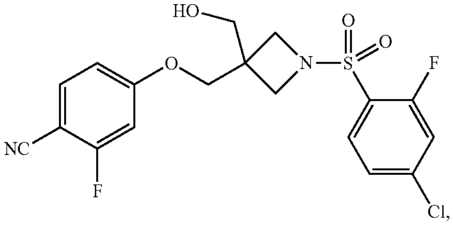
,
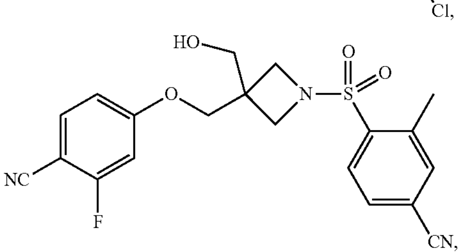
,
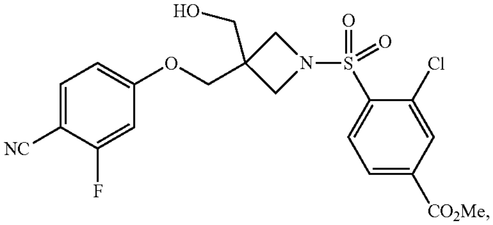
,
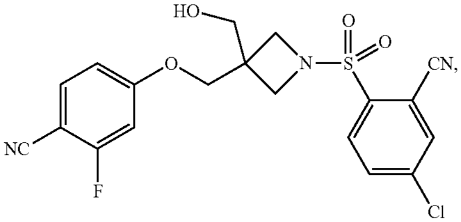
-continued
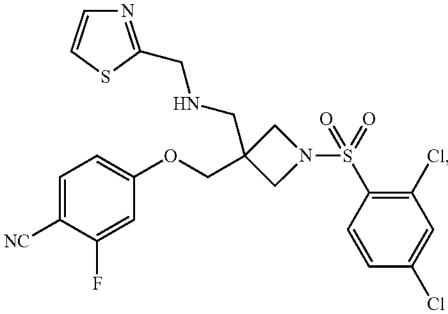
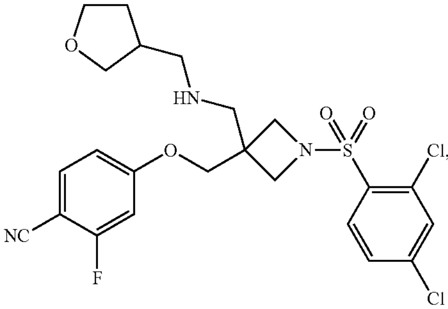
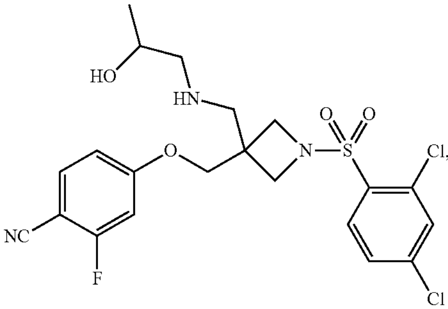
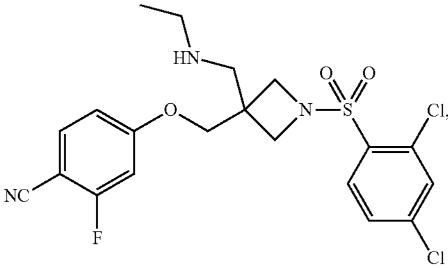
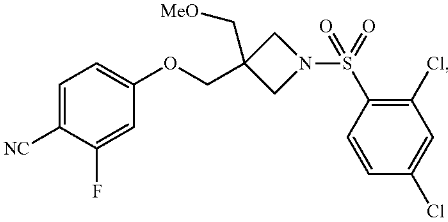

-continued
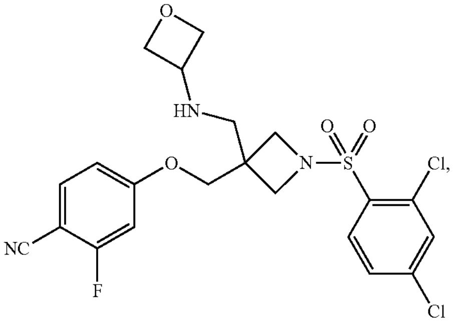
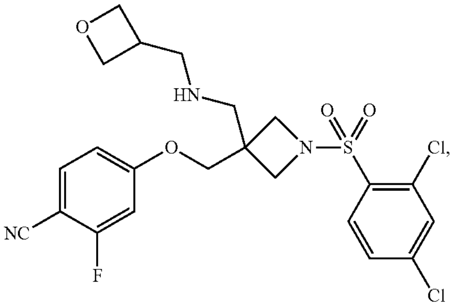
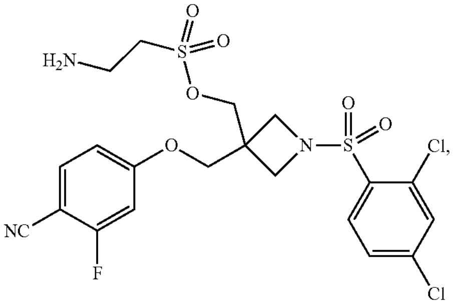
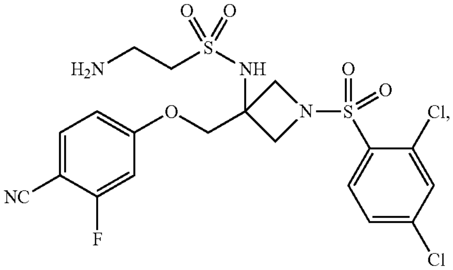
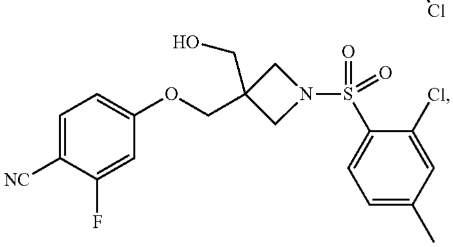
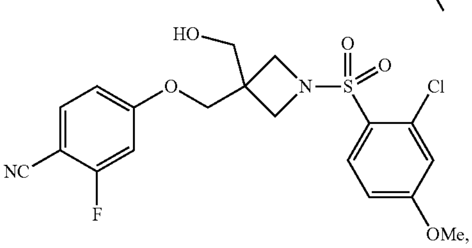
-continued
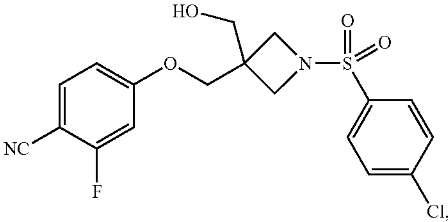
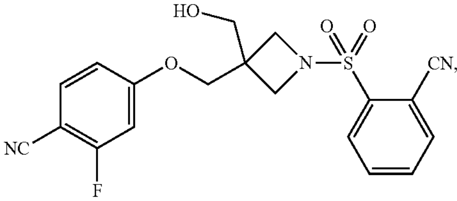
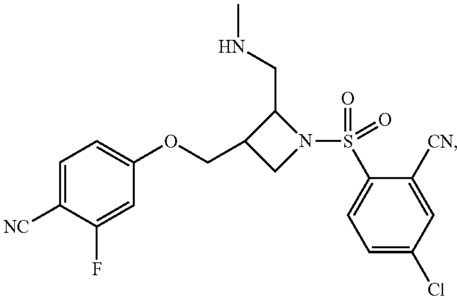
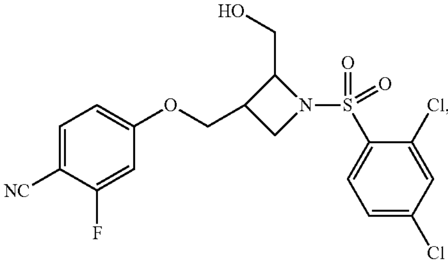
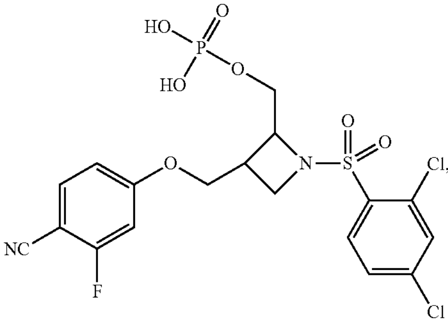
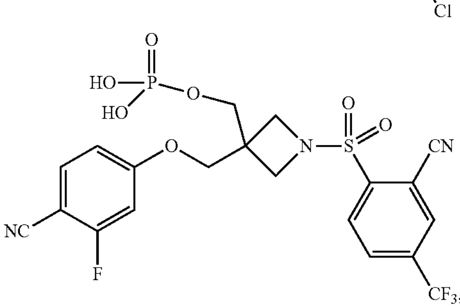

-continued
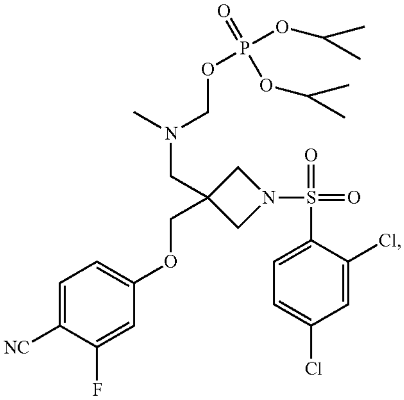
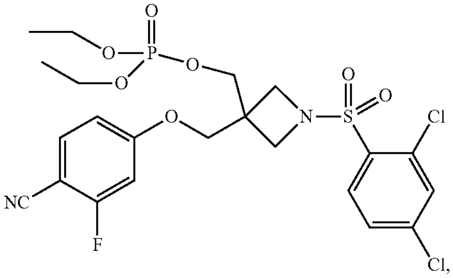
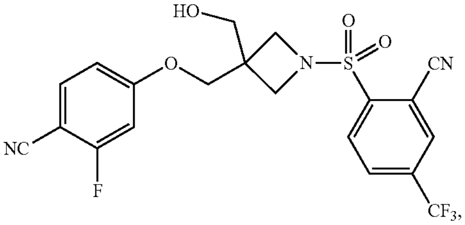
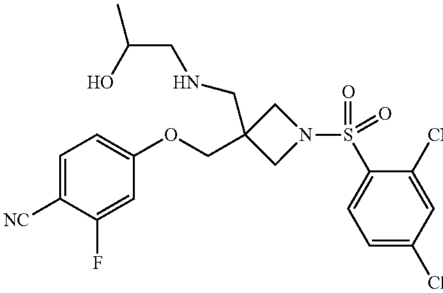
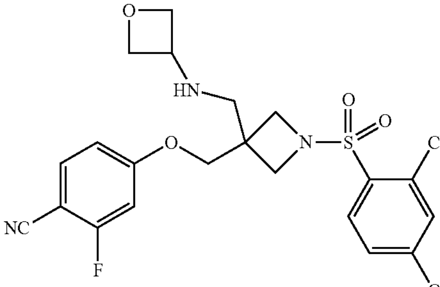
-continued
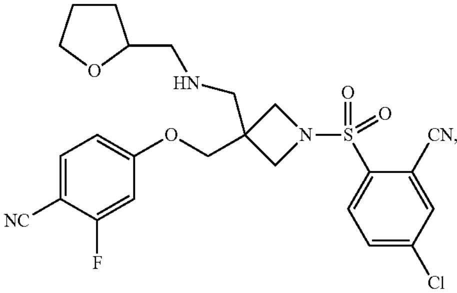
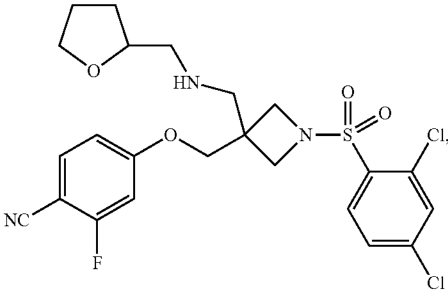
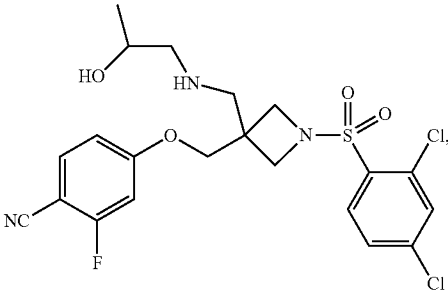
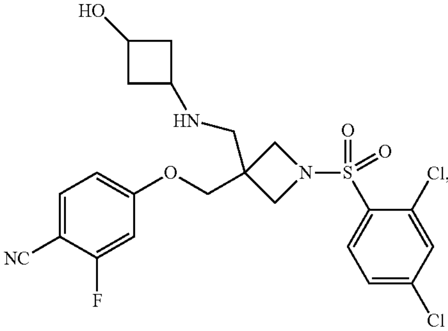
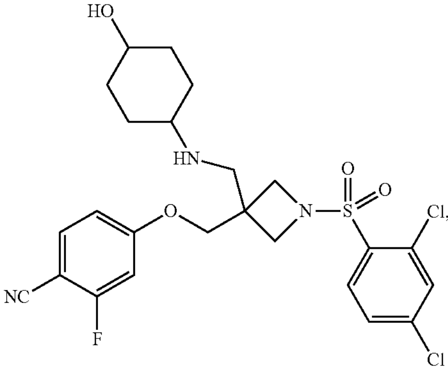

-continued
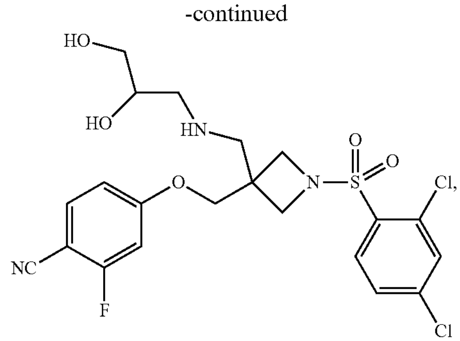
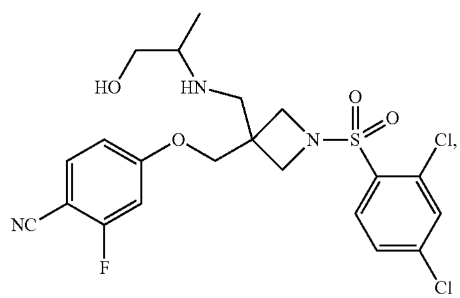
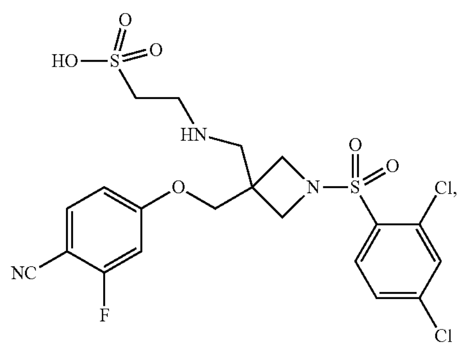
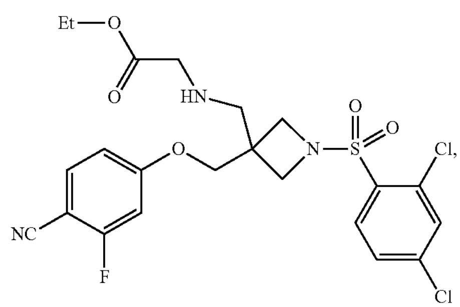
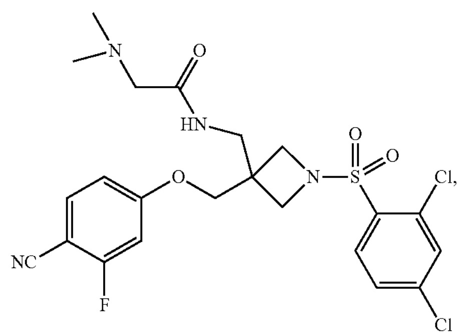
-continued
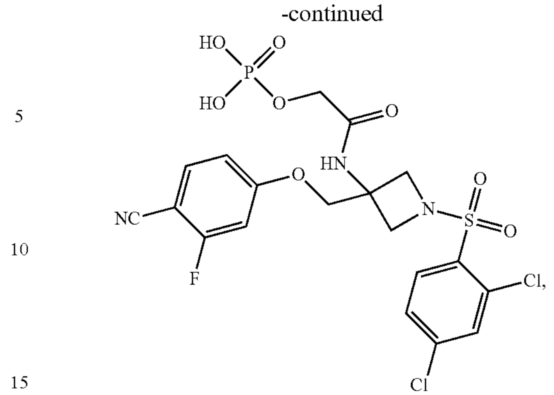
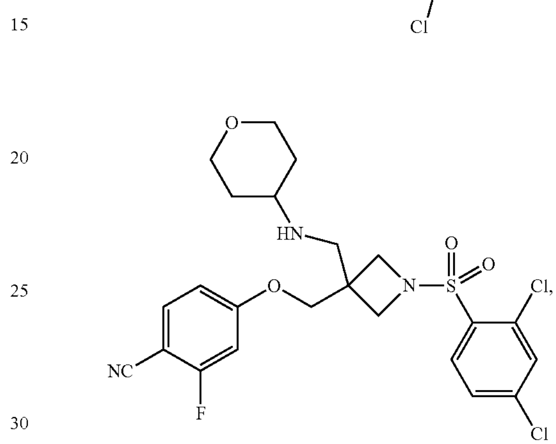
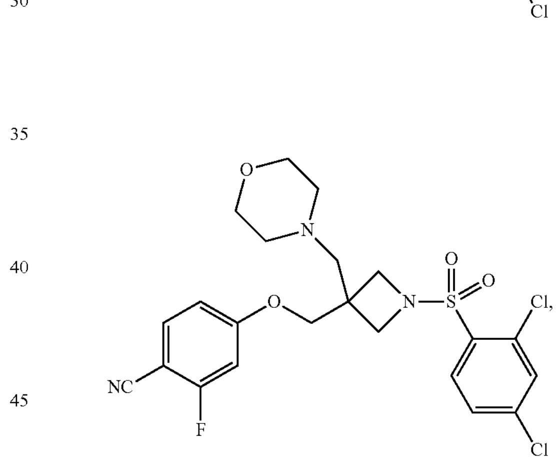
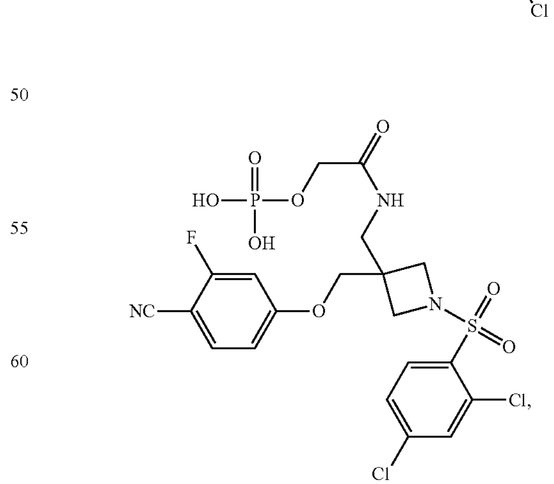

-continued
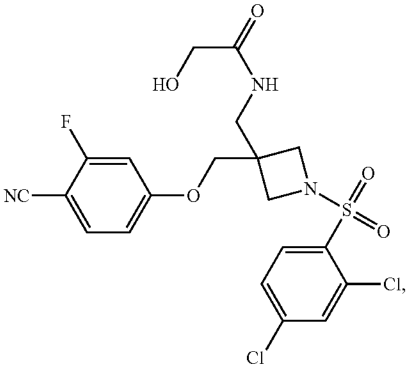
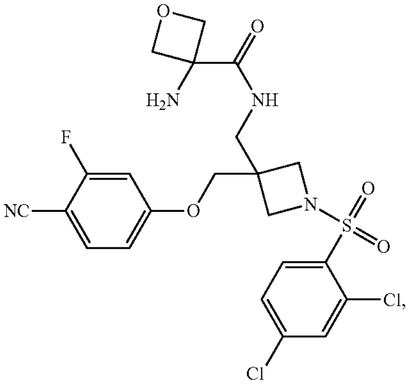
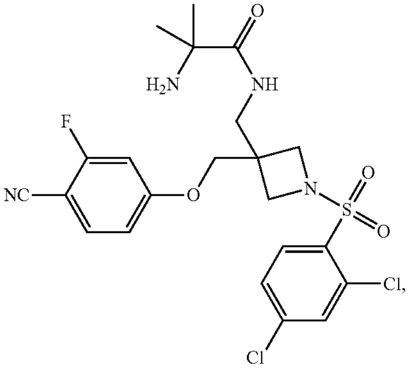
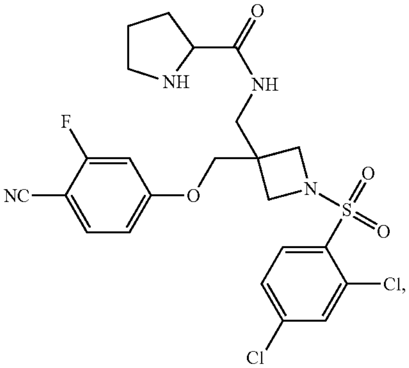
-continued
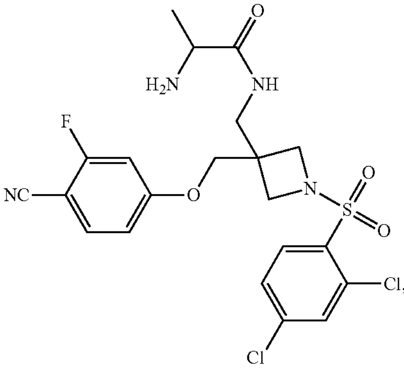
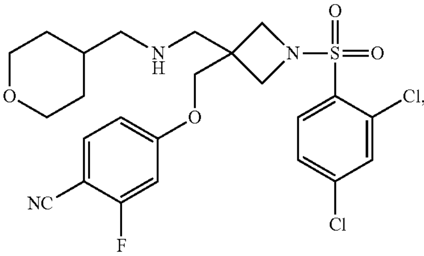
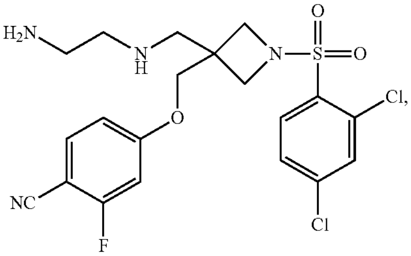
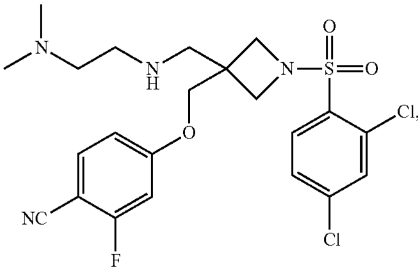
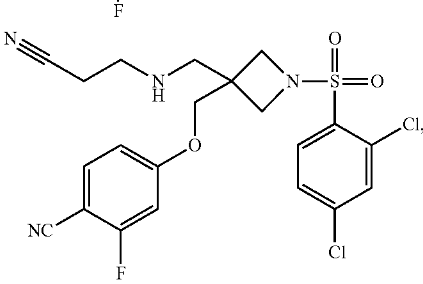
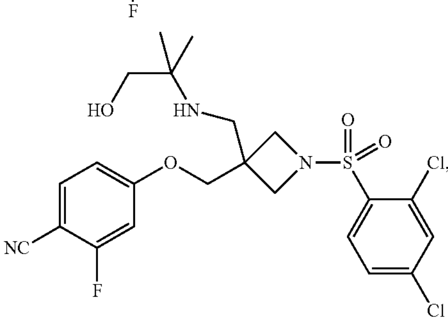

-continued
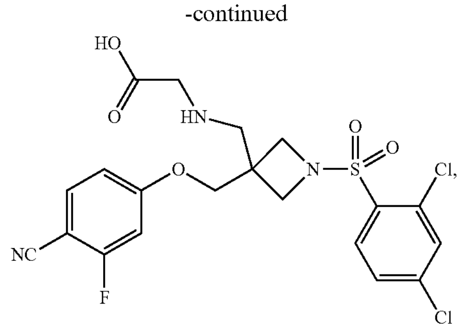
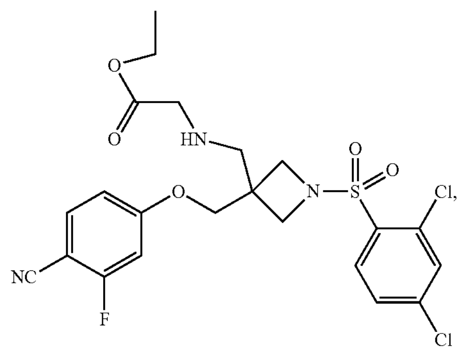
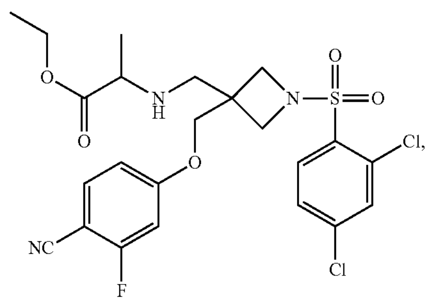
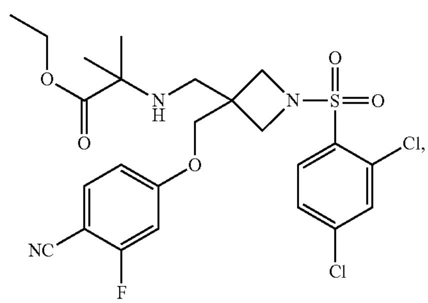
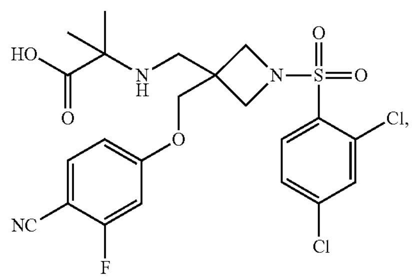
-continued
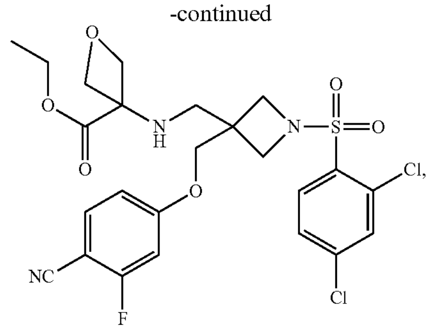
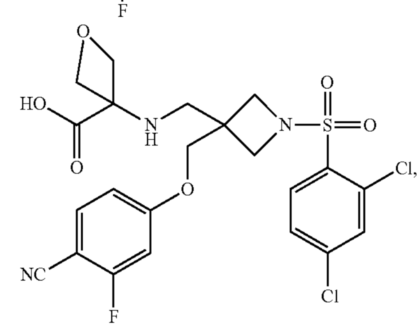
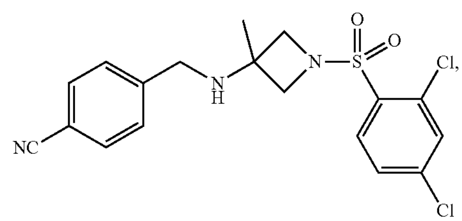
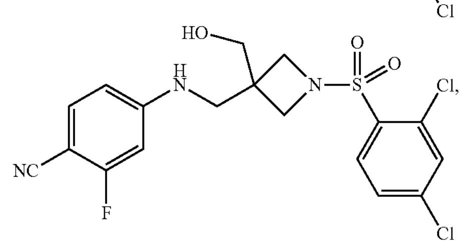
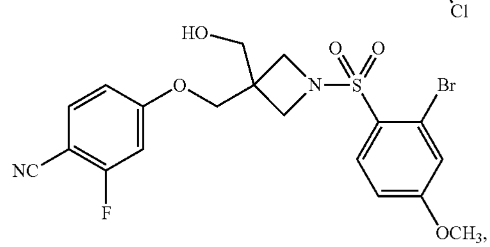
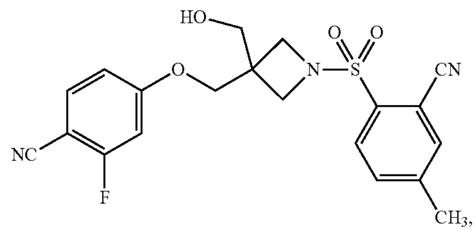
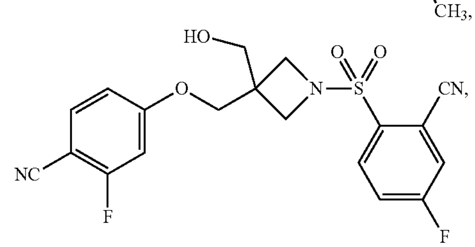

-continued
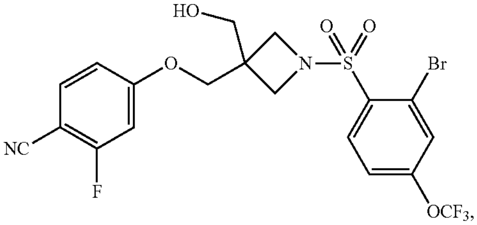
,
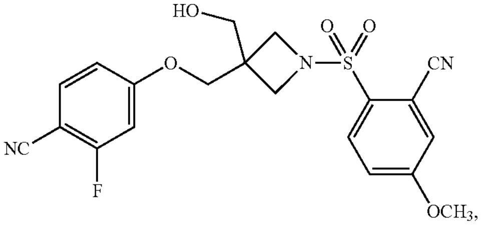
,
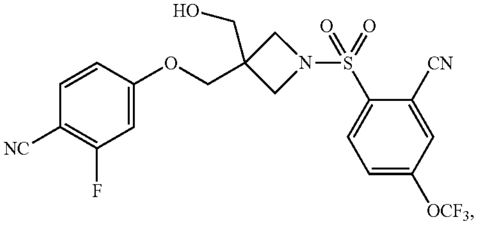
,
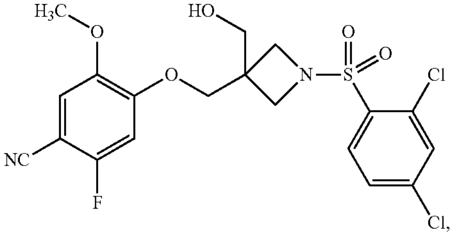
,
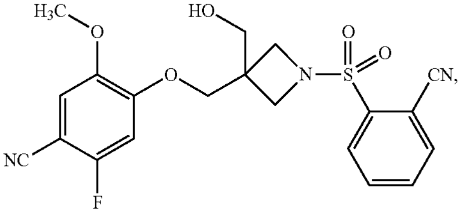
,
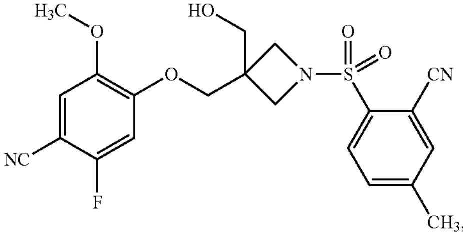
,
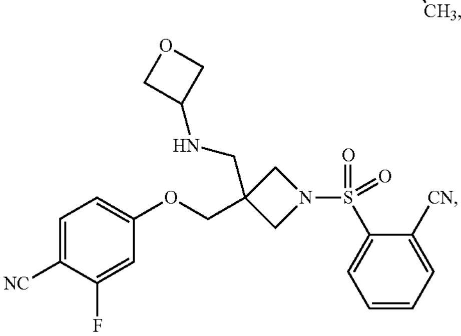
,
-continued
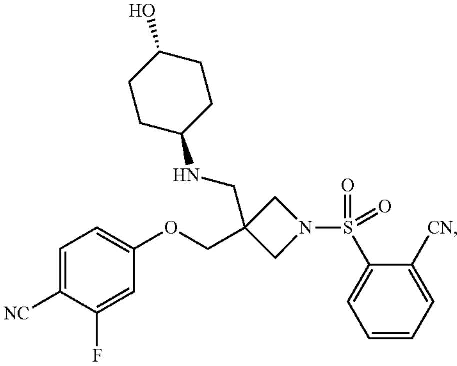
,
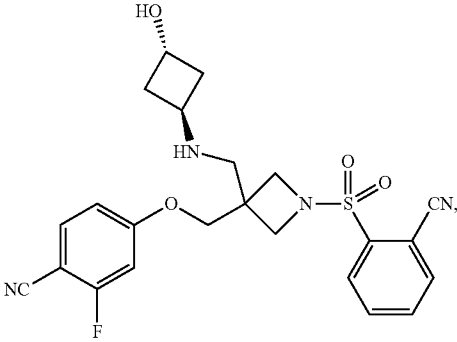
,
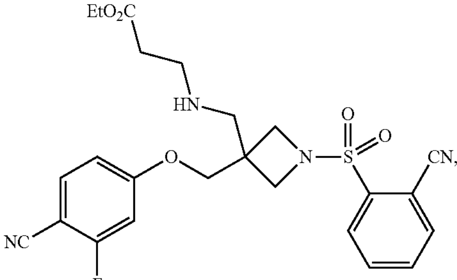
,
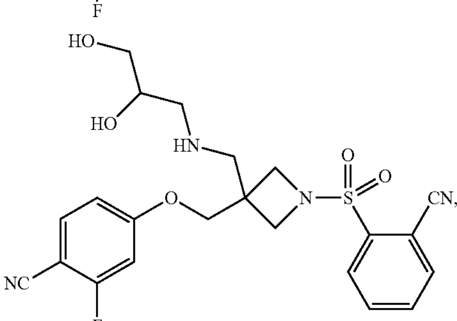
,
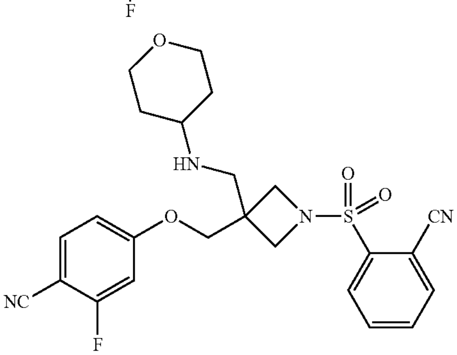
and -continued

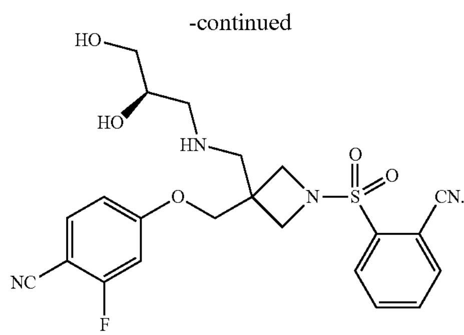

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

It should be understood that the compound may possess tautomeric forms, as well as geometric isomers, and that these also constitute embodiments of the disclosure.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, 35S, $^{18}F$, and $^{36}Cl$, respectively. Substitution with heavier isotopes such as deuterium, i.e. $^{2}H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

In some embodiments, in compounds of formula (I), any hydrogen atom may be deuterium.

The disclosed compounds may act or function as antagonists of TRPV4. In certain embodiments, the disclosed compounds can inhibit TRPV4 with an $IC_{50}$ ranging from about 0.1 nM to about 50 μM, from about 0.1 nM to about 10 μM, from about 0.1 nM to about 1 μM, from about 0.1 nM to about 100 nM, or from about 0.1 nM to about 50 nM. In certain embodiments, the disclosed compounds can inhibit TRPV4 with an $IC_{50}$ of less than 50 μM, less than 49 μM, less than 48 μM, less than 47 μM, less than 46 μM, less than 45 μM, less than 44 μM, less than 43 μM, less than 42 μM, less than 41 μM, less than 40 μM, less than 39 μM, less than 38 μM, less than 37 μM, less than 36 μM, less than 35 μM, less than 34 μM, less than 33 μM, less than 32 μM, less than 31 μM, less than 30 μM, less than 29 μM, less than 28 μM, less than 27 μM, less than 26 μM, less than 25 μM, less than 24 μM, less than 23 μM, less than 22 μM, less than 21 μM, less than 20 μM, less than 19 μM, less than 18 μM, less than 17 μM, less than 16 μM, less than 15 μM, less than 14 μM, less than 13 μM, less than 12 μM, less than 11 μM, less than 10 μM, less than 9 μM, less than 8 μM, less than 7 μM, less than 6 μM, less than 5 μM, less than 4 μM, less than 3 μM, less than 2 μM, less than 1 μM, less than 950 nM, less than 900 nM, less than 850 nM, less than 800 nM, less than 750 nM, less than 700 nM, less than 650 nM, less than 600 nM, less than 550 nM, less than 500 nM, less than 450 nM, less than 400 nM, less than 350 nM, less than 300 nM, less than 250 nM, less than 200 nM, less than 150 nM, less than 100 nM, less than 50 nM, less than 10 nM, less than 5 nM, or less than 1 nM.

The disclosed compounds may be selective modulators of TRPV4 over other TRPV receptors, such as TRPV3.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. PHARMACEUTICAL COMPOSITIONS

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention (e.g., a compound of formula (I)) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, PA) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of an active compound (e.g., a compound of formula (I)) and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I)), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I)), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

4. METHODS OF TREATMENT

The disclosed compounds may be used in methods for treatment of TRPV4 related medical disorders and/or diseases. The methods of treatment may comprise administering to a subject in need of such treatment a composition comprising a therapeutically effective amount of the compound of formula (I), or a pharmaceutically acceptable salt thereof.

The compounds can be administered to a subject in need thereof to modulate TRPV4, for a variety of diverse biological processes.

The compounds may be useful for treating and preventing certain diseases and disorders in humans and animals related to TRPV4 dysfunction. Treatment or prevention of such diseases and disorders can be effected by modulating TRPV4 in a subject, by administering a compound or composition of the disclosure, either alone or in combination with another active agent as part of a therapeutic regimen to a subject in need thereof.

In combination therapy, the other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The compounds may be useful for treating or preventing a disease or disorder associated with dysfunction of TPRV4, like ocular diseases, such as retinopathies including nonproliferative and proliferative diabetic retinopathy and retinopathy of prematurity, glaucoma, macular degeneration, age-related macular degeneration (wet and dry), retinitis pigmentosa, Stargardt disease, macular edema, uveitis, ocular hypertension, and retinal infections including those with cytomegalovirus. The disease may be chronic, or it may be acute. The compounds and pharmaceutical compositions disclosed herein may also be used to prevent blast-induced ocular injury mediated by, for example, IEDs, increased G forces during flight and mechanical trauma. In an embodiment, the compounds and pharmaceutical compositions disclosed herein may be used for treating or preventing glaucoma.

It is possible that the vertebrate retina, which is exposed to systemic blood pressure, hydrostatic pressure form the CSF, and intrinsic IOP, contains one or more pressure-sensitive TRP and/or piezo channels. Pathological elevations in IOP or systemic pressure represent primary risk factors for many conditions such as glaucoma, a group of inherited optic neuropathies characterized by apoptotic loss of RGCs, degeneration of the optic nerve, and progressive loss of visual fields. The cellular pathophysiology of glaucoma is not well understood, in part because the mechanisms that couple the mechanical stimulus (ΔIOP) to cellular signal transduction remain to be characterized.

The compounds and compositions disclosed herein may be useful for the treatment or prevention of diseases and disorders other than ocular diseases, for which an antagonist of a TRPV4 channel may be beneficial. For example, the compounds of formula (I) may be useful in the treatment and/or prevention of disorders of the bladder, heart failure, lung edema, atherosclerosis, disorders related to intestinal edema, post-surgical abdominal edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, overactive bladder, pain, motor neuron disorders, genetic gain of function disorders, cardiovascular disease, renal dysfunction, osteoarthritis crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, or flatulence.

Also provided is a method for the treatment of one or more disorders, for which TRPV4 receptor modulation is predicted to be beneficial, in a subject comprising the step of administering to the subject at least one disclosed compound; at least one disclosed pharmaceutical composition; and/or at least one disclosed product in a dosage and amount effective to treat the disorder in the subject.

The disclosure is directed to the use of described chemical compositions to treat diseases or disorders in patients (preferably human) wherein TRPV4 receptor modulation would be predicted to have a therapeutic effect, such as atherosclerosis, disorders related to intestinal edema, fluid retention, sepsis, hypertension, inflammation, bone related dysfunctions and congestive heart failure, pulmonary disorders, overactive bladder, pain, motor neuron disorders, genetic gain of function disorders, cardiovascular disease, renal dysfunction, osteoarthritis, intestinal irregularity (hyperreactivity/hyporeactivity) by administering one or more disclosed compounds or products.

Also provided is a method for the treatment of a disorder in a mammal comprising the step of administering to the mammal at least one disclosed compound, composition, or medicament.

The compounds are further useful in a method for the prevention, treatment, control, amelioration, or reduction of risk of the diseases, disorders and conditions noted herein. The compounds are further useful in a method for the prevention, treatment, control, amelioration, or reduction of risk of the aforementioned diseases, disorders and conditions in combination with other agents.

Additionally, various ocular traumas are capable of having long-term degenerative effects on the eye. For example, a subject that is near an explosion can develop subsequent degenerative conditions due to the compressive impact of the explosion on the eyes. In some cases such damage may not be immediate, but can develop over time. Treatments for such ocular trauma can include delivering a TRPV4 antagonist into the eye following such trauma to moderate, decrease, or eliminate associated long-term effects.

Furthermore, in some cases apoptosis of RGCs can be associated with ocular conditions having a degenerative component. In some aspects, antagonists to TRPV4 receptors can have a neuroprotective effect on at least RGCs, thus treating or moderating the damaging effects of such conditions. It is noted that treatment of an eye with a TRPV4 antagonist can be beneficial for those subjects experiencing an increase in IOP as well as for those subjects that do not exhibit IOP or have moderate increases in IOP.

In one aspect, a TRPV4 antagonist can provide protection against pressure-induced $Ca^{2+}$ overloads under in vitro and in vivo conditions. Such an antagonist reduces IOP in the anterior chamber of eye, suggesting that it regulates fluid production/absorption in the trabecular meshwork of the anterior eye, and blocks pressure-induced apoptosis of RGCs.

It is known that the TRPV4 ion channel is involved in modulating calcium flux, and is implicated in the retinal remodeling that occurs during chronic increases in IOP (Ryskamp et al, J. Neuroscience 2011, 31(19), 7089-7101, incorporated herein). In certain embodiments, the compounds of formula (I) can antagonize excessive TRPV4 activation. The regulation of IOP by modulating fluid production in the anterior eye can be used for treating ocular diseases, particularly glaucoma.

5. KITS

In one aspect, the disclosure provides kits comprising at least one disclosed compound or a pharmaceutically acceptable salt thereof, and optionally one or more of:

(a) at least one agent known to modulate TRPV4 activity;

(b) at least one agent known to treat a disorder associated with TPRV4 activity;

(c) instructions for treating a disorder associated with TPRV4 activity; or (d) instructions for administering the compound in connection with ocular therapy.

In some embodiments, the at least one disclosed compound and the at least one agent are co-formulated. In some embodiments, the at least one disclosed compound and the at least one agent are co-packaged. The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

That the disclosed kits can be employed in connection with disclosed methods of use.

The kits may contain information, instructions, or both that use of the kit will provide treatment for medical conditions in mammals (particularly humans). The information and instructions may be in the form of words, pictures, or both, and the like. In addition or in the alternative, the kit may include the compound, a composition, or both; and information, instructions, or both, regarding methods of application of compound, or of composition, preferably with the benefit of treating or preventing medical conditions in mammals (e.g., humans).

The compounds and processes of the invention will be better understood by reference to the following examples, which are intended as an illustration of and not a limitation upon the scope of the invention.

6. EXAMPLES

The following Examples are offered as illustrative as a partial scope and particular embodiments of the disclosure and are not meant to be limiting of the scope of the disclosure. Abbreviations and chemical symbols have their usual and customary meanings unless otherwise indicated. Unless otherwise indicated, the compounds described herein have been prepared, isolated and characterized using the Schemes and other methods disclosed herein or may be prepared using same.

The preparation of starting materials that are commercially available, described in the literature, or readily obtainable by those skilled in the art is not described. It will be appreciated by the skilled person that where it is stated that compounds were prepared analogously to earlier examples or intermediates, the reaction time, number of equivalents of reagents, and temperature, can be modified for each specific reaction and that it may be necessary or desirable to employ different work-up or purification techniques.

The following abbreviations may be used: lithium bis(trimethylsilyl)amide (LHMDS), diisopropyl azodicarboxylate (DIAD), trifluoroacetic acid (TFA), dichloromethane (DCM), triethylamine ($Et_3N$), N,N-diisopropylethylamine (DIPEA), ethyl acetate (EtOAc), triphenylphosphine ($PPh_3$), hexafluorophosphate azabenzotriazole tetramethyl uronium (HATU), ethanol (EtOH), lithium tri-tert-butoxyaluminum hydride ($LiAlH(Ot\text{-}Bu)_3$), borane dimethyl sulfide complex ($BH_3 \cdot SMe_2$), N,N-dimethylaminopyridine (DMAP), acetonitrile ($CH_3CN$), diethyl ether ($Et_2O$), tetrahydrofuran (THF), dimethylsulfoxide (DMSO), N,N'-dimethylformamide (DMF), sodium triacetoxyborohydride ($NaBH(OAc)_3$), acetic acid (AcOH), 1,2-dichloethane (DCE), sodium acetate (NaOAc), sodium cyanoborohydride ($NaBH_3CN$), tert-butyldimethylsilyl chloride (TBS-Cl), and tetrabutlyammonium fluoride (TBAF).

General Methods. All reactions requiring anhydrous conditions were conducted in oven or flame-dried glassware. Commercially available reagents were used as received; otherwise, materials were purified accordingly following Purification of Laboratory Chemicals protocols. Dichloromethane, N,N'-dimethylformamide, toluene, acetonitrile and tetrahydrofuran were degassed with nitrogen and passed through a solvent purification system (Innovative Technologies Pure Solv). Dry 1,4-dioxane was purchased from Acros Organics in a Acros Seal™ bottle. Triethylamine and N,N-diisopropylethylamine were stored over 4 Å molecular sieves or distilled over 4 Å molecular sieves prior to usage. Microwave reactions were done in CEM Discover System Model 908005. Reactions were monitored by TLC and visualized by a dual short wave/long wave UV lamp and stained with either ethanolic solutions of KMnO4 or 12-phosphomolybdic acid. Flash chromatography was performed on Merck silica gel Kieselgel 60 (230-400 mesh) from EM Science with the indicated HPLC grade solvent or with an automated medium pressure column chromatography system (Teledyne ISCO CombiFlash RF75 or CombiFlash Rf+). Reverse phase HPLC was conducted on a Waters HPLC Semi Prep 150B system with Sunfire C18 Prep Column or Atlantis T3 Prep Column. LCMS data were collected on Thermo Scientific™ UltiMate™ 3000 UHPLC with electrochemical detector with a fluorescence detector monitored at either 214 or 254 nm. LC/MS/MS data were collected on a ThermoFinnigan TSQ Quantum with Genesis Lightn C18, 4 uM 50 mm column (ID 2.1 mm) in either positive or negative mode. Mobile phases consisted of acetonitrile (0.1% formic acid) and water (0.1% formic acid) for positive ion mode and methanol (5 mM ammonium bicarbonate) and water (5 mM ammonium bicarbonate) for negative ion mode. $^1$H NMR spectra were recorded at 500 MHz, 400 MHz, and 300 MHz, and 13C at 125 MHz. Proton resonances were reported relative to the deuterated solvent peak: 7.27 ppm for CDCl3, 3.31 ppm (center line signal) for $CD_3OD$, 2.50 for DMSO-$d_6$ and 4.79 for $D_2O$ using the following format: chemical shift (6) [multiplicity (s singlet, br s broad singlet, d doublet, t triplet q quartet, m multiplet)]. Carbon resonances were reported as chemical shifts (6) in parts per million, relative to the center line signal of the respective solvent peak: 77.23 ppm for CDCl3 and 49.15 ppm for $CD_3OD$.

Example 1—Compound 1

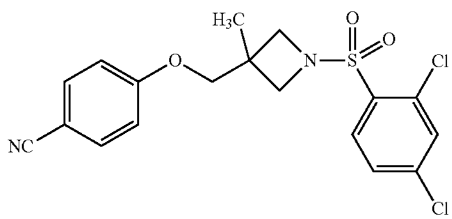 [SMILES: CC1(COc2ccc(C#N)cc2)CN(S(=O)(=O)c2ccc(Cl)cc2Cl)C1]

4-((1-((2,4-Dichlorophenyl)sulfonyl)-3-methylazetidin-3-yl)methoxy)benzonitrile was prepared according to Scheme 1:

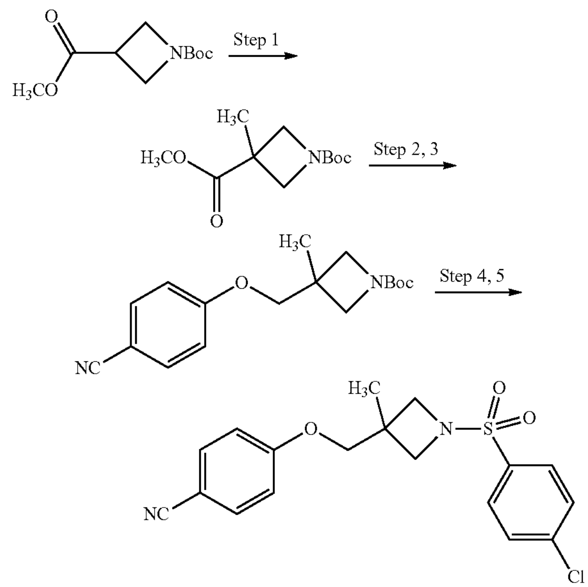

Reagents: Step 1) LiHMDS, $CH_3I$, THF, −78° C. to rt; 2) $LiBH_4$, THF, $CH_3OH$; 3) DIAD, $PPh_3$, 4-hydroxybenzonitrile, THF; 4) TFA, DCM; 5) 2,4-dichlorobenzenesulfonyl chloride, $Et_3N$, DCM.

Step 1. 1-(tert-Butyl) 3-methyl 3-methylazetidine-1,3-dicarboxylate. A solution of LHMDS (1.0 M in THF, 11.3 mL) was added to dry THF (30 mL) in a 3-neck flask under $N_2$, and the mixture cooled to −78° C. A solution of 1-(tert-butyl) 3-methyl azetidine-1,3-dicarboxylate (2.00 g, 9.29 mmol) in dry THF (20 mL) was added dropwise, and the mixture was stirred at −78° C. for 20 min. A solution of methyl iodide (0.75 mL, 12.05 mmol) in dry THF (8 mL) was added dropwise, and the mixture was warmed to rt while stirring for 3 days. The reaction was quenched with half-saturated $NH_4Cl$ (200 mL) and extracted with EtOAc (200 mL). The organic layer was washed with brine (200 mL), dried over $Na_2SO_4$, filtered and concentrated in vacuo. The residue was purified by flash chromatography (Hexanes/EtOAc) to give the title compound (1.07 g) as a light yellow oil. $^1$H NMR (500 MHz, CDCl3) δ ppm 4.21 (d, 2H), 3.75 (s, 3H), 3.67 (d, 2H), 1.53 (s, 3H), 1.44 (s, 9H).

Step 2. tert-Butyl 3-(hydroxymethyl)-3-methylazetidine-1-carboxylate. $LiBH_4$ (208 mg, 9.54 mmol) was added to a solution of 1-(tert-butyl) 3-methyl 3-methylazetidine-1,3-dicarboxylate (1.07 g, 4.67 mmol) in dry THF (40 mL), and the mixture was stirred at rt under $N_2$ for 19 h. $CH_3OH$ (10 mL) was added to the reaction mixture along with another portion of $LiBH_4$ (510 mg, 23.39 mmol), and stirring continued at rt for 25 h. A third portion of $LiBH_4$ (510 mg, 23.39 mmol) was added and the mixture stirred for another 25 h. The reaction was quenched with half-saturated $NH_4Cl$ (100 mL) and extracted with EtOAc (2×50 mL). The extracts were washed with brine (75 mL), dried over $Na_2SO_4$, filtered and concentrated in vacuo. The residue was purified by flash chromatography (Hexanes/EtOAc) to give the title compound (800 mg) as a colorless semi-solid. $^1$H NMR (500 MHz, $CDCl_3$) δ ppm 3.76 (d, 2H), 3.56-3.62 (m, 2H), 3.54 (d, 2H), 2.00-2.05 (m, 1H), 1.43 (s, 9H), 1.25 (s, 3H).

Step 3. tert-Butyl 3-((4-cyanophenoxy)methyl)-3-methylazetidine-1-carboxylate. Neat DIAD (0.17 mL, 0.86 mmol) was added dropwise to a solution of tert-butyl 3-(hydroxymethyl)-3-methylazetidine-1-carboxylate (103 mg, 0.512 mmol), 4-hydroxybenzonitrile (70 mg, 0.588 mmol), and $PPh_3$ (230 mg, 0.877 mmol) in dry THF (5 mL), and the mixture was stirred at rt under $N_2$ for 18 h. The reaction mixture was diluted with EtOAc (30 mL), washed with sat. aq. $NaHCO_3$ (2×25 mL) and brine (25 mL), dried over $Na_2SO_4$, filtered and concentrated in vacuo. The residue was purified by flash chromatography (Hexanes/EtOAc) to give the title compound (234 mg) in about 60% purity.

Step 4. 4-((3-Methylazetidin-3-yl)methoxy)benzonitrile. A mixture of tert-butyl 3-((4-cyanophenoxy)methyl)-3-methylazetidine-1-carboxylate (ca. 60% pure, 234 mg, 0.46 mmol) and TFA (1.5 mL) in dry DCM (7 mL) was stirred at rt under $N_2$ for 24 h. The reaction mixture was concentrated in vacuo and the residue was partitioned into 1 M HCl (15 mL) and DCM (15 mL). The aqueous layer was washed with another portion of DCM (15 mL), made basic (ca. pH 12) with 1 M NaOH (20 mL), and extracted with DCM (3×15 mL). The extracts were dried over $Na_2SO_4$, filtered and concentrated in vacuo to give the title compound (60 mg) as a colorless oil. $^1$H NMR (500 MHz, $CDCl_3$) δ ppm 7.54-7.63 (m, 2H), 6.95-7.01 (m, 2H), 4.03 (s, 2H), 3.58 (d, 2H), 3.45 (d, 2H), 2.07 (br s, 1H), 1.38 (s, 3H).

Step 5. 4-((1-((2,4-Dichlorophenyl)sulfonyl)-3-methylazetidin-3-yl)methoxy)benzonitrile. Solid 2,4-dichlorobenzenesulfonyl chloride (80 mg, 0.33 mmol) was added to a solution of 4-((3-methylazetidin-3-yl)methoxy)benzonitrile (60 mg, 0.30 mmol) and $Et_3N$ (85 μL, 0.61 mmol) in dry DCM (3 mL), and the mixture was stirred at rt under $N_2$ for 18 h. The reaction mixture was concentrated in vacuo and the residue was purified by flash chromatography (Hexanes/EtOAc) to give the title compound (106 mg) as a foam. $^1$H NMR (500 MHz, $CDCl_3$) δ ppm 7.98 (d, 1H), 7.58-7.62 (m, 2H), 7.57 (d, 1H), 7.38 (dd, 1H), 6.88-6.94 (m, 2H), 4.02 (d, 2H), 3.95 (s, 2H), 3.79 (d, 2H), 1.41 (s, 3H). LCMS $[M+H]^+$ 410.9, 412.9.

Example 2—Compound 2

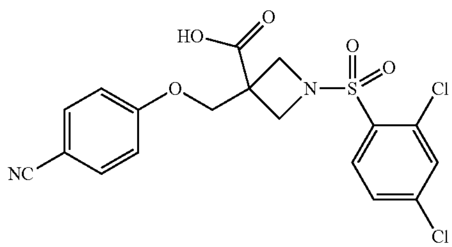 [SMILES: N#Cc1ccc(OCC2(C(=O)O)CN(S(=O)(=O)c3ccc(Cl)cc3Cl)C2)cc1]

3-((4-Cyanophenoxy)methyl)-1-((2,4-dichlorophenyl)sulfonyl)azetidine-3-carboxylic acid was prepared according to Scheme 2:

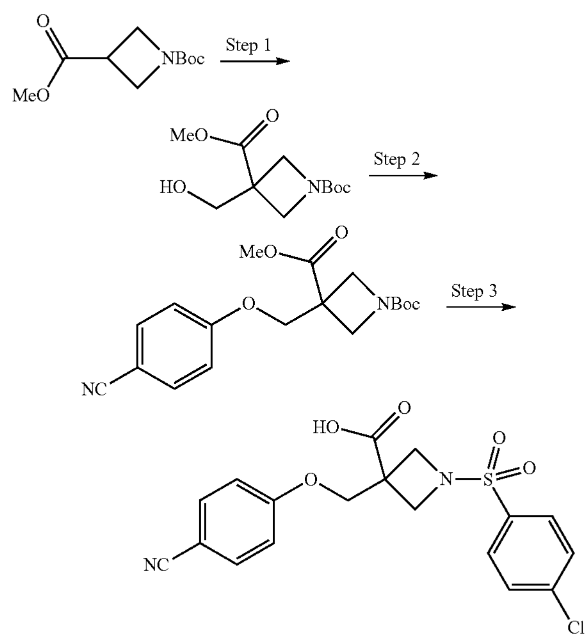

Reagents: Step 1) LHMDS, paraformaldehyde, THF, −78° C. to rt; 2) DIAD, $PPh_3$, 4-hydroxybenzonitrile, THF; 3) TFA, DCM; 2,4-dichlorobenzenesulfonyl chloride, NaOH, $H_2O$, DCM.

Step 1. 1-(tert-Butyl) 3-methyl 3-(hydroxymethyl)azetidine-1,3-dicarboxylate. A dry 3-neck 250 mL flask equipped with an addition funnel was placed under an atmosphere of $N_2$ and charged with dry THF (60 mL). That was cooled to −78° C. and LHMDS (1.0 M in THF, 11.8 mL, 11.8 mmol) was added. A solution of 1-(tert-butyl) 3-methyl azetidine-1,3-dicarboxylate (2.10 g, 9.75 mmol) in dry THF (25 mL) was added dropwise, and the mixture was stirred at −78° C. under $N_2$ for 1.5 h. In a separate flask under $N_2$, paraformaldehyde (3.56 g, 118.7 mmol) was heated with a heat gun, and the formaldehyde gas generated was bubbled into the reaction mixture. The reaction was warmed to rt while stirring for 18 h. The reaction mixture was quenched with half-saturated $NH_4Cl$ (200 mL) and extracted with EtOAc (2×100 mL). The organics were washed with brine (200 mL), dried over $Na_2SO_4$, filtered and concentrated in vacuo. The residue was purified by flash chromatography (Hexanes/EtOAc) to give the title compound (268 mg) as a light yellow oil. $^1H$ NMR (500 MHz, $CDCl_3$) δ ppm 4.15 (d, 2H), 4.04 (d, 2H), 3.91-3.98 (m, 2H), 3.80 (s, 3H), 2.27-2.36 (m, 1H), 1.44 (s, 9H).

Step 2. 1-(tert-Butyl) 3-methyl 3-((4-cyanophenoxy)methyl)azetidine-1,3-dicarboxylate. Neat DIAD (0.32 mL, 1.63 mmol) was added dropwise to a solution of 1-(tert-butyl) 3-methyl 3-(hydroxymethyl)azetidine-1,3-dicarboxylate (268 mg, 1.09 mmol), 4-hydroxybenzonitrile (144 mg, 1.21 mmol), and $PPh_3$ (430 mg, 1.64 mmol) in dry THF (10 mL), and the mixture was stirred at rt under $N_2$ for 27 h. The reaction mixture was diluted with EtOAc (50 mL), washed with sat. aq. $NaHCO_3$ (2×50 mL) and brine (50 mL), dried over $Na_2SO_4$, filtered and concentrated in vacuo. The residue was taken up in EtOAc (50 mL), washed with aq. $K_2CO_3$ (3×50 mL) and brine (50 mL), dried over $Na_2SO_4$, filtered and concentrated in vacuo. The reaction mixture was purified by flash chromatography (Hexanes/EtOAc) to give the title compound as a colorless oil (444 mg, ~50% purity) mixed with DIAD byproduct. $^1H$ NMR (500 MHz, $CDCl_3$) δ ppm 7.60 (d, 2H), 6.97 (d, 2H), 4.35 (s, 2H), 4.27 (d, 2H), 3.95 (d, 2H), 3.80 (s, 3H), 1.40-1.48 (m, 9H).

Step 3. 3-((4-Cyanophenoxy)methyl)-1-((2,4-dichlorophenyl)sulfonyl)azetidine-3-carboxylic acid. A mixture of 1-(tert-butyl) 3-methyl 3-((4-cyanophenoxy)methyl)azetidine-1,3-dicarboxylate (444 mg, 50% purity, 0.64 mmol), TFA (2 mL), and DCM (10 mL) was stirred at rt under $N_2$ for 3 h. The reaction mixture was concentrated in vacuo, and the residue was taken up in 1 M HCl (25 mL) and extracted with DCM (2×25 mL). The aqueous layer was made basic with 1 M NaOH (35 mL) and extracted with DCM (3×25 mL). The aqueous layer was concentrated in vacuo to a total volume of about 20 mL (with lots of inorganic salts precipitating). Solid NaOH (49 mg, 1.23 mmol), DCM (10 mL), and water were added so that stirring was thorough. Solid 2,4-dichlorobenzenesulfonyl chloride (324 mg, 1.32 mmol) was added in one portion and the biphasic mixture was stirred vigorously at rt under $N_2$ for 7 days. Aqueous 1 M HCl (10 mL), was added and the reaction mixture diluted with $H_2O$ until all of the salts dissolved and extracted with DCM (3×25 mL). The extracts were dried over $Na_2SO_4$, filtered and concentrated in vacuo. The residue was purified by flash chromatography ($DCM/CH_3OH/AcOH$). Product fractions were concentrated in vacuo and toluene/$CH_3OH$ and $Et_2O$ were added and removed under vacuum in succession to give the title compound (82 mg) as a white solid. $^1H$ NMR (500 MHz, DMSO-$d_6$) δ ppm 7.99 (d, 1H), 7.96 (d, 1H), 7.77 (d, 2H), 7.68 (dd, 1H), 7.06 (d, 2H), 4.37 (s, 2H), 4.23 (d, 2H), 4.06 (d, 2H). LCMS $[M+H]^+$ 441.0, 443.0.

Example 3—Compound 3

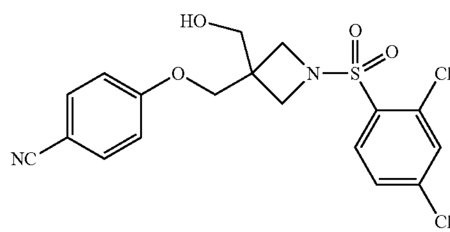 [SMILES: N#Cc1ccc(OCC2(CO)CN(S(=O)(=O)c3ccc(Cl)cc3Cl)C2)cc1]

4-((1-((2,4-Dichlorophenyl)sulfonyl)-3-(hydroxymethyl)azetidin-3-yl)methoxy)benzonitrile was prepared according to Scheme 3:

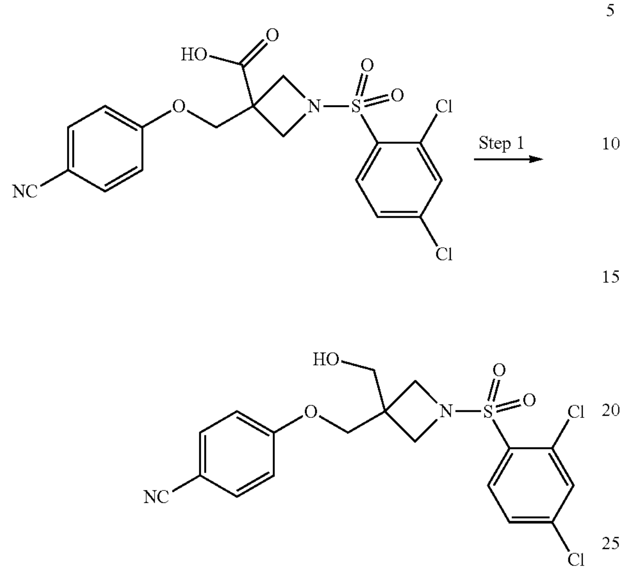

Reagents: Step 1) $BH_3$·THF, THF.

Step 1. A solution of $BH_3$·THF (1.0 M in THF, 0.22 mL, 0.22 mmol) was added dropwise to 3-((4-cyanophenoxy)methyl)-1-((2,4-dichlorophenyl)sulfonyl)azetidine-3-carboxylic acid (32 mg, 0.07 mmol) in dry THF (2 mL) at 0° C. under $N_2$. The mixture was warmed to rt while stirring for 19 h. The reaction mixture was quenched with half-saturated $NH_4Cl$ (5 mL) and extracted with EtOAc (2×10 mL). The organics were washed with brine (10 mL), dried over $Na_2SO_4$, filtered and concentrated in vacuo. The residue was purified by flash chromatography (Hexanes/EtOAc) to give the title compound (8.9 mg) as a thick, colorless oil. $^1H$ NMR (500 MHz, $CDCl_3$) δ ppm 7.98 (d, 1H), 7.60 (d, 2H), 7.56 (d, 1H), 7.39 (dd, 1H), 6.93 (d, 2H), 4.16 (s, 2H), 3.96-4.01 (m, 2H), 3.92-3.96 (m, 2H), 3.91 (s, 2H). LCMS $[M+H]^+$ 427.0, 429.0.

Example 4—Compound 4

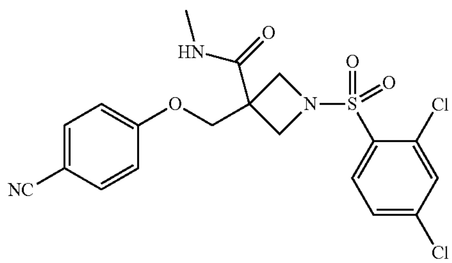 [SMILES: CNC(=O)C1(COc2ccc(C#N)cc2)CN(S(=O)(=O)c2ccc(Cl)cc2Cl)C1]

3-((4-Cyanophenoxy)methyl)-1-((2,4-dichlorophenyl)sulfonyl)-N-methylazetidine-3-carboxamide was prepared according to Scheme 4:

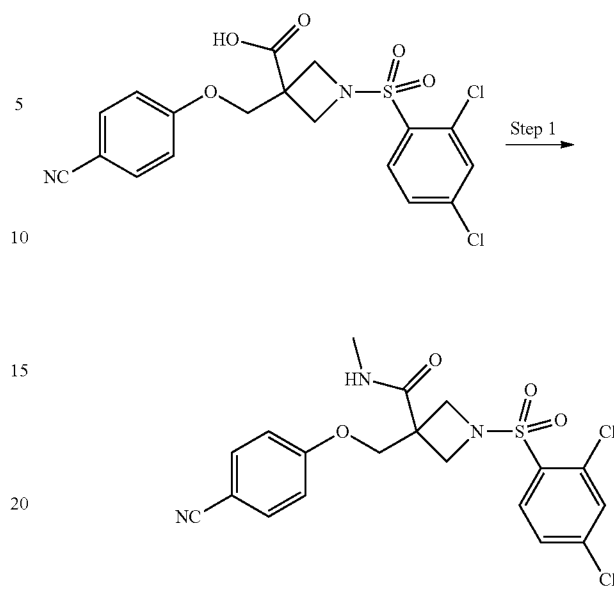

Reagents: Step 1) HATU, $CH_3NH_2$, DIPEA, DMF.

Step 1. A mixture of DIPEA (18 μL, 0.10 mmol) and methylamine (2.0 M in THF, 0.08 mL, 0.160 mmol) were added to a mixture of 3-((4-cyanophenoxy)methyl)-1-((2,4-dichlorophenyl)sulfonyl)azetidine-3-carboxylic acid (14.7 mg, 0.033 mmol) and HATU (18.0 mg, 0.047 mmol) in dry DMF (0.5 mL), and the reaction mixture was stirred at rt for 4 h. The reaction mixture was diluted with EtOAc (2 mL), washed with sat. aq. $NaHCO_3$ (2×2 mL) and brine (2 mL), dried over $Na_2SO_4$, filtered and concentrated in vacuo. The residue was purified by flash chromatography (Hexanes/EtOAc) to give the title compound (7.2 mg) as a white solid. $^1H$ NMR (500 MHz, $CDCl_3$) δ ppm 7.98 (d, 1H), 7.62 (d, 2H), 7.58 (d, 1H), 7.41 (dd, 1H), 6.95 (d, 2H), 6.14 (br s, 1H), 4.33 (s, 2H), 4.28 (d, 2H), 4.09 (d, 2H), 2.88 (d, 3H). LCMS $[M+H]^+$ 453.9, 456.0.

Example 5—Compound 5

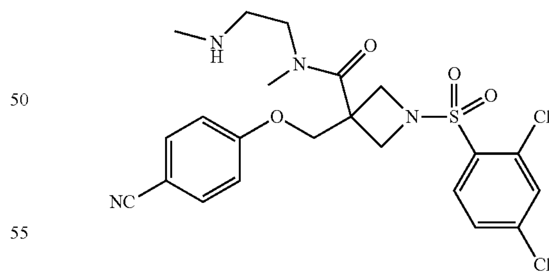

3-((4-Cyanophenoxy)methyl)-1-((2,4-dichlorophenyl)sulfonyl)-N-methyl-N-(2-(methylamino)ethyl)azetidine-3-carboxamide was prepared in a similar fashion to Scheme 4. $^1H$ NMR (mixture of rotamers, 500 MHz, $CDCl_3$) δ ppm 7.97 (d, 1H), 7.61 (d, 2H), 7.56 (d, 1H), 7.38 (dd, 1H), 6.96 (d, 2H), 4.53 and 4.47 (d, 2H), 4.44 and 4.37 (s, 2H), 3.96-4.06 (m, 2H), 3.43-3.52 (m, 2H), 3.14-3.22 (m, 1H), 2.96 and 2.92 (s, 3H), 2.69-2.81 (m, 2H), 2.39 (s, 3H). LCMS $[M+H]^+$ 511.0, 513.0.

Example 6—Compound 6

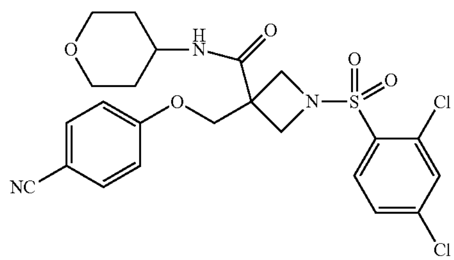 [SMILES: N#Cc1ccc(OCC2(C(=O)NC3CCOCC3)CN(S(=O)(=O)c3ccc(Cl)cc3Cl)C2)cc1]

3-((4-cyanophenoxy)methyl)-1-((2,4-dichlorophenyl)sulfonyl)-N-(tetrahydro-2H-pyran-4-yl)azetidine-3-carboxamide was prepared in a similar fashion to Scheme 4. $^1H$ NMR (500 MHz, $CDCl_3$) δ ppm 7.98 (d, 1H), 7.60-7.66 (m, 2H), 7.58 (d, 1H), 7.41 (dd, 1H), 6.92-6.99 (m, 2H), 5.99 (d, 1H), 4.33 (s, 2H), 4.27 (d, 2H), 4.10 (d, 2H), 3.98-4.06 (m, 1H), 3.90-3.97 (m, 2H), 3.42-3.52 (m, 2H), 1.84-1.93 (m, 2H), 1.40-1.52 (m, 2H). LCMS $[M+H]^+$ 523.9, 526.0.

Example 7—Compound 7

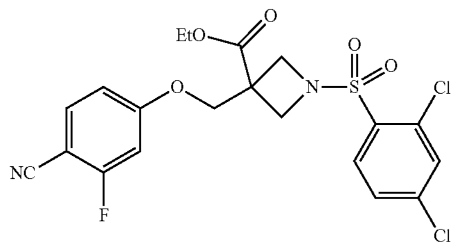

Ethyl 3-((4-cyano-3-fluorophenoxy)methyl)-1-((2,4-dichlorophenyl)sulfonyl)azetidine-3-carboxylate was prepared according to Scheme 5:

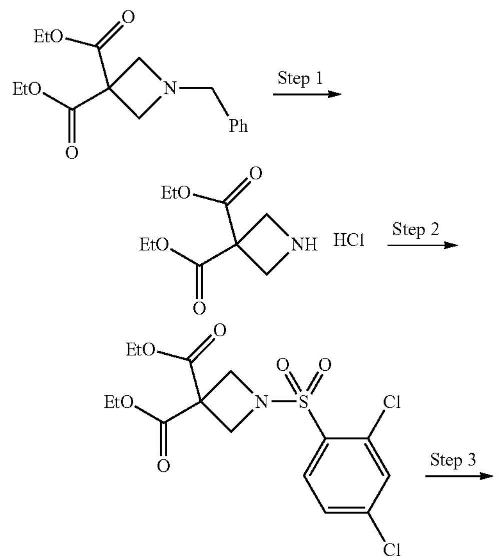

-continued

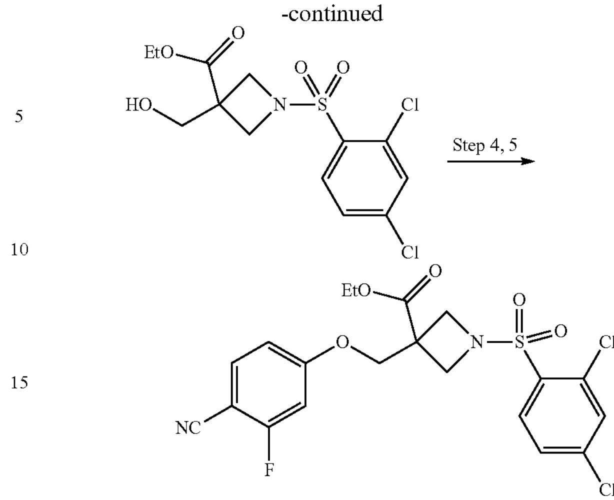

Reagents: Step 1) $Pd(OH)_2/C$, HCl, EtOH; 2) 2,4-dichlorobenzenesulfonyl chloride, $Et_3N$, DCM; 3) $LiAlH(Ot\text{-}Bu)_3$, THF; 4) methanesulfonyl chloride, $Et_3N$, DCM; 5) 2-fluoro-4-hydroxybenzonitrile, $K_2CO_3$, $CH_3CN$, A.

Step 1. Diethyl azetidine-3,3-dicarboxylate hydrochloride. A mixture of $Pd(OH)_2$ (20 wt. % on carbon, ca. 50% water, 1.548 g), diethyl 1-benzylazetidine-3,3-dicarboxylate (prepared according to Syn. Commun. 2003, 33, 3347-3353, 7.613 g, 26.12 mmol), and HCl (4.0 M in dioxane, 7.20 mL, 28.80 mmol) in EtOH (200 mL) was stirred under an atmosphere of $H_2$ for 18 h. The mixture was filtered through a pad of celite, rinsing with $CH_3OH$, and the filtrate was concentrated in vacuo to give the title compound (6.209 g) as a pale yellow oil. $^1H$ NMR (500 MHz, $CDCl_3$) δ ppm 10.06 (br s, 1H), 4.49 (br s, 4H), 4.31 (q, 4H), 1.26-1.35 (m, 6H).

Step 2. Diethyl 1-((2,4-dichlorophenyl)sulfonyl)azetidine-3,3-dicarboxylate. Neat $Et_3N$ (11.5 mL, 82.50 mmol) and 2,4-dichlorobenzenesulfonyl chloride (8.15 g, 33.2 mmol) were added to a solution of diethyl azetidine-3,3-dicarboxylate hydrochloride (6.209 g, 26.12 mmol) in dry DCM (250 mL), and the mixture was stirred at rt under $N_2$ for 20 h. The reaction mixture was poured into sat. aq. $NaHCO_3$ (500 mL) and extracted with DCM (2×500 mL). The extracts were dried over $Na_2SO_4$, filtered and concentrated in vacuo. The residue was purified by flash chromatography on silica gel (Hexanes/EtOAc) to give the title compound (8.80 g) as a colorless oil. $^1H$ NMR (500 MHz, $CDCl_3$) δ ppm 7.95 (d, 1H), 7.55 (d, 1H), 7.37 (dd, 1H), 4.40 (s, 4H), 4.25 (q, 4H), 1.27 (t, 6H).

Step 3. Ethyl 1-((2,4-dichlorophenyl)sulfonyl)-3-(hydroxymethyl)azetidine-3-carboxylate. A solution of $LiAlH(Ot\text{-}Bu)_3$ (1.0 M in THF, 45.5 mL, 45.5 mmol) was added dropwise via addition funnel to a solution of diethyl 1-((2,4-dichlorophenyl)sulfonyl)azetidine-3,3-dicarboxylate (8.8 g, 21.45 mmol) in dry THF (200 mL) at 0° C. under $N_2$. The mixture was warmed to rt while stirring for 22 h. The reaction mixture was diluted with EtOAc (500 mL), washed with 1 M HCl (2×500 mL) and brine (500 mL), dried over $Na_2SO_4$, filtered and concentrated in vacuo. The residue was purified by flash chromatography (Hexanes/EtOAc) to give the title compound (5.88 g) as a white crystalline solid. $^1H$ NMR (500 MHz, $CDCl_3$) δ ppm 7.93-8.00 (m, 1H), 7.53-7.58 (m, 1H), 7.35-7.40 (m, 1H), 4.32 (d, 2H), 4.20-4.27 (m, 2H), 3.96 (s, 2H), 3.92 (d, 2H), 1.26-1.32 (m, 3H).

Step 4. Ethyl 1-((2,4-dichlorophenyl)sulfonyl)-3-(((methylsulfonyl)oxy)methyl)azetidine-3-carboxylate. Neat methanesulfonyl chloride (1.40 mL, 18.08 mmol) was added dropwise to a solution of ethyl 1-((2,4-dichlorophenyl)sulfonyl)-3-(hydroxymethyl)azetidine-3-carboxylate (5.88 g, 15.97 mmol) and $Et_3N$ (3.4 mL, 24.4 mmol) in dry DCM (200 mL) and the mixture was stirred at rt under $N_2$ for 3 h. The reaction mixture was poured into sat. aq. $NaHCO_3$ (500 mL) and extracted with DCM (2×500 mL). The extracts were dried over $Na_2SO_4$, filtered and concentrated in vacuo to give the title compound (6.67 g) as an orange oil. $^1H$ NMR (500 MHz, $CDCl_3$) δ ppm 7.96 (d, 1H), 7.56 (d, 1H), 7.36-7.41 (m, 1H), 4.55 (s, 2H), 4.38 (d, 2H), 4.25 (q, 2H), 4.00 (d, 2H), 3.07 (s, 3H), 1.27-1.32 (m, 3H).

Step 5. Ethyl 3-((4-cyano-3-fluorophenoxy)methyl)-1-((2,4-dichlorophenyl)sulfonyl)azetidine-3-carboxylate. A mixture of ethyl 1-((2,4-dichlorophenyl)sulfonyl)-3-(((methylsulfonyl)oxy)methyl)azetidine-3-carboxylate (5.33 g, 11.94 mmol), 2-fluoro-4-hydroxybenzonitrile (1.96 g, 14.33 mmol), and $K_2CO_3$ (3.30 g, 23.87 mmol) in dry $CH_3CN$ (50 mL) was stirred at 80° C. under $N_2$ for 20 h. The reaction mixture was cooled, diluted with EtOAc (500 mL), washed with 2 M $K_2CO_3$ (2×400 mL) and brine (2×400 mL), dried over $Na_2SO_4$, filtered and concentrated in vacuo to give the title compound as a thick, colorless oil (5.59 g, 11.47 mmol). $^1H$ NMR (500 MHz, $CDCl_3$) δ ppm 7.97 (d, 1H), 7.56-7.58 (m, 1H), 7.52-7.55 (m, 1H), 7.39 (dd, 1H), 6.78 (dd, 1H), 6.73 (dd, 1H), 4.41 (d, 2H), 4.36 (s, 2H), 4.25 (q, 2H), 4.10 (d, 2H), 1.27 (t, 3H). LCMS $[M+H]^+$ 487, 488.

Example 8—Compound 8

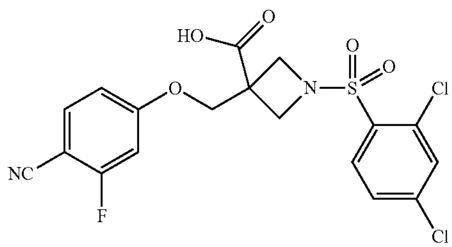 [SMILES: N#Cc1ccc(OCC2(C(=O)O)CN(S(=O)(=O)c3ccc(Cl)cc3Cl)C2)cc1F]

3-((4-Cyano-3-fluorophenoxy)methyl)-1-((2,4-dichlorophenyl)sulfonyl)azetidine-3-carboxylic acid was prepared according to Scheme 6:

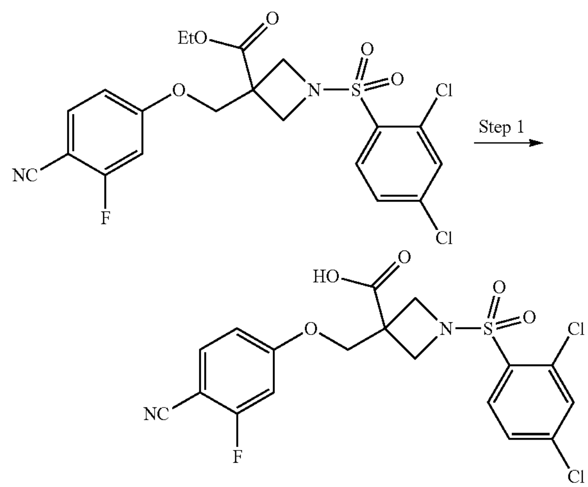

Reagents: Step 1) 4 M aq. NaOH, THF.

Step 1. Aqueous 4M NaOH (5.30 mL, 21.2 mmol) was added to a solution of ethyl 3-((4-cyano-3-fluorophenoxy)methyl)-1-((2,4-dichlorophenyl)sulfonyl)azetidine-3-carboxylate (1.02 g, 2.09 mmol) in THF (20 mL), and the mixture was stirred at rt under $N_2$ for 3 h. The reaction mixture was concentrated in vacuo to remove THF, made acidic with 1 M HCl (50 mL), diluted with water (50 mL), saturated with solid NaCl and extracted with DCM (3×100 mL). The extracts were dried over $Na_2SO_4$, filtered and concentrated in vacuo to give the title compound (910 mg) as a white foam. $^1H$ NMR (500 MHz, $CDCl_3$) δ ppm 7.97 (d, 1H), 7.53-7.59 (m, 2H), 7.39 (dd, 1H), 6.79 (dd, 1H), 6.75 (dd, 1H), 4.47 (d, 2H), 4.39 (s, 2H), 4.13 (d, 2H). LCMS $[M+H]^+$ 459, 461.

Example 9—Compound 9

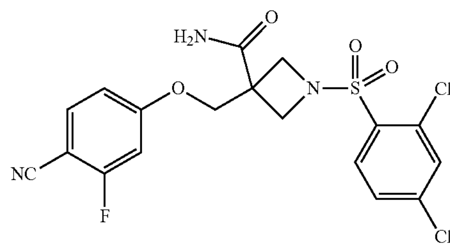

3-((4-Cyano-3-fluorophenoxy)methyl)-1-((2,4-dichlorophenyl)sulfonyl)azetidine-3-carboxamide was prepared according to Scheme 7:

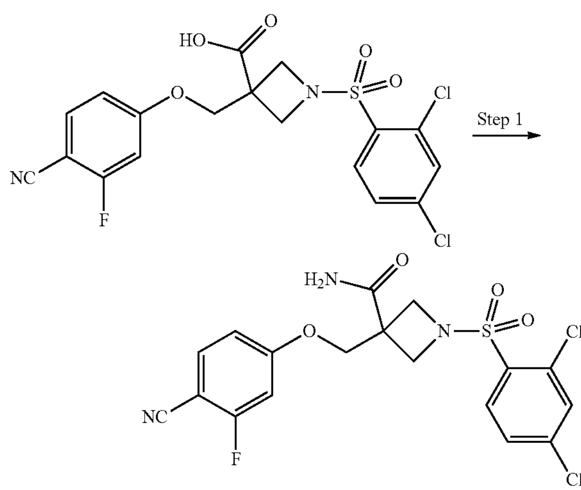

Reagents: Step 1) HATU, $NH_3$, DIPEA, DMF

Step 1. Neat DIPEA (32 μL, 0.184 mmol) was added to a solution of 3-((4-cyano-3-fluorophenoxy)methyl)-1-((2,4-dichlorophenyl)sulfonyl)azetidine-3-carboxylic acid (27.0 mg, 0.059 mmol) and HATU (28.5 mg, 0.075 mmol) in dry DMF (2 mL) under $N_2$, and the mixture was stirred at rt for 30 min. Ammonia gas was bubbled through the reaction mixture for 5 min, and the mixture was stirred at rt for 19 h. The reaction mixture was diluted with EtOAc (10 mL), washed with sat. aq. $NaHCO_3$ (2×10 mL) and brine (2×10 mL), dried over $Na_2SO_4$, filtered and concentrated in vacuo. The residue was purified by flash chromatography (Hexanes/

EtOAc) to give the title compound (5.0 mg) as a yellow oil. $^1H$ NMR (500 MHz, $CDCl_3$) δ ppm 7.99 (d, 1H), 7.55-7.61 (m, 2H), 7.42 (dd, 1H), 6.79 (dd, 1H), 6.75 (dd, 1H), 6.18 (br s, br s, 1H), 5.60 (br s, br s, 1H), 4.34 (s, 2H), 4.28 (d, 2H), 4.16 (d, 2H). LCMS $[M+H]^+$ 458.0, 460.0.

Example 10—Compound 10

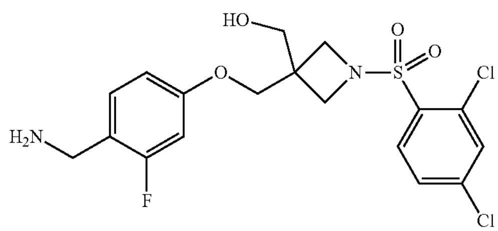 [SMILES: NCc1ccc(OCC2(CO)CN(S(=O)(=O)c3ccc(Cl)cc3Cl)C2)cc1F]

(3-((4-(Aminomethyl)-3-fluorophenoxy)methyl)-1-((2,4-dichlorophenyl)sulfonyl)azetidin-3-yl)methanol was prepared according to Scheme 8

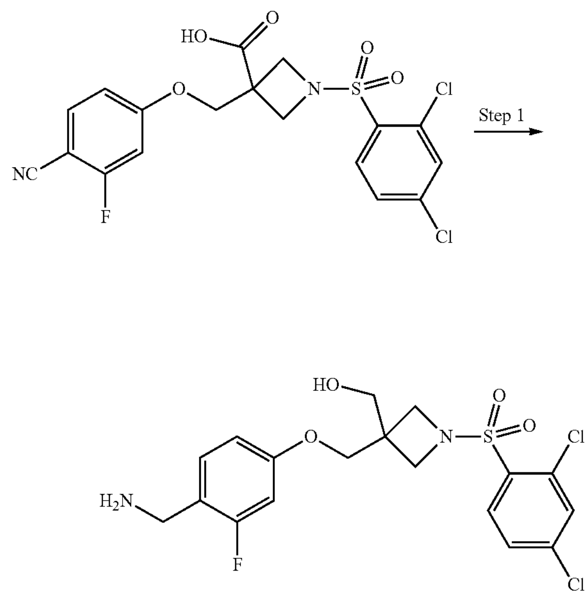 [SMILES: N#Cc1ccc(OCC2(C(=O)O)CN(S(=O)(=O)c3ccc(Cl)cc3Cl)C2)cc1F ; NCc1ccc(OCC2(CO)CN(S(=O)(=O)c3ccc(Cl)cc3Cl)C2)cc1F]

Reagents: Step 1) $BH_3$·THF, THF.

Step 1. A solution of $BH_3$·THF (1.0 M in THF, 1.65 mL) was added dropwise to a solution of 3-((4-cyano-3-fluorophenoxy)methyl)-1-((2,4-dichlorophenyl)sulfonyl)azetidine-3-carboxylic acid (248 mg, 0.54 mmol) in dry THF (5 mL) at 0° C. under $N_2$. The mixture was warmed to rt while stirring for 21 h. The reaction mixture was quenched with 1 M HCl (10 mL), neutralized with sat. aq. $NaHCO_3$ (35 mL) and extracted with EtOAc (2×35 mL). The organics were washed with brine (35 mL), dried ($Na_2SO_4$), filtered and concentrated in vacuo. The residue was purified by flash chromatography on silica gel (EtOAc/Hexanes then DCM/$CH_3OH/NH_4OH$) to give the title compound (111 mg) as a white foam. $^1H$ NMR (500 MHz, DMSO-$d_6$) δ ppm 7.96 (d, 1H), 7.95 (d, 1H), 7.67 (dd, 1H), 7.32 (t, 1H), 6.55-6.61 (m, 2H), 5.06 (t, 1H), 3.93 (s, 2H), 3.76-3.82 (m, 4H), 3.64 (s, 2H), 3.52 (d, 2H), 1.98 (br s, 2H). LCMS $[M+H]^+$ 449.

Example 11—Compound 11

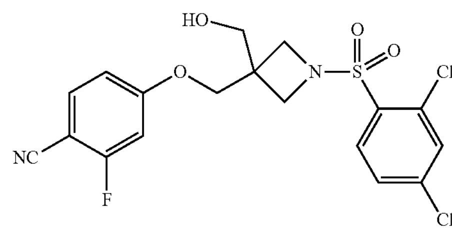 [SMILES: N#Cc1ccc(OCC2(CO)CN(S(=O)(=O)c3ccc(Cl)cc3Cl)C2)cc1F]

4-((1-((2,4-Dichlorophenyl)sulfonyl)-3-(hydroxymethyl)azetidin-3-yl)methoxy)-2-fluorobenzonitrile was prepared according to Scheme 9:

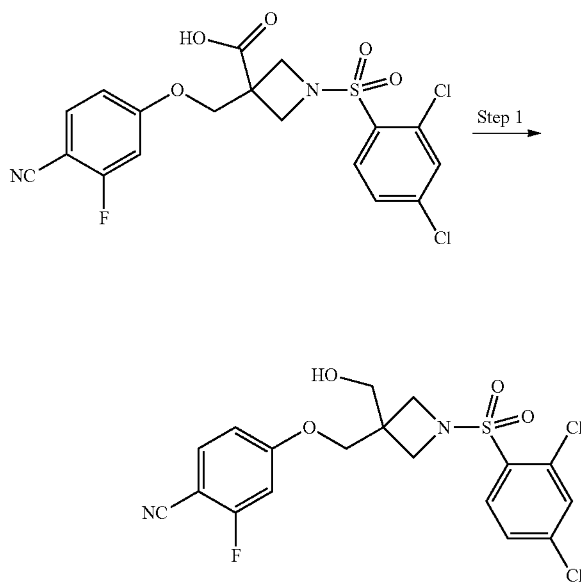 [SMILES: N#Cc1ccc(OCC2(C(=O)O)CN(S(=O)(=O)c3ccc(Cl)cc3Cl)C2)cc1F ; N#Cc1ccc(OCC2(CO)CN(S(=O)(=O)c3ccc(Cl)cc3Cl)C2)cc1F]

Reagents: Step 1) $BH_3 \cdot SMe_2$ (1.0 M in THF), THF.

Step 1. A solution of $BH_3 \cdot SMe_2$ (0.30 mL, 3.16 mmol) was added dropwise to 3-((4-cyano-3-fluorophenoxy)methyl)-1-((2,4-dichlorophenyl)sulfonyl)azetidine-3-carboxylic acid (971 mg, 2.12 mmol) in dry THF (20 mL) at 0° C. under $N_2$. The mixture was warmed to rt while stirring for 20 h. The reaction mixture was quenched with 1 M NaOH (15 mL), poured into sat. aq. $NaHCO_3$ (100 mL), and extracted with EtOAc (2×75 mL). The organics were washed with brine (75 mL), dried over $Na_2SO_4$, filtered and concentrated in vacuo. The residue was purified by flash chromatography (Hexanes/EtOAc) to give the title compound as a thick colorless oil (760 mg, 1.71 mmol). $^1H$ NMR (500 MHz, $CDCl_3$) δ ppm 7.98 (d, 1H), 7.57 (d, 1H), 7.53 (dd, 1H), 7.39 (dd, 1H), 6.75 (dd, 1H), 6.71 (dd, 1H), 4.16 (s, 2H), 3.95-3.99 (m, 2H), 3.92-3.95 (m, 2H), 3.90 (d, 2H), 1.75 (t, 1H). LCMS $[M+H]^+$ 445, 447. LC/MS/MS $[M-H]^-$ 442.7.

Example 12—Compound 12

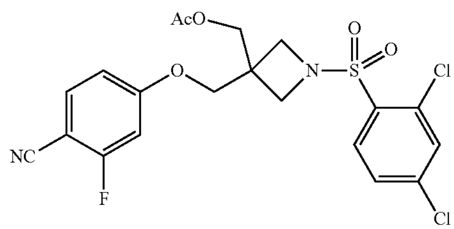

(3-((4-Cyano-3-fluorophenoxy)methyl)-1-((2,4-dichlorophenyl)sulfonyl)azetidin-3-yl)methyl acetate was prepared according to Scheme 10:

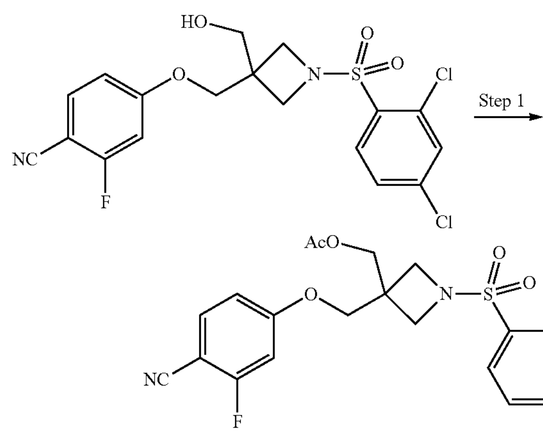

Reagents: Step 1) acetic anhydride, $Et_3N$, DMAP, DCM.

Step 1. Catalytic DMAP was added to a solution of 4-((1-((2,4-dichlorophenyl)sulfonyl)-3-(hydroxymethyl)azetidin-3-yl)methoxy)-2-fluorobenzonitrile (19.7 mg, 0.044 mmol), $Et_3N$ (12 μL, 0.088 mmol), and acetic anhydride (10 μL, 0.088 mmol) in dry DCM (0.5 mL), and the mixture was stirred at rt for 6 h. The reaction mixture was directly purified by flash chromatography on silica gel (EtOAc/Hexanes) to give the title compound (20.1 mg) as a thick, colorless oil. $^1$H NMR (500 MHz, $CDCl_3$) δ ppm 7.97 (d, 1H), 7.52-7.59 (m, 2H), 7.39 (dd, 1H), 6.76 (dd, 1H), 6.71 (dd, 1H), 4.32 (s, 2H), 4.12 (s, 2H), 4.01 (d, 2H), 3.96 (d, 2H), 2.07 (s, 3H). LCMS $[M+H]^+$ 487, 489.

Example 13—Compound 13

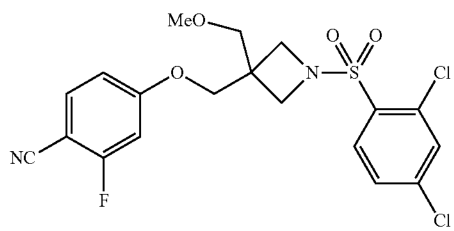 [SMILES: COCC1(COc2ccc(C#N)c(F)c2)CN(S(=O)(=O)c2ccc(Cl)cc2Cl)C1]

4-((1-((2,4-Dichlorophenyl)sulfonyl)-3-(methoxymethyl)azetidin-3-yl)methoxy)-fluorobenzonitrile was prepared according to Scheme 11:

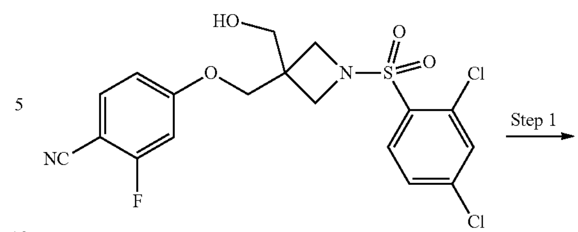

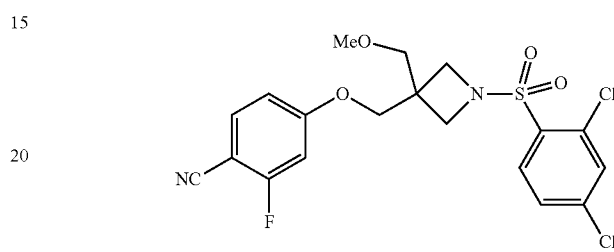

Reagents: Step 1) NaH, $CH_3I$, THF.

Step 1. To an oven-dried flask charged with a stir bar, NaH (9.2 mg, 0.383 mmol) was added and the flask was capped and placed under $N_2$ atmosphere, and dry THF (0.5 mL) was added. A solution of 4-((1-((2,4-dichlorophenyl)sulfonyl)-3-(hydroxymethyl)azetidin-3-yl)methoxy)-2-fluorobenzonitrile (53.2 mg, 0.119 mmol) in dry THF (0.5 mL) was added dropwise, followed by addition of a solution of $CH_3I$ (16.0 μL, 0.257 mmol) in dry THF (0.5 mL), and the mixture was stirred at rt for 20 h. The reaction mixture was diluted with EtOAc (15 mL) and washed with sat. aq. $NaHCO_3$ (2×10 mL) with brine (2×10 mL). The organic layer was dried over $Na_2SO_4$, decanted, and concentrated in vacuo. The residue was purified by flash chromatography on silica gel (Hexanes/EtOAc) to give the title compound (17.2 mg) as a white solid. $^1$H NMR (500 MHz, $CDCl_3$) δ ppm 7.97 (d, 1H), 7.56-7.59 (m, 1H), 7.53 (dd, 1H), 7.39 (dd, 1H), 6.74 (dd, 1H), 6.69 (dd, 1H), 4.09 (s, 2H), 3.97 (d, 2H), 3.88-3.92 (m, 2H), 3.57 (s, 2H), 3.34 (s, 3H).

Example 14—Compound 14

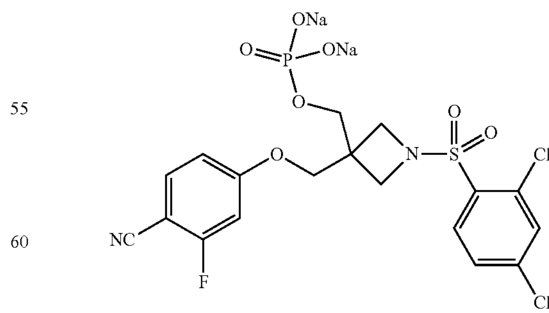

Sodium (3-((4-cyano-3-fluorophenoxy)methyl)-1-((2,4-dichlorophenyl)sulfonyl)azetidin-3-yl)methyl phosphate was prepared according to Scheme 12:

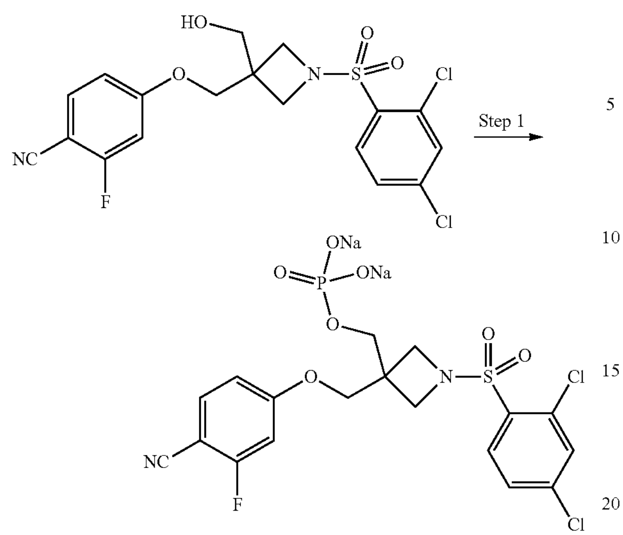

Reagents: Step 1) phosphorus(V) oxychloride, $Et_3N$, THF.

Step 1. Neat phosphorus(V) oxychloride (30 μL, 0.32 mmol) was added dropwise to a solution of 4-((1-((2,4-dichlorophenyl)sulfonyl)-3-(hydroxymethyl)azetidin-3-yl)methoxy)-2-fluorobenzonitrile (89 mg, 0.20 mmol) and $Et_3N$ (56 μL, 0.40 mmol) in dry THF (2.0 mL), and the mixture was stirred at rt for 3 h. The reaction mixture was quenched with 1 M NaOH (5 mL), diluted with $H_2O$ (10 mL) and washed with EtOAc (2×15 mL). The aqueous layer was acidified to pH 1 with 6 M HCl and extracted with DCM (3×20 mL). The extracts were dried over $Na_2SO_4$, filtered and concentrated to dryness to give the phosphate ester (83 mg, 0.16 mmol). The residue was dissolved in $CH_3OH$ and THF, and 0.1 M aq. $NaHCO_3$ (3.2 mL) was added. The mixture was concentrated to dryness and the residue was concentrated from dry $CH_3OH$ twice to give the title compound as a white solid (85 mg, 0.15 mmol). $^{1}H$ NMR (500 MHz, $CD_3OD$) δ ppm 8.03 (d, 1H), 7.75 (d, 1H), 7.63 (dd, 1H), 7.56 (dd, 1H), 6.92 (dd, 1H), 6.85 (dd, 1H), 4.17 (s, 2H), 4.01-4.08 (m, 4H), 3.91 (d, 2H). LCMS $[M+H]^+$ 524.9, 526.9. LC/MS/MS $[M-H]^-$ 522.8.

Example 15—Compound 15

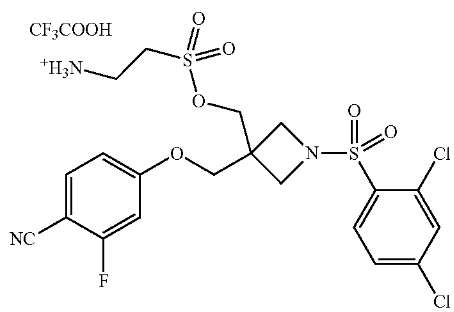 [SMILES: "CF3COOH" ; N#Cc1ccc(OCC2(COS(=O)(=O)CC[NH3+])CN(S(=O)(=O)c3ccc(Cl)cc3Cl)C2)cc1F]

(3-((4-Cyano-3-fluorophenoxy)methyl)-1-((2,4-dichlorophenyl)sulfonyl)azetidin-3-yl)methyl 2-aminoethane-1-sulfonate trifluoroacetate salt was prepared according to Scheme 13:

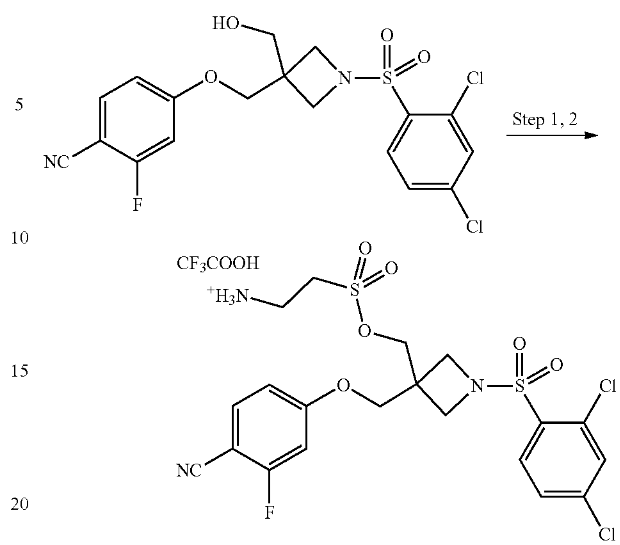

Reagents: Step 1) N-Boc taurine chloride, $Et_3N$, DCM 2) TFA, DCM.

Step 1. (3-((4-Cyano-3-fluorophenoxy)methyl)-1-((2,4-dichlorophenyl)sulfonyl)azetidin-3-yl)methyl 2-((tert-butoxycarbonyl)amino)ethane-1-sulfonate. A solution of 4-((1-((2,4-dichlorophenyl)sulfonyl)-3-(hydroxymethyl)azetidin-3-yl)methoxy)-2-fluorobenzonitrile (34 mg, 0.077 mmol) and $Et_3N$ (22 μL, 0.16 mmol) in dry DCM (1 mL) was added to a mixture of N-Boc taurine hydrochloride (24 mg, 0.10 mmol), prepared as in *Nucleosides, Nucleotides, and Nucleic Acids* 2013, 32, 599, in dry DCM (0.5 mL) and the mixture was stirred at rt for 3 days. The reaction mixture was directly purified by flash chromatography (EtOAc/Hexanes) to afford the title compound (29 mg) as a colorless oil.

Step 2. (3-((4-Cyano-3-fluorophenoxy)methyl)-1-((2,4-dichlorophenyl)sulfonyl)azetidin-3-yl)methyl 2-aminoethane-1-sulfonate trifluoroacetate salt. Neat TFA (0.1 mL) was added to a solution of (3-((4-cyano-3-fluorophenoxy)methyl)-1-((2,4-dichlorophenyl)sulfonyl)azetidin-3-yl)methyl 2-((tert-butoxycarbonyl)amino)ethane-1-sulfonate (29 mg, 0.044 mmol) in dry DCM (1 mL), and the mixture was stirred at rt for 2 h. The reaction mixture was concentrated to dryness, concentrated to dryness from dioxane twice and $Et_2O$ twice to afford the title compound (30 mg) as a viscous yellow oil. $^{1}H$ NMR (500 MHz, DMSO-$d_6$) δ ppm 7.91-8.06 (m, 5H), 7.85 (t, 1H), 7.67 (dd, 1H), 7.06 (dd, 1H), 6.88 (dd, 1H), 4.50 (s, 2H), 4.21 (s, 2H), 3.89-3.98 (m, 4H), 3.69 (t, 2H), 3.15-3.24 (m, 2H). LCMS $[M+H]^+$ 552.0, 554.1.

Example 16—Compound 16

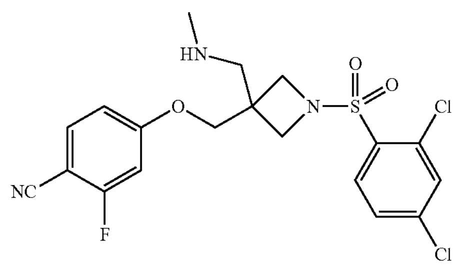 [SMILES: CNCC1(COc2ccc(C#N)c(F)c2)CN(S(=O)(=O)c2ccc(Cl)cc2Cl)C1]

4-((1-((2,4-Dichlorophenyl)sulfonyl)-3-((methylamino)methyl)azetidin-3-yl)methoxy)-2-fluorobenzonitrile hydrochloride was prepared according to Scheme 14:

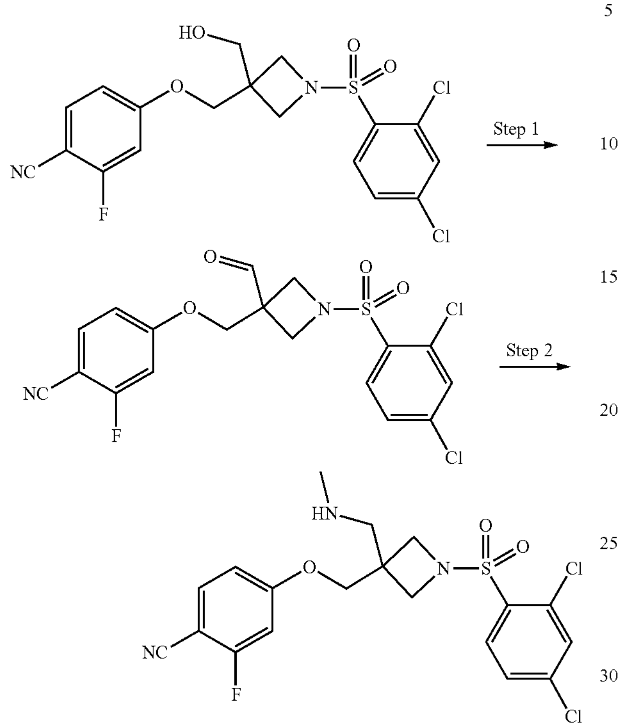

Reagents: Step 1) $Et_3N$, oxalyl chloride, DMSO, DCM; −78° C. 2) $CH_3NH_2$, $NaBH(OAc)_3$, AcOH, DCE.

Step 1. 4-((1-((2,4-Dichlorophenyl)sulfonyl)-3-formylazetidin-3-yl)methoxy)-2-fluorobenzonitrile. A solution of DMSO (0.560 mL, 7.887 mmol) in dry DCM (3 mL) was added dropwise to a solution of oxalyl chloride (0.350 mL, 4.027 mmol) in dry DCM (3 mL) at −78° C. under $N_2$. The mixture was stirred for 10 min, a solution of 4-((1-((2,4-dichlorophenyl)sulfonyl)-3-(hydroxymethyl)azetidin-3-yl)methoxy)-2-fluorobenzonitrile (760 mg, 1.707 mmol) in dry DCM (10 mL) was added dropwise. The mixture was stirred at −78° C. for 30 min, $Et_3N$ (1.30 mL, 9.326 mmol) was added dropwise. The mixture was warmed to rt while stirring for 22 h. The reaction mixture was poured into sat. aq. $NaHCO_3$ (100 mL) and extracted with DCM (3×50 mL). The extracts were dried over $Na_2SO_4$, filtered and concentrated in vacuo to give the crude title compound (681.1 mg) as a yellow oil. $^1H$ NMR (500 MHz, $CDCl_3$) δ ppm 9.87-9.93 (m, 1H), 7.96-8.00 (m, 1H), 7.51-7.60 (m, 2H), 7.39-7.43 (m, 1H), 6.76-6.80 (m, 1H), 6.72-6.76 (m, 1H), 4.38 (s, 2H), 4.30 (s, 2H), 4.15-4.20 (m, 2H).

Step 2. 4-((1-((2,4-Dichlorophenyl)sulfonyl)-3-((methylamino)methyl)azetidin-3-yl)methoxy)-2-fluorobenzonitrile hydrochloride. Solid $NaBH(OAc)_3$ (310 mg, 1.46 mmol) was added to a solution of 4-((1-((2,4-dichlorophenyl)sulfonyl)-3-formylazetidin-3-yl)methoxy)-2-fluorobenzonitrile (258 mg, 0.58 mmol), methylamine (2.0 M in THF, 0.73 mL, 1.46 mmol), and acetic acid (2 drops) in dry DCE (5 mL), and the mixture was stirred at rt for 22 h. The reaction mixture was poured into sat. aq. $NaHCO_3$ (100 mL) and extracted with DCM (3×50 mL). The extracts were dried over $Na_2SO_4$, decanted, and concentrated in vacuo. The residue was purified by flash chromatography on silica gel (Hexanes/EtOAc/$CH_3OH$). A solution of HCl (4.0 M in dioxane) was added to purified material and concentrated. The solid was triturated with $CH_3OH/Et_2O$ and the precipitate was collected by vacuum filtration to give the title compound (106 mg) as a white solid. $^1H$ NMR (500 MHz, DMSO-$d_6$) δ ppm 8.79 (br s, br s, 2H), 7.97 (m, 2H), 7.86 (m, 1H), 7.67 (dd, 1H), 7.01 (dd, 1H), 6.87 (dd, 1H), 4.23 (s, 2H), 4.02 (d, 2H), 3.87 (d, 2H), 3.33 (m, 2H), 2.58 (br s, br s, 3H). LCMS $[M+H]^+$ 458, 460.

Example 17—Compound 17

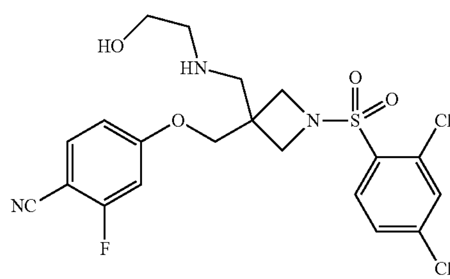 [SMILES: N#Cc1ccc(OCC2(CNCCO)CN(S(=O)(=O)c3ccc(Cl)cc3Cl)C2)cc1F]

4-((1-((2,4-Dichlorophenyl)sulfonyl)-3-(((2-hydroxyethyl)amino)methyl)azetidin-3-yl)methoxy)-2-fluorobenzonitrile was prepared in a similar fashion as in Scheme 14 from 4-((1-((2,4-dichlorophenyl)sulfonyl)-3-formylazetidin-3-yl)methoxy)-2-fluorobenzonitrile and ethanolamine. $^1H$ NMR (500 MHz, $CDCl_3$) δ ppm 7.98 (d, 1H), 7.57 (d, 1H), 7.54 (dd, 1H), 7.39 (dd, 1H), 6.75 (dd, 1H), 6.72 (dd, 1H), 4.13 (s, 2H), 3.89-3.97 (m, 4H), 3.62-3.67 (m, 2H), 2.97 (s, 2H), 2.77-2.83 (m, 2H). LCMS $[M+H]^+$ 488, 490.

Example 18—Compound 18

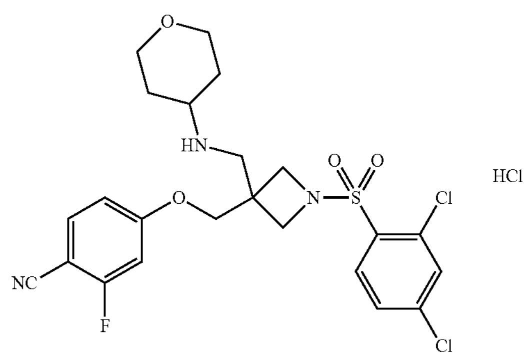 [SMILES: N#Cc1ccc(OCC2(CNC3CCOCC3)CN(S(=O)(=O)c3ccc(Cl)cc3Cl)C2)cc1F ; Cl]

4-((1-((2,4-Dichlorophenyl)sulfonyl)-3-(((tetrahydro-2H-pyran-4-yl)amino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and 4-aminotetrahydropyran. $^1H$ NMR (free base) (500 MHz, $CDCl_3$) δ ppm 7.98 (d, 1H), 7.57 (d, 1H), 7.53 (dd, 1H), 7.39 (dd, 1H), 6.74 (dd, 1H), 6.71 (dd, 1H), 4.11-4.13 (m, 2H), 3.90-3.97 (m, 4H), 3.85-3.90 (m, 2H), 3.31-3.40 (m, 2H), 2.95 (s, 2H), 2.55-2.66 (m, 1H), 1.78 (d, 2H), 1.30 (d, 2H). LCMS $[M+H]^+$ 528, 530.

Example 19—Compound 19

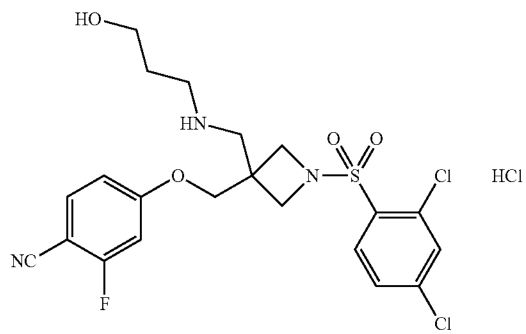 [SMILES: N#Cc1ccc(OCC2(CNCCCO)CN(S(=O)(=O)c3ccc(Cl)cc3Cl)C2)cc1F ; Cl]

4-((1-((2,4-Dichlorophenyl)sulfonyl)-3-(((3-hydroxypropyl)amino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and 3-amino-1-propanol. $^{1}$H NMR (free base) (500 MHz, $CDCl_3$) δ ppm 7.97 (d, 1H), 7.56 (d, 1H), 7.54 (dd, 1H), 7.37-7.40 (m, 1H), 6.75 (dd, 1H), 6.71 (dd, 1H), 4.09-4.12 (m, 2H), 3.87-3.96 (m, 4H), 3.73-3.78 (m, 2H), 2.97 (s, 2H), 2.86 (t, 2H), 1.70 (quin, 2H). LCMS $[M+H]^+$ 502, 504.

Example 20—Compound 20

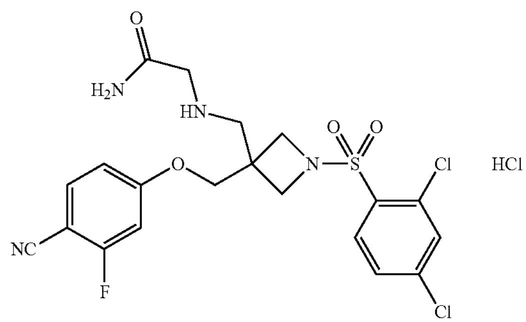 [SMILES: N#Cc1ccc(OCC2(CNCC(N)=O)CN(S(=O)(=O)c3ccc(Cl)cc3Cl)C2)cc1F ; Cl]

2-(((3-((4-Cyano-3-fluorophenoxy)methyl)-1-((2,4-dichlorophenyl)sulfonyl)azetidin-3-yl)methyl)amino)acetamide hydrochloride was prepared in a similar fashion as in Scheme 14 from 4-((1-((2,4-dichlorophenyl)sulfonyl)-3-formylazetidin-3-yl)methoxy)-2-fluorobenzonitrile and glycinamide hydrochloride. $^{1}$H NMR (free base) (500 MHz, $CDCl_3$) δ ppm 7.97 (d, 1H), 7.52-7.58 (m, 2H), 7.39 (dd, 1H), 6.76 (dd, 1H), 6.72 (dd, 1H), 6.48 (br s, 1H), 5.41-5.49 (m, 1H), 4.13-4.16 (m, 2H), 3.97-4.02 (m, 2H), 3.90-3.95 (m, 2H), 3.34 (s, 2H), 2.97 (s, 2H). LCMS $[M+H]^+$ 501, 503.

Example 21—Compound 21

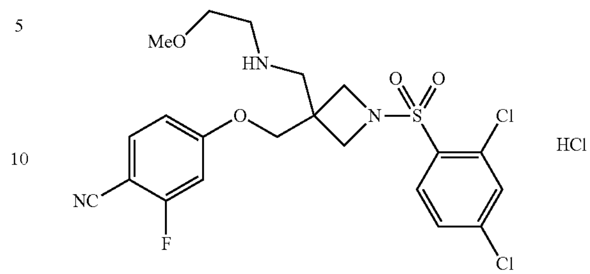

4-((1-((2,4-dichlorophenyl)sulfonyl)-3-(((2-methoxyethyl)amino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and 2-methoxyethylamine. $^{1}$H NMR (free base) (500 MHz, $CDCl_3$) δ ppm 7.97 (d, 1H), 7.56 (d, 1H), 7.50-7.55 (m, 1H), 7.38 (dd, 1H), 6.68-6.77 (m, 2H), 4.13 (s, 2H), 3.91-3.96 (m, 2H), 3.87 (d, 2H), 3.43 (t, 2H), 3.32 (s, 3H), 2.94 (s, 2H), 2.76 (t, 2H). LCMS $[M+H]^+$ 502, 504.

Example 22—Compound 22

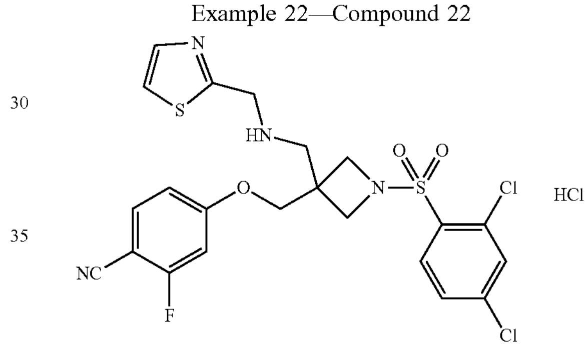

4-((1-((2,4-dichlorophenyl)sulfonyl)-3-(((thiazol-2-ylmethyl)amino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and thiazol-2-ylmethanamine. $^{1}$H NMR (free base) (500 MHz, $CDCl_3$) δ ppm 8.10 (s, 1H), 7.97 (d, 1H), 7.70 (d, 1H), 7.55 (d, 1H), 7.54-7.51 (m, 1H), 7.38 (dd, 1H), 6.74 (dd, 1H), 6.70 (dd, 1H), 4.17 (s, 2H), 4.15 (s, 2H), 3.96 (d, 2H), 3.92 (d, 2H), 3.04 (s, 2H). LCMS $[M+H]^+$ 541, 543.

Example 23—Compound 23

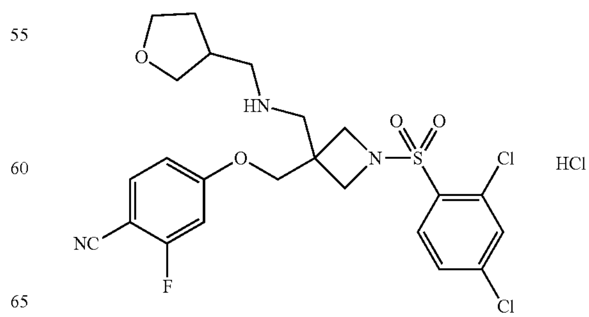

4-((1-((2,4-Dichlorophenyl)sulfonyl)-3-((((tetrahydrofuran-3-yl)methyl)amino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and (tetrahydrofuran-3-yl)methanamine. $^1$H NMR (free base) (500 MHz, $CDCl_3$) δ ppm 7.91 (d, 1H), 7.44-7.52 (m, 2H), 7.32 (dd, 1H), 6.61-6.71 (m, 2H), 4.05 (s, 2H), 3.80-3.89 (m, 4H), 3.70-3.78 (m, 2H), 3.62-3.68 (m, 1H), 3.41 (dd, 1H), 2.86 (q, 2H), 2.47-2.60 (m, 2H), 2.18-2.28 (m, 1H), 1.87-1.99 (m, 1H), 1.47 (dd, 1H). LCMS $[M+H]^+$ 528, 530.

Example 24—Compound 24

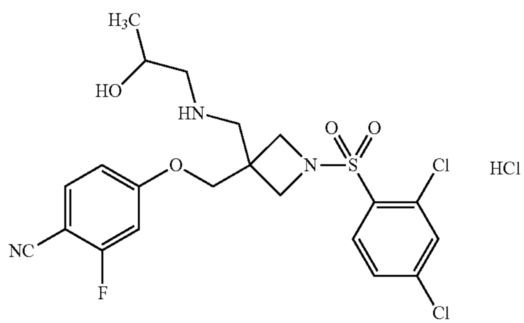 [SMILES: CC(O)CNCC1(COc2ccc(C#N)c(F)c2)CN(S(=O)(=O)c2ccc(Cl)cc2Cl)C1 ; Cl]

4-((1-((2,4-Dichlorophenyl)sulfonyl)-3-(((2-hydroxypropyl)amino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and 1-amino-2-propanol. $^1$H NMR (free base) (500 MHz, $CDCl_3$) δ ppm 7.91 (d, 1H), 7.43-7.53 (m, 2H), 7.32 (dd, 1H), 6.62-6.72 (m, 2H), 4.07 (s, 2H), 3.83-3.90 (m, 4H), 3.67-3.75 (m, 1H), 2.85-2.97 (m, 2H), 2.66 (dd, 1H), 2.39 (dd, 1H), 1.08 (d, 3H). LCMS $[M+H]^+$ 502, 504.

Example 25—Compound 25

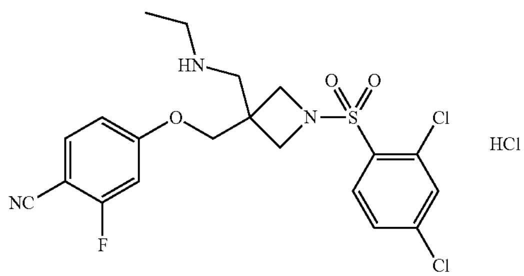 [SMILES: CCNCC1(COc2ccc(C#N)c(F)c2)CN(S(=O)(=O)c2ccc(Cl)cc2Cl)C1 ; Cl]

4-((1-((2,4-Dichlorophenyl)sulfonyl)-3-((ethylamino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and ethylamine (2.0 M in THF). $^1$H NMR (free base) (500 MHz, $CDCl_3$) δ ppm 7.97 (d, 1H), 7.50-7.59 (m, 2H), 7.39 (dd, 1H), 6.69-6.78 (m, 2H), 4.12 (s, 2H), 3.92-3.96 (m, 2H), 3.86-3.90 (m, 2H), 2.93 (s, 2H), 2.64 (q, 2H), 1.06 (t, 3H). LCMS $[M+H]^+$ 472, 474.

Example 26—Compound 26

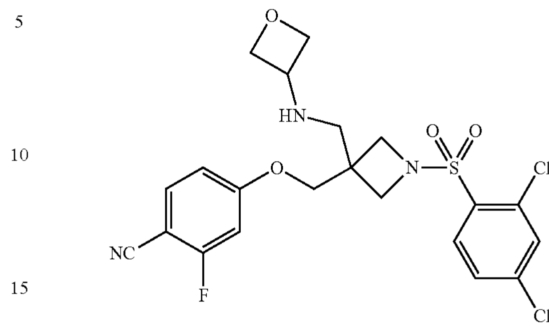

4-((1-((2,4-Dichlorophenyl)sulfonyl)-3-((oxetan-3-ylamino)methyl)azetidin-3-yl)methoxy)-2-fluorobenzonitrile was prepared in a similar fashion as in Scheme 14 from 4-((1-((2,4-dichlorophenyl)sulfonyl)-3-formylazetidin-3-yl)methoxy)-2-fluorobenzonitrile and oxetan-3-amine. $^1$H NMR (500 MHz, $CDCl_3$) δ ppm 7.97 (d, 1H), 7.52-7.58 (m, 2H), 7.39 (dd, 1H), 6.75 (dd, 1H), 6.71 (dd, 1H), 4.80 (t, 2H), 4.37 (t, 2H), 4.12-4.15 (m, 2H), 3.85-3.96 (m, 5H), 2.90 (s, 2H). LCMS $[M+H]^+$ 500, 502.

Example 27—Compound 27

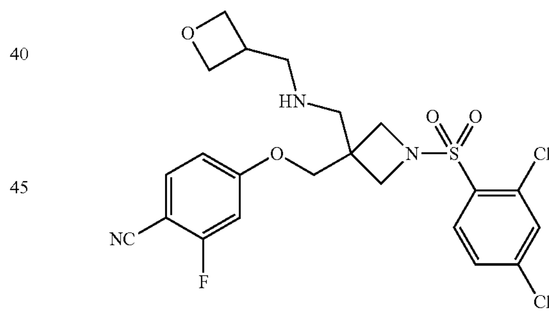

4-((1-((2,4-Dichlorophenyl)sulfonyl)-3-(((oxetan-3-ylmethyl)amino)methyl)azetidin-3-yl)methoxy)-2-fluorobenzonitrile was prepared in a similar fashion as in Scheme 14 from 4-((1-((2,4-dichlorophenyl)sulfonyl)-3-formylazetidin-3-yl)methoxy)-2-fluorobenzonitrile and 3-oxetanemethanamine. $^1$H NMR (500 MHz, $CDCl_3$) δ ppm 7.97 (d, 1H), 7.51-7.58 (m, 2H), 7.36-7.40 (m, 1H), 6.74 (dd, 1H), 6.70 (dd, 1H), 4.76 (dd, 2H), 4.34 (t, 2H), 4.11 (s, 2H), 3.85-3.94 (m, 4H), 2.97-3.08 (m, 1H), 2.91-2.97 (m, 4H). LCMS $[M+H]^+$ 514, 516.

Example 28—Compound 28

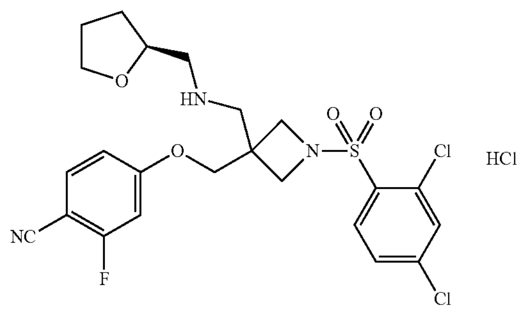 [SMILES: N#Cc1ccc(OCC2(CNC[C@@H]3CCCO3)CN(S(=O)(=O)c3ccc(Cl)cc3Cl)C2)cc1F ; Cl]

(S)-4-((1-((2,4-dichlorophenyl)sulfonyl)-3-((((tetrahydrofuran-2-yl)methyl)amino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and (S)-tetrahydrofurfurylamine. $^1$H NMR (500 MHz, DMSO-$d_6$) δ ppm 9.21 (br s, 1H), 9.04 (br s, 1H), 7.97 (dd, 1H), 7.86 (t, 1H), 7.67 (dd, 2H), 6.98 (dd, 1H), 6.84 (dd, 1H), 4.23-4.29 (m, 2H), 3.98 (d, 2H), 3.90 (d, 2H), 3.74-3.82 (m, 1H), 3.63-3.71 (m, 1H), 3.30-3.48 (m, 3H), 3.10 (br s, 1H), 2.94 (br s, 1H), 1.93-2.04 (m, 1H), 1.75-1.90 (m, 2H), 1.49-1.59 (m, 1H). LCMS $[M+H]^+$ 528, 530.

Example 29—Compound 29

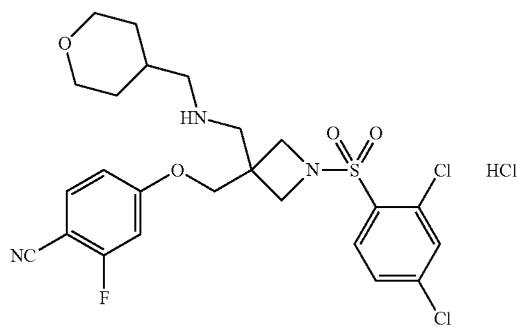 [SMILES: N#Cc1ccc(OCC2(CNCC3CCOCC3)CN(S(=O)(=O)c3ccc(Cl)cc3Cl)C2)cc1F ; Cl]

4-((1-((2,4-Dichlorophenyl)sulfonyl)-3-((((tetrahydro-2H-pyran-4-yl)methyl)amino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and 4-aminomethyltetrahydropyran. $^1$H NMR (500 MHz, DMSO-$d_6$) δ ppm 9.01-8.82 (m, 2H), 8.03-7.95 (m, 2H), 7.91-7.83 (m, 1H), 7.69 (dd, 1H), 6.99 (dd, 1H), 6.85 (dd, 1H), 4.29 (s, 2H), 4.03 (d, 2H), 3.92 (d, 2H), 3.89-3.81 (m, 2H), 3.43-3.37 (m, 2H), 3.26 (td, 2H), 2.93-2.84 (m, 2H), 2.11-1.98 (m, 1H), 1.73-1.63 (m, 2H), 1.30-1.14 (m, 2H). LCMS $[M+H]^+$ 542, 544.

Example 30—Compound 30

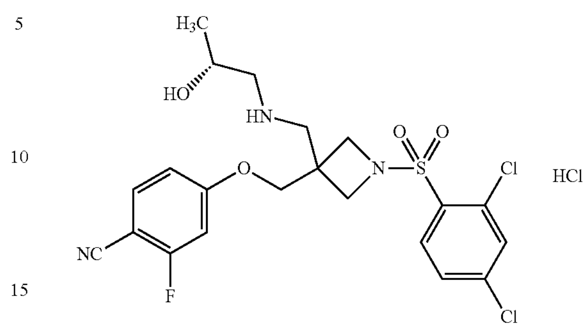

(R)-4-((1-((2,4-Dichlorophenyl)sulfonyl)-3-(((2-hydroxypropyl)amino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and (R)-(−)-1-amino-2-propanol. $^1$H NMR (500 MHz, DMSO-$d_6$) δ ppm 8.95-8.78 (m, 2H), 8.02-7.96 (m, 2H), 7.90-7.85 (m, 1H), 7.69 (dd, 1H), 7.01 (dd, 1H), 6.87 (dd, 1H), 5.50-5.29 (m, 1H), 4.28 (s, 2H), 4.09-3.97 (m, 3H), 3.94-3.88 (m, 2H), 3.45-3.37 (m, 2H), 3.07-2.98 (m, 1H), 2.86-2.76 (m, 1H), 1.11 (d, 3H). LCMS $[M+H]^+$ 502, 504.

Example 31—Compound 31

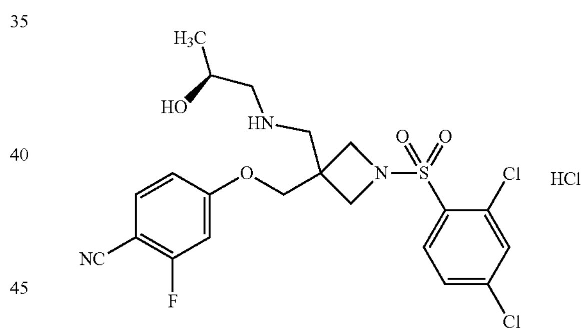

(S)-4-((1-((2,4-dichlorophenyl)sulfonyl)-3-(((2-hydroxypropyl)amino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and (S)-(+)-1-amino-2-propanol. $^1$H NMR (500 MHz, DMSO-$d_6$) δ ppm 8.96-8.78 (m, 2H), 8.01-7.96 (m, 2H), 7.91-7.85 (m, 1H), 7.69 (dd, 1H), 7.01 (dd, 1H), 6.87 (dd, 1H), 5.50-5.30 (m, 1H), 4.28 (s, 2H), 4.08-3.97 (m, 3H), 3.94-3.88 (m, 2H), 3.46-3.39 (m, 2H), 3.07-2.99 (m, 1H), 2.86-2.76 (m, 1H), 1.11 (d, 3H). LCMS $[M+H]^+$ 502, 504.

Example 32—Compound 32

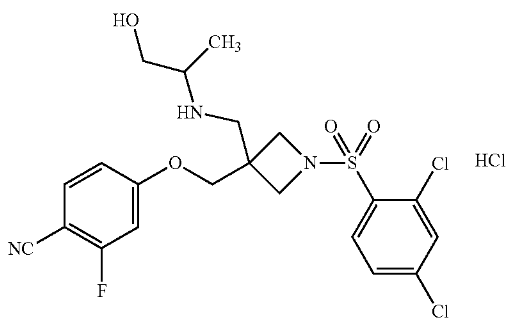 [SMILES: CC(CO)NCC1(COc2ccc(C#N)c(F)c2)CN(S(=O)(=O)c2ccc(Cl)cc2Cl)C1 ; Cl]

4-((1-((2,4-Dichlorophenyl)sulfonyl)-3-(((1-hydroxypropan-2-yl)amino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and (+/−) alaninol. $^1$H NMR (500 MHz, DMSO-$d_6$) δ ppm 8.90-8.65 (m, 2H), 8.03-7.96 (m, 2H), 7.91-7.85 (m, 1H), 7.69 (dd, 1H), 6.99 (dd, 1H), 6.86 (dd, 1H), 5.41 (s, 1H), 4.27 (s, 2H), 4.02-3.96 (m, 2H), 3.96-3.90 (m, 2H), 3.73-3.64 (m, 2H), 3.59-3.52 (m, 1H), 3.52-3.45 (m, 1H), 3.37-3.28 (m, 1H), 1.23 (d, 3H). LCMS $[M+H]^+$ 502, 504.

Example 33—Compound 33

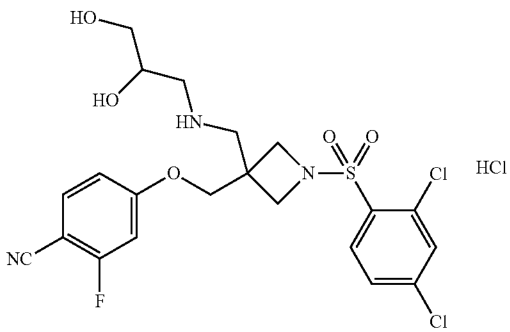 [SMILES: N#Cc1ccc(OCC2(CNCC(O)CO)CN(S(=O)(=O)c3ccc(Cl)cc3Cl)C2)cc1F ; Cl]

4-((1-((2,4-Dichlorophenyl)sulfonyl)-3-(((2,3-dihydroxypropyl)amino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and 3-amino-1,2-propanediol. $^1$H NMR (500 MHz, $CD_3OD$) δ ppm 8.05-8.00 (m, 1H), 7.77 (d, 1H), 7.71 (dd, 1H), 7.58-7.54 (m, 1H), 7.01 (dd, 1H), 6.97 (dd, 1H), 4.39-4.33 (m, 2H), 4.10-4.02 (m, 4H), 4.01-3.95 (m, 1H), 3.68-3.64 (m, 1H), 3.64-3.62 (m, 1H), 3.62-3.55 (m, 2H), 3.28-3.26 (m, 1H), 3.20-3.14 (m, 1H). LCMS $[M+H]^+$ 518, 520.

Example 34—Compound 34

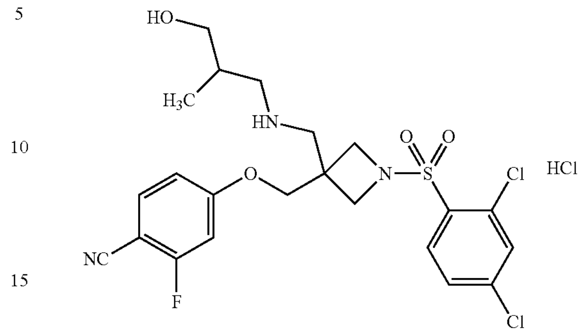

4-((1-((2,4-Dichlorophenyl)sulfonyl)-3-(((3-hydroxy-2-methylpropyl)amino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and 3-amino-2-methylpropan-1-ol. $^1$H NMR (500 MHz, $CD_3OD$) δ ppm 8.02 (d, 1H), 7.76 (d, 1H), 7.69 (dd, 1H), 7.56 (dd, 1H), 6.99 (dd, 1H), 6.95 (dd, 1H), 4.35 (s, 2H), 3.98-4.11 (m, 4H), 3.71-3.78 (m, 1H), 3.54-3.59 (m, 1H), 3.43-3.51 (m, 2H), 3.06-3.17 (m, 2H), 2.16-2.27 (m, 1H), 0.93 (d, 3H). LCMS $[M+H]^+$ 516, 518.

Example 35—Compound 35

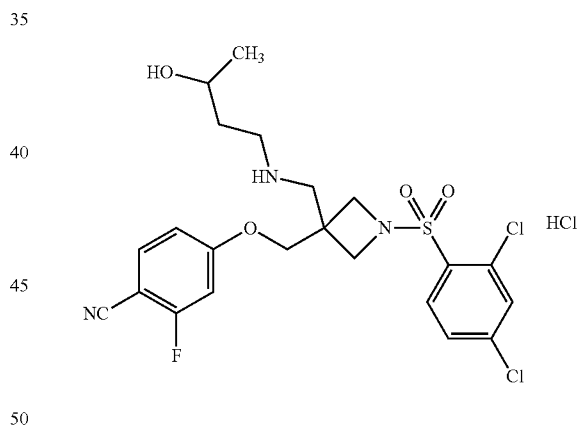

4-((1-((2,4-dichlorophenyl)sulfonyl)-3-(((3-hydroxybutyl)amino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and 4-amino-2-butanol. $^1$H NMR (500 MHz, $CD_3OD$) δ ppm 8.02 (d, 1H), 7.77 (d, 1H), 7.70 (dd, 1H), 7.53-7.58 (m, 1H), 6.98 (dd, 2H), 6.94 (dd, 2H), 4.32 (s, 2H), 4.00-4.08 (m, 4H), 3.95 (s, 1H), 3.44-3.57 (m, 2H), 3.20-3.27 (m, 2H), 1.84 (d, 1H), 1.77 (s, 1H), 1.18-1.24 (m, 3H). LCMS $[M+H]^+$ 516, 518.

Example 36—Compound 36

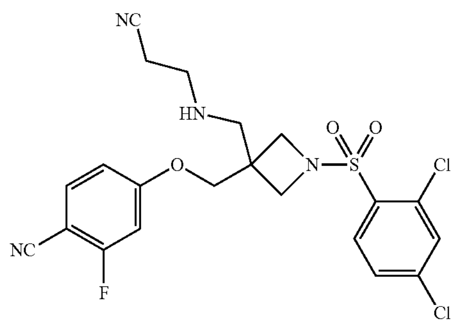 [SMILES: N#CCCNCC1(COc2ccc(C#N)c(F)c2)CN(S(=O)(=O)c2ccc(Cl)cc2Cl)C1]

4-((3-(((2-Cyanoethyl)amino)methyl)-1-((2,4-dichlorophenyl)sulfonyl)azetidin-3-yl)methoxy)-2-fluorobenzonitrile was prepared in a similar fashion as in Scheme 14 from 4-((1-((2,4-dichlorophenyl)sulfonyl)-3-formylazetidin-3-yl)methoxy)-2-fluorobenzonitrile and 3-aminopropionitrile. $^1$H NMR (500 MHz, $CDCl_3$) δ ppm 7.96-7.99 (m, 1H), 7.56-7.58 (m, 1H), 7.51-7.55 (m, 1H), 7.37-7.41 (m, 1H), 6.74-6.77 (m, 1H), 6.70-6.74 (m, 1H), 4.11 (s, 2H), 3.85-3.96 (m, 4H), 2.93 (s, 2H), 2.84-2.88 (m, 2H), 2.44-2.48 (m, 2H). LCMS $[M+H]^+$ 497, 499.

Example 37—Compound 37

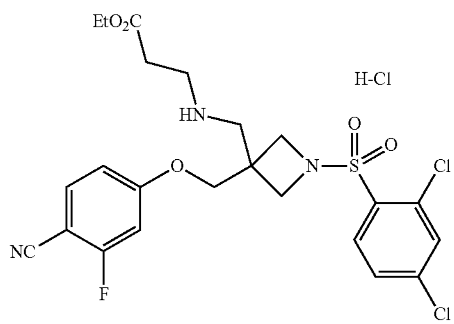

Ethyl 3-(((3-((4-Cyano-3-fluorophenoxy)methyl)-1-((2,4-dichlorophenyl)sulfonyl)azetidin-3-yl)methyl)amino)propanoate hydrochloride was prepared in a similar fashion as in Scheme 14 from 4-((1-((2,4-dichlorophenyl)sulfonyl)-3-formylazetidin-3-yl)methoxy)-2-fluorobenzonitrile and β-alanine ethyl ester hydrochloride and NaOAc instead of AcOH. $^1$H NMR (500 MHz, DMSO-$d_6$) δ ppm 8.91-9.08 (m, 2H), 7.94-8.04 (m, 2H), 7.87 (t, 1H), 7.67 (d, 1H), 7.00 (d, 1H), 6.86 (d, 1H), 4.25 (s, 2H), 4.08 (q, 2H), 4.01 (d, 2H), 3.88 (d, 2H), 3.35-3.46 (m, 2H), 3.13-3.28 (m, 2H), 2.77-2.88 (m, 2H), 1.15-1.26 (m, 3H). LCMS $[M+H]^+$ 544.0, 546.1.

Example 38—Compound 38

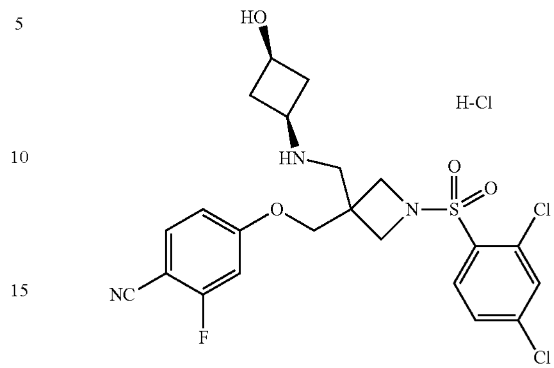

4-((1-((2,4-Dichlorophenyl)sulfonyl)-3-((((cis)-3-hydroxycyclobutyl)amino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and cis-3-aminocyclobutanol hydrochloride and NaOAc. $^1$H NMR (500 MHz, $CD_3OD$) δ ppm 8.02 (d, 1H), 7.77 (d, 1H), 7.71 (dd, 1H), 7.56 (dd, 1H), 6.98 (dd, 1H), 6.93 (dd, 1H), 4.29 (s, 2H), 4.07-4.14 (m, 1H), 3.98-4.06 (m, 4H), 3.33-3.43 (m, 3H), 2.67-2.78 (m, 2H), 2.01-2.14 (m, 2H). LCMS $[M+H]^+$ 514.1, 516.2.

Example 39—Compound 39

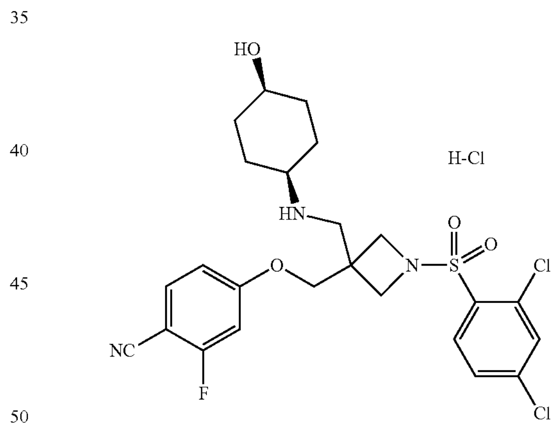

4-((1-((2,4-Dichlorophenyl)sulfonyl)-3-((((cis)-4-hydroxycyclohexyl)amino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and cis-4-aminocyclohexanol hydrochloride and NaOAc. $^1$H NMR (500 MHz, $CD_3OD$) δ ppm 8.03 (d, 1H), 7.78 (d, 1H), 7.68-7.74 (m, 1H), 7.57 (dd, 1H), 6.97 (dd, 1H), 6.93 (dd, 1H), 4.29 (s, 2H), 4.05-4.09 (m, 2H), 3.98-4.04 (m, 3H), 3.54 (s, 2H), 3.13-3.23 (m, 1H), 1.88-1.96 (m, 4H), 1.78-1.87 (m, 2H), 1.54-1.65 (m, 2H). LCMS $[M+H]^+$ 542.1, 544.1.

Example 40—Compound 40

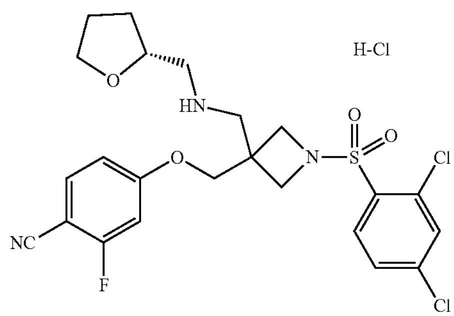 [SMILES: N#Cc1ccc(OCC2(CNC[C@H]3CCCO3)CN(S(=O)(=O)c3ccc(Cl)cc3Cl)C2)cc1F ; "H-Cl"]

(R)-4-((1-((2,4-dichlorophenyl)sulfonyl)-3-((((tetrahydrofuran-2-yl)methyl)amino)methyl)azetidin-3-yl)methoxy)-2-fluorobenzonitrile hydrochloride was prepared in a similar fashion as in Scheme 14 from 4-((1-((2,4-dichlorophenyl)sulfonyl)-3-formylazetidin-3-yl)methoxy)-2-fluorobenzonitrile and [(2R)-oxolan-2-yl]methanamine hydrochloride and NaOAc. $^1$H NMR (500 MHz, DMSO-$d_6$+$K_2CO_3$) 6 ppm 7.96-8.00 (m, 2H), 7.80-7.86 (m, 1H), 7.68 (dd, 1H), 7.05 (dd, 1H), 6.86 (dd, 1H), 4.11 (s, 2H), 3.77-3.84 (m, 4H), 3.64-3.77 (m, 3H), 3.52-3.61 (m, 2H), 2.68-2.78 (m, 2H), 1.68-1.88 (m, 3H), 1.39-1.49 (m, 1H). LCMS [M+H]$^+$ 528.1, 530.1.

Example 41—Compound 41

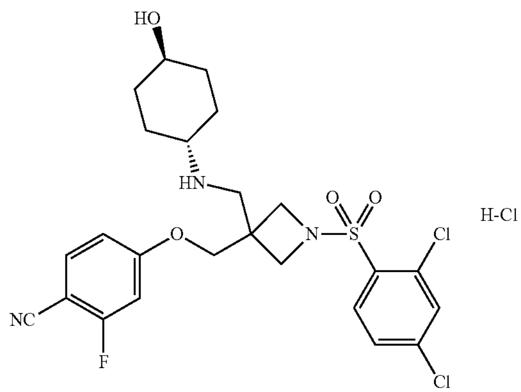

4-((1-((2,4-Dichlorophenyl)sulfonyl)-3-((((trans)-4-hydroxycyclohexyl)amino)methyl)azetidin-3-yl)methoxy)-2-fluorobenzonitrile hydrochloride was prepared according to Scheme 15:

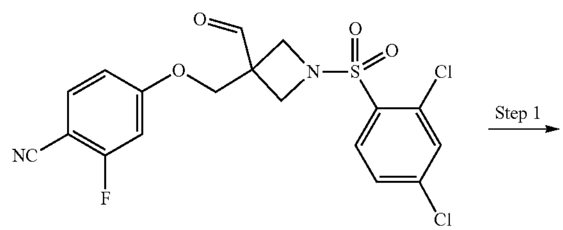

-continued

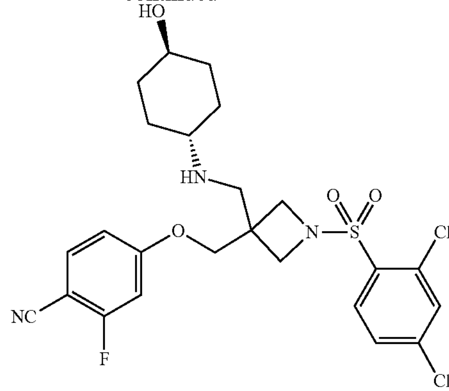

Reagents: Step 1) $NaBH_3CN$, trans-4-aminocyclohexanol, $CH_3OH$.

Step 1. Trans-4-aminocyclohexanol (18.3 mg, 0.159 mmol) was added to a solution of 4-((1-((2,4-dichlorophenyl)sulfonyl)-3-formylazetidin-3-yl)methoxy)-2-fluorobenzonitrile (50.1 mg, 0.113 mmol) in $CH_3OH$ (1 mL) and stirred until fully dissolved. $NaBH_3CN$ (12.8 mg, 0.204 mmol) was added and the mixture was stirred at rt for 18 h. The reaction mixture was poured into 2 M $K_2CO_3$ (15 mL) and extracted with DCM (3×10 mL). The extracts were dried over $Na_2SO_4$, decanted, and concentrated in vacuo. The residue was purified by flash chromatography on silica gel (Hexanes/EtOAC/$CH_3OH$) to give the title compound (21.9 mg) as a white solid. $^1$H NMR (500 MHz, DMSO-$d_6$) δ ppm 8.81-8.71 (m, 2H), 8.02-7.96 (m, 2H), 7.88 (dd, 1H), 7.69 (dd, 1H), 7.00 (dd, 1H), 6.86 (dd, 1H), 4.26 (s, 2H), 3.98 (d, 2H), 3.91 (d, 2H), 3.73-3.69 (m, 1H), 3.69-3.64 (m, 1H), 3.52-3.48 (m, 1H), 3.48-3.44 (m, 1H), 2.09-2.00 (m, 2H), 1.92-1.84 (m, 2H), 1.50-1.37 (m, 2H), 1.21-1.10 (m, 2H). LCMS [M+H]$^+$ 542, 544.

Example 42—Compound 42

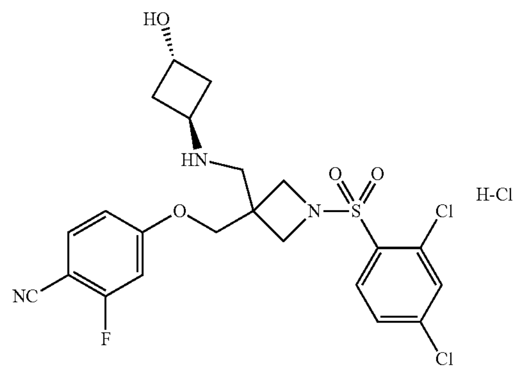

4-((1-((2,4-Dichlorophenyl)sulfonyl)-3-((((trans)-3-hydroxycyclobutyl)amino)methyl)azetidin-3-yl)methoxy)-2-fluorobenzonitrile hydrochloride was prepared in a similar fashion as in Scheme 15 from 4-((1-((2,4-dichlorophenyl)sulfonyl)-3-formylazetidin-3-yl)methoxy)-2-fluorobenzonitrile and trans-3-aminocyclobutan-1-ol. $^1$H NMR (500 MHz, $CD_3OD$) δ ppm 8.02 (d, 1H), 7.77 (d, 1H), 7.71 (dd, 1H), 7.56 (dd, 1H), 6.98 (dd, 1H), 6.93 (dd, 1H), 4.44-4.51 (m, 1H), 4.29 (s, 2H), 4.01-4.08 (m, 4H), 3.93-4.00 (m, 1H), 3.39 (s, 2H), 2.47-2.56 (m, 2H), 2.35 (br s, 2H). LCMS $[M+H]^+$ 514, 516.

Example 43—Compound 43

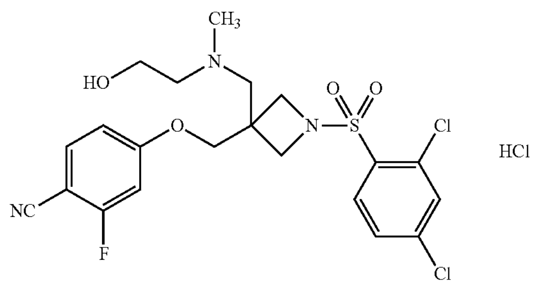 [SMILES: CN(CCO)CC1(COc2ccc(C#N)c(F)c2)CN(S(=O)(=O)c2ccc(Cl)cc2Cl)C1 ; Cl]

4-((1-((2,4-Dichlorophenyl)sulfonyl)-3-(((2-hydroxyethyl)(methyl)amino)methyl)azetidin-3-yl)methoxy)-2-fluorobenzonitrile hydrochloride was prepared according to Scheme 16:

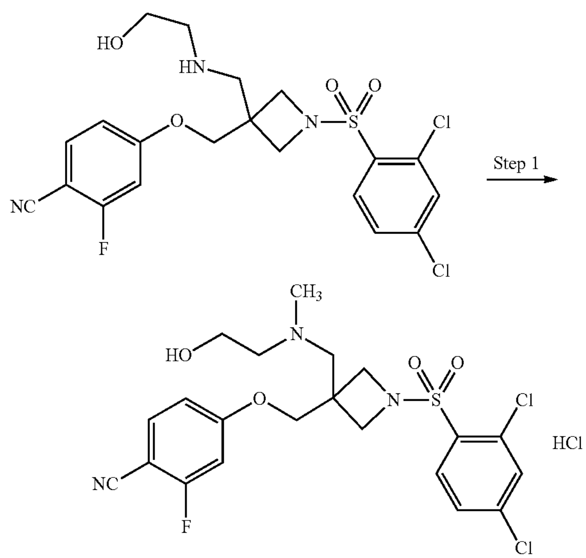

Reagents: Step 1) $NaBH(OAc)_3$, formaldehyde 37% by wt, AcOH, DCE.

Step 1. Solid $NaBH(OAc)_3$ (16.9 mg, 0.0798 mmol) was added to a solution of 4-((1-((2,4-dichlorophenyl)sulfonyl)-3-(((2-hydroxyethyl)amino)methyl)azetidin-3-yl)methoxy)-2-fluorobenzonitrile (15 mg, 0.031 mmol), formaldehyde (37 wt % in $H_2O$, 16 μL, 0.16 mmol), and acetic acid (1 drop) in dry DCE (1 mL) and mixture was stirred at rt for 16 h. The reaction mixture was the poured into sat. aq. $NaHCO_3$ (15 mL) and extracted with DCM (3×10 mL). The extracts were dried over $Na_2SO_4$, decanted, and concentrated in vacuo. The residue was purified by flash chromatography on silica gel (Hexanes/EtOAc/$CH_3OH$) to give the title compound (7.7 mg) as a thick colorless oil. $^1H$ NMR (free base) (500 MHz, $CDCl_3$) δ ppm 7.97 (d, 1H), 7.56 (d, 1H), 7.54 (dd, 1H), 7.38 (dd, 1H), 6.77 (dd, 1H), 6.73 (dd, 1H), 4.20 (s, 2H), 3.98 (d, 2H), 3.90 (d, 2H), 3.56 (t, 2H), 2.79 (s, 2H), 2.52-2.58 (m, 2H), 2.22 (s, 3H). LCMS $[M+H]^+$ 502, 504.

Example 44—Compound 44

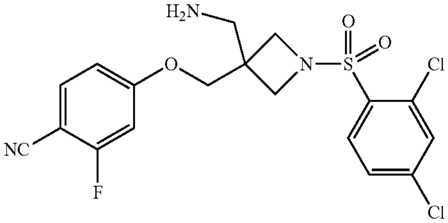 [SMILES: N#Cc1ccc(OCC2(CN)CN(S(=O)(=O)c3ccc(Cl)cc3Cl)C2)cc1F]

4-((3-(Aminomethyl)-1-((2,4-dichlorophenyl)sulfonyl)azetidin-3-yl)methoxy)-2-fluorobenzonitrile was prepared according to Scheme 17:

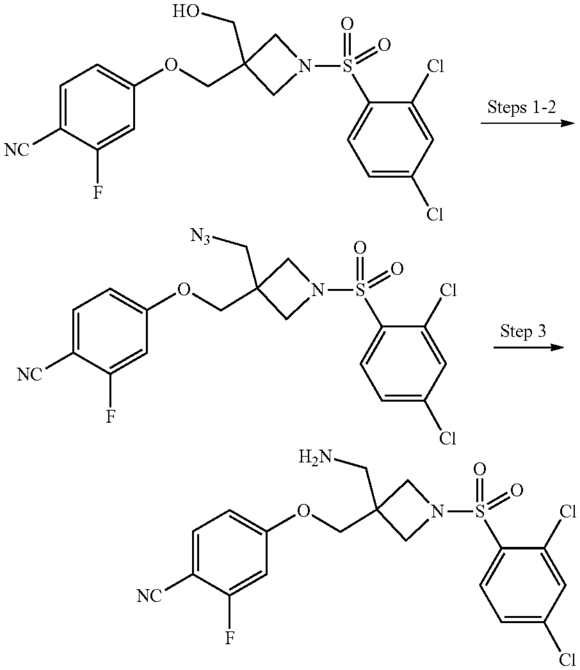

Reagents: Step 1) methanesulfonyl chloride, $Et_3N$, DCM; 2) $NaN_3$, DMF; 3) Zn, $NH_4Cl$, $CH_3OH$.

Step 1. (3-((4-Cyano-3-fluorophenoxy)methyl)-1-((2,4-dichlorophenyl)sulfonyl)azetidin-3-yl)methyl methanesulfonate. Neat methanesulfonyl chloride (0.16 mL, 2.06 mmol) was added dropwise to a solution of 4-((1-((2,4-dichlorophenyl)sulfonyl)-3-(hydroxymethyl)azetidin-3-yl)methoxy)-2-fluorobenzonitrile (760 mg, 1.71 mmol) and $Et_3N$ (0.36 mL, 2.58 mmol) in dry DCM (20 mL), and the mixture was stirred at rt under $N_2$ for 1 h. The reaction mixture was poured into saturated aqueous $NaHCO_3$ (100 mL) and extracted with DCM (2×100 mL). The extracts were dried over $Na_2SO_4$, filtered and concentrated to dryness to afford the title compound (909 mg) as an off-white foam.

Step 2. 4-((3-(Azidomethyl)-1-((2,4-dichlorophenyl)sulfonyl)azetidin-3-yl)methoxy)-2-fluorobenzonitrile. A mixture of (3-((4-cyano-3-fluorophenoxy)methyl)-1-((2,4-dichlorophenyl)sulfonyl)azetidin-3-yl)methyl methanesulfonate (909 mg, 1.71 mmol) and $NaN_3$ (566 mg, 8.71 mmol) in dry DMF (5 mL) was stirred at 50° C. for 16 h. The reaction mixture was cooled, diluted with EtOAc (75 mL), washed with saturated aqueous $NaHCO_3$ (2×50 mL) and brine (50 mL), dried over $Na_2SO_4$, filtered and concentrated to dryness to afford the title compound (755 mg) as a nearly colorless oil. $^1H$ NMR (500 MHz, $CDCl_3$) δ ppm 7.97 (d, 1H), 7.52-7.60 (m, 2H), 7.36-7.42 (m, 1H), 6.68-6.80 (m, 2H), 4.08-4.12 (m, 2H), 3.94-3.99 (m, 2H), 3.88-3.93 (m, 2H), 3.74 (s, 2H).

Step 3. 4-((3-(Aminomethyl)-1-((2,4-dichlorophenyl)sulfonyl)azetidin-3-yl)methoxy)-2-fluorobenzonitrile. A mixture of 4-((3-(azidomethyl)-1-((2,4-dichlorophenyl)sulfonyl)azetidin-3-yl)methoxy)-2-fluorobenzonitrile (755 mg, 1.61 mmol), $NH_4Cl$ (437 mg, 8.17 mmol), and zinc dust (2.09 g, 32.0 mmol) in $CH_3OH$ (20 mL) was stirred at rt under $N_2$ for 3 h. The reaction mixture was diluted with DCM (ca. 20 mL) and filtered through celite, rinsing with DCM/$CH_3OH$. The filtrate was concentrated to dryness and purified by flash chromatography (Hexanes/EtOAc/$CH_3OH$) to afford the title compound (583 mg) as a white solid. $^1H$ NMR (500 MHz, DMSO-$d_6$) δ ppm 7.92-8.01 (m, 2H), 7.84 (t, 1H), 7.63-7.70 (m, 1H), 6.99 (dd, 1H), 6.83 (dd, 1H), 5.07 (br. s, 2H), 4.12 (s, 2H), 3.84-3.90 (m, 2H), 3.78-3.83 (m, 2H), 2.96 (s, 2H). LCMS $[M+H]^+$ 444, 446.

Example 45—Compound 45

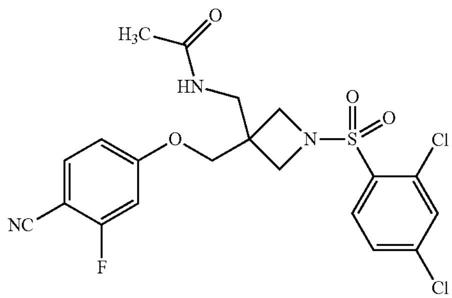 [SMILES: CC(=O)NCC1(COc2ccc(C#N)c(F)c2)CN(S(=O)(=O)c2ccc(Cl)cc2Cl)C1]

N-((3-((4-Cyano-3-fluorophenoxy)methyl)-1-((2,4-dichlorophenyl)sulfonyl)azetidin-3-yl)methyl)acetamide was prepared as follows. Acetyl chloride (8 μL, 0.113 mmol) was added dropwise to a solution of 4-((3-(aminomethyl)-1-((2,4-dichlorophenyl)sulfonyl)azetidin-3-yl)methoxy)-2-fluorobenzonitrile (8.9 mg, 0.020 mmol) and $Et_3N$ (15 μL, 0.108 mmol) in dry DCM (0.5 mL) and the mixture was stirred at rt for 2 h. The reaction mixture was poured into sat. aq. $NaHCO_3$ (5 mL) and extracted with DCM (2×5 mL). The extracts were dried over $Na_2SO_4$, decanted, and concentrated to dryness. The residue was purified by flash chromatography on silica gel (Hexanes/EtOAc) to give the title compound (3.8 mg) as a colorless oil. $^1H$ NMR (500 MHz, $CDCl_3$) δ ppm 7.97 (d, 1H), 7.57 (d, 1H), 7.54 (dd, 1H), 7.40 (dd, 1H), 6.74 (dd, 1H), 6.70 (dd, 1H), 5.85 (t, 1H), 4.06 (s, 2H), 3.91-3.99 (m, 4H), 3.60 (d, 2H), 2.02 (s, 3H). LCMS $[M+H]^+$ 486, 488.

Example 46—Compound 46

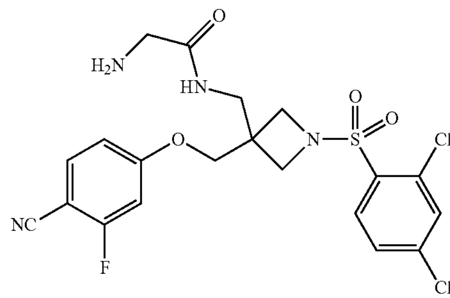 [SMILES: N#Cc1ccc(OCC2(CNC(=O)CN)CN(S(=O)(=O)c3ccc(Cl)cc3Cl)C2)cc1F]

2-Amino-N-((3-((4-cyano-3-fluorophenoxy)methyl)-1-((2,4-dichlorophenyl)sulfonyl)azetidin-3-yl)methyl)acetamide was prepared according to Scheme 18:

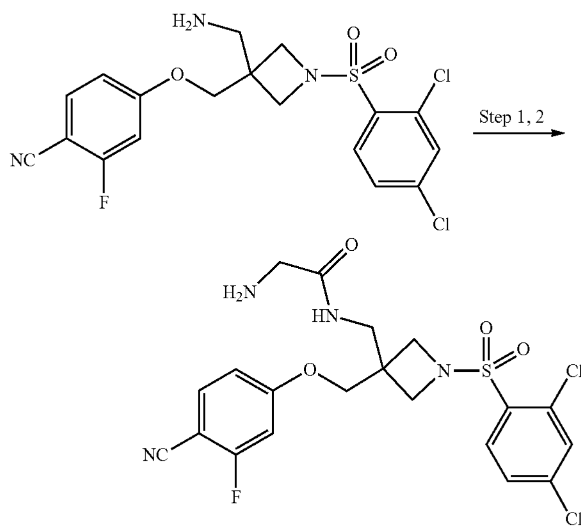

Reagents: Step 1) Boc-glycine, HATU, DIPEA, DMF; 2) TFA, DCM.

Step 1. tert-Butyl (2-(((3-((4-cyano-3-fluorophenoxy)methyl)-1-((2,4-dichlorophenyl)sulfonyl)azetidin-3-yl)methyl)amino)-2-oxoethyl)carbamate. A mixture of 4-((3-(aminomethyl)-1-((2,4-dichlorophenyl)sulfonyl)azetidin-3-yl)methoxy)-2-fluorobenzonitrile (43 mg, 0.10 mmol), Boc-glycine (21 mg, 0.12 mmol), HATU (46 mg, 0.12 mmol), and DIPEA (60 μL, 0.34 mmol) in dry DMF (1 mL) was stirred at rt for 18 h. The reaction mixture was diluted with EtOAc (10 mL), washed with saturated aqueous $NaHCO_3$ (2×10 mL) and brine (2×10 mL), dried over $Na_2SO_4$, decanted, and concentrated. The residue was purified by flash chromatography (EtOAc/Hexanes) to afford the title compound, which was immediately carried-on to the next step.

Step 2. 2-Amino-N-((3-((4-cyano-3-fluorophenoxy)methyl)-1-((2,4-dichlorophenyl)sulfonyl)azetidin-3-yl)methyl)acetamide. A mixture of tert-butyl (2-(((3-((4-cyano-3-fluorophenoxy)methyl)-1-((2,4-dichlorophenyl)sulfonyl)azetidin-3-yl)methyl)amino)-2-oxoethyl)carbamate (0.10 mmol) and TFA (0.25 mL) in dry DCM (0.75 mL) was stirred at rt for 2 h and concentrated. The residue was added to saturated aqueous $NaHCO_3$ (10 mL) and extracted with DCM (3×10 mL). The extracts were dried over $Na_2SO_4$, decanted, and concentrated, and the residue was purified by flash chromatography ($DCM/CH_3OH/NH_4OH$) to afford the title compound (20 mg) as a white solid. $^1H$ NMR (500 MHz, $CDCl_3$) δ ppm 7.96 (d, 1H), 7.87-7.94 (m, 1H), 7.51-7.59 (m, 2H), 7.39 (dd, 1H), 6.76 (dd, 1H), 6.71 (dd, 1H), 4.08 (s, 2H), 3.97-4.01 (m, 2H), 3.92-3.97 (m, 2H), 3.63 (d, 2H), 3.39 (s, 2H). LCMS $[M+H]^+$ 501.1, 503.1.

Example 47—Compound 47

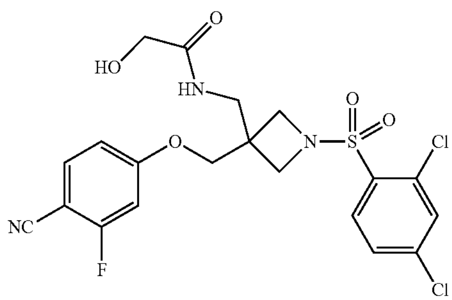 [SMILES: N#Cc1ccc(OCC2(CNC(=O)CO)CN(S(=O)(=O)c3ccc(Cl)cc3Cl)C2)cc1F]

N-((3-((4-Cyano-3-fluorophenoxy)methyl)-1-((2,4-dichlorophenyl)sulfonyl)azetidin-3-yl)methyl)-2-hydroxyacetamide was prepared in a similar fashion as in Scheme 18 from 4-((3-(aminomethyl)-1-((2,4-dichlorophenyl)sulfonyl)azetidin-3-yl)methoxy)-2-fluorobenzonitrile and glycolic acid. $^1H$ NMR (500 MHz, $CDCl_3$) δ ppm 7.96 (d, 1H), 7.56 (d, 1H), 7.52-7.55 (m, 1H), 7.36-7.41 (m, 1H), 6.96-7.03 (m, 1H), 6.76 (dd, 1H), 6.72 (dd, 1H), 4.18 (d, 2H), 4.10 (s, 2H), 4.03 (d, 2H), 3.95 (d, 2H), 3.67 (d, 2H), 2.42 (t, 1H). LCMS $[M+H]^+$ 502.0, 504.0.

Example 48—Compound 48

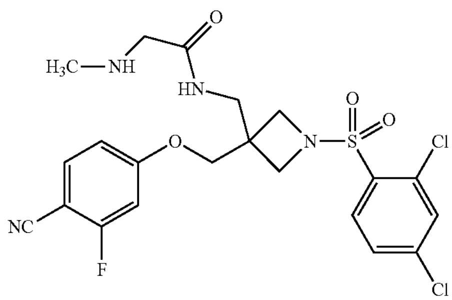 [SMILES: CNCC(=O)NCC1(COc2ccc(C#N)c(F)c2)CN(S(=O)(=O)c2ccc(Cl)cc2Cl)C1]

N-((3-((4-Cyano-3-fluorophenoxy)methyl)-1-((2,4-dichlorophenyl)sulfonyl)azetidin-3-yl)methyl)-2-(methylamino)acetamide was prepared in a similar fashion as in Scheme 18 from 4-((3-(aminomethyl)-1-((2,4-dichlorophenyl)sulfonyl)azetidin-3-yl)methoxy)-2-fluorobenzonitrile and Boc-sarcosine. $^1H$ NMR (500 MHz, $CDCl_3$) δ ppm 7.96 (d, 1H), 7.73-7.81 (m, 1H), 7.51-7.58 (m, 2H), 7.38 (dd, 1H), 6.75 (dd, 1H), 6.71 (dd, 1H), 4.08 (s, 2H), 3.92-3.99 (m, 4H), 3.63 (d, 2H), 3.27 (s, 2H), 2.42 (s, 3H), 1.75 (br s, 1H). LCMS $[M+H]^+$ 515.0, 517.1.

Example 49—Compound 49

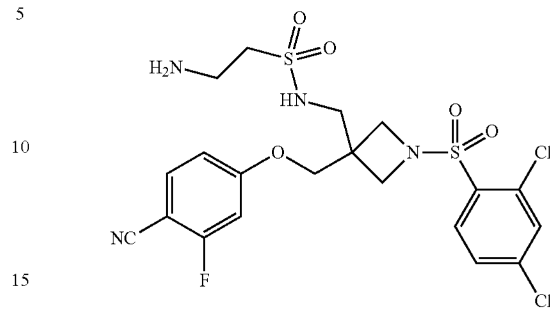

2-Amino-N-((3-((4-cyano-3-fluorophenoxy)methyl)-1-((2,4-dichlorophenyl)sulfonyl)azetidin-3-yl)methyl)ethane-1-sulfonamide was prepared in a similar fashion as in Scheme 13 from 4-((3-(aminomethyl)-1-((2,4-dichlorophenyl)sulfonyl)azetidin-3-yl)methoxy)-2-fluorobenzonitrile and Boc-taurine chloride. $^1H$ NMR (500 MHz, $CDCl_3$) δ ppm 7.97 (d, 1H), 7.57 (d, 1H), 7.52-7.56 (m, 1H), 7.40 (dd, 1H), 6.75 (dd, 1H), 6.70 (dd, 1H), 5.76-5.94 (m, 2H), 4.16 (s, 2H), 3.91-4.00 (m, 4H), 3.45 (s, 2H), 3.24-3.31 (m, 2H), 3.07-3.13 (m, 2H). LCMS $[M+H]^+$ 550.9, 553.0.

Example 50—Compound 50

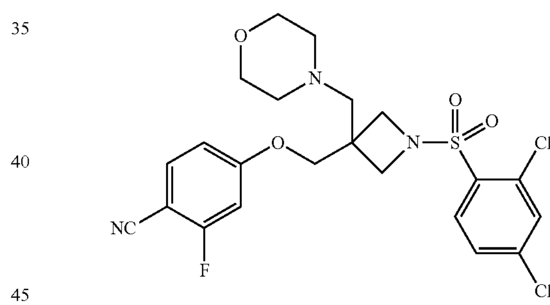

4-((1-((2,4-Dichlorophenyl)sulfonyl)-3-(morpholinomethyl)azetidin-3-yl)methoxy)-2-fluorobenzonitrile hydrochloride was prepared according to Scheme 19:

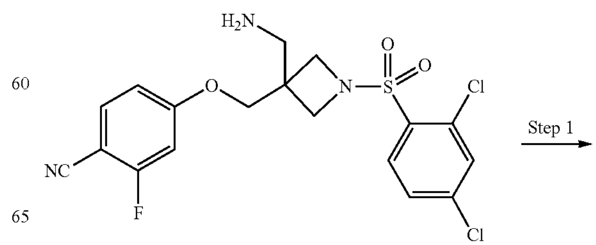

-continued

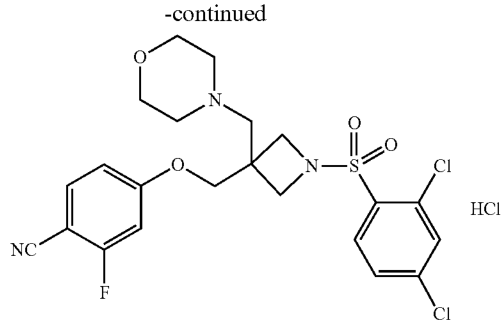

Reagents: Step 1) 2-bromoethyl ether, $K_2CO_3$, $CH_3CN$, 85° C.

Step 1. A solution of 2-bromoethyl ether (19 μL, 0.15 mmol) in dry $CH_3CN$ (1.0 mL) was added to 4-((3-(aminomethyl)-1-((2,4-dichlorophenyl)sulfonyl)azetidin-3-yl)methoxy)-2-fluorobenzonitrile (44 mg, 0.10 mmol) and $K_2CO_3$, and the mixture was stirred at 85° C. in a capped vial for 16 h. The reaction mixture was cooled, diluted with EtOAc (10 mL), washed with saturated aqueous $NaHCO_3$ (2×10 mL) and brine (10 mL), dried over $Na_2SO_4$, decanted and concentrated. The residue was purified by flash chromatography (EtOAc/Hexanes). Product fractions were concentrated, converted to the HCl salt with 4.0 M HCl in dioxane, and concentrated to dryness to afford the title compound (33 mg, 0.06 mmol) as a white solid. $^1$H NMR (500 MHz, DMSO-$d_6$+$K_2CO_3$) 6 ppm 7.94-7.99 (m, 2H), 7.82 (t, 1H), 7.67 (dd, 1H), 7.07 (dd, 1H), 6.89 (dd, 1H), 4.16 (s, 2H), 3.86 (d, 2H), 3.78 (d, 2H), 3.39-3.46 (m, 4H), 2.51 (s, 2H), 2.23-2.32 (m, 4H). LCMS $[M+H]^+$ 514.1, 516.1.

Example 51—Compound 51

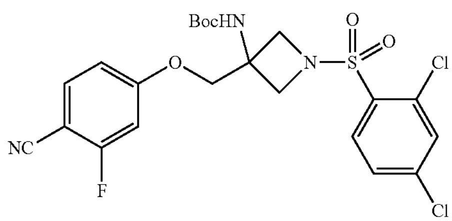 [SMILES: CC(C)(C)OC(=O)NC1(COc2ccc(C#N)c(F)c2)CN(S(=O)(=O)c2ccc(Cl)cc2Cl)C1]

tert-Butyl (3-((4-cyano-3-fluorophenoxy)methyl)-1-((2,4-dichlorophenyl)sulfonyl)azetidin-3-yl)carbamate was prepared according to Scheme 20:

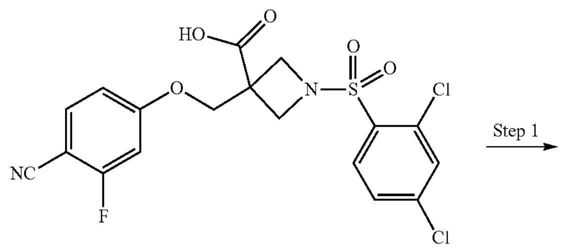

-continued

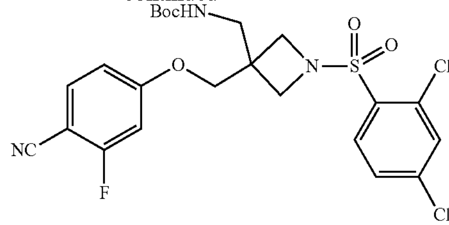

Reagents: Step 1) Diphenyl phosphoryl azide, $Et_3N$, toluene, 100° C.; tert-butanol, 100° C.

Step 1. Neat $Et_3N$ (50 μL, 0.36 mmol) and diphenyl phosphoryl azide (70 μL, 0.33 mmol) were added to a suspension of 3-((4-cyano-3-fluorophenoxy)methyl)-1-((2,4-dichlorophenyl)sulfonyl)azetidine-3-carboxylic acid (124 mg, 0.27 mmol) in toluene (4 mL), and the mixture was stirred at 100° C. under $N_2$ for 17 h. The reaction mixture was cooled to rt, tert-butanol (2 mL) was added, and it was heated to 100° C. for another 4 h. The reaction mixture was cooled, concentrated in vacuo to remove most of the toluene and tert-butanol, taken up in EtOAc (15 mL), washed with sat. aq. $NaHCO_3$ (2×15 mL) and brine (15 mL), dried over $Na_2SO_4$, filtered and concentrated in vacuo. The residue was purified by flash chromatography (Hexanes/EtOAc) to give the title compound (33.8 mg) as a colorless glass. $^1$H NMR (500 MHz, $CDCl_3$) δ ppm 7.97 (d, 1H), 7.51-7.58 (m, 2H), 7.39 (dd, 1H), 6.77 (dd, 1H), 6.73 (dd, 1H), 4.98 (br. s, 1H), 4.29 (s, 2H), 4.21 (d, 2H), 4.08 (d, 2H), 1.42 (s, 9H). LCMS $[M+H]^+$ 530.1, 531.8.

Example 52—Compound 52

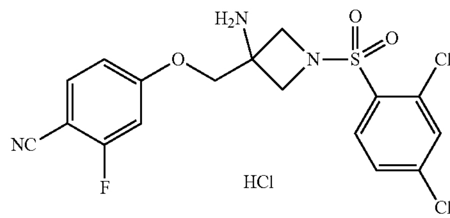 [SMILES: N#Cc1ccc(OCC2(N)CN(S(=O)(=O)c3ccc(Cl)cc3Cl)C2)cc1F ; Cl]

4-((3-Amino-1-((2,4-dichlorophenyl)sulfonyl)azetidin-3-yl)methoxy)-2-fluorobenzonitrile hydrochloride salt was prepared according to Scheme 21:

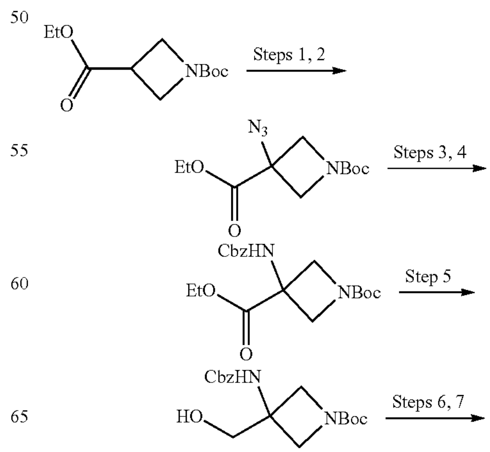

-continued

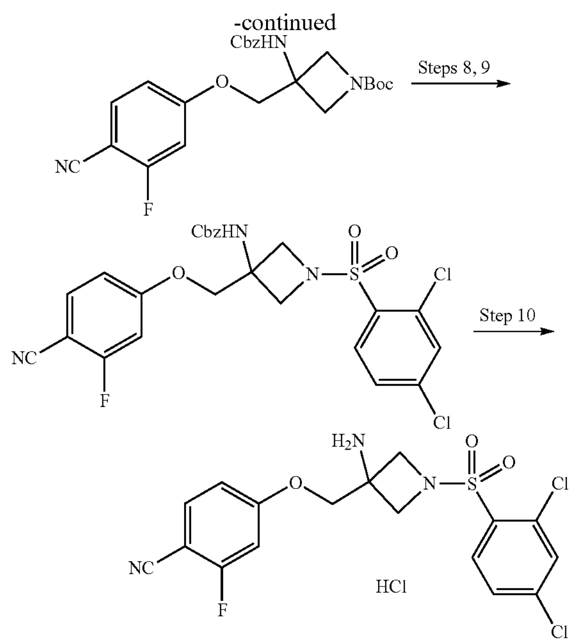

Reagents: Step 1) LHMDS, THF, −78° C.; $CBr_4$; 2) $NaN_3$, DMSO; 3) $H_2$, Pd/C, EtOH; 4) benzyl chloroformate, sat. aq. $NaHCO_3$, dioxane; 5) $LiAlH(Ot\text{-}Bu)_3$, THF; 6) methanesulfonyl chloride, $Et_3N$, DCM; 7) 2-fluoro-4-hydroxybenzonitrile, $K_2CO_3$, $CH_3CN$, A; 8) TFA, DCM; 9) 2,4-dichlorobenzenesulfonyl chloride, $Et_3N$, DCM; 10) TFA, 50° C.

Step 1. 1-(tert-Butyl) 3-ethyl 3-bromoazetidine-1,3-dicarboxylate. A mixture of LHMDS (1.0 M in THF/ethyl benzene, 15.8 mL, 15.8 mmol) and dry THF (60 mL) under $N_2$ was cooled to −78° C. A solution of ethyl 1-boc-azetidine-3-carboxylate (3.01 g, 13.1 mmol) in dry THF (30 mL) was added dropwise, and the mixture was stirred at −78° C. for 15 min. A solution of $CBr_4$ (6.56 g, 19.8 mmol) in dry THF (30 mL) was added dropwise, and the mixture was warmed to rt and stirred for 20 h. The reaction mixture was diluted with $Et_2O$ (350 mL), washed with saturated aqueous $NaHCO_3$ (2×250 mL) and brine (250 mL), dried over $Na_2SO_4$, decanted and concentrated. The residue was purified by flash chromatography (EtOAc/Hexanes) to afford the title compound (2.53 g) as an orange oil. $^1H$ NMR (500 MHz, $CDCl_3$) δ ppm 4.64 (dd, 2H), 4.25-4.33 (m, 4H), 1.45 (s, 9H), 1.33 (t, 3H).

Step 2. 1-(tert-Butyl) 3-ethyl 3-azidoazetidine-1,3-dicarboxylate. A mixture of 1-(tert-butyl) 3-ethyl 3-bromoazetidine-1,3-dicarboxylate (2.53 g, 8.2 mmol) and $NaN_3$ (1.59 g, 24.5 mmol) in dry DMSO (20 mL) was stirred at 50° C. under $N_2$ for 18 h. The reaction mixture was cooled, diluted with $Et_2O$ (250 mL), washed with saturated aqueous $NaHCO_3$ (150 mL) and brine (2×150 mL), dried over $Na_2SO_4$, filtered and concentrated to dryness to afford the title compound (2.10 g) as a yellow oil. $^1H$ NMR (500 MHz, $CDCl_3$) δ ppm 4.30-4.36 (m, 4H), 3.97 (d, 2H), 1.45 (s, 9H), 1.36 (t, 3H).

Step 3. 1-(tert-Butyl) 3-ethyl 3-aminoazetidine-1,3-dicarboxylate. A mixture of 1-(tert-butyl) 3-ethyl 3-azidoazetidine-1,3-dicarboxylate (1.93 g, 7.15 mmol) and Pd/C (300 mg, 10 wt %, 50% $H_2O$, Degussa) in EtOH (70 mL) was stirred under and atmosphere of $H_2$ for 16 h. The reaction mixture was filtered through celite and the filtrate was concentrated to dryness to afford the title compound (1.73 g) as a yellow oil. $^1H$ NMR (500 MHz, $CDCl_3$) δ ppm 4.22-4.32 (m, 4H), 3.79 (d, 2H), 2.37 (br. s, 2H), 1.44 (s, 9H), 1.31 (t, 3H).

Step 4. 1-(tert-Butyl) 3-ethyl 3-(((benzyloxy)carbonyl)amino)azetidine-1,3-dicarboxylate. A mixture of 1-(tert-butyl) 3-ethyl 3-aminoazetidine-1,3-dicarboxylate (1.89 g, 7.72 mmol) and benzyl chloroformate (1.76 mL, 12.4 mmol) in saturated aqueous $NaHCO_3$ (40 mL) and dioxane (40 mL) was stirred vigorously under $N_2$ for 4 days. The reaction mixture was diluted with EtOAc (250 mL), washed with saturated aqueous $NaHCO_3$ (200 mL) and brine (200 mL), dried over $Na_2SO_4$, decanted, and concentrated. The residue was purified by flash chromatography (EtOAc/Hexanes) to afford the title compound as a colorless oil (2.49 g) that partially solidified. $^1H$ NMR (500 MHz, $CDCl_3$) δ ppm 7.29-7.41 (m, 5H), 5.58 (br. s, 1H), 5.13 (s, 2H), 4.22-4.39 (m, 4H), 4.07-4.22 (m, 2H), 1.45 (s, 9H), 1.23-1.34 (m, 3H).

Step 5. tert-Butyl 3-(((benzyloxy)carbonyl)amino)-3-(hydroxymethyl)azetidine-1-carboxylate. $LiAlH(Ot\text{-}Bu)_3$ (1.0M in THF, 15.3 mL) was added dropwise to a solution of 1-(tert-butyl) 3-ethyl 3-(((benzyloxy)carbonyl)amino) azetidine-1,3-dicarboxylate (2.31 g, 6.11 mmol) in dry THF at rt under $N_2$, and the mixture was stirred for 22 h. The reaction mixture was diluted with EtOAc (250 mL), washed with 1M HCl (2×150 mL) and brine (150 mL), dried over $Na_2SO_4$, filtered and concentrated to dryness to afford the title compound (1.89 g) as a white solid. $^1H$ NMR (500 MHz, $CDCl_3$) δ ppm 7.31-7.40 (m, 5H), 5.34 (br. s, 1H), 5.09 (s, 2H), 3.93-4.02 (m, 2H), 3.82-3.92 (m, 4H), 2.63 (br. s, 1H), 1.43 (s, 9H).

Step 6. tert-Butyl 3-(((benzyloxy)carbonyl)amino)-3-(((methylsulfonyl)oxy)methyl)azetidine-1-carboxylate. To a solution of tert-butyl 3-(((benzyloxy)carbonyl)amino)-3-(hydroxymethyl)azetidine-1-carboxylate (1.94 g, 5.8 mmol) in dry DCM (50 mL) was added $Et_3N$ (1.2 mL, 8.6 mmol) and methanesulfonyl chloride (0.53 mL, 6.8 mmol). The mixture was stirred at rt under $N_2$ for 3 h, poured into sat. aq. $NaHCO_3$ (100 mL) and extracted with DCM (2×100 mL). The extracts were dried over $Na_2SO_4$, filtered and concentrated to dryness to afford the title compound (2.36 g) as a light orange foam. $^1H$ NMR (500 MHz, $CDCl_3$) δ ppm 7.29-7.44 (m, 5H), 5.41 (br s, 1H), 5.10 (s, 2H), 4.50 (s, 2H), 3.88-4.00 (m, 4H), 2.95 (s, 3H), 1.43 (s, 9H).

Step 7. tert-Butyl 3-(((benzyloxy)carbonyl)amino)-3-((4-cyano-3-fluorophenoxy)methyl)azetidine-1-carboxylate. A mixture of tert-butyl 3-(((benzyloxy)carbonyl)amino)-3-(((methylsulfonyl)oxy)methyl)azetidine-1-carboxylate (2.36 g, 5.7 mmol), 2-fluoro-4-hydroxybenzonitrile (936 mg, 6.8 mmol), and $K_2CO_3$ (1.59 g, 11.5 mmol) in dry $CH_3CN$ (50 mL) was stirred at reflux under $N_2$ for 16 h. The reaction mixture was cooled, diluted with EtOAc (250 mL), washed with 2M $K_2CO_3$ (4×150 mL) and brine (150 mL), dried over $Na_2SO_4$, decanted, and concentrated. The residue was purified by flash chromatography (EtOAc/Hexanes) to afford the title compound (1.81 g) as a foam. $^1H$ NMR (500 MHz, $CDCl_3$) δ ppm 7.51 (dd, 1H), 7.29-7.39 (m, 5H), 6.66-6.81 (m, 2H), 5.30 (br. s, 1H), 5.08 (s, 2H), 4.29 (m, 2H), 3.95-4.08 (m, 4H), 1.44 (s, 9H).

Step 8. Benzyl (3-((4-cyano-3-fluorophenoxy)methyl) azetidin-3-yl)carbamate trifluoroacetate salt. A mixture of tert-butyl 3-(((benzyloxy)carbonyl)amino)-3-((4-cyano-3-fluorophenoxy)methyl)azetidine-1-carboxylate (1.81 g, 3.97 mmol) and TFA (10 mL) in dry DCM (40 mL) was stirred at rt under $N_2$ for 2 h. The reaction mixture was concentrated to dryness to afford the crude title compound as a foam (2.21 g).

Step 9. Benzyl (3-((4-cyano-3-fluorophenoxy)methyl)-1-((2,4-dichlorophenyl)sulfonyl)azetidin-3-yl)carbamate. A mixture of benzyl (3-((4-cyano-3-fluorophenoxy)methyl)azetidin-3-yl)carbamate trifluoroacetate (2.21 g, 3.97 mmol), $Et_3N$ (1.70 mL, 12.2 mmol), and 2,4-dichlorobenzenesulfonyl chloride (1.17 g, 4.77 mmol) in dry DCM (40 mL) was stirred at rt under $N_2$ for 18 h. The reaction mixture was poured into saturated aqueous $NaHCO_3$ (100 mL) and extracted with DCM (2×100 mL). The extracts were dried over $Na_2SO_4$, decanted, and concentrated, and the residue was purified by flash chromatography (EtOAc/Hexanes) to afford the title compound (2.07 g) as a foam. $^1H$ NMR (500 MHz, $CDCl_3$) δ ppm 7.97 (d, 1H), 7.56 (d, 1H), 7.52 (dd, 1H), 7.38 (dd, 1H), 7.28-7.36 (m, 5H), 6.65-6.78 (m, 2H), 5.26 (br s, 1H), 5.07 (s, 2H), 4.30 (br s, 2H), 4.24 (d, 2H), 4.11 (d, 2H).

Step 10. 4-((3-Amino-1-((2,4-dichlorophenyl)sulfonyl)azetidin-3-yl)methoxy)-2-fluorobenzonitrile hydrochloride salt. A mixture of benzyl (3-((4-cyano-3-fluorophenoxy)methyl)-1-((2,4-dichlorophenyl)sulfonyl)azetidin-3-yl)carbamate (883 mg, 1.56 mmol) and TFA (12 mL) was stirred at 50° C. for 7 h. The reaction mixture was concentrated, taken up in DCM, poured into saturated aqueous $NaHCO_3$ (100 mL) and extracted with DCM (3×75 mL). The extracts were dried over $Na_2SO_4$, decanted, and concentrated, and the residue was purified by flash chromatography twice ($DCM/CH_3OH/NH_4OH$ and $Hexanes/EtOAc/CH_3OH$). The pure product was treated with 4M HCl in dioxane, concentrated, and triturated with $CH_3OH/Et_2O$. The precipitate was collected by vacuum filtration to afford the title compound (216 mg) as a white solid. $^1H$ NMR (500 MHz, DMSO-$d_6$) δ ppm 9.05 (br s, 3H), 7.93-8.01 (m, 2H), 7.87 (t, 1H), 7.65 (dd, 1H), 7.12 (dd, 1H), 6.96 (dd, 1H), 4.43 (s, 2H), 4.23 (d, 2H), 4.04 (d, 2H). LCMS $[M+H]^+$ 430.0, 432.0.

Example 53—Compound 53

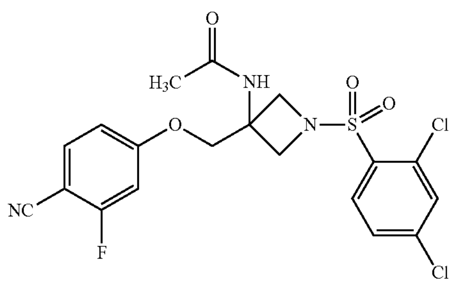 [SMILES: CC(=O)NC1(COc2ccc(C#N)c(F)c2)CN(S(=O)(=O)c2ccc(Cl)cc2Cl)C1]

N-(3-((4-Cyano-3-fluorophenoxy)methyl)-1-((2,4-dichlorophenyl)sulfonyl)azetidin-3-yl)acetamide was prepared as follows. Neat triethylamine (10 μL, 0.072 mmol) and acetyl chloride (0.33 mL, 0.1 M in DCM) were added to a suspension of 4-((3-amino-1-((2,4-dichlorophenyl)sulfonyl)azetidin-3-yl)methoxy)-2-fluorobenzonitrile hydrochloride (10.4 mg, 0.022 mmol) in dry DCM (0.5 mL), and the mixture was stirred at rt for 24 h. Additional triethylamine (40 μL, 0.287 mmol) and acetyl chloride (16 μL, 0.225 mmol) were added and stirring continued for another 18 h. The mixture was quenched with $CH_3OH$ (0.5 mL), diluted with DCM (5 mL), dry-loaded onto celite, and purified by flash chromatography (EtOAc/Hexanes) to give the title compound (7.2 mg) as a light yellow solid. $^1H$ NMR (500 MHz, $CDCl_3$) δ ppm 7.97 (d, 1H), 7.51-7.58 (m, 2H), 7.39

(dd, 1H), 6.75 (dd, 1H), 6.70 (dd, 1H), 5.90 (s, 1H), 4.34 (s, 2H), 4.20 (d, 2H), 4.14 (d, 2H), 2.00 (s, 3H). LCMS $[M+H]^+$ 472.0, 474.1.

Example 54—Compound 54

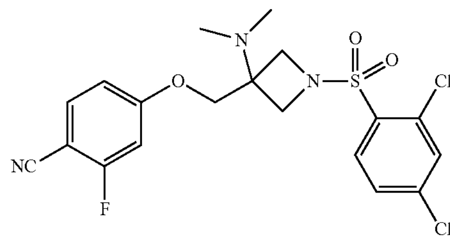 [SMILES: CN(C)C1(COc2ccc(C#N)c(F)c2)CN(S(=O)(=O)c2ccc(Cl)cc2Cl)C1]

4-((1-((2,4-Dichlorophenyl)sulfonyl)-3-(dimethylamino)azetidin-3-yl)methoxy)-2-fluorobenzonitrile was prepared as follows. A mixture of 4-((3-amino-1-((2,4-dichlorophenyl)sulfonyl)azetidin-3-yl)methoxy)-2-fluorobenzonitrile hydrochloride (10.8 mg, 0.023 mmol) and formaldehyde (37% aq., 1.9 μL, 0.03 mmol) in dry THF (0.25 mL) was stirred at rt for 15 min. $NaBH(OAc)_3$ (21 mg, 0.1 mmol) was added, and the mixture was stirred at rt for 23 h. The reaction mixture was quenched with sat. aq. $NaHCO_3$ (1 mL) and extracted with EtOAc (2×1 mL). The extracts were dried over $Na_2SO_4$, decanted, and concentrated in vacuo. The residue was purified by flash chromatography ($Hexanes/EtOAc/CH_3OH$) to give the title compound (5.1 mg) as a white solid (~80% purity). $^1H$ NMR (500 MHz, $CDCl_3$) δ ppm 7.97 (d, 1H), 7.52-7.58 (m, 2H), 7.38 (dd, 1H), 6.79 (dd, 1H), 6.74 (dd, 1H), 4.24 (s, 2H), 4.03 (d, 2H), 3.91 (d, 2H), 2.31 (s, 6H). LCMS $[M+H]^+$ 458.1, 460.1.

Example 55—Compound 55

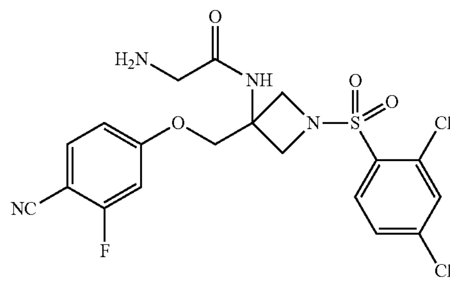 [SMILES: N#Cc1ccc(OCC2(NC(=O)CN)CN(S(=O)(=O)c3ccc(Cl)cc3Cl)C2)cc1F]

2-Amino-N-(3-((4-cyano-3-fluorophenoxy)methyl)-1-((2,4-dichlorophenyl)sulfonyl)azetidin-3-yl)acetamide was prepared according to Scheme 22:

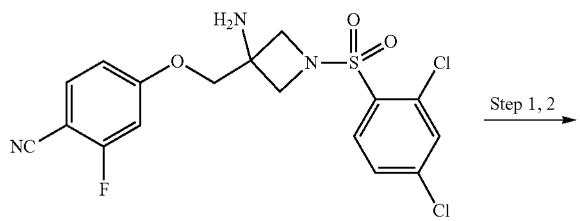

-continued

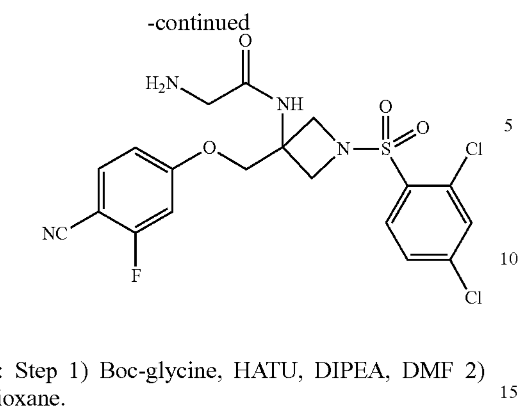

Reagents: Step 1) Boc-glycine, HATU, DIPEA, DMF 2) HCl in dioxane.

Step 1. tert-Butyl (2-((3-((4-cyano-3-fluorophenoxy)methyl)-1-((2,4-dichlorophenyl)sulfonyl)azetidin-3-yl)amino)-2-oxoethyl)carbamate. A mixture of 4-((3-amino-1-((2,4-dichlorophenyl)sulfonyl)azetidin-3-yl)methoxy)-2-fluorobenzonitrile hydrochloride (25 mg, 0.053 mmol), Boc-glycine (12 mg, 0.067 mmol), HATU (24 mg, 0.063 mmol), and DIPEA (28 μL, 0.16 mmol) in dry DMF (0.4 mL) was stirred at rt for 17 h. The reaction mixture was diluted with EtOAc (10 mL), washed with saturated aqueous $NaHCO_3$ (2×7 mL) and brine (7 mL), dried over $Na_2SO_4$, decanted and concentrated. The residue was purified by flash chromatography (EtOAc/Hexanes) to afford the title compound.

Step 2. 2-Amino-N-(3-((4-cyano-3-fluorophenoxy)methyl)-1-((2,4-dichlorophenyl)sulfonyl)azetidin-3-yl)acetamide. A mixture of tert-butyl (2-((3-((4-cyano-3-fluorophenoxy)methyl)-1-((2,4-dichlorophenyl)sulfonyl)azetidin-3-yl)amino)-2-oxoethyl)carbamate (0.053 mmol) and 4.0 M HCl in dioxane (1.0 mL) was stirred at rt for 18 hr concentrated to dryness. The residue was purified by flash chromatography ($DCM/CH_3OH/NH_4OH$) to afford the title compound (9.8 mg) as a white solid. $^1H$ NMR (500 MHz, $CDCl_3$) δ ppm 7.93-8.01 (m, 2H), 7.49-7.59 (m, 2H), 7.39 (dd, 1H), 6.67-6.78 (m, 2H), 4.34 (s, 2H), 4.27 (d, 2H), 4.18 (d, 2H), 3.30-3.39 (m, 2H). LCMS $[M+H]^+$ 487.1, 489.0.

Example 56—Compound 56

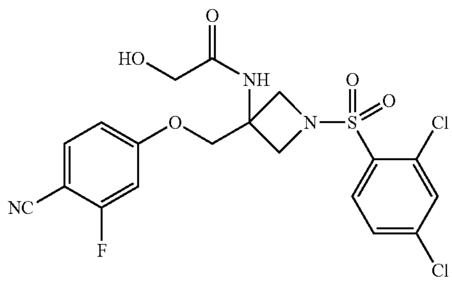 [SMILES: N#Cc1ccc(OCC2(NC(=O)CO)CN(S(=O)(=O)c3ccc(Cl)cc3Cl)C2)cc1F]

N-(3-((4-Cyano-3-fluorophenoxy)methyl)-1-((2,4-dichlorophenyl)sulfonyl)azetidin-3-yl)-2-hydroxyacetamide was prepared in a similar fashion as in Scheme 22 from 4-((3-amino-1-((2,4-dichlorophenyl)sulfonyl)azetidin-3-yl)methoxy)-2-fluorobenzonitrile hydrochloride and glycolic acid. $^1H$ NMR (500 MHz, $CDCl_3$) δ ppm 7.97 (d, 1H), 7.57 (d, 1H), 7.54 (dd, 1H), 7.39 (dd, 1H), 7.03 (s, 1H), 6.76 (dd, 1H), 6.71 (dd, 1H), 4.36 (s, 2H), 4.28 (d, 2H), 4.19 (d, 2H), 4.13 (s, 2H), 2.81 (s, 1H). LCMS $[M+H]^+$ 488.1, 490.1.

Example 57—Compound 57

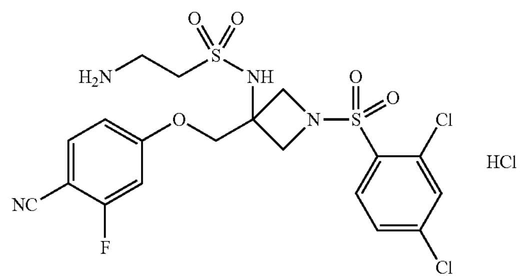 [SMILES: N#Cc1ccc(OCC2(NS(=O)(=O)CCN)CN(S(=O)(=O)c3ccc(Cl)cc3Cl)C2)cc1F ; Cl]

2-Amino-N-(3-((4-cyano-3-fluorophenoxy)methyl)-1-((2,4-dichlorophenyl)sulfonyl)azetidin-3-yl)ethane-1-sulfonamide hydrochloride was prepared in a similar fashion as in Scheme 13 from 4-((3-amino-1-((2,4-dichlorophenyl)sulfonyl)azetidin-3-yl)methoxy)-2-fluorobenzonitrile hydrochloride and Boc-taurine chloride. $^1H$ NMR (500 MHz, DMSO-$d_6$) δ ppm 8.58 (s, 1H), 8.05 (br s, 3H), 7.94-7.99 (m, 2H), 7.86 (t, 1H), 7.67 (dd, 1H), 7.17 (dd, 1H), 6.97 (dd, 1H), 4.34 (s, 2H), 4.16 (d, 2H), 4.01 (d, 2H), 3.36-3.42 (m, 2H), 3.08-3.17 (m, 2H). LCMS $[M+H]^+$ 537.1, 538.9.

Example 58—Compound 58

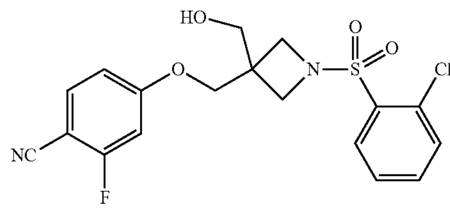 [SMILES: N#Cc1ccc(OCC2(CO)CN(S(=O)(=O)c3ccccc3Cl)C2)cc1F]

4-((1-((2-Chlorophenyl)sulfonyl)-3-(hydroxymethyl)azetidin-3-yl)methoxy)-2-fluorobenzonitrile was prepared according to Scheme 23:

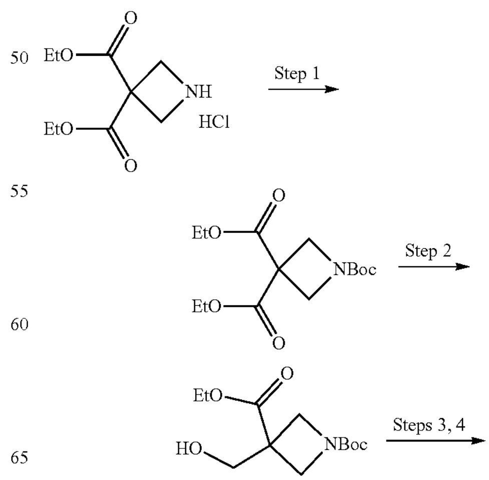

-continued

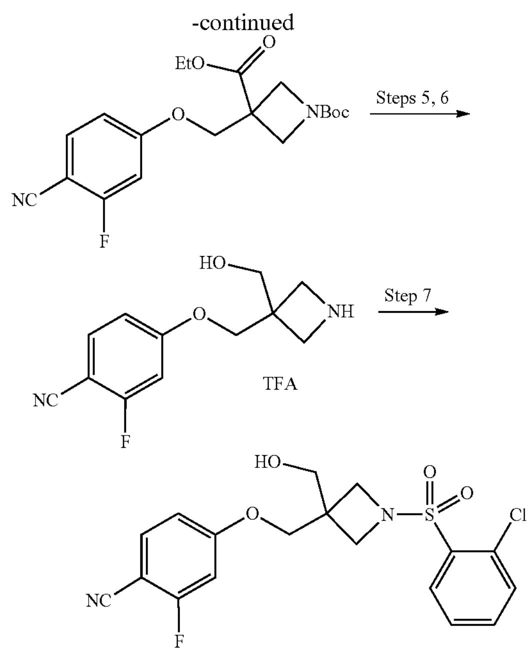

Reagents: Step 1) Di-tert-butyl dicarbonate, sat. aq. $NaHCO_3$, dioxane; 2) $LiAlH(Ot\text{-}Bu)_3$, THF; 3) methanesulfonyl chloride, $Et_3N$, DCM; 4) 2-fluoro-4-hydroxybenzonitrile, $K_2CO_3$, $CH_3CN$, A; 5) $LiAlH(Ot\text{-}Bu)_3$, THF; 6) TFA, DCM; 7) 2-chlorobenzenesulfonyl chloride, $Et_3N$, DCM.

Step 1. 1-(tert-Butyl) 3,3-diethyl azetidine-1,3,3-tricarboxylate. A mixture of diethyl azetidine-3,3-dicarboxylate hydrochloride (3.46 g, 14.55 mmol), di-tert-butyl dicarbonate (4.7 mL, 20.5 mmol), sat. aq. $NaHCO_3$ (75 mL) and dioxane (75 mL) was stirred vigorously at rt for 18 h. The reaction mixture was diluted with sat. aq. $NaHCO_3$ (100 mL) and water and extracted with EtOAc (3×100 mL). The extracts were washed with brine (200 mL), dried over $Na_2SO_4$, filtered and concentrated to dryness. The residue was purified by flash chromatography on silica gel (Hexanes/EtOAc) to give the title compound (4.02 g) as a colorless oil. $^1H$ NMR (500 MHz, $CDCl_3$) δ ppm 4.23-4.29 (m, 8H), 1.44 (s, 9H), 1.28 (t, 6H).

Step 2. 1-(tert-Butyl) 3-ethyl 3-(hydroxymethyl)azetidine-1,3-dicarboxylate. $LiAlH(Ot\text{-}Bu)_3$ (1.0 M in THF, 27.5 mL) was added dropwise by addition funnel to a solution of 1-(tert-butyl) 3,3-diethyl azetidine-1,3,3-tricarboxylate (4.02 g, 13.3 mmol) in dry THF (120 mL) at 0° C. under $N_2$. The mixture was warmed to rt and stirred for 18 h. The reaction mixture was diluted with EtOAc (150 mL) and washed with 1 M HCl (200 mL). The aqueous layer was extracted with EtOAc (150 mL) and the combined organics were washed with brine (200 mL), dried over $Na_2SO_4$, filtered and concentrated to give the title compound (3.85 g) as a colorless oil. $^1H$ NMR (500 MHz, $CDCl_3$) δ ppm 4.26 (q, 2H), 4.15 (d, 2H), 3.95 (s, 2H), 3.81 (d, 2H), 1.45 (s, 9H), 1.32 (t, 3H).

Step 3. 1-(tert-Butyl) 3-ethyl 3-(((methylsulfonyl)oxy)methyl)azetidine-1,3-dicarboxylate. Methanesulfonyl chloride (0.17 mL, 2.2 mmol) was added dropwise to a solution of 1-(tert-butyl) 3-ethyl 3-(hydroxymethyl)azetidine-1,3-dicarboxylate (460 mg, 1.774 mmol) and $Et_3N$ (0.37 mL, 2.654 mmol) in dry DCM (12 mL), and the mixture was stirred at rt for 2.5 h. The reaction mixture was poured into sat. aq. $NaHCO_3$ (75 mL) and extracted with DCM (3×35 mL). The extracts were dried over $Na_2SO_4$, filtered and concentrated in vacuo to give the crude title compound (679 mg) as a colorless oil.

Step 4. 1-(tert-Butyl) 3-ethyl 3-((4-cyano-3-fluorophenoxy)methyl)azetidine-1,3-dicarboxylate. A mixture of crude 1-(tert-butyl) 3-ethyl 3-(((methylsulfonyl)oxy)methyl)azetidine-1,3-dicarboxylate (679 mg, 2.2 mmol), 2-fluoro-4-hydroxybenzonitrile (294 mg, 2.14 mmol), and $K_2CO_3$ (493 mg, 3.6 mmol) in dry DMF (10 mL) was stirred at 85° C. under $N_2$ for 18 h. The reaction mixture was cooled, diluted with $Et_2O$ (100 mL), washed with 2M $K_2CO_3$ (2×75 mL) and brine (75 mL), dried over $Na_2SO_4$, filtered and concentrated to dryness. The residue was purified by flash chromatography on silica gel (Hexanes/EtOAc) to give the title compound as a thick colorless oil (590 mg, 1.56 mmol). $^1H$ NMR (500 MHz, $CDCl_3$) δ ppm 7.54 (dd, 1H), 6.78 (dd, 1H), 6.74 (dd, 1H), 4.35 (s, 2H), 4.22-4.30 (m, 4H), 3.93 (d, 2H), 1.45 (s, 9H), 1.28 (t, 3H).

Step 5. tert-Butyl 3-((4-cyano-3-fluorophenoxy)methyl)-3-(hydroxymethyl)azetidine-1-carboxylate. A solution of $LiAlH(Ot\text{-}Bu)_3$ (1.0 M in THF, 4.4 mL) was added dropwise to a solution of 1-(tert-butyl) 3-ethyl 3-((4-cyano-3-fluorophenoxy)methyl)azetidine-1,3-dicarboxylate (590 mg, 1.56 mmol) in dry THF (12 mL) at 0° C. under $N_2$. The mixture was warmed to rt and stirred for 4 days. The reaction mixture was diluted with EtOAc (50 mL), washed with 1 M HCl (2×50 mL) and brine (50 mL), dried over $Na_2SO_4$, filtered and concentrated to dryness to give the title compound (523 mg) as a thick colorless oil. $^1H$ NMR (500 MHz, $CDCl_3$) δ ppm 7.54 (dd, 1H), 6.79 (dd, 1H), 6.75 (dd, 1H), 4.18 (s, 2H), 3.91 (s, 2H), 3.77-3.83 (m, 4H), 1.45 (s, 9H).

Step 6. 3-((4-Cyano-3-fluorophenoxy)methyl)-3-(hydroxymethyl)azetidin-1-ium trifluoroacetate salt. A mixture of tert-butyl 3-((4-cyano-3-fluorophenoxy)methyl)-3-(hydroxymethyl)azetidine-1-carboxylate (523 mg, 1.555 mmol) and TFA (1.5 mL) in dry DCM (15 mL) was stirred at rt under $N_2$ for 3 h. The reaction mixture was concentrated to dryness, concentrated again from DCE, toluene and $CH_3OH$, and finally $Et_2O$, to give the title compound (577 mg) as a thick colorless oil that slowly solidified.

Step 7. 4-((1-((2-Chlorophenyl)sulfonyl)-3-(hydroxymethyl)azetidin-3-yl)methoxy)-2-fluorobenzonitrile. 2-Chlorobenzenesulfonyl chloride (12.0 mg, 0.057 mmol) was added to a solution of 3-((4-cyano-3-fluorophenoxy)methyl)-3-(hydroxymethyl)azetidin-1-ium trifluoroacetate salt (19.6 mg, 0.056 mmol) and $Et_3N$ (31 μL, 0.222 mmol) in dry DCM (0.5 mL), and the mixture was stirred at rt for 6 h. The mixture was concentrated and purified by flash chromatography on silica gel (Hexanes/DCM/$CH_3CN$) to give the target compound (13.1 mg) as a colorless glass. $^1H$ NMR (500 MHz, $CDCl_3$) δ ppm 8.05 (dd, 1H), 7.49-7.59 (m, 3H), 7.38-7.44 (m, 1H), 6.75 (dd, 1H), 6.69 (dd, 1H), 4.16 (s, 2H), 3.97 (d, 2H), 3.93 (d, 2H), 3.90 (s, 2H), 1.72 (br s, 1H). LCMS $[M+H]^+$ 411, 413.

Example 59—Compound 59

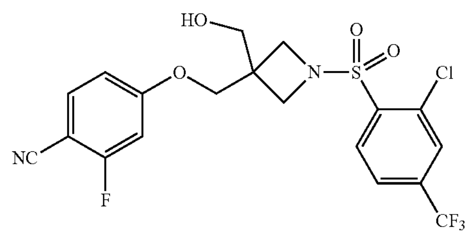 [SMILES: N#Cc1ccc(OCC2(CO)CN(S(=O)(=O)c3ccc(C(F)(F)F)cc3Cl)C2)cc1F]

4-((1-((2-Chloro-4-(trifluoromethyl)phenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 2-chloro-4-(trifluoromethyl)benzenesulfonyl chloride. $^1H$ NMR (500 MHz, $CDCl_3$) δ ppm 8.18 (d, 1H), 7.81 (d, 1H), 7.66 (dd, 1H), 7.54 (dd, 1H), 6.69-6.78 (m, 2H), 4.17 (s, 2H), 3.97-4.06 (m, 4H), 3.92 (s, 2H), 1.71 (br s, 1H). LCMS $[M+H]^+$ 479, 481.

Example 60—Compound 60

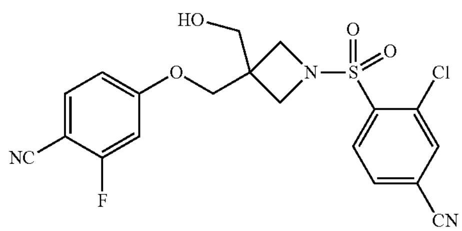 [SMILES: N#Cc1ccc(S(=O)(=O)N2CC(CO)(COc3ccc(C#N)c(F)c3)C2)c(Cl)c1]

4-((1-((2-Chloro-4-cyanophenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 2-chloro-4-cyanobenzenesulfonyl chloride. $^1H$ NMR (500 MHz, $CDCl_3$) δ ppm 8.16 (d, 1H), 7.83 (d, 1H), 7.69 (dd, 1H), 7.55 (dd, 1H), 6.79 (dd, 1H), 6.74 (dd, 1H), 4.18 (s, 2H), 4.05 (d, 2H), 4.01 (d, 2H), 3.91 (s, 2H), 1.70 (br. s, 1H). LCMS $[M+H]^+$ 436.

Example 61—Compound 61

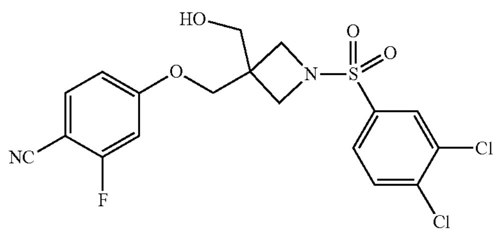 [SMILES: N#Cc1ccc(OCC2(CO)CN(S(=O)(=O)c3ccc(Cl)c(Cl)c3)C2)cc1F]

4-((1-((3,4-Dichlorophenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 3,4-dichlorobenzenesulfonyl chloride. $^1H$ NMR (500 MHz, $CDCl_3$) δ ppm 7.93-7.97 (m, 1H), 7.65-7.72 (m, 2H), 7.48-7.55 (m, 1H), 6.55-6.63 (m, 2H), 4.04 (s, 2H), 3.79 (s, 2H), 3.72-3.78 (m, 4H), 1.70 (br s, 1H). LCMS $[M+H]^+$ 445, 447.

Example 62—Compound 62

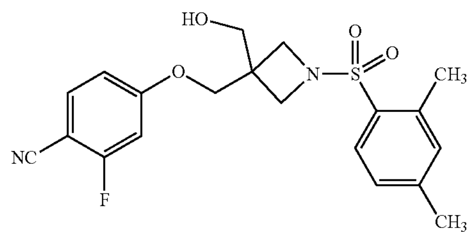 [SMILES: Cc1ccc(S(=O)(=O)N2CC(CO)(COc3ccc(C#N)c(F)c3)C2)c(C)c1]

4-((1-((2,4-Dimethylphenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 2,4-dimethylbenzenesulfonyl chloride. $^1H$ NMR (500 MHz, $CDCl_3$) δ ppm 7.82 (d, 1H), 7.51 (dd, 1H), 7.10-7.17 (m, 2H), 6.72 (dd, 1H), 6.64 (dd, 1H), 4.11 (s, 2H), 3.88 (d, 2H), 3.77 (d, 2H), 3.73 (d, 2H), 2.61 (s, 3H), 2.39 (s, 3H), 1.69 (t, 1H). LCMS $[M+H]^+$ 405.

Example 63—Compound 63

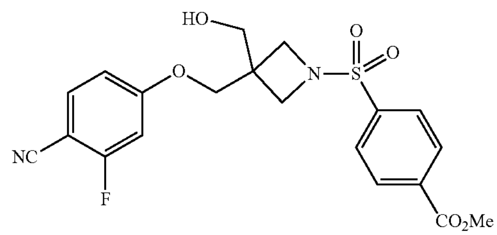 [SMILES: COC(=O)c1ccc(S(=O)(=O)N2CC(CO)(COc3ccc(C#N)c(F)c3)C2)cc1]

Methyl 4-((3-((4-cyano-3-fluorophenoxy)methyl)-3-(hydroxymethyl)azetidin-1-yl)sulfonyl)benzoate was prepared in a similar fashion as in Scheme 23 from 3-((4-cyano-3-fluorophenoxy)methyl)-3-(hydroxymethyl)azetidin-1-ium trifluoroacetate salt and methyl 4-(chlorosulfonyl)benzoate. $^1H$ NMR (500 MHz, $CDCl_3$) δ ppm 8.25 (d, 2H), 7.93 (d, 2H), 7.48 (dd, 1H), 6.58 (dd, 1H), 6.48 (dd, 1H), 3.99 (s, 3H), 3.98 (s, 2H), 3.68-3.77 (m, 6H), 1.61 (t, 1H). LCMS $[M+H]^+$ 435.

Example 64—Compound 64

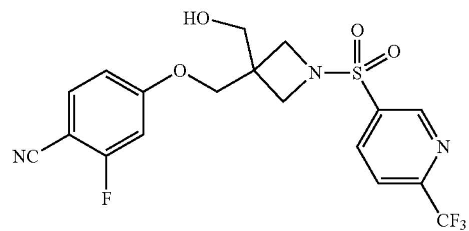 [SMILES: N#Cc1ccc(OCC2(CO)CN(S(=O)(=O)c3ccc(C(F)(F)F)nc3)C2)cc1F]

2-Fluoro-4-((3-(hydroxymethyl)-1-((6-(trifluoromethyl)pyridin-3-yl)sulfonyl)azetidin-3-yl)methoxy)benzonitrile was prepared in a similar fashion as in Scheme 23 from 3-((4-cyano-3-fluorophenoxy)methyl)-3-(hydroxymethyl)azetidin-1-ium trifluoroacetate salt and 6-(trifluoromethyl)

pyridine-3-sulfonyl chloride. $^1$H NMR (500 MHz, $CDCl_3$) δ ppm 9.18 (d, 1H), 8.34 (dd, 1H), 7.92 (d, 1H), 7.47-7.56 (m, 1H), 6.56-6.66 (m, 2H), 4.06 (s, 2H), 3.80-3.88 (m, 4H), 3.78 (d, 2H), 1.62 (t, 1H). LCMS $[M+H]^+$ 446.

Example 65—Compound 65

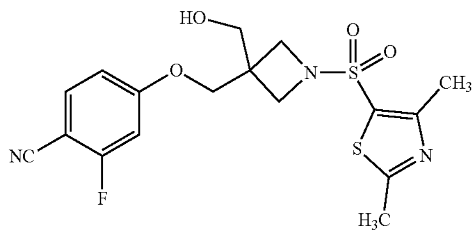 [SMILES: Cc1nc(C)c(S(=O)(=O)N2CC(CO)(COc3ccc(C#N)c(F)c3)C2)s1]

4-((1-((2,4-Dimethylthiazol-5-yl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 2,4-dimethylthiazole-5-sulfonyl chloride. $^1$H NMR (500 MHz, $CDCl_3$) δ ppm 7.53 (dd, 1H), 6.69 (dd, 1H), 6.63 (dd, 1H), 4.08 (s, 2H), 3.81-3.87 (m, 4H), 3.75-3.80 (m, 2H), 2.73 (s, 3H), 2.67 (s, 3H), 1.69 (t, 1H). LCMS $[M+H]^+$ 412.

Example 66—Compound 66

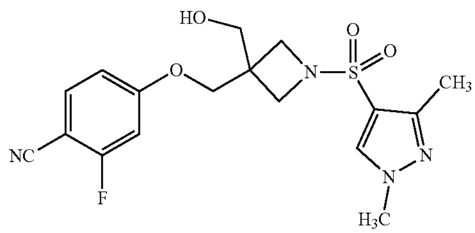 [SMILES: Cc1nn(C)cc1S(=O)(=O)N1CC(CO)(COc2ccc(C#N)c(F)c2)C1]

4-((1-((1,3-Dimethyl-1H-pyrazol-4-yl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 1,3-dimethyl-1H-pyrazole-4-sulfonyl chloride. $^1$H NMR (500 MHz, $CDCl_3$) δ ppm 7.76 (s, 1H), 7.53 (dd, 1H), 6.70 (dd, 1H), 6.65 (dd, 1H), 4.08 (s, 2H), 3.89 (s, 3H), 3.85 (s, 2H), 3.72 (d, 2H), 3.67 (d, 2H), 2.45 (s, 3H). LCMS $[M+H]^+$ 395.

Example 67—Compound 67

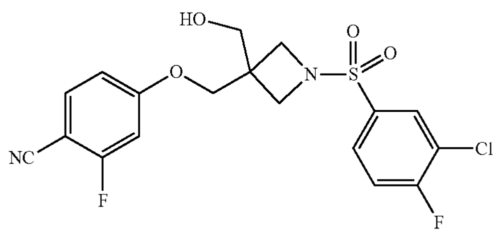

4-((1-((3-chloro-4-fluorophenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 3-chloro-4-fluorobenzenesulfonyl chloride. $^1$H NMR (500 MHz, $CDCl_3$) δ ppm 7.95 (dd, 1H), 7.74-7.80 (m, 1H), 7.52 (dd, 1H), 7.36 (t, 1H), 6.60-6.68 (m, 2H), 4.07 (s, 2H), 3.71-3.80 (m, 6H), 1.66 (t, 1H). LCMS $[M+H]^+$ 429, 431.

Example 68—Compound 68

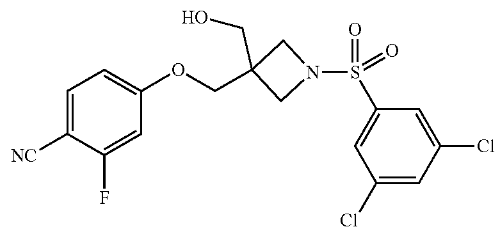 [SMILES: N#Cc1ccc(OCC2(CO)CN(S(=O)(=O)c3cc(Cl)cc(Cl)c3)C2)cc1F]

4-((1-((3,5-Dichlorophenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 3,5-dichlorobenzenesulfonyl chloride. $^1$H NMR (500 MHz, $CDCl_3$) δ ppm 7.74 (d, 2H), 7.63-7.66 (m, 1H), 7.53 (dd, 1H), 6.67 (dd, 1H), 6.62 (dd, 1H), 4.07 (s, 2H), 3.74-3.83 (m, 6H), 1.60 (t, 1H). LCMS $[M+H]^+$ 445, 447.

Example 69—Compound 69

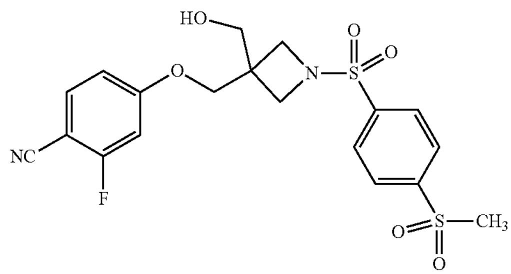 [SMILES: CS(=O)(=O)c1ccc(S(=O)(=O)N2CC(CO)(COc3ccc(C#N)c(F)c3)C2)cc1]

2-Fluoro-4-((3-(hydroxymethyl)-1-((4-(methylsulfonyl)phenyl)sulfonyl)azetidin-3-yl)methoxy)benzonitrile was prepared in a similar fashion as in Scheme 23 from 3-((4-cyano-3-fluorophenoxy)methyl)-3-(hydroxymethyl)azetidin-1-ium trifluoroacetate salt and 4-(methylsulfonyl)benzenesulfonyl chloride. $^1$H NMR (500 MHz, DMSO-$d_6$) δ ppm 8.19-8.25 (m, 2H), 8.06-8.11 (m, 2H), 7.69-7.75 (m, 1H), 6.97 (dd, 1H), 6.62 (dd, 1H), 4.98 (t, 1H), 3.94 (s, 2H), 3.64 (s, 4H), 3.37 (d, 2H), 3.32 (s, 3H). LCMS $[M+H]^+$ 455.

Example 70—Compound 70

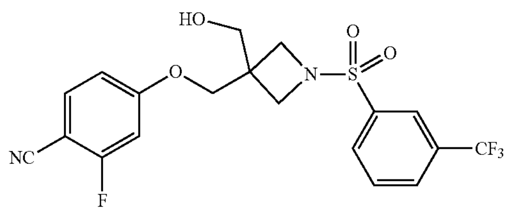 [SMILES: N#Cc1ccc(OCC2(CO)CN(S(=O)(=O)c3cccc(C(F)(F)F)c3)C2)cc1F]

2-Fluoro-4-((3-(hydroxymethyl)-1-((3-(trifluoromethyl) phenyl)sulfonyl)azetidin-3-yl)methoxy)benzonitrile was prepared in a similar fashion as in Scheme 23 from 3-((4-cyano-3-fluorophenoxy)methyl)-3-(hydroxymethyl)azetidin-1-ium trifluoroacetate salt and 3-(trifluoromethyl)benzenesulfonyl chloride. $^1H$ NMR (500 MHz, $CDCl_3$) δ ppm 8.14 (s, 1H), 8.07 (d, 1H), 7.94 (d, 1H), 7.76 (t, 1H), 7.51 (dd, 1H), 6.62 (dd, 1H), 6.56 (dd, 1H), 4.04 (s, 2H), 3.72-3.81 (m, 6H), 1.57 (t, 1H). LCMS $[M+H]^+$ 445.

Example 71—Compound 71

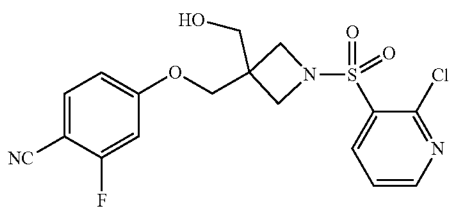 [SMILES: N#Cc1ccc(OCC2(CO)CN(S(=O)(=O)c3cccnc3Cl)C2)cc1F]

4-((1-((2-chloropyridin-3-yl)sulfonyl)-3-(hydroxymethyl) azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 2-chloropyridine-3-sulfonyl chloride. $^1H$ NMR (500 MHz, $CDCl_3$) δ ppm 8.58 (dd, 1H), 8.36 (dd, 1H), 7.54 (dd, 1H), 7.42 (dd, 1H), 6.78 (dd, 1H), 6.73 (dd, 1H), 4.18 (s, 2H), 4.06 (d, 2H), 4.02 (d, 2H), 3.93 (d, 2H), 1.76 (t, 1H). LCMS $[M+H]^+$ 453, 455.

Example 72—Compound 72

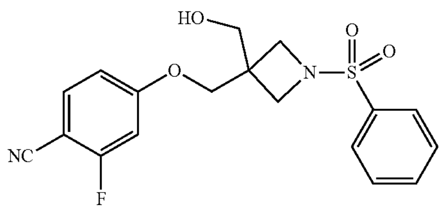 [SMILES: N#Cc1ccc(OCC2(CO)CN(S(=O)(=O)c3ccccc3)C2)cc1F]

2-Fluoro-4-((3-(hydroxymethyl)-1-(phenylsulfonyl)azetidin-3-yl)methoxy)benzonitrile was prepared in a similar fashion as in Scheme 23 from 3-((4-cyano-3-fluorophenoxy) methyl)-3-(hydroxymethyl)azetidin-1-ium trifluoroacetate salt and benzenesulfonyl chloride. $^1H$ NMR (500 MHz, $CDCl_3$) δ ppm 7.85-7.90 (m, 2H), 7.68-7.74 (m, 1H), 7.59-7.65 (m, 2H), 7.49 (dd, 1H), 6.59 (dd, 1H), 6.52 (dd, 1H), 3.97 (s, 2H), 3.71-3.77 (m, 4H), 3.66-3.71 (m, 2H), 1.58 (t, 1H). LCMS $[M+H]^+$ 377.

Example 73—Compound 73

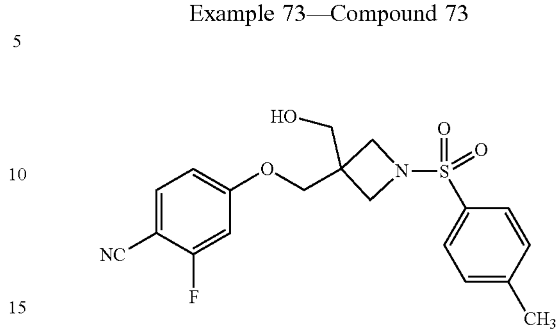

2-Fluoro-4-((3-(hydroxymethyl)-1-tosylazetidin-3-yl) methoxy)benzonitrile was prepared in a similar fashion as in Scheme 23 from 3-((4-cyano-3-fluorophenoxy)methyl)-3-(hydroxymethyl)azetidin-1-ium trifluoroacetate salt and 4-methyl-benzenesulfonyl chloride. $^1H$ NMR (500 MHz, $CDCl_3$) δ ppm 7.73-7.79 (m, 2H), 7.50 (dd, 1H), 7.41 (d, 2H), 6.59 (dd, 1H), 6.46 (dd, 1H), 3.95 (s, 2H), 3.77 (d, 2H), 3.71 (d, 2H), 3.66 (d, 2H), 2.50 (s, 3H), 1.57 (t, 1H). LCMS $[M+H]^+$ 391.

Example 74—Compound 74

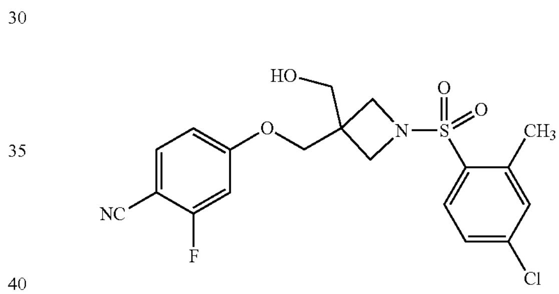

4-((1-((4-Chloro-2-methylphenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 2-methyl-4-chlorobenzenesulfonyl chloride. $^1H$ NMR (500 MHz, $CDCl_3$) δ ppm 7.89 (d, 1H), 7.54 (dd, 1H), 7.35 (d, 1H), 7.31 (dd, 1H), 6.73 (dd, 1H), 6.70 (dd, 1H), 4.14 (s, 2H), 3.90 (s, 2H), 3.80-3.84 (m, 2H), 3.75-3.79 (m, 2H), 2.63 (s, 3H), 1.67 (br s, 1H).

Example 75—Compound 75

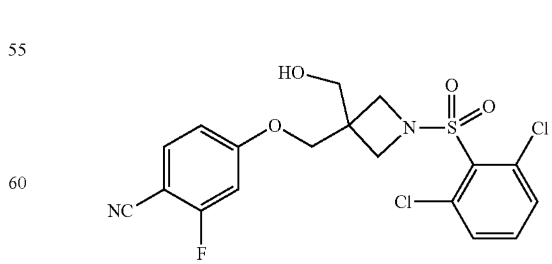

4-((1-((2,6-Dichlorophenyl)sulfonyl)-3-(hydroxymethyl) azetidin-3-yl)methoxy)-2-fluorobenzonitrile was prepared in a similar fashion as in Scheme 23 from 3-((4-cyano-3- fluorophenoxy)methyl)-3-(hydroxymethyl)azetidin-1-ium trifluoroacetate salt and 2,6-dichlorobenzenesulfonyl chloride. $^1$H NMR (500 MHz, $CDCl_3$) δ ppm 7.53 (dd, 1H), 7.48 (d, 2H), 7.32-7.38 (m, 1H), 6.77 (dd, 1H), 6.71 (dd, 1H), 4.18 (s, 2H), 4.04-4.09 (m, 2H), 3.99-4.03 (m, 2H), 3.93 (s, 2H), 1.71 (br s, 1H).

Example 76—Compound 76

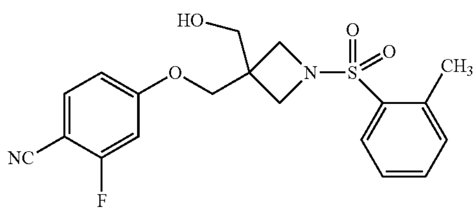 [SMILES: Cc1ccccc1S(=O)(=O)N1CC(CO)(COc2ccc(C#N)c(F)c2)C1]

2-Fluoro-4-((3-(hydroxymethyl)-1-(o-tolylsulfonyl)azetidin-3-yl)methoxy)benzonitrile was prepared in a similar fashion as in Scheme 23 from 3-((4-cyano-3-fluorophenoxy)methyl)-3-(hydroxymethyl)azetidin-1-ium trifluoroacetate salt and 2-methyl-benzenesulfonyl chloride. $^1$H NMR (500 MHz, $CDCl_3$) δ ppm 7.92-7.98 (m, 1H), 7.46-7.55 (m, 2H), 7.31-7.38 (m, 2H), 6.73 (dd, 1H), 6.68 (dd, 1H), 4.13 (s, 2H), 3.89 (s, 2H), 3.79-3.83 (m, 2H), 3.75-3.78 (m, 2H), 2.65 (s, 3H), 1.82 (br s, 1H).

Example 77—Compound 77

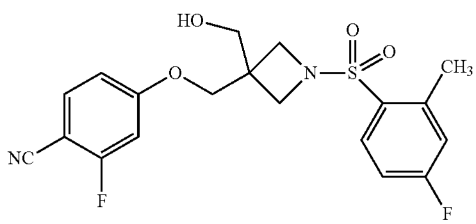 [SMILES: Cc1cc(F)ccc1S(=O)(=O)N1CC(CO)(COc2ccc(C#N)c(F)c2)C1]

2-Fluoro-4-((1-((4-fluoro-2-methylphenyl)sulfonyl)-3-(hydroxymethyl)azetidin-3-yl)methoxy)benzonitrile was prepared in a similar fashion as in Scheme 23 from 3-((4-cyano-3-fluorophenoxy)methyl)-3-(hydroxymethyl)azetidin-1-ium trifluoroacetate salt and 2-methyl-4-fluorobenzenesulfonyl chloride. $^1$H NMR (500 MHz, $CDCl_3$) δ ppm 7.97 (dd, 1H), 7.53 (dd, 1H), 6.97-7.08 (m, 2H), 6.75 (dd, 1H), 6.71 (dd, 1H), 4.16 (s, 2H), 3.90 (s, 2H), 3.79-3.84 (m, 2H), 3.74-3.79 (m, 2H), 2.65 (s, 3H), 1.62-1.73 (m, 1H).

Example 78—Compound 78

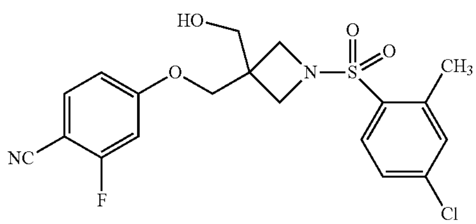 [SMILES: Cc1cc(Cl)ccc1S(=O)(=O)N1CC(CO)(COc2ccc(C#N)c(F)c2)C1]

4-((1-((4-Chloro-2-fluorophenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 2-fluoro-4-chlorobenzenesulfonyl chloride. $^1$H NMR (500 MHz, $CDCl_3$) δ ppm 7.79-7.86 (m, 1H), 7.52 (dd, 1H), 7.28-7.36 (m, 2H), 6.67 (dd, 1H), 6.63 (dd, 1H), 4.10 (s, 2H), 3.85-3.91 (m, 4H), 3.84 (s, 2H), 1.78 (br s, 1H).

Example 79—Compound 79

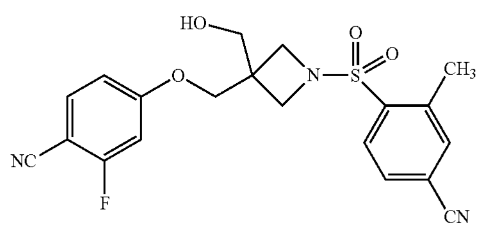 [SMILES: Cc1cc(C#N)ccc1S(=O)(=O)N1CC(CO)(COc2ccc(C#N)c(F)c2)C1]

4-((1-((4-Cyano-2-methylphenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 2-methyl-4-cyanobenzenesulfonyl chloride. $^1$H NMR (500 MHz, $CDCl_3$) δ ppm 8.06 (d, 1H), 7.59-7.66 (m, 2H), 7.49-7.57 (m, 1H), 6.77 (dd, 1H), 6.73 (dd, 1H), 4.17 (s, 2H), 3.87-3.94 (m, 4H), 3.82-3.87 (m, 2H), 2.68 (s, 3H), 1.84 (br s, 1H).

Example 80—Compound 80

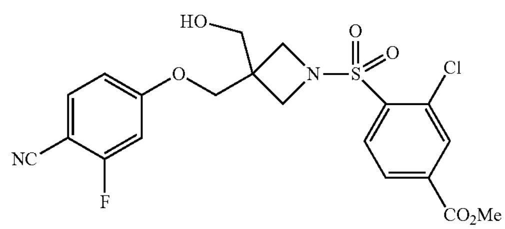 [SMILES: COC(=O)c1ccc(S(=O)(=O)N2CC(CO)(COc3ccc(C#N)c(F)c3)C2)c(Cl)c1]

Methyl 3-chloro-4-((3-((4-cyano-3-fluorophenoxy)methyl)-3-(hydroxymethyl)azetidin-1-yl)sulfonyl)benzoate was prepared in a similar fashion as in Scheme 23 from 3-((4-cyano-3-fluorophenoxy)methyl)-3-(hydroxymethyl)azetidin-1-ium trifluoroacetate salt and methyl 3-chloro-4-(chlorosulfonyl) benzoate. $^1$H NMR (500 MHz, $CDCl_3$) δ ppm 8.19 (d, 1H), 8.11 (d, 1H), 8.03 (dd, 1H), 7.52 (dd, 1H), 6.75 (dd, 1H), 6.69 (dd, 1H), 4.16 (s, 2H), 3.94-4.03 (m, 7H), 3.90 (s, 2H), 1.64-1.84 (m, 1H).

Example 81—Compound 81

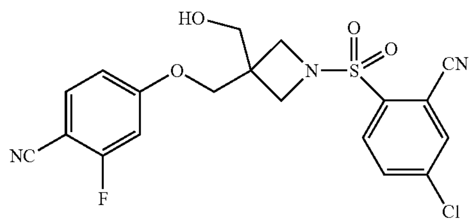 [SMILES: N#Cc1ccc(OCC2(CO)CN(S(=O)(=O)c3ccc(Cl)cc3C#N)C2)cc1F]

4-((1-((4-Chloro-2-cyanophenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 2-cyano-4-chloro-benzenesulfonyl chloride. $^1$H NMR (500 MHz, $CDCl_3$) δ ppm 8.01 (d, 1H), 7.85 (d, 1H), 7.71 (dd, 1H), 7.54 (dd, 1H), 6.76 (dd, 1H), 6.71 (dd, 1H), 4.17 (s, 2H), 3.96-4.05 (m, 4H), 3.90 (s, 2H), 1.67-1.76 (m, 1H). LC/MS/MS $[M-H]^-$ 479.8.

Example 82—Compound 82

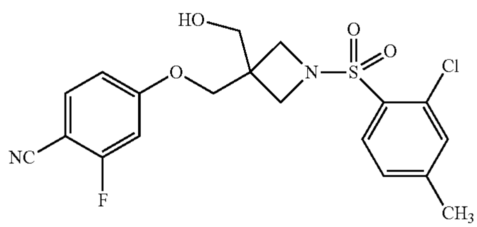 [SMILES: Cc1ccc(S(=O)(=O)N2CC(CO)(COc3ccc(C#N)c(F)c3)C2)c(Cl)c1]

4-((1-((2-Chloro-4-methylphenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 2-chloro-4-methylbenzenesulfonyl chloride. $^1$H NMR (500 MHz, $CDCl_3$) δ ppm 7.91 (d, 1H), 7.52 (t, 1H), 7.37 (s, 1H), 7.20 (d, 1H), 6.73 (dd, 1H), 6.65 (dd, 1H), 4.14 (s, 2H), 3.83-3.99 (m, 6H), 2.42 (s, 3H), 1.74 (br s, 1H).

Example 83—Compound 83

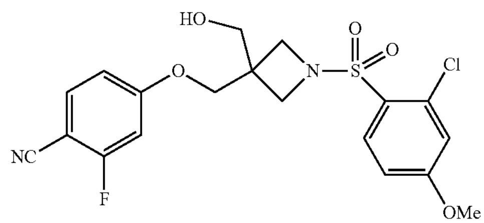 [SMILES: COc1ccc(S(=O)(=O)N2CC(CO)(COc3ccc(C#N)c(F)c3)C2)c(Cl)c1]

4-((1-((2-chloro-4-methoxyphenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 2-chloro-4-methoxybenzenesulfonyl chloride. $^1$H NMR (500 MHz, $CDCl_3$) δ ppm 7.96 (d, 1H), 7.52 (dd, 1H), 7.06 (d, 1H), 6.88 (dd, 1H), 6.74 (dd, 1H), 6.67 (dd, 1H), 4.14 (s, 2H), 3.82-3.94 (m, 9H), 1.81 (br s, 1H).

Example 84—Compound 84

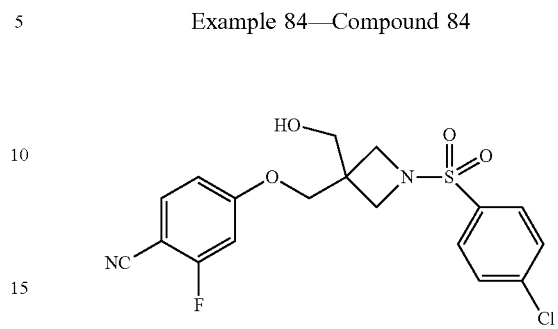

4-((1-((4-Chlorophenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 4-chlorobenzenesulfonyl chloride. $^1$H NMR (500 MHz, $CDCl_3$) δ ppm 7.79-7.84 (m, 2H), 7.57-7.62 (m, 2H), 7.51 (t, 1H), 6.53-6.61 (m, 2H), 3.99 (s, 2H), 3.77 (s, 2H), 3.66-3.75 (m, 4H), 1.66 (br s, 1H).

Example 85—Compound 85

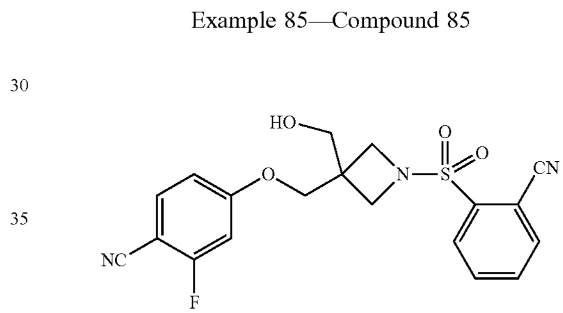

4-((1-((2-Cyanophenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 2-cyanobenzenesulfonyl chloride. $^1$H NMR (500 MHz, $CDCl_3$) δ ppm 8.09 (dd, 1H), 7.90 (dd, 1H), 7.69-7.80 (m, 2H), 7.53 (dd, 1H), 6.66-6.79 (m, 2H), 4.17 (s, 2H), 3.97-4.04 (m, 4H), 3.90 (d, 2H), 1.75 (t, 1H).

Example 86—Compound 86

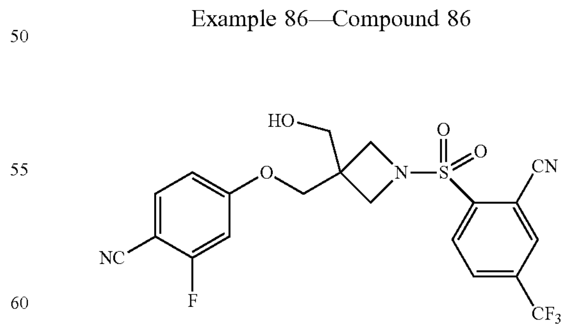

4-((1-((2-Cyano-4-(trifluoromethyl)phenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 2-cyano-4-trifluoromethylbenzenesulfonyl chloride. $^1H$ NMR (500 MHz, $CDCl_3$) δ ppm 8.23 (d, 1H), 8.13 (d, 1H), 7.98-8.02 (m, 1H), 7.53 (dd, 1H), 6.76 (dd, 1H), 6.71-6.74 (m, 1H), 4.18 (s, 2H), 4.02-4.10 (m, 4H), 3.91 (s, 2H), 1.84 (br s, 1H).

Example 87—Compound 87

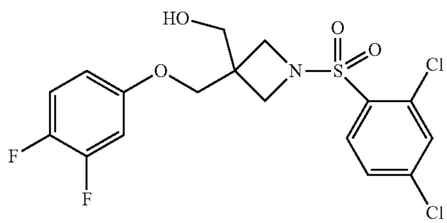 [SMILES: O=S(=O)(c1ccc(Cl)cc1Cl)N1CC(CO)(COc2ccc(F)c(F)c2)C1]

(1-((2,4-Dichlorophenyl)sulfonyl)-3-((3,4-difluorophenoxy)methyl)azetidin-3-yl)methanol was prepared according to Scheme 24:

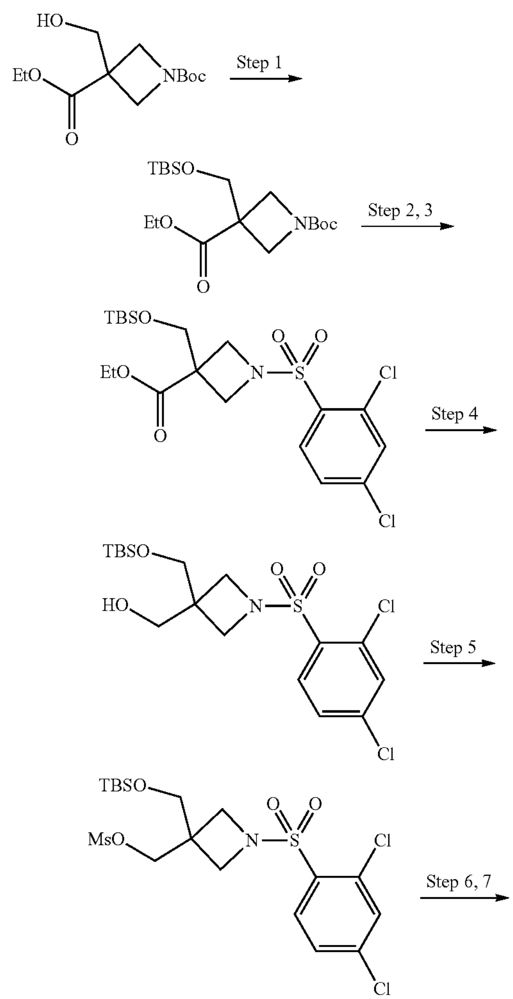

-continued

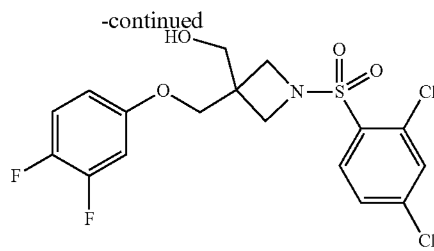

Reagents: Step 1) TBS-$C_1$, imidazole, DMF; 2) TFA, DCM; 3) 2,4-dichlorobenzenesulfonyl chloride, $Et_3N$, DCM; 4) $LiAlH(Ot-Bu)_3$, THF; 5) methanesulfonyl chloride, $Et_3N$, DCM; 6) 3,4-difluorophenol, $K_2CO_3$, DMF, 85° C.; 7) TBAF, THF.

Step 1. 1-(tert-Butyl) 3-ethyl 3-(((tert-butyldimethylsilyl)oxy)methyl)azetidine-1,3-dicarboxylate. A mixture of 1-(tert-butyl) 3-ethyl 3-(hydroxymethyl)azetidine-1,3-dicarboxylate (3.85 g 13.3 mmol), tert-butyldimethylsilyl chloride (2.48 g, 16.46 mmol), and imidazole (1.84 g, 27.1 mmol) in dry DMF (50 mL) was stirred at rt under $N_2$ for 20 h. More tert-butyldimethylsilyl chloride (1.38 g, 9.17 mmol) and imidazole (0.95 g, 14 mmol) were added and stirring continued for 3 days. The reaction mixture was diluted with EtOAc (300 mL), washed with 1M HCl (2×150 mL) and brine (150 mL), dried over $Na_2SO_4$, filtered and concentrated to dryness. The residue was purified by flash chromatography on silica gel (Hexanes/EtOAc) to give the title compound (4.84 g) as a colorless oil. $^1H$ NMR (500 MHz, $CDCl_3$) δ ppm 4.20 (q, 2H), 4.10 (d, 2H), 3.88 (s, 2H), 3.83 (d, 2H), 1.43 (s, 9H), 1.28 (t, 3H), 0.87 (s, 9H), 0.05 (s, 6H).

Step 2. Ethyl 3-(((tert-butyldimethylsilyl)oxy)methyl)azetidine-3-carboxylate trifluoroacetate salt. A mixture of 1-(tert-butyl) 3-ethyl 3-(((tert-butyldimethylsilyl)oxy)methyl)azetidine-1,3-dicarboxylate (832 mg, 2.00 mmol) and TFA (2.0 mL) in dry DCM (20 mL) was stirred at rt under $N_2$ for 2 h. The reaction mixture was concentrated to dryness, concentrated from toluene twice and $Et_2O$ once to give the title compound (840 mg), which was carried-on crude.

Step 3. Ethyl 3-(((tert-butyldimethylsilyl)oxy)methyl)-1-((2,4-dichlorophenyl)sulfonyl)azetidine-3-carboxylate. 2,4-dichlorobenzenesulfonyl chloride (467 mg, 1.9 mmol) was added to a solution of ethyl 3-(((tert-butyldimethylsilyl)oxy)methyl)azetidine-3-carboxylate trifluoroacetate (840 mg, 2.00 mmol theoretical) and $Et_3N$ (0.70 mL, 5.02 mmol) in dry DCM (20 mL), and the mixture was stirred at rt under $N_2$ for 20 h. The reaction mixture was poured into sat. aq. $NaHCO_3$ (50 mL) and extracted with DCM (3×35 mL). The extracts were dried over $Na_2SO_4$, filtered and concentrated to dryness. The residue was purified by flash chromatography on silica gel (Hexanes/EtOAc) to give the desilylated by-product as a colorless oil (187 mg) and the title compound (617 mg) as a colorless oil. $^1H$ NMR (500 MHz, $CDCl_3$) δ ppm 7.96 (d, 1H), 7.54 (d, 1H), 7.36 (dd, 1H), 4.24 (d, 2H), 4.19 (q, 2H), 3.99 (d, 2H), 3.89 (s, 2H), 1.26 (t, 3H), 0.82-0.87 (m, 9H), 0.02-0.06 (m, 6H).

Step 4. (3-(((tert-Butyldimethylsilyl)oxy)methyl)-1-((2,4-dichlorophenyl)sulfonyl)azetidin-3-yl)methanol. A solution of $LiAlH(Ot-Bu)_3$ (1M in THF, 5 mL) was added dropwise to a solution of ethyl 3-(((tert-butyldimethylsilyl)oxy)methyl)-1-((2,4-dichlorophenyl)sulfonyl)azetidine-3-carboxylate (809 mg, 1.68 mmol) in dry THF (12 mL) at 0° C. under $N_2$. The mixture was warmed to rt and stirred for 20 h. Another portion of $LiAlH(Ot-Bu)_3$ (1M in THF, 1.7 mL) was added dropwise, and stirred for 22 h. The reaction mixture was diluted with EtOAc (100 mL), washed with 1M HCl (2×75 mL) and brine (75 mL), dried over $Na_2SO_4$, filtered and concentrated to give the title compound (720 mg) as a colorless oil. $^1$H NMR (500 MHz, $CDCl_3$) δ ppm 7.97 (d, 1H), 7.55 (d, 1H), 7.37 (dd, 1H), 3.74-3.83 (m, 8H), 0.85-0.90 (m, 9H), 0.05-0.09 (m, 6H).

Step 5. (3-(((tert-Butyldimethylsilyl)oxy)methyl)-1-((2,4-dichlorophenyl)sulfonyl)azetidin-3-yl)methyl methanesulfonate. Methanesulfonyl chloride (0.13 mL, 1.68 mmol) was added dropwise to a solution of (3-(((tert-butyldimethylsilyl)oxy)methyl)-1-((2,4-dichlorophenyl)sulfonyl)azetidin-3-yl)methanol (620 mg, 1.41 mmol) and $Et_3N$ (0.39 mL, 2.8 mmol) in dry DCM (12 mL), and the mixture was stirred at rt under $N_2$ for 2 h. The reaction mixture was concentrated to dryness and the residue was purified by flash chromatography on silica gel (Hexanes/EtOAc) to give the title compound (684 mg) as a colorless oil. $^1$H NMR (500 MHz, $CDCl_3$) δ ppm 7.96 (d, 1H), 7.56 (d, 1H), 7.38 (dd, 1H), 4.33 (s, 2H), 3.81-3.89 (m, 4H), 3.73 (s, 2H), 3.04 (s, 3H), 0.85-0.90 (m, 9H), 0.04-0.08 (m, 6H).

Step 6. 3-(((tert-Butyldimethylsilyl)oxy)methyl)-1-((2,4-dichlorophenyl)sulfonyl)-3-((3,4-difluorophenoxy)methyl)azetidine. A mixture of (3-(((tert-butyldimethylsilyl)oxy)methyl)-1-((2,4-dichlorophenyl)sulfonyl)azetidin-3-yl)methyl methanesulfonate (32.6 mg, 0.06 mmol), 3,4-difluorophenol (10.4 mg, 0.08 mmol), and $K_2CO_3$ (17.9 mg, 0.13 mmol) in dry DMF (0.5 mL) was stirred at 85° C. for 18 h. The reaction mixture was cooled, diluted with EtOAc (10 mL), washed with 2M $K_2CO_3$ (2×5 mL) and brine (2×5 mL), dried over $Na_2SO_4$, filtered and concentrated to dryness to give the crude title compound (31.8 mg).

Step 7. (1-((2,4-Dichlorophenyl)sulfonyl)-3-((3,4-difluorophenoxy)methyl)azetidin-3-yl)methanol. To solid 3-(((tert-butyldimethylsilyl)oxy)methyl)-1-((2,4-dichlorophenyl)sulfonyl)-3-((3,4-difluorophenoxy)methyl)azetidine (31.8 mg, 0.06 mmol) in dry THF (0.5 mL), was added TBAF (1M in THF, 0.175 mL) and the mixture stirred at rt for 20 h. The reaction mixture was diluted with EtOAc (10 mL), washed with sat. aq. $NaHCO_3$ (2×5 mL) and brine (2×5 mL), dried over $Na_2SO_4$, filtered and concentrated to dryness. The residue was purified by flash chromatography on silica gel (Hexanes/EtOAc) to give the title compound (18.4 mg) as a colorless oil. $^1$H NMR (500 MHz, $CDCl_3$) δ ppm 7.98 (d, 1H), 7.57 (d, 1H), 7.39 (dd, 1H), 7.03-7.11 (m, 1H), 6.66-6.72 (m, 1H), 6.54-6.59 (m, 1H), 4.05 (s, 2H), 3.91-3.97 (m, 4H), 3.90 (s, 2H), 1.65 (br. s, 1H). LCMS $[M+H]^+$ 438, 440.

Example 88—Compound 88

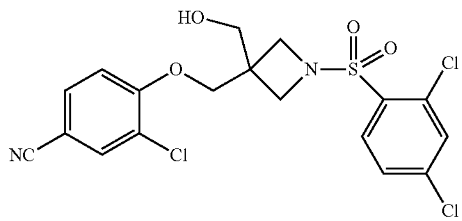 [SMILES: N#Cc1ccc(OCC2(CO)CN(S(=O)(=O)c3ccc(Cl)cc3Cl)C2)c(Cl)c1]

3-Chloro-4-((1-((2,4-dichlorophenyl)sulfonyl)-3-(hydroxymethyl)azetidin-3-yl)methoxy)benzonitrile was prepared in a similar fashion as in Scheme 24 from (3-(((tert-butyldimethylsilyl)oxy)methyl)-1-((2,4-dichlorophenyl)sulfonyl)azetidin-3-yl)methyl methanesulfonate and 3-chloro-4-hydroxybenzonitrile. $^1$H NMR (500 MHz, $CDCl_3$) δ ppm 7.98 (d, 1H), 7.66 (d, 1H), 7.53-7.59 (m, 2H), 7.36-7.41 (m, 1H), 7.00 (d, 1H), 4.26 (s, 2H), 3.92-4.03 (m, 6H), 1.79 (t, 1H). LCMS $[M+H]^+$ 461, 463.

Example 89—Compound 89

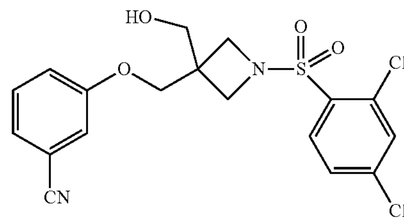 [SMILES: N#Cc1cccc(OCC2(CO)CN(S(=O)(=O)c3ccc(Cl)cc3Cl)C2)c1]

3-((1-((2,4-Dichlorophenyl)sulfonyl)-3-(hydroxymethyl)azetidin-3-yl)methoxy)benzonitrile was prepared in a similar fashion as in Scheme 24 from (3-(((tert-butyldimethylsilyl)oxy)methyl)-1-((2,4-dichlorophenyl)sulfonyl)azetidin-3-yl)methyl methanesulfonate and 3-cyanophenol. $^1$H NMR (500 MHz, $CDCl_3$) δ ppm 7.98 (d, 1H), 7.57 (d, 1H), 7.36-7.42 (m, 2H), 7.27-7.30 (m, 1H), 7.08-7.15 (m, 2H), 4.13 (s, 2H), 3.93-4.00 (m, 4H), 3.91 (s, 2H), 1.77 (br. s, 1H). LCMS $[M+H]^+$ 427, 429.

Example 90—Compound 90

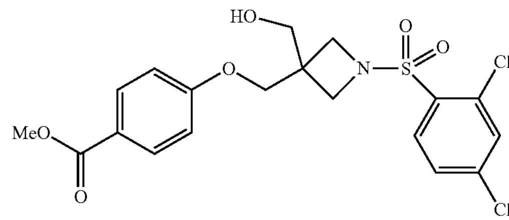 [SMILES: COC(=O)c1ccc(OCC2(CO)CN(S(=O)(=O)c3ccc(Cl)cc3Cl)C2)cc1]

Methyl 4-((1-((2,4-dichlorophenyl)sulfonyl)-3-(hydroxymethyl)azetidin-3-yl)methoxy)benzoate was prepared in a similar fashion as in Scheme 24 from (3-(((tert-butyldimethylsilyl)oxy)methyl)-1-((2,4-dichlorophenyl)sulfonyl)azetidin-3-yl)methyl methanesulfonate and methyl 4-hydroxybenzoate. $^1$H NMR (500 MHz, $CDCl_3$) δ ppm 7.97-8.01 (m, 3H), 7.57 (d, 1H), 7.39 (dd, 1H), 6.85-6.90 (m, 2H), 4.16 (s, 2H), 3.93-4.00 (m, 4H), 3.92 (s, 2H), 3.89 (s, 3H), 1.72 (br. s, 1H). LCMS $[M+H]^+$ 460, 462.

Example 91—Compound 91

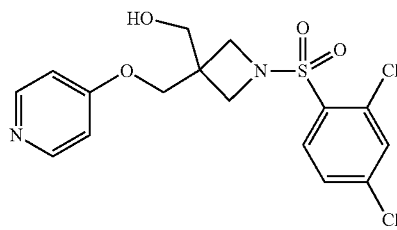 [SMILES: O=S(=O)(c1ccc(Cl)cc1Cl)N1CC(CO)(COc2ccncc2)C1]

(1-((2,4-Dichlorophenyl)sulfonyl)-3-((pyridin-4-yloxy)methyl)azetidin-3-yl)methanol was prepared in a similar fashion as in Scheme 24 from (3-(((tert-butyldimethylsilyl)oxy)methyl)-1-((2,4-dichlorophenyl)sulfonyl)azetidin-3-yl)methyl methanesulfonate and 4-hydroxypyridine. $^1$H NMR (500 MHz, $CDCl_3$) δ ppm 8.37 (d, 2H), 7.98 (d, 1H), 7.56 (d, 1H), 7.38 (dd, 1H), 6.71 (d, 2H), 4.12 (s, 2H), 3.92-3.98 (m, 4H), 3.90 (s, 2H). LCMS $[M+H]^+$ 403, 405.

Example 92—Compound 92

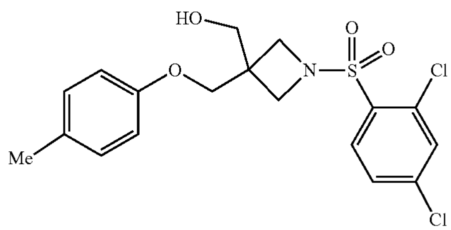 [SMILES: Cc1ccc(OCC2(CO)CN(S(=O)(=O)c3ccc(Cl)cc3Cl)C2)cc1]

(1-((2,4-Dichlorophenyl)sulfonyl)-3-((p-tolyloxy)methyl)azetidin-3-yl)methanol was prepared in a similar fashion as in Scheme 24 from (3-(((tert-butyldimethylsilyl)oxy)methyl)-1-((2,4-dichlorophenyl)sulfonyl)azetidin-3-yl)methyl methanesulfonate and p-cresol. $^1$H NMR (500 MHz, $CDCl_3$) δ ppm 7.98 (d, 1H), 7.56 (d, 1H), 7.38 (dd, 1H), 7.08 (d, 2H), 6.74 (d, 2H), 4.08 (s, 2H), 3.91-3.96 (m, 4H), 3.90 (s, 2H), 2.29 (s, 3H), 1.76 (br s, 1H). LCMS $[M+H]^+$ 416, 418.

Example 93—Compound 93

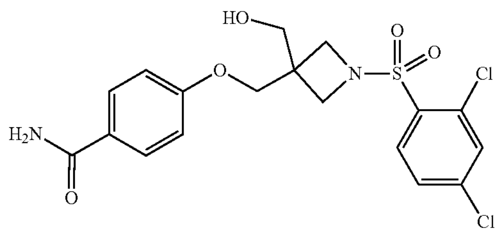 [SMILES: NC(=O)c1ccc(OCC2(CO)CN(S(=O)(=O)c3ccc(Cl)cc3Cl)C2)cc1]

4-((1-((2,4-Dichlorophenyl)sulfonyl)-3-(hydroxymethyl)azetidin-3-yl)methoxy)benzamide was prepared in a similar fashion as in Scheme 24 from (3-(((tert-butyldimethylsilyl)oxy)methyl)-1-((2,4-dichlorophenyl)sulfonyl)azetidin-3-yl)methyl methanesulfonate and 4-hydroxybenzamide. $^1$H NMR (500 MHz, DMSO-$d_6$) δ ppm 7.97 (d, 1H), 7.94 (d, 1H), 7.78-7.85 (m, 3H), 7.67 (dd, 1H), 7.14-7.18 (br s, 1H), 6.79-6.84 (m, 2H), 5.07-5.14 (m, 1H), 4.00 (s, 2H), 3.78-3.84 (m, 4H), 3.53-3.56 (m, 2H). LCMS $[M+H]^+$ 445, 447.

Example 94—Compound 94

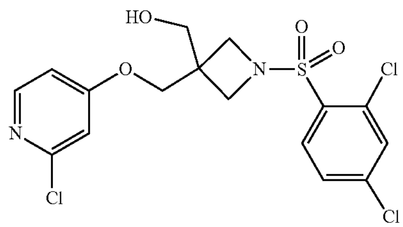 [SMILES: O=S(=O)(c1ccc(Cl)cc1Cl)N1CC(CO)(COc2ccnc(Cl)c2)C1]

(3-(((2-Chloropyridin-4-yl)oxy)methyl)-1-((2,4-dichlorophenyl)sulfonyl)azetidin-3-yl)methanol was prepared in a similar fashion as in Scheme 24 from (3-(((tert-butyldimethylsilyl)oxy)methyl)-1-((2,4-dichlorophenyl)sulfonyl)azetidin-3-yl)methyl methanesulfonate and 2-chloropyridin-4-ol. $^1$H NMR (500 MHz, $CDCl_3$) δ ppm 8.20 (d, 1H), 7.98 (d, 1H), 7.57 (d, 1H), 7.39 (dd, 1H), 6.82 (d, 1H), 6.72 (dd, 1H), 4.16 (s, 2H), 3.93-3.97 (m, 4H), 3.91 (d, 2H), 1.90-1.95 (m, 1H). LCMS $[M+H]^+$ 437, 439.

Example 95—Compound 95

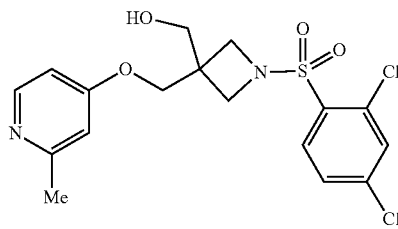 [SMILES: Cc1cc(OCC2(CO)CN(S(=O)(=O)c3ccc(Cl)cc3Cl)C2)ccn1]

(1-((2,4-Dichlorophenyl)sulfonyl)-3-(((2-methylpyridin-4-yl)oxy)methyl)azetidin-3-yl)methanol was prepared in a similar fashion as in Scheme 24 from (3-(((tert-butyldimethylsilyl)oxy)methyl)-1-((2,4-dichlorophenyl)sulfonyl)azetidin-3-yl)methyl methanesulfonate and 2-methylpyridin-4-ol. $^1$H NMR (500 MHz, $CDCl_3$) δ ppm 8.26 (d, 1H), 7.98 (d, 1H), 7.57 (d, 1H), 7.39 (dd, 1H), 6.56-6.64 (m, 2H), 4.13 (s, 2H), 3.91-3.97 (m, 4H), 3.90 (s, 2H), 2.52 (s, 3H). LCMS $[M+H]^+$ 417, 419.

Example 96—Compound 96

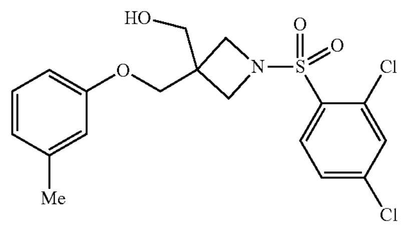 [SMILES: Cc1cccc(OCC2(CO)CN(S(=O)(=O)c3ccc(Cl)cc3Cl)C2)c1]

(1-((2,4-Dichlorophenyl)sulfonyl)-3-((m-tolyloxy)methyl)azetidin-3-yl)methanol was prepared in a similar fashion as in Scheme 24 from (3-(((tert-butyldimethylsilyl)oxy)methyl)-1-((2,4-dichlorophenyl)sulfonyl)azetidin-3-yl)methyl methanesulfonate and m-cresol. $^1$H NMR (500 MHz, $CDCl_3$) δ ppm 7.98 (d, 1H), 7.56 (d, 1H), 7.38 (dd, 1H), 7.17

(t, 1H), 6.80 (d, 1H), 6.62-6.68 (m, 2H), 4.08 (s, 2H), 3.92-3.97 (m, 4H), 3.91 (s, 2H), 2.33 (s, 3H), 1.83 (br. s, 1H). LCMS $[M+H]^+$ 416, 418.

Example 97—Compound 97

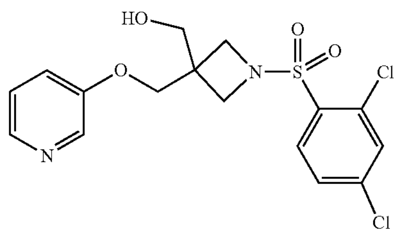 [SMILES: O=S(=O)(c1ccc(Cl)cc1Cl)N1CC(CO)(COc2cccnc2)C1]

(1-((2,4-Dichlorophenyl)sulfonyl)-3-((pyridin-3-yloxy)methyl)azetidin-3-yl)methanol was prepared in a similar fashion as in Scheme 24 from (3-(((tert-butyldimethylsilyl)oxy)methyl)-1-((2,4-dichlorophenyl)sulfonyl)azetidin-3-yl)methyl methanesulfonate and 3-hydroxypyridine. $^1$H NMR (500 MHz, $CDCl_3$) δ ppm 8.21-8.29 (m, 2H), 7.98 (d, 1H), 7.57 (d, 1H), 7.39 (dd, 1H), 7.21-7.24 (m, 1H), 7.15-7.18 (m, 1H), 4.16 (s, 2H), 3.94-3.99 (m, 4H), 3.93 (s, 2H), 1.94-2.37 (m, 1H). LCMS $[M+H]^+$ 403, 405.

Example 98—Compound 98

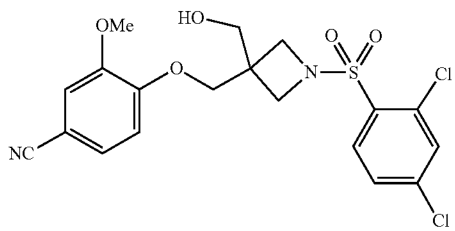 [SMILES: COc1cc(C#N)ccc1OCC1(CO)CN(S(=O)(=O)c2ccc(Cl)cc2Cl)C1]

4-((1-((2,4-Dichlorophenyl)sulfonyl)-3-(hydroxymethyl)azetidin-3-yl)methoxy)-3-methoxybenzonitrile was prepared in a similar fashion as in Scheme 24 from (3-(((tert-butyldimethylsilyl)oxy)methyl)-1-((2,4-dichlorophenyl)sulfonyl)azetidin-3-yl)methyl methanesulfonate and 4-hydroxy-3-methoxybenzonitrile. $^1$H NMR (500 MHz, $CDCl_3$) δ ppm 7.97 (d, 1H), 7.55 (d, 1H), 7.37 (dd, 1H), 7.23-7.29 (m, 1H), 7.08 (d, 1H), 6.92 (d, 1H), 4.23 (s, 2H), 3.90-4.00 (m, 6H), 3.84 (s, 3H).

Example 99—Compound 99

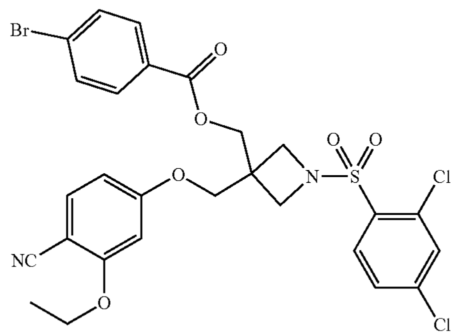 [SMILES: CCOc1cc(OCC2(COC(=O)c3ccc(Br)cc3)CN(S(=O)(=O)c3ccc(Cl)cc3Cl)C2)ccc1C#N]

(3-((4-Cyano-3-ethoxyphenoxy)methyl)-1-((2,4-dichlorophenyl)sulfonyl)azetidin-3-yl)methyl 4-bromobenzoate was prepared according to Scheme 25:

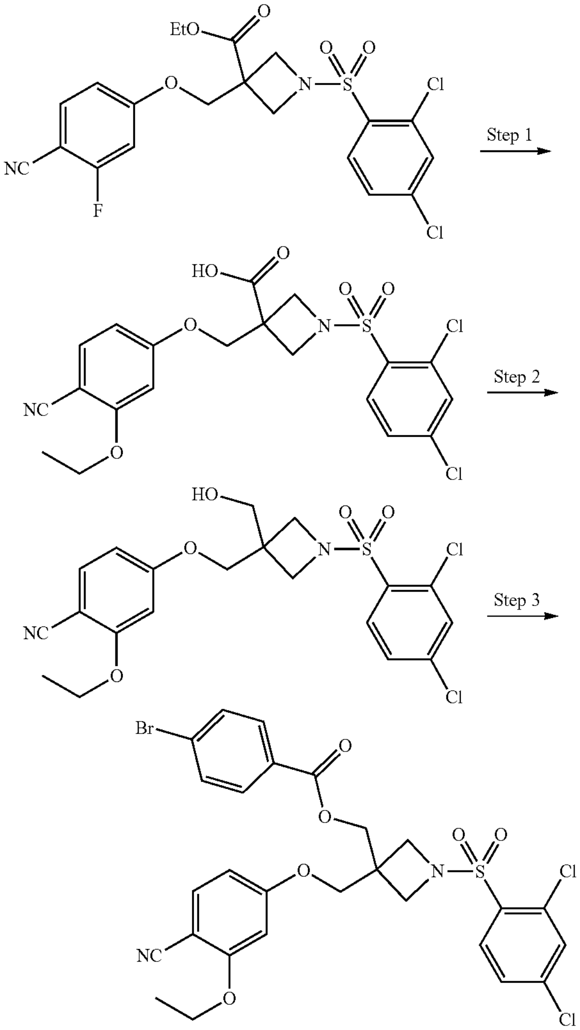

Reagents: Step 1) 4 M aq. NaOH, THF, EtOH; 2) $BH_3 \cdot SMe_2$, THF; 3) 4-Bromobenzoyl chloride, $Et_3N$, DCM.

Step 1. 3-((4-Cyano-3-ethoxyphenoxy)methyl)-1-((2,4-dichlorophenyl)sulfonyl)azetidine-3-carboxylic acid. Aqueous NaOH (4M, 10 mL) was added to a solution of ethyl 3-((4-cyano-3-fluorophenoxy)methyl)-1-((2,4-dichlorophenyl)sulfonyl)azetidine-3-carboxylate (1.96 g, 4.0 mmol) in THF (25 mL) and EtOH (25 mL), and the mixture was stirred at rt under $N_2$ for 16 h. The reaction mixture was concentrated in vacuo to remove most of the THF and EtOH, acidified with 1 M HCl (100 mL), diluted with water (100 mL), saturated with solid NaCl and extracted with DCM (3×150 mL). The extracts were dried over $Na_2SO_4$, filtered and concentrated in vacuo to give a mixture of 3-((4-cyano-3-fluorophenoxy)methyl)-1-((2,4-dichlorophenyl)sulfonyl)azetidine-3-carboxylic acid and the title compound (1.86 g).

Step 2. 4-((1-((2,4-Dichlorophenyl)sulfonyl)-3-(hydroxymethyl)azetidin-3-yl)methoxy)-2-ethoxybenzonitrile. A solution of $BH_3 \cdot SMe_2$ (0.3 mL, 3.16 mmol) was added dropwise to a mixture of 3-((4-cyano-3-fluorophenoxy)methyl)-1-((2,4-dichlorophenyl)sulfonyl)azetidine-3-carboxylic acid and 3-((4-cyano-3-ethoxyphenoxy)methyl)-1-((2,4-dichlorophenyl)sulfonyl)azetidine-3-carboxylic acid (941 mg, 2.0 mmol) in dry THF (20 mL) at 0° C. under $N_2$. The mixture was warmed to rt while stirring for 20 h. The reaction mixture was quenched with 4M NaOH (50 mL), poured into sat. aq. $NaHCO_3$ (200 mL) and extracted with EtOAc (2×350 mL). The organics were washed with brine (250 mL), dried over $Na_2SO_4$, filtered and concentrated in vacuo. The residue was purified by flash chromatography (Hexanes/EtOAc) to give a mixture of 4-((1-((2,4-dichlorophenyl)sulfonyl)-3-(hydroxymethyl)azetidin-3-yl)methoxy)-2-fluorobenzonitrile and the title compound (703 mg) as a thick colorless oil.

Step 3. (3-((4-Cyano-3-ethoxyphenoxy)methyl)-1-((2,4-dichlorophenyl)sulfonyl)azetidin-3-yl)methyl 4-bromobenzoate. Solid 4-bromobenzoyl chloride (1.15 g, 5.24 mmol) was added to a solution of a mixture of 4-((1-((2,4-dichlorophenyl)sulfonyl)-3-(hydroxymethyl)azetidin-3-yl)methoxy)-2-fluorobenzonitrile and 4-((1-((2,4-dichlorophenyl)sulfonyl)-3-(hydroxymethyl)azetidin-3-yl)methoxy)-2-ethoxybenzonitrile (1.94 g, 4.4 mmol) and $Et_3N$ (0.95 mL, 6.82 mmol) in dry DCM (45 mL) and the mixture was stirred at rt under $N_2$ for 4 h. The reaction mixture was concentrated in vacuo and the residue was purified by flash chromatography (Hexanes/EtOAc) to give the title compound (103 mg) as a white solid. $^1H$ NMR (500 MHz, $CDCl_3$) δ ppm 7.98 (d, 1H), 7.84-7.89 (m, 2H), 7.57-7.63 (m, 2H), 7.53 (d, 1H), 7.48 (d, 1H), 7.38 (dd, 1H), 6.40-6.50 (m, 2H), 4.56 (s, 2H), 4.19 (s, 2H), 4.03-4.14 (m, 6H), 1.48 (t, 3H).

Example 100—Compound 100

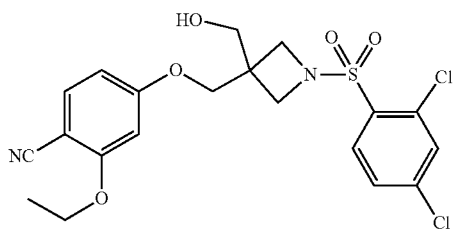 [SMILES: CCOc1cc(OCC2(CO)CN(S(=O)(=O)c3ccc(Cl)cc3Cl)C2)ccc1C#N]

4-((1-((2,4-Dichlorophenyl)sulfonyl)-3-(hydroxymethyl)azetidin-3-yl)methoxy)-2-ethoxybenzonitrile was prepared as follows. Aqueous NaOH (1M, 1.15 mL) was added to a solution of 4-((1-((2,4-dichlorophenyl)sulfonyl)-3-(hydroxymethyl)azetidin-3-yl)methoxy)-2-ethoxybenzonitrile (74.6 mg, 0.11 mmol) in THF (0.5 mL) and EtOH (0.5 mL), and the mixture was stirred at rt for 1 h. The reaction mixture was diluted with EtOAc (20 mL) and washed with sat. aq. $NaHCO_3$ (3×15 mL), dried over $Na_2SO_4$, filtered and concentrated in vacuo. The residue was purified by flash chromatography (Hexanes/EtOAc) to give the title compound (25.2 mg) as a white solid. $^1H$ NMR (500 MHz, $CDCl_3$) δ ppm 7.98 (d, 1H), 7.56 (d, 1H), 7.47 (d, 1H), 7.38 (dd, 1H), 6.47 (dd, 1H), 6.43 (d, 1H), 4.14 (s, 2H), 4.08-4.14 (m, 2H), 3.91-4.00 (m, 4H), 3.90 (s, 2H), 1.66-1.72 (m, 1H), 1.48 (t, 3H). LCMS $[M+H]^+$ 471, 472.

Example 101—Compound 101

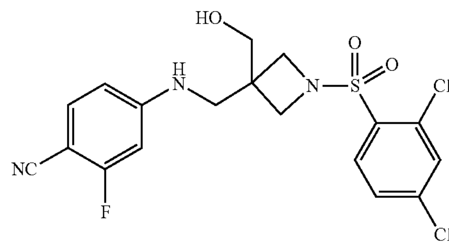 [SMILES: N#Cc1ccc(NCC2(CO)CN(S(=O)(=O)c3ccc(Cl)cc3Cl)C2)cc1F]

4-(((1-((2,4-dichlorophenyl)sulfonyl)-3-(hydroxymethyl)azetidin-3-yl)methyl)amino)-2-fluorobenzonitrile was prepared according to Scheme 26:

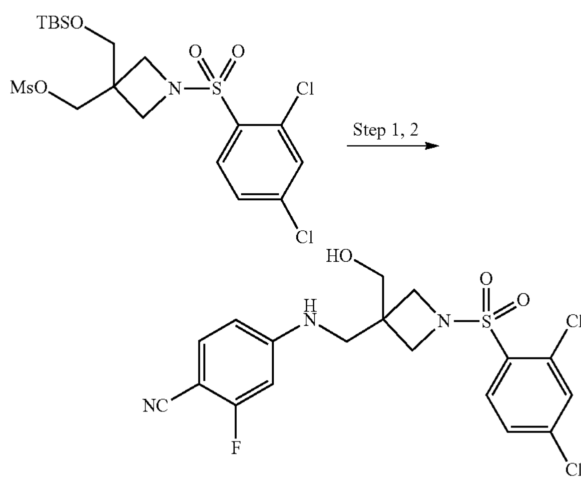

Reagents: Step 1) 4-amino-2-fluorobenzonitrile, LHMDS (1.0 M in THF), NaI, DMF, 70° C.; 2) TBAF, THF.

Step 1. 4-(((3-(((tert-Butyldimethylsilyl)oxy)methyl)-1-((2,4-dichlorophenyl)sulfonyl)azetidin-3-yl)methyl)amino)-2-fluorobenzonitrile. A solution of LHMDS (1.0 M in THF, 0.20 mL) was added to a mixture of 4-amino-2-fluorobenzonitrile (27.8 mg, 0.20 mmol) and NaI (5.6 mg, 0.037 mmol) in dry DMF (0.4 mL) at rt under $N_2$. After stirring for 15 min. a solution of (3-(((tert-butyldimethylsilyl)oxy)methyl)-1-((2,4-dichlorophenyl)sulfonyl)azetidin-3-yl)methyl methanesulfonate (51 mg, 0.10 mmol) in dry DMF (0.8 mL) was added dropwise, and the mixture was stirred at 70° C. for 22 h. The reaction mixture was cooled, diluted with EtOAc (10 mL), washed with sat. aq. $NaHCO_3$ (10 mL), brine (2×10 mL), dried over $Na_2SO_4$, filtered and concentrated in vacuo. The residue was purified by flash chromatography (EtOAc/Hexanes) to give the title compound (4.3 mg) as a yellow oil. $^1H$ NMR (500 MHz, $CDCl_3$) δ ppm 7.96 (d, 1H), 7.56 (d, 1H), 7.38 (dd, 1H), 7.32 (dd, 1H), 6.32 (dd, 1H), 6.28 (dd, 1H), 5.19 (t, 1H), 3.82-3.85 (m, 2H), 3.81 (s, 2H), 3.77-3.80 (m, 2H), 3.40 (d, 2H), 0.92 (s, 9H), 0.10 (s, 6H).

Step 2. 4-(((1-((2,4-Dichlorophenyl)sulfonyl)-3-(hydroxymethyl)azetidin-3-yl)methyl)amino)-2-fluorobenzonitrile. A solution of TBAF (1.0 M in THF, 40 μL) was added dropwise to a solution of 4-(((3-(((tert-butyldimethylsilyl)oxy)methyl)-1-((2,4-dichlorophenyl)sulfonyl)azetidin-3-yl)methyl)amino)-2-fluorobenzonitrile (4.3 mg, 0.01 mmol) in dry THF (0.5 mL), and the mixture was stirred at rt for 5 h. The reaction mixture was dry-loaded onto silica gel and purified by flash chromatography (EtOAc/Hexanes) to give the title compound (1.4 mg) as a yellow oil. $^1H$ NMR (500 MHz, $CDCl_3$) δ ppm 7.96 (d, 1H), 7.56 (d, 1H), 7.38 (dd, 1H), 7.33 (t, 1H), 6.37 (dd, 1H), 6.33 (dd, 1H), 5.11 (s, 1H), 3.88-3.94 (m, 4H), 3.82 (d, 2H), 3.44 (d, 2H), 3.35 (s, 1H). LCMS $[M+H]^+$ 443.9, 446.1.

Example 102—Compound 102

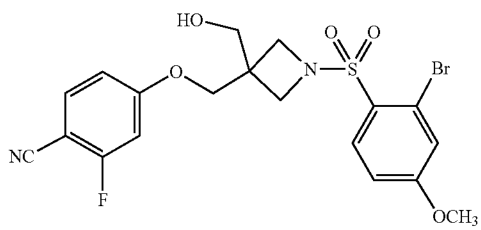 [SMILES: COc1ccc(S(=O)(=O)N2CC(CO)(COc3ccc(C#N)c(F)c3)C2)c(Br)c1]

4-((1-((2-Bromo-4-methoxyphenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 2-bromo-4-methoxybenzenesulfonyl chloride. $^1H$ NMR (500 MHz, $CDCl_3$) δ ppm 8.00 (d, 1H), 7.53 (dd, 1H), 7.28 (d, 1H), 6.92 (dd, 1H), 6.76 (dd, 1H), 6.70 (dd, 1H), 4.16 (s, 2H), 3.85-3.94 (m, 9H), 1.68 (br. s, 1H).

Example 103—Compound 103

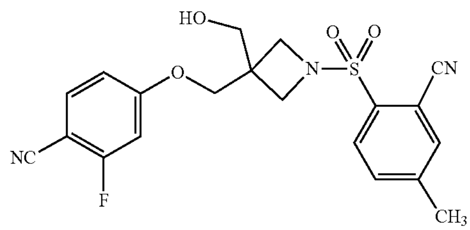 [SMILES: Cc1ccc(S(=O)(=O)N2CC(CO)(COc3ccc(C#N)c(F)c3)C2)c(C#N)c1]

4-((1-((2-Cyano-4-methylphenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 2-cyano-4-methylbenzenesulfonyl chloride. $^1H$ NMR (500 MHz, $CDCl_3$) δ ppm 7.96 (d, 1H), 7.70 (s, 1H), 7.49-7.57 (m, 2H), 6.75 (dd, 1H), 6.66 (dd, 1H), 4.16 (s, 2H), 3.92-4.01 (m, 4H), 3.89 (s, 2H), 2.50 (s, 3H), 1.76 (br. s., 1H).

Example 104—Compound 104

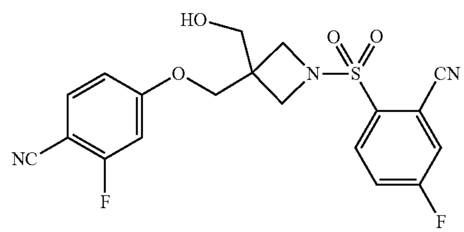 [SMILES: N#Cc1ccc(OCC2(CO)CN(S(=O)(=O)c3ccc(F)cc3C#N)C2)cc1F]

4-((1-((2-Cyano-4-fluorophenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 2-cyano-4-fluorobenzenesulfonyl chloride. $^1H$ NMR (500 MHz, $CDCl_3$) δ ppm 8.10 (dd, 1H), 7.59 (dd, 1H), 7.54 (dd, 1H), 7.41-7.46 (m, 1H), 6.78 (dd, 1H), 6.73 (dd, 1H), 4.18 (s, 2H), 3.97-4.04 (m, 4H), 3.90 (s, 2H), 1.75 (br. s, 1H).

Example 105—Compound 105

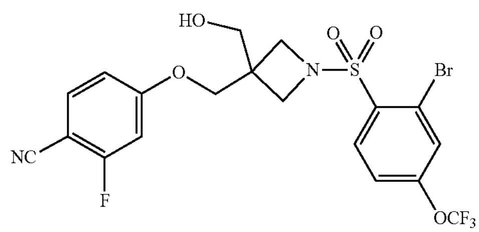 [SMILES: N#Cc1ccc(OCC2(CO)CN(S(=O)(=O)c3ccc(OC(F)(F)F)cc3Br)C2)cc1F]

4-((1-((2-Bromo-4-(trifluoromethoxy)phenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl) azetidin-1-ium trifluoroacetate salt and 2-bromo-4-trifluoromethoxybenzenesulfonyl chloride. $^1H$ NMR (500 MHz, $CDCl_3$) δ ppm 8.13 (d, 1H), 7.61 (d, 1H), 7.53 (dd, 1H), 7.26-7.32 (m, 1H), 6.77 (dd, 1H), 6.73 (dd, 1H), 4.18 (s, 2H), 3.94-4.02 (m, 4H), 3.92 (s, 2H), 1.74 (br. s., 1H).

Example 106—Compound 106

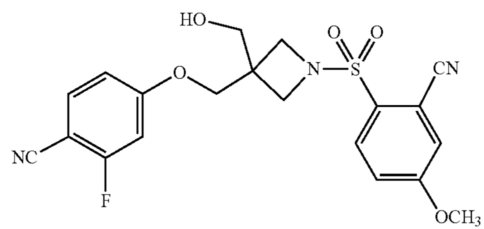 [SMILES: COc1ccc(S(=O)(=O)N2CC(CO)(COc3ccc(C#N)c(F)c3)C2)c(C#N)c1]

4-((1-((2-Cyano-4-methoxyphenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl)azetidin-1-ium trifluoroacetate salt and 2-cyano-4-methoxybenzenesulfonyl chloride. $^1H$ NMR (500 MHz, $CDCl_3$) δ ppm 7.99 (d, 1H), 7.52 (dd, 1H), 7.35 (d, 1H), 7.18 (dd, 1H), 6.75 (dd, 1H), 6.67 (dd, 1H), 4.16 (s, 2H), 3.90-3.99 (m, 7H), 3.89 (s, 2H), 1.82 (br. s, 1H).

Example 107—Compound 107

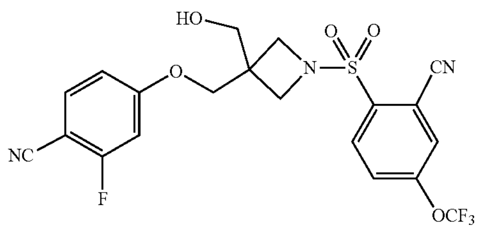 [SMILES: N#Cc1ccc(OCC2(CO)CN(S(=O)(=O)c3ccc(OC(F)(F)F)cc3C#N)C2)cc1F]

4-((1-((2-Cyano-4-trifluoromethoxyphenyl)sulfonyl)-3-(hydroxymethyl)azetidin-3-yl)methoxy)-2-fluorobenzonitrile was prepared in a similar fashion as in Scheme 23 from 3-((4-cyano-3-fluorophenoxy)methyl)-3-(hydroxymethyl) azetidin-1-ium trifluoroacetate salt and 2-cyano-4-trifluoromethoxybenzenesulfonyl chloride. $^1$H NMR (500 MHz, $CDCl_3$) δ ppm 8.14 (d, 1H), 7.70 (d, 1H), 7.50-7.59 (m, 2H), 6.77 (dd, 1H), 6.73 (dd, 1H), 4.19 (s, 2H), 3.99-4.08 (m, 4H), 3.91 (s, 2H), 1.74 (br. s., 1H).

Example 108—Compound 108

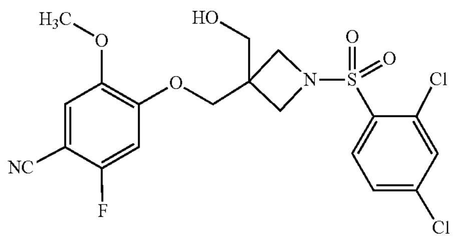 [SMILES: COc1cc(C#N)c(F)cc1OCC1(CO)CN(S(=O)(=O)c2ccc(Cl)cc2Cl)C1]

4-((1-((2,4-Dichlorophenyl)sulfonyl)-3-(hydroxymethyl) azetidin-3-yl)methoxy)-2-fluoro-5-methoxybenzonitrile was prepared in a similar fashion as in Scheme 23 from 3-((4-cyano-5-fluoro-2-methoxyphenoxy)methyl)-3-(hydroxymethyl)azetidin-1-ium trifluoroacetate salt and 2,4-dichlorobenzenesulfonyl chloride. $^1$H NMR (500 MHz, $CDCl_3$) δ ppm 7.97 (d, 1H), 7.55 (d, 1H), 7.37 (dd, 1H), 6.95 (d, 1H), 6.73 (d, 1H), 4.21 (s, 2H), 3.96-4.00 (m, 2H), 3.90-3.95 (m, 4H), 3.82 (s, 3H), 2.06-2.13 (m, 1H).

Example 109—Compound 109

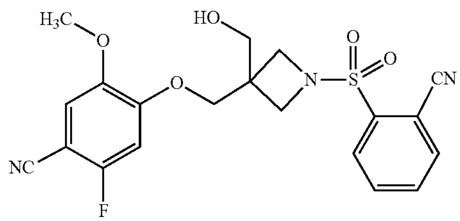 [SMILES: COc1cc(C#N)c(F)cc1OCC1(CO)CN(S(=O)(=O)c2ccccc2C#N)C1]

4-((1-((2-Cyanophenyl)sulfonyl)-3-(hydroxymethyl)azetidin-3-yl)methoxy)-2-fluoro-5-methoxybenzonitrile was prepared in a similar fashion as in Scheme 23 from 3-((4-cyano-5-fluoro-2-methoxyphenoxy)methyl)-3-(hydroxymethyl) azetidin-1-ium trifluoroacetate salt and 2-cyanobenzenesulfonyl chloride. $^1$H NMR (500 MHz, DMSO-$d_6$) δ ppm 8.15 (dd, 1H), 8.03 (dd, 1H), 7.91-7.96 (m, 1H), 7.86-7.91 (m, 1H), 7.39 (d, 1H), 7.19 (d, 1H), 4.97 (t, 1H), 4.08 (s, 2H), 3.80 (d, 2H), 3.75 (s, 3H), 3.72 (d, 2H), 3.40 (d, 2H).

Example 110—Compound 110

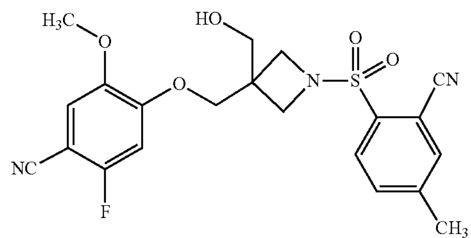 [SMILES: COc1cc(C#N)c(F)cc1OCC1(CO)CN(S(=O)(=O)c2ccc(C)cc2C#N)C1]

4-((1-((2-Cyano-4-methylphenyl)sulfonyl)-3-(hydroxymethyl)azetidin-3-yl)methoxy)-2-fluoro-5-methoxybenzonitrile was prepared in a similar fashion as in Scheme 23 from 3-((4-cyano-5-fluoro-2-methoxyphenoxy)methyl)-3-(hydroxymethyl)azetidin-1-ium trifluoroacetate salt and 2-cyano-4-methylbenzenesulfonyl chloride. $^1$H NMR (500 MHz, $CDCl_3$) δ ppm 7.95 (d, 1H), 7.68 (s, 1H), 7.50-7.55 (m, 1H), 6.94 (d, 1H), 6.72 (d, 1H), 4.22 (s, 2H), 3.97-4.01 (m, 2H), 3.93-3.97 (m, 2H), 3.90 (s, 2H), 3.82 (s, 3H), 2.48 (s, 3H), 2.08 (br. s., 1H).

Example 111—Compound 111

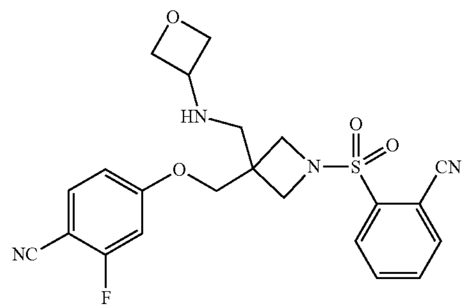 [SMILES: N#Cc1ccc(OCC2(CNC3COC3)CN(S(=O)(=O)c3ccccc3C#N)C2)cc1F]

4-((1-((2-Cyanophenyl)sulfonyl)-3-((oxetan-3-ylamino) methyl)azetidin-3-yl)methoxy)-2-fluorobenzonitrile was prepared in a similar fashion as in Scheme 14 from 4-((1-((2-cyanophenyl)sulfonyl)-3-(hydroxymethyl)azetidin-3-yl) methoxy)-2-fluorobenzonitrile and oxetan-3-amine. $^1$H NMR (500 MHz, $CDCl_3$) δ ppm 8.09 (dd, 1H), 7.90 (dd, 1H), 7.74 (m, 2H), 7.54 (dd, 1H), 6.76 (dd, 1H), 6.71 (dd, 1H), 4.80 (t, 2H), 4.37 (t, 2H), 4.16 (s, 2H), 3.98-4.03 (m, 2H), 3.88-3.96 (m, 3H), 2.91 (s, 2H). LCMS $[M+H]^+$ 456.9.

Example 112—Compound 112

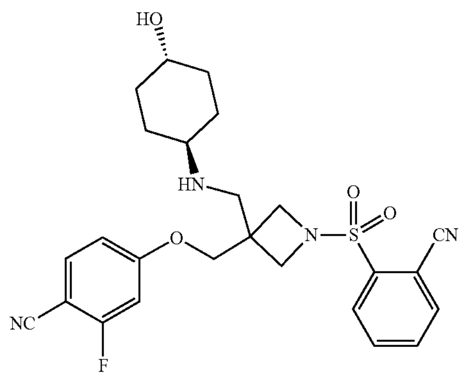 [SMILES: N#Cc1ccc(OCC2(CN[C@H]3CC[C@H](O)CC3)CN(S(=O)(=O)c3ccccc3C#N)C2)cc1F]

4-((1-((2-Cyanophenyl)sulfonyl)-3-(((trans-4-hydroxycyclohexyl)amino)methyl)azetidin-3-yl)methoxy)-2-fluorobenzonitrile was prepared in a similar fashion as in Scheme 14 from 4-((1-((2-cyanophenyl)sulfonyl)-3-(hydroxymethyl)azetidin-3-yl)methoxy)-2-fluorobenzonitrile and trans-4-aminocyclohexanol. $^1$H NMR (500 MHz, $CDCl_3$) δ ppm 8.08 (dd, 1H), 7.90 (dd, 1H), 7.69-7.79 (m, 2H), 7.52 (dd, 1H), 6.74 (dd, 1H), 6.69 (dd, 1H), 4.12 (s, 2H), 3.94-3.99 (m, 2H), 3.91 (d, 2H), 3.59 (tt, 1H), 2.90-2.96 (m, 2H), 2.38 (tt, 1H), 1.83-1.99 (m, 4H), 1.23-1.33 (m, 2H), 0.99-1.10 (m, 2H).

Example 113—Compound 113

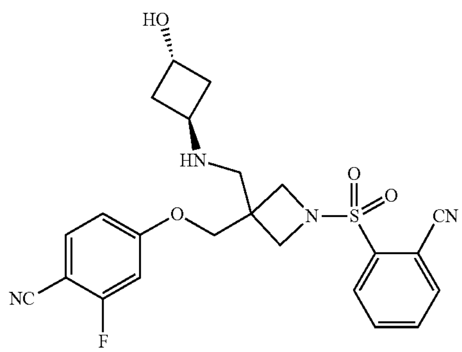 [SMILES: N#Cc1ccc(OCC2(CN[C@H]3C[C@H](O)C3)CN(S(=O)(=O)c3ccccc3C#N)C2)cc1F]

4-((1-((2-Cyanophenyl)sulfonyl)-3-(((trans-3-hydroxycyclobutyl)amino)methyl)azetidin-3-yl)methoxy)-2-fluorobenzonitrile was prepared in a similar fashion as in Scheme 14 from 4-((1-((2-cyanophenyl)sulfonyl)-3-(hydroxymethyl)azetidin-3-yl)methoxy)-2-fluorobenzonitrile and trans-3-aminocyclobutan-1-ol. $^1$H NMR (500 MHz, $CDCl_3$) δ ppm 8.08 (dd, 1H), 7.90 (dd, 1H), 7.69-7.80 (m, 2H), 7.53 (dd, 1H), 6.75 (dd, 1H), 6.69 (dd, 1H), 4.39-4.46 (m, 1H), 4.11-4.15 (m, 2H), 3.96-4.01 (m, 2H), 3.88-3.93 (m, 2H), 3.36-3.43 (m, 1H), 2.81 (s, 2H), 2.05-2.13 (m, 2H), 1.96-2.04 (m, 2H). LCMS $[M+H]^+$ 470.9.

Example 114—Compound 114

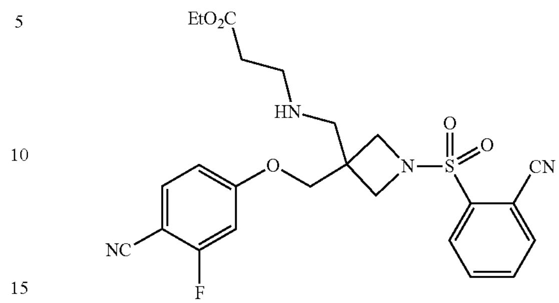

Ethyl 3-(((3-((4-cyano-3-fluorophenoxy)methyl)-1-((2-cyanophenyl)sulfonyl)azetidin-3-yl)methyl)amino)propanoate was prepared in a similar fashion as in Scheme 14 from 4-((1-((2-cyanophenyl)sulfonyl)-3-(hydroxymethyl)azetidin-3-yl)methoxy)-2-fluorobenzonitrile and ethyl 3-aminopropanoate. $^1$H NMR (500 MHz, $CDCl_3$) δ ppm 8.08 (dd, 1H), 7.90 (dd, 1H), 7.69-7.79 (m, 2H), 7.52 (dd, 1H), 6.75 (dd, 1H), 6.70 (dd, 1H), 4.08-4.15 (m, 4H), 3.95-4.00 (m, 2H), 3.89-3.94 (m, 2H), 2.93 (s, 2H), 2.86 (t, 2H), 2.44 (t, 2H), 1.21-1.25 (m, 3H). LCMS $[M+H]^+$ 501.1.

Example 115—Compound 115

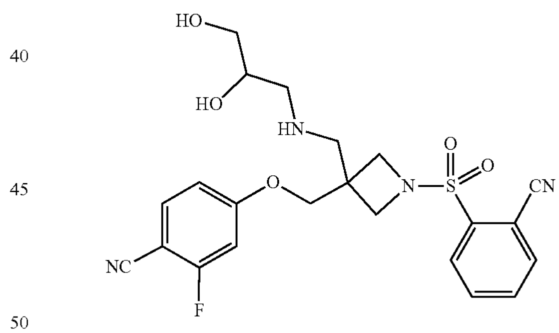

4-((1-((2-Cyanophenyl)sulfonyl)-3-(((2,3-dihydroxypropyl)amino)methyl)azetidin-3-yl)methoxy)-2-fluorobenzonitrile was prepared in a similar fashion as in Scheme 14 from 4-((1-((2-cyanophenyl)sulfonyl)-3-(hydroxymethyl)azetidin-3-yl)methoxy)-2-fluorobenzonitrile and 3-aminopropane-1,2-diol. $^1$H NMR (500 MHz, $CDCl_3$) δ ppm 8.05-8.11 (m, 1H), 7.90 (dd, 1H), 7.69-7.80 (m, 2H), 7.49-7.55 (m, 1H), 6.75 (dd, 1H), 6.70 (dd, 1H), 4.12-4.16 (m, 2H), 3.95-4.02 (m, 4H), 3.77 (m, 1H), 3.68-3.73 (m, 1H), 3.56 (dd, 1H), 2.92-3.03 (m, 2H), 2.78-2.84 (m, 1H), 2.73 (dd, 1H). LCMS $[M+H]^+$ 475.1.

Example 116—Compound 116

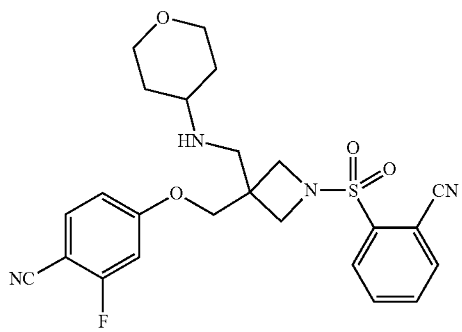 [SMILES: N#Cc1ccc(OCC2(CNC3CCOCC3)CN(S(=O)(=O)c3ccccc3C#N)C2)cc1F]

4-((1-((2-Cyanophenyl)sulfonyl)-3-(((tetrahydro-2H-pyran-4-yl)amino)methyl)azetidin-3-yl)methoxy)-2-fluorobenzonitrile was prepared in a similar fashion as in Scheme 14 from 4-((1-((2-cyanophenyl)sulfonyl)-3-(hydroxymethyl)azetidin-3-yl)methoxy)-2-fluorobenzonitrile and 4-aminotetrahydropyran. $^1$H NMR (500 MHz, $CDCl_3$) δ ppm 8.09 (dd, 1H), 7.90 (dd, 1H), 7.69-7.79 (m, 2H), 7.49-7.55 (m, 1H), 6.75 (dd, 1H), 6.69 (dd, 1H), 4.12-4.16 (m, 2H), 3.89-4.00 (m, 8H), 3.35 (m, 1H), 2.96 (s, 2H), 2.56-2.65 (m, 1H), 1.73-1.82 (m, 2H), 1.30 (dd, 2H). LCMS $[M+H]^+$ 484.5.

Example 117—Compound 117

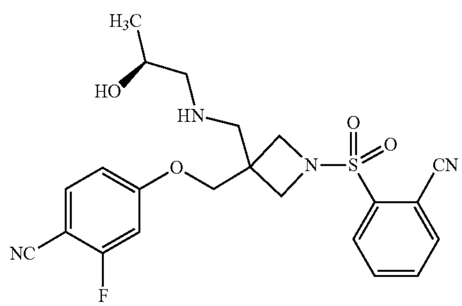 [SMILES: C[C@H](O)CNCC1(COc2ccc(C#N)c(F)c2)CN(S(=O)(=O)c2ccccc2C#N)C1]

(S)-4-((1-((2-Cyanophenyl)sulfonyl)-3-(((2-hydroxypropyl)amino)methyl)azetidin-3-yl)methoxy)-2-fluorobenzonitrile was prepared in a similar fashion as in Scheme 14 from 4-((1-((2-cyanophenyl)sulfonyl)-3-(hydroxymethyl)azetidin-3-yl)methoxy)-2-fluorobenzonitrile and (S)-1-aminopropan-2-ol. $^1$H NMR (500 MHz, $CDCl_3$) δ ppm 8.08 (dd, 1H), 7.90 (dd, 1H), 7.69-7.79 (m, 2H), 7.49-7.56 (m, 1H), 6.76 (dd, 1H), 6.70 (dd, 1H), 4.13-4.17 (m, 2H), 3.94-4.02 (m, 4H), 3.74-3.82 (m, 1H), 2.91-3.05 (m, 2H), 2.69-2.75 (m, 1H), 2.46 (dd, 1H), 1.12-1.16 (m, 3H). LCMS $[M+H]^+$ 458.8.

Example 118. Biological Activity

The biological activity of the TRPV4 antagonists of the present disclosure was assessed as follows.

Assessing TRPV4 Antagonist Activity and Potency ($IC_{50}$) in Human Embryonic Kidney Cells Fluorometric cell-based $Ca^{2+}$ flux assays were performed to assess TRPV4 antagonist activity and determine potency ($IC_{50}$ values) in human embryonic kidney-293 cells (HEK-293) that stably overexpress human TRPV4. The assays were performed according to methods described in: Deering-Rice, C. E., Johansen, M. E., Roberts, J. K., Thomas, K. C., Romero, E. G., Lee, J., Yost, G. S., Veranth, J. M., and Reilly, C. A. (2012), *Mol. Pharmacol.* 81(3), 411-419; Shapiro, D., Deering-Rice, C. E., Romero, E. G., Hughen, R. W., Light, A. R., Veranth, J. M., and Reilly, C. A. (2013), *Chem Res. Toxicol.,* 26, 750-758; and Deering-Rice, C. E., Mitchell, V. K., Romero, E. G., Abdel Aziz, M. H., and Reilly, C. A. (2014), *Pharmacol. Res. & Perspectives.* 2(5), 1-10.

The HEK-293 cells stably overexpressing human TRPV4 were grown to confluence in 2% (w/v) gelatin-coated 96-well plates in DMEM:F12 media supplemented with 5% fetal bovine serum, 1× penicillin/streptomycin (Invitrogen) and Geneticin (300 μg/mL).

The HEK-293 cells were prepared for assay by replacing the growth media with a 1:1 solution of LHC-9 and Fluo 4-Direct (Invitrogen) reagent containing Fluo 4-AM, pluronic F-127, probenecid, and a proprietary quencher dye. The cells were then incubated at 37° C. for 1 h in a cell culture incubator. The cells were subsequently washed by replacing the loading solution with LHC-9 containing 1 mM water-soluble probenecid (Invitrogen), 750 μM Trypan Red (ATT Bioquest), and a test compound (at various concentrations). The cells were incubated for an additional 30 minutes at 37° C. to allow for Fluo 4-AM cleavage and activation, as well as equilibration to both the test compounds and Fluo 4.

An agonist treatment solution (90 nM GSK1016790A, a potent activator of TRPV4) was prepared in LHC9 at 3× concentration and 25 μL was added to 50 μL of media on the cells in 96 well plates, providing a final concentration of 30 nM. Changes in cellular fluorescence were monitored with a BMG Labtech NOVOStar fluorescence plate reader for 1 minute at 37° C. Data were quantified as the maximum rate of change in fluorescence intensity (max ΔF/s), corrected for media only treatment (negative control), and represented as the percentage of response relative to the no antagonist control. A minimum of three replicates were used for each treatment condition, with a minimum of 8 concentrations to derive the $IC_{50}$ values reported for each antagonist. The $IC_{50}$ values for each antagonist, which are shown in Table 4 below, were calculated according to methods described in the assays were performed according to methods described in: Deering-Rice, C. E., Johansen, M. E., Roberts, J. K., Thomas, K. C., Romero, E. G., Lee, J., Yost, G. S., Veranth, J. M., and Reilly, C. A. (2012), *Mol. Pharmacol.* 81(3), 411-419; Shapiro, D., Deering-Rice, C. E., Romero, E. G., Hughen, R. W., Light, A. R., Veranth, J. M., and Reilly, C. A. (2013), *Chem Res. Toxicol.,* 26, 750-758; and Deering-Rice, C. E., Mitchell, V. K., Romero, E. G., Abdel Aziz, M. H., and Reilly, C. A. (2014), *Pharmacol. Res. & Perspectives.* 2(5), 1-10.

TABLE 4

| Compound | TRPV4 IC50 (μM) | Parent MW |
|---|---|---|
| 1 | 0.51 | 411.3 |
| 2 | ≥50 | 441.3 |
| 3 | 0.27 | 427.3 |
| 4 | 4.6 | 454.3 |
| 5 | 2.25 | 511.4 |
| 6 | 12.9 | 524.4 |
| 7 | 5 | 487.3 |
| 8 | 50 | 459.3 |

TABLE 4-continued

| Compound | TRPV4 IC50 (μM) | Parent MW |
|---|---|---|
| 9 | 1.09 | 458.3 |
| 10 | 10 | 449.3 |
| 11 | 0.052-0.061 | 445.3 |
| 12 | 0.303 | 487.3 |
| 13 | 0.062 | 459.3 |
| 14 | 0.070 | 525.3 |
| 15 | 0.021 | 552.4 |
| 16 | 0.0006 | 458.3 |
| 17 | 0.0002-0.0006 | 488.4 |
| 18 | 0.0007 | 528.4 |
| 19 | 0.0005 | 502.4 |
| 20 | 0.153 | 501.4 |
| 21 | 0.0187 | 502.4 |
| 22 | 0.117 | 541.4 |
| 23 | 0.0041 | 528.4 |
| 24 | 0.0009 | 502.4 |
| 25 | 0.001 | 472.4 |
| 26 | 0.008 | 500.4 |
| 27 | 0.001 | 514.4 |
| 28 | 0.0087 | 528.4 |
| 29 | 0.0052 | 542.5 |
| 30 | 0.0003 | 502.4 |
| 31 | 0.0004 | 502.4 |
| 32 | 0.0003 | 502.4 |
| 33 | 0.0003 | 518.4 |
| 34 | 0.0002 | 516.4 |
| 35 | 0.0007 | 516.4 |
| 36 | 0.010 | 497.4 |
| 37 | 0.0033 | 544.4 |
| 38 | 0.0018 | 514.4 |
| 39 | 0.0013 | 542.5 |
| 40 | 0.0134 | 528.4 |
| 41 | 0.0003 | 542.5 |
| 42 | 0.0013 | 514.4 |
| 43 | 1 | 502.4 |
| 44 | 0.0087 | 444.3 |
| 45 | 3.0 | 486.3 |
| 46 | 0.052 | 501.4 |
| 47 | 0.348 | 502.3 |
| 48 | 0.252 | 515.4 |
| 49 | 0.11 | 551.4 |
| 50 | 0.794 | 514.4 |
| 51 | 3.35 | 530.4 |
| 52 | 0.024-0.066 | 430.3 |
| 53 | 0.088 | 472.3 |
| 54 | 1.24 | 458.3 |
| 55 | 0.023 | 487.3 |
| 56 | 0.1 | 488.3 |
| 57 | 0.053 | 537.4 |
| 58 | 0.413 | 410.8 |
| 59 | 0.481 | 478.8 |
| 60 | 0.054 | 435.9 |
| 61 | 1 | 445.3 |
| 62 | 0.472 | 404.5 |
| 63 | 5 | 434.4 |
| 64 | 5 | 445.4 |
| 65 | 5 | 411.5 |
| 66 | 10 | 394.4 |
| 67 | 5 | 428.8 |
| 68 | 5 | 445.3 |
| 69 | 5 | 454.5 |
| 70 | 5 | 444.4 |
| 71 | 1 | 411.8 |
| 72 | 5 | 376.4 |
| 73 | 3 | 390.4 |
| 74 | 0.52 | 424.9 |
| 75 | >1.3 | 445.3 |
| 76 | >2.5 | 390.4 |
| 77 | >2.5 | 408.4 |
| 78 | 0.1-0.5 | 428.8 |
| 79 | >1.3 | 415.4 |
| 80 | >0.85 | 468.9 |
| 81 | 0.005 | 435.9 |
| 82 | >0.027 | 424.9 |
| 83 | >0.064 | 440.9 |
| 84 | >0.302 | 410.8 |
| 85 | 0.0049 | 401.4 |
| 86 | 0.0223 | 469.4 |
| 87 | 1-3 | 438.3 |
| 88 | 0.5 | 461.7 |
| 89 | 1-3 | 427.3 |
| 90 | ≈5 | 460.3 |
| 91 | ≈5 | 403.3 |
| 92 | ≈5 | 416.3 |
| 93 | ≈5 | 445.3 |
| 94 | ≈3 | 437.7 |
| 95 | ≈3 | 417.3 |
| 97 | ≈5 | 403.3 |
| 98 | 0.0672 | 457.3 |
| 99 | >1 | 654.4 |
| 100 | >1 | 471.4 |
| 101 | 0.136 | 444.3 |
| 102 | 0.231 | 485.3 |
| 103 | 0.0147 | 415.4 |
| 104 | 0.0293 | 419.4 |
| 105 | 1.2 | 539.3 |
| 106 | 0.145 | 431.4 |
| 107 | 0.080 | 485.4 |
| 108 | 0.528 | 475.3 |
| 109 | 0.940 | 431.4 |
| 110 | 0.241 | 445.5 |
| 111 | 0.0476 | 456.5 |
| 112 | 0.00029 | 498.6 |
| 113 | 0.00079 | 470.5 |
| 114 | 0.00645 | 500.6 |
| 115 | 0.00198 | 474.5 |
| 116 | 0.00041 | 484.5 |
| 117 | 0.0016 | 458.5 |

TRPV4 Selectivity

To determine selectivity of the various test compounds for TRPV4, select compounds with activity in the TRPV4 fluorometric cell-based $Ca^{2+}$ flux assays were also tested for inhibition of human TRPA1 stably over-expressed in HEK-293 cells, TRPM8 stably over-expressed in HEK-293 cells, TRPV3 stably over-expressed in HEK-293 cells, and TRPV1 stably overexpressed in human lung epithelial (BEAS-2B) cells. The assays were conducted substantially as described above for HEK-293 cells that stably overexpress TRPV4, although for TRPV1, the BEAS-2B cells were maintained in LHC-9 media containing Geneticin (300 μg/mL) and were loaded with Fluo-4AM at room temperature. The agonist for TRPA1 was 2,4-ditert butylphenol (50 μM), for TRPM8 was icilin (50 μM), for TRPV3 was carvacrol (300 μM), and for TRPV1 was nonivamide (5 μM). All other aspects of the assay described above were the same. For Compound 11, the $IC_{50}$ values for TRPA1, TRPM8, TRPV3 and TRPV1 were 52.0 μM, 14.4 μM, >100 μM, and 24.3 μM, respectively. For Compound 52, the $IC_{50}$ values for TRPA1, TRPM8, TRPV3 and TRPV1 were 89.6 μM, 35.9 μM, >100 μM, and 60.0 μM, respectively. These results show that Compound 11 and Compound 16 are substantially more selective for TRPV4. For Compound 16, the $IC_{50}$ values for TRPA1, TRPM8, TRPV3 and TRPV1 were 20.7 μM, 17.8 μM, >100 μM, and 6.0 μM, respectively. For Compound 17, the $IC_{50}$ values for TRPA1, TRPM8, TRPV3 and TRPV1 were >35.5 μM, 25.4 μM, >50 μM, and 5.3 μM, respectively.

In Vitro Screening Assay in Ocular Cells

Fluorometric cell-based $Ca^{2+}$ flux assays were performed on several test compounds according to methods described herein and in [Ryskamp et al., J Neurosci 34(47): 15689, 2014; Ryskamp et al., Sci Rep 6:30583, 2016 and Jo et al., Proc Natl Acad Sci U.S.A. 113(14): 3885, 2016] to assess TRPV4 antagonist activity and potency ($IC_{50}$ values) of the test compounds in human primary trabecular meshwork (TM) cells, Müller cells and retinal microvascular endothelial cells.

The trabecular meshwork is an area of tissue in the eye located around the base of the cornea, near the ciliary body, and is responsible for draining the aqueous humor from the eye via the anterior chamber. TM cells are believed to represent the primary source of the resistance to the outflow of aqueous humor from the anterior eye, and thus a primary determinant of intraocular pressure (IOP), which is believed to be the primary cause of glaucoma. Increases in IOP may increase the stiffness and contractility in (TM) cells by increasing intracellular calcium levels. TRPV4 antagonists may decrease the pressure-induced calcium elevations in (TM) cells, thereby decreasing IOP due to suppression of their contractile response. Primary™ cells were isolated from the juxtacanalicular and corneoscleral regions of the human eye, and were grown in Trabecular Meshwork Cell Medium (ScienCell, Catalog #6591) at 37° C. and 5% $CO_2$.

Müller cells are the primary macroglia in the retina. Müller cells function as a pressure and volume sensor, strongly express TRPV4 channels, and are believed to contribute to the inflammatory response that is associated with, and may contribute to, glaucomatous neurodegeneration [Ryskamp et al., J Neurosci. 34(47):15689-700, 2014]. TRPV4 antagonists may mitigate pressure-induced, calcium-dependent reactive gliosis, glial swelling/edema and inflammatory signaling in the retina. Müller glial cells and retinal ganglion cells (RGCs) were dissociated from mouse retinas digested in L-15 containing papain (7 U/ml; Worthington) for 1 hour at room temperature.

Microvascular endothelial cells (MVECs), the key component of the blood-retina barrier, regulate the passage of oxygen and metabolites to the inner retina and mediate functional hyperemia, light-induced increase in retinal blood flow. The cells strongly express TRPV4 channels which may transduce their responses to shear flow, swelling and stretch into changes in the intracellular calcium concentration. TRPV4 antagonists appear to regulate retinal vascular tone and functional hyperemic responses. Primary MVECs, isolated from human retinal capillary tissue, were purchased from Cell Systems (ACBRI 181) and cells at passages 3-5 were grown in human endothelial growth medium (EBM-2, Lonza, CC-3156 & CC4176) at 37° C. and 5% $CO_2$.

Fluorometric cell-based $Ca^{2+}$ flux assays were performed according to methods described herein and in [Ryskamp et al., J Neurosci 34(47): 15689, 2014 and Jo et al., J Neurosci 35(39): 13525, 2015] to assess TRPV4 antagonist activity and determine potency ($IC_{50}$ values) in the TM cells, Müller cells and MVECs. Activity was determined following stimulation of the cells with the TRPV4 selective agonist GSK1016790A (25 nM for (TM) cells and Müller cells, and 10 nM for MVECs) in the presence of different test compounds at various concentrations. More specifically, an aliquot of the agonist compound was prepared at 10 mM in DMSO and dissolved in saline buffer at the testing concentration (10-25 nM). Calcium levels were determined in cells loaded with 5 μM Fura-2-AM (Life Technologies) calcium indicator dye for 15-30 minutes at room temperature and perfused with isotonic saline (pH 7.4) containing (in mM): 98.5 NaCl, 5 KCl, 3 $MgCl_2$, 2 $CaCl_2$), 10 HEPES, 10 D-glucose, 93 mannitol. Epifluorescence imaging of calcium levels was performed using inverted Nikon Ti microscopes with 40× (1.3 N.A. oil & 0.8 N.A. water) objectives and Nikon Elements software. Data were quantified as described in [Ryskamp et al., J Neurosci 34(47): 15689, 2014 and Molnar et al., J Neurosci 36(11): 3184]. Calculated $IC_{50}$ values, which are shown in Table 4 below, represent averages across cells (3-6 slides) from at least three separate experiments with 20-100 cells per treatment condition.

The data show that agonist (GSK1016790A) and swelling-induced calcium responses mediated by TRPV4 channels are inhibited by Compound 11 with $IC_{50}$ values from ~0.01 μM to ~0.03 μM and Compound 52 with $IC_{50}$ values from ~0.01 μM to ~0.04 μM. In contrast, HC067047 inhibits TRPV4-mediated calcium responses in ocular cells with $IC_{50}$ values from ~0.5 to ~1.6 μM. The differences in potency across cell types may reflect different molecular configurations (heteromerization, phosphorylation) of the TRPV4 channel.

In Vivo Assay to Assess Lowering of IOP in a Mouse Model of Ocular Hypertension

A tonometric assay was used to measured IOP changes in mice models of ocular hypertension over a period of weeks following topical application of the compounds.

To prepare the mice models of ocular hypertension, mice were anesthetized with an intraperitoneal (IP) injection of ketamine/xylazine (90 mg/10 mg/kg of body weight). Eye drops of 0.5% proparacaine hydrochloride with 1% tropicamide ophthalmic solution (Bausch & Lomb) were applied to numb and dilate the eyes of the mice. IOP was elevated in the ipsilateral eye by injecting 2 μl of polystyrene microbeads (7.8 μm FluoSpheres; Bangs Laboratories) with a Hamilton syringe into the anterior chamber over 60 seconds. The contralateral eye was injected with phosphate buffered saline (PBS).

A rebound tonometer was used to measure IOP at 1, 2, 6 and 10 hours post-injection after topical administration of Compounds 11 and 52 and timolol, a known medication for treatment of IOP associated with ocular hypertension and glaucoma. The IOP was determined from the means of 10 to 20 readings, following the protocol described in Ryskamp et al., Sci Rep 6:30583, 2016. As shown in FIG. 1, topical administration of Compound 11 (1 μM and 10 μM) and Compound 52 (1 μM and 10 μM), as well as of 0.5% timolol, each lowered the IOP and protected RGCs in the mouse model of ocular hypertension. This confirms the effectiveness of the TRPV4 antagonist HC067047, which lowered IOP in hypertensive mouse eyes when applied at 0.3-1.0 mM [Ryskamp et al., Sci Rep 6:30583, 2016].

The in vivo data shows that single topical applications of Compounds 11 and 52 at low concentrations [1 μM and 10 μM] effectively lower IOP within the earliest determination time-frame (1 hour). The effectiveness is comparable to the effect of 0.5% timolol, the standard IOP-lowering drug in current clinical practice that targets the secondary (uveoscleral) outflow pathway. TRPV4 blockers facilitate aqueous fluid drainage through the conventional outflow pathway (Ryskamp et al., 2016) and can be employed in IOP-lowering as adjuncts to timolol and/or latanoprost (Xalatan). Given that timolol application was associated with significant side effects, including blurred vision, drooping eyelid, burning eye, headache, drowsiness, numbness, dry mouth, nausea, diarrhea, mood changes, irregular heartbeat, and loss of appetite, and prostaglandin analogs (Xalatan) when applied to lower IOP were shown to induce blurred vision, burning/stinging/redness of the eye, headache, dizziness, joint pain, chest pain, browning of the iris, watery eyes, eyelash growth and vision changes, the TRPV4 antagonists of the present disclosure may be used as alternatives to timolol, Xalatan and other currently used IOP-lowering drugs.

In Vivo Assay to Assess Lowering of IOP in a Dog Model of Ocular Hypertension

The present invention is further supported by the finding that Compound 52 lowers IOP in ocular hypertensive dogs.

Homozygous Beagels with autosomal recessive missense mutation in the ADAMTS10 gene develop significant IOP elevations due to decreased outflow facility for aqueous humor, resulting in open angle glaucoma that manifests as optic nerve head cupping and optic neuropathy. The carbonic anhydrase inhibitor dorzolamide HCl produces 3.8-5.0 mm Hg IOP lowering in OAG-affected dogs (Gelatt K N, MacKay E O, Vet Ophthalmol. 2001 March; 4(1):61-7.), a combination of dorzolamide and timolol effects 6.6-8.4 mm Hg reduction in IOP (Plummer C E, MacKay E O, Gelatt K N, Vet Ophthalmol. 2006 July-August; 9(4):245-9; Scardillo A, Pugliese M, De Majo M, Niutta P P, Pugliese A., Vet Ther. 2010 11(3):E1-6) whereas IOP in glaucomatous dogs is unaffected by Rho inhibitors (Leary K A, Lin K T, Steibel J P, Harman C D, Komiromy A M, Vet Ophthalmol. 2019 Dec. 24).

8 drops of Compound 52 (200 mM in hydroxypropyl methylcellulose solution, stock dissolved in DMSO) were administered to the Beagels at 7 AM for 1.5 hours. Control eyes received the vehicle (hydroxypropyl methylcellulose eyedrop with proper dilution of DMSO). IOP was measured by tonometry at 9:00 AM (6 readings per event, averaged) in dogs under topical anesthesia (N=5 OAG, N=5 non-symptomatic dogs). General ophthalmic examinations were performed by slit lamp biomicroscopy (Kowa SL-17 Portable Slit Lamp; Kowa Company, Ltd.) and indirect ophthalmoscopy (Keeler All Pupil II headset; Keeler Instruments; Pan Retinal 2.2D condensing lens; Volk Optical) to detect potential treatment-related adverse effects.

Compound 52 was well-tolerated by the dogs (N=10) with no observable signs of ocular discomfort or conjunctival hyperemia. The mean baseline IOP was 45.5 mm Hg. Topical application of Compound 52 significantly lowered IOP to the average level of 36.6 mm Hg.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A compound of formula (I),

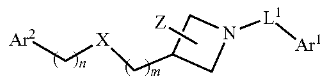

(I)

or a pharmaceutically acceptable salt thereof, wherein:

$L^1$ is —C(O)—, —$S(O_2)$—, or —S(O)—;

X is O or $NR^1$;

m is 1, 2, 3, or 4;

n is 0;

$Ar^1$ and $Ar^2$ are each independently selected from a 6-10 membered aryl or a 5-10 membered heteroaryl;

Z is $CHR^2R^3$, $COR^4$, or $NHR^5$;

$R^1$ is selected from hydrogen and $C_1$-$C_4$alkyl;

$R^2$, $R^3$, $R^4$, and $R^5$ are each independently selected from the group consisting of hydrogen, hydroxy, $C_1$-$C_6$alkyl, hydroxy-$C_1$-$C_6$alkyl, $C_1$-$C_6$alkoxy, $C_1$-$C_6$alkoxy-$C_1$-$C_6$alkyl, phosphate, $C_1$-$C_6$alkyl phosphate, $C_4$-$C_8$heterocyclyl, $NR^6R^7$, —$OC(O)R^8$, —$C(O)R^9$, —$S(O)_2R^{10}$, and —$OS(O)_2R^{11}$;

$R^6$, $R^7$, $R^8$, $R^9$, $R^{10}$, and $R^{11}$ are each independently selected from the group consisting of hydrogen, $C_1$-$C_6$alkyl, $C_1$-$C_6$heteroalkyl, $C_1$-$C_6$alkoxy, $C_4$-$C_8$cycloalkyl, $C_4$-$C_8$heterocyclyl, $C_6$-$C_8$aryl, $C_5$-$C_8$-heteroaryl, $C_1$-$C_6$alkoxy-$C_1$-$C_6$alkyl, $C_6$-$C_8$aryl-$C_1$-$C_6$alkyl, $C_5$-$C_8$heteroaryl-$C_1$-$C_6$alkyl, $C_5$-$C_8$heterocyclyl-$C_1$-$C_6$alkyl, amino-$C_1$-$C_6$alkyl, hydroxy-$C_1$-$C_6$alkyl, hydroxy-$C_3$-$C_8$cycloalkyl, cyano-$C_1$-$C_6$alkyl, hydroxysulfonyl-$C_1$-$C_6$alkyl, phosphate-$C_1$-$C_6$alkyl, alkylphosphate-$C_1$-$C_6$alkyl, —$COR^{12}$, and —$CR^{13}R^{14}C(O)R^{15}$;

$R^{12}$ is selected from the group consisting of $C_1$-$C_6$alkyl, $C_1$-$C_6$heteroalkyl, $C_1$-$C_6$alkoxy, amino-$C_1$-$C_6$alkyl, $C_4$-$C_8$heterocyclyl, hydroxy-$C_1$-$C_6$alkyl, amino-$C_4$-$C_8$heterocyclyl, phosphate-$C_1$-$C_6$alkyl, and $C_1$-$C_6$alkyl phosphate;

$R^{13}$ and $R^{14}$ are each independently selected from the group consisting of hydrogen, $C_1$-$C_6$alkyl and, $C_1$-$C_6$heteroalkyl, or optionally taken together with the atoms to which they are attached to form a ring; and $R^{15}$ is hydroxy, $C_1$-$C_6$alkoxy or amino;

wherein each aryl, heteroaryl, cycloalkyl, or heterocycle is independently unsubstituted or substituted with one or more substituents independently selected from cyano, halo, $C_1$-$C_6$alkyl, $C_1$-$C_6$alkoxy, amino-$C_1$-$C_6$alkyl, haloalkyl, sulfonyl, —C(O)—$C_1$-$C_6$alkoxy, and —C(O)—$NH_2$.

2. The compound of claim 1, or a pharmaceutical salt thereof, wherein $L^1$ is —$S(O_2)$—.

3. The compound of claim 1, or a pharmaceutical salt thereof, wherein $Ar^1$ is selected from a 5-membered heteroaryl, a 6-membered aryl, or a 6-membered heteroaryl, wherein each aryl or heteroaryl is unsubstituted or substituted with one or two substituents independently selected from cyano, halo, $C_1$-$C_6$alkyl, $C_1$-$C_6$alkoxy, haloalkyl, sulfonyl, and —C(O)—$C_1$-$C_6$alkoxy.

4. The compound of claim 3, or a pharmaceutical salt thereof, wherein the halo is fluoro or chloro.

5. The compound of claim 3, or a pharmaceutical salt thereof, wherein the haloalkyl is trifluoromethyl.

6. The compound of claim 1, or a pharmaceutical salt thereof, wherein $Ar^1$ is,

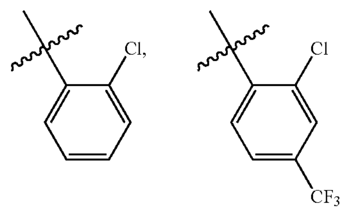

-continued

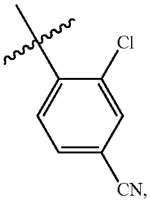 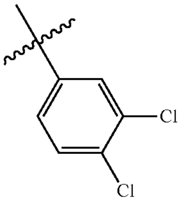, 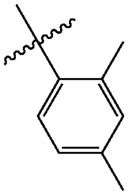,

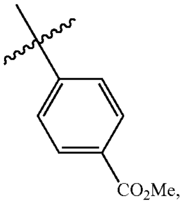 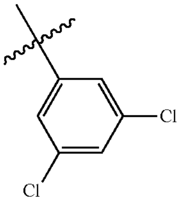,

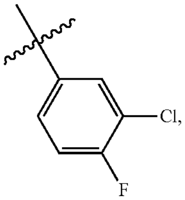 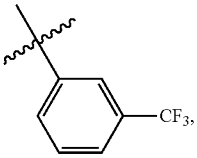 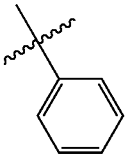,

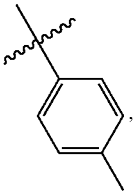, 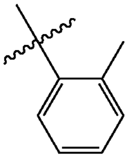, 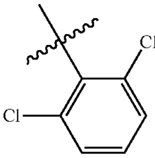,

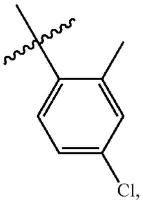 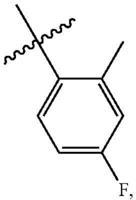 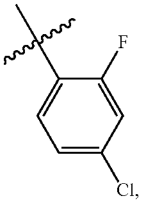

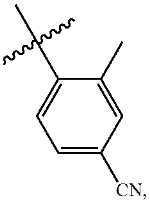 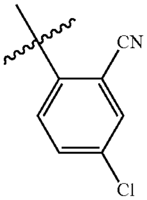, 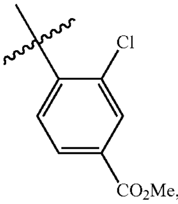

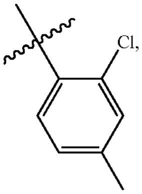 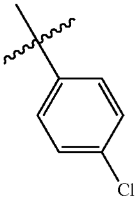, 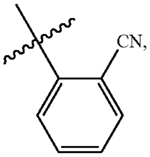

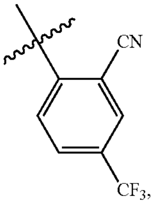 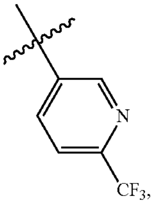

-continued

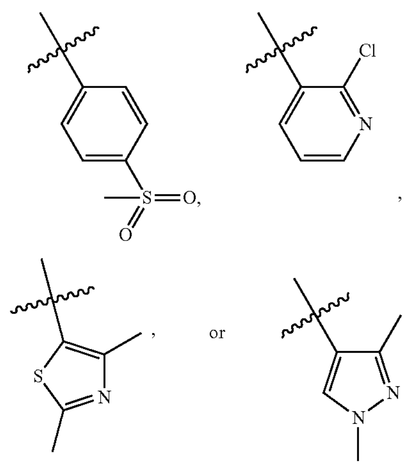

7. The compound of claim 1, or a pharmaceutical salt thereof, wherein $Ar^1$ is

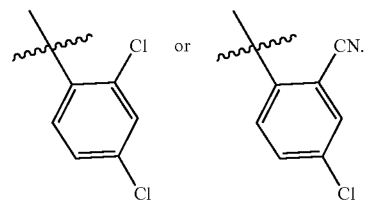 [SMILES: *c1ccc(Cl)cc1Cl ; *c1ccc(Cl)cc1C#N]

8. The compound of claim 1, or a pharmaceutical salt thereof, wherein $Ar^2$ is selected from a 5-membered heteroaryl, a 6-membered aryl, or a 6-membered heteroaryl, wherein each aryl or heteroaryl is unsubstituted or substituted with one or two substituents independently selected from cyano, halo, $C_1$-$C_6$alkyl, $C_1$-$C_6$alkoxy, —C(O)—$C_1$-$C_6$alkoxy, and —C(O)—$NH_2$.

9. The compound of claim 8, or a pharmaceutical salt thereof, wherein the halo is fluoro or chloro.

10. The compound of claim 1, or a pharmaceutical salt thereof, wherein $Ar^2$ is

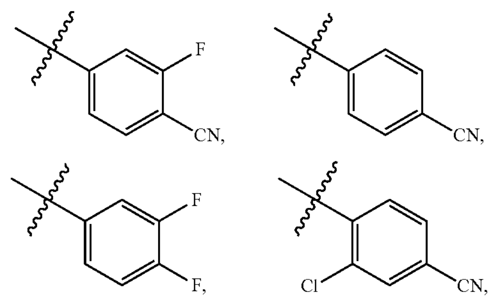

-continued

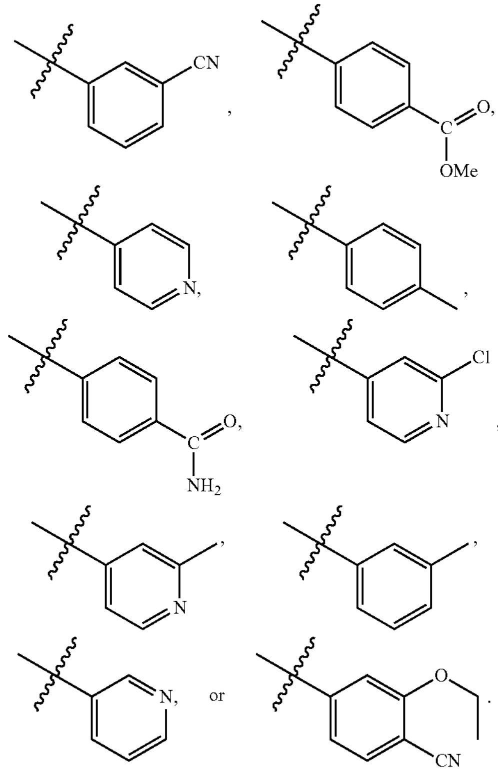

11. The compound of claim 1, or a pharmaceutical salt thereof, wherein $Ar^2$ is

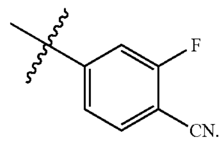 [SMILES: *c1ccc(C#N)c(F)c1]

12. The compound of claim 1, or a pharmaceutical salt thereof, wherein

Z is $CHR^2R^3$, $COR^4$, or $NHR^5$;

$R^2$ and $R^3$ are each independently selected from the group consisting of hydrogen, hydroxy, $C_1$-$C_6$alkoxy, $C_4$-$C_8$heterocyclyl, phosphate, $NR^6R^7$, —$OC(O)R^8$, and —$S(O)_2R^{10}$;

$R^4$ is selected from the group consisting of hydroxy, $C_1$-$C_6$alkoxy, and $NR^6R^7$;

$R^5$ is selected from the group consisting of hydrogen, $C_1$-$C_6$alkyl, —$C(O)R^9$, and —$S(O)_2R^{10}$;

$R^6$ and $R^7$ are each independently selected from the group consisting of hydrogen, $C_1$-$C_6$alkyl, $C_1$-$C_6$heteroalkyl, $C_4$-$C_8$heterocyclyl, $C_1$-$C_6$alkoxy-$C_1$-$C_6$alkyl, $C_5$-$C_8$heteroaryl-$C_1$-$C_6$alkyl, $C_5$-$C_8$heterocyclyl-$C_1$-$C_6$alkyl, amino-$C_1$-$C_6$alkyl, hydroxy-$C_1$-$C_6$alkyl, hydroxy-$C_3$-$C_8$cycloalkyl, cyano-$C_1$-$C_6$alkyl, hydroxysulfonyl-$C_1$-$C_6$alkyl, alkylphosphate-$C_1$-$C_6$alkyl, —$COR^{12}$, and —$CHR^{13}C(O)R^{14}$;

$R^8$ is $C_6$-$C_8$aryl or $C_5$-$C_8$-heteroaryl;

$R^9$ is selected from the group consisting of $C_1$-$C_6$alkyl, $C_1$-$C_6$heteroalkyl, amino-$C_1$-$C_6$alkyl, hydroxy-$C_1$-$C_6$alkyl, or —$COR^{12}$;

$R^{10}$ is amino-$C_1$-$C_6$alkyl;

$R^{12}$ is selected from the group consisting of $C_1$-$C_6$alkyl, $C_1$-$C_6$heteroalkyl, $C_1$-$C_6$alkoxy, amino-$C_1$-$C_6$alkyl, $C_4$-$C_8$heterocyclyl, amino-$C_4$-$C_8$heterocyclyl, phosphate-$C_1$-$C_6$alkyl, and $C_1$-$C_6$alkyl phosphate;

$R^{13}$ and $R^{14}$ are each independently selected from the group consisting of hydrogen and $C_1$-$C_6$alkyl; and $R^{15}$ is selected from the group consisting of hydroxy, $C_1$-$C_6$alkoxy and amino.

13. The compound of claim 1, or a pharmaceutical salt thereof, wherein Z is —$CH_2OH$, —$C(O)OH$, —$NH_2$, —$NHC(O)CH_3$, —$CH_2NH_2$, —$CH_2NHCH_3$, —$CH_2NH(CH_2)_2OH$, —$CH_2NH(CH_2)_3OH$, —$CH_2NH(C_5H_9O)$, —$CH_2NH(CH_2)_2OCH_3$, —$CH_2NHCH_2CH_3$, or —$CH_2NHCH_2CH(OH)CH_3$.

14. The compound of claim 1, or a pharmaceutical salt thereof, wherein m is 1.

15. The compound of claim 1, or a pharmaceutical salt thereof, wherein X is O and n is 0.

16. The compound of claim 1, or a pharmaceutical salt thereof, wherein X is $NR^1$.

17. The compound of claim 16, or a pharmaceutical salt thereof, wherein $R^1$ is hydrogen.

18. The compound of claim 16, or a pharmaceutical salt thereof, wherein n is 0.

19. The compound of claim 1, selected from the group consisting of:

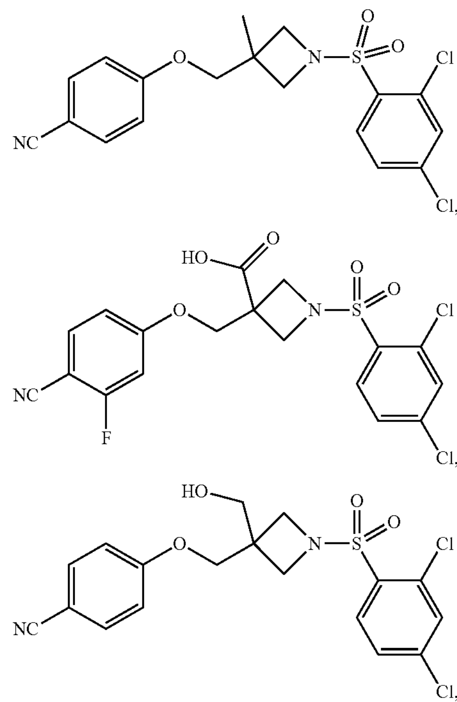

-continued
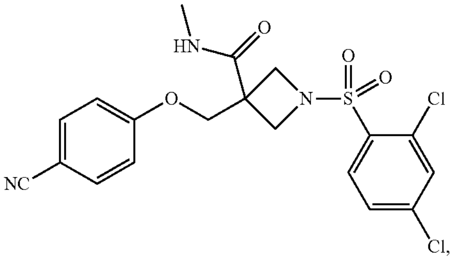,
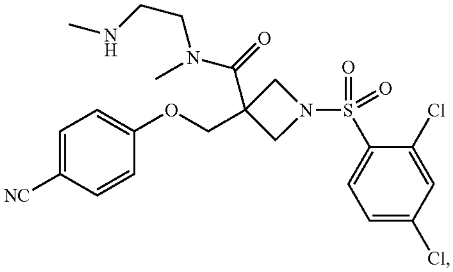,
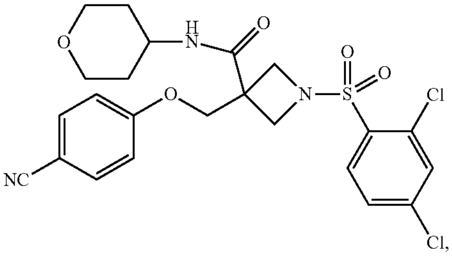,
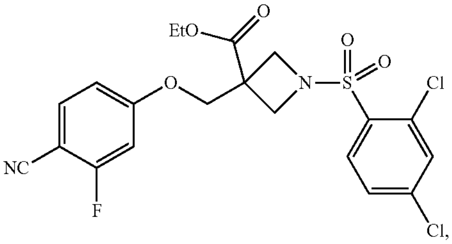,
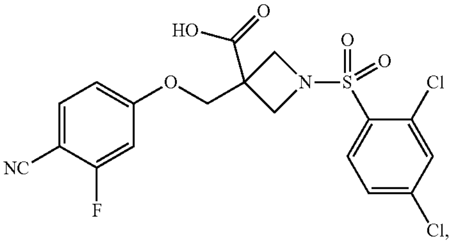,
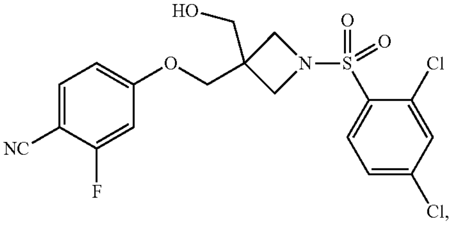,
-continued
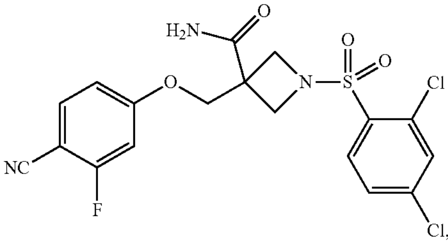,
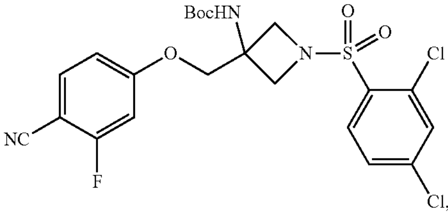,
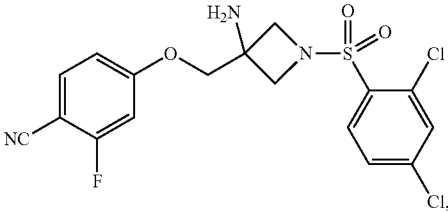,
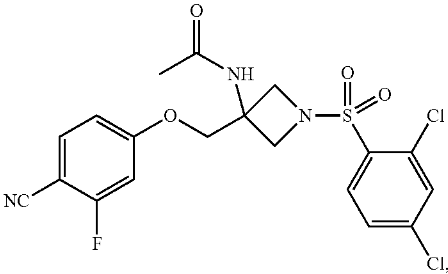,
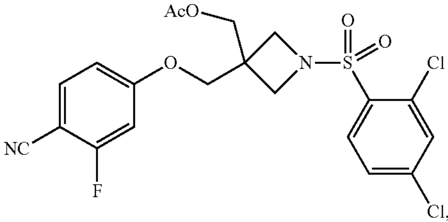,
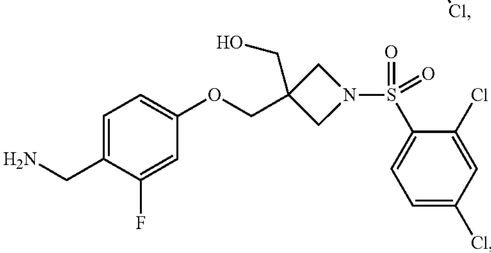,
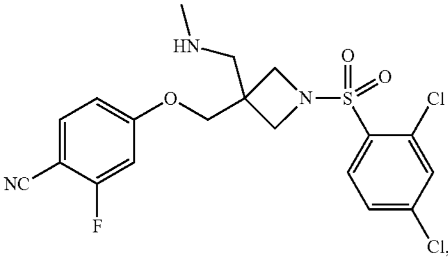, -continued
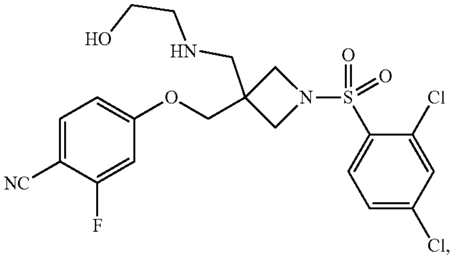
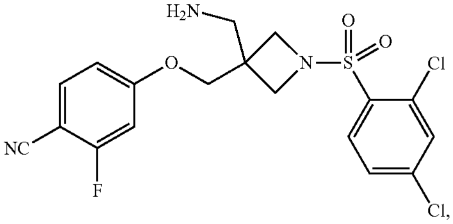
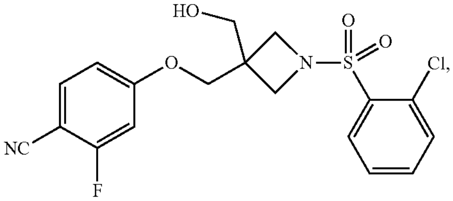
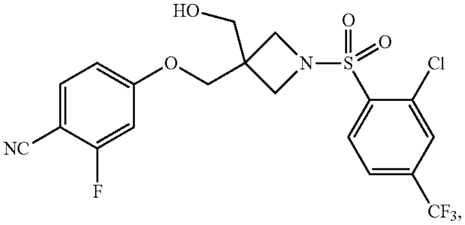
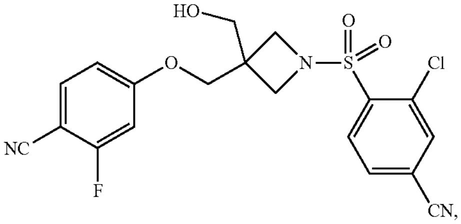
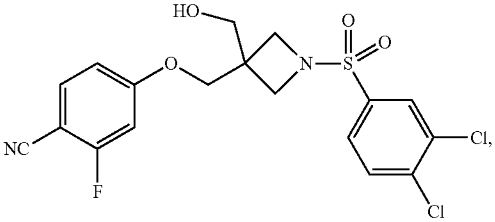
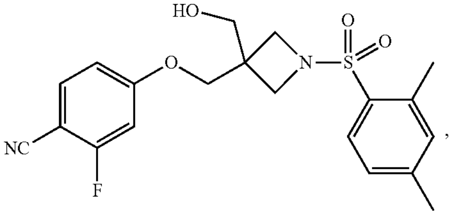
-continued
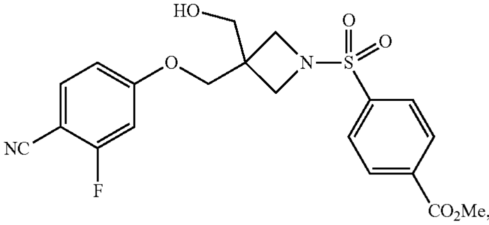
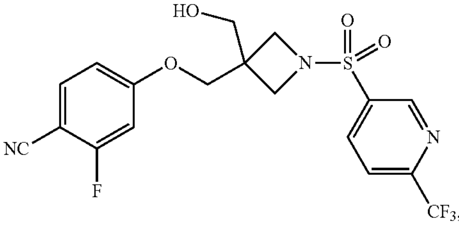
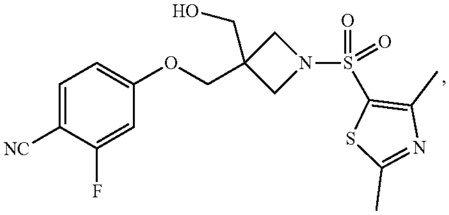
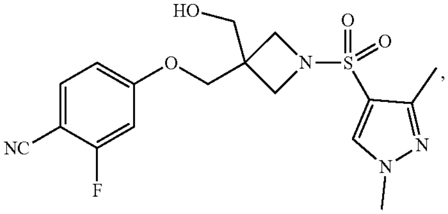
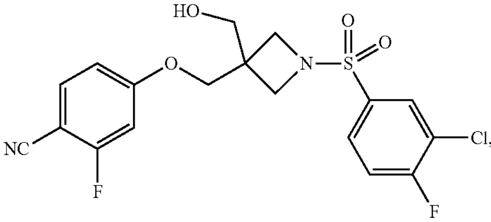
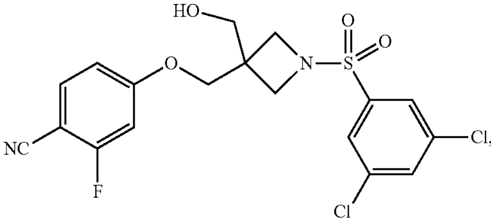
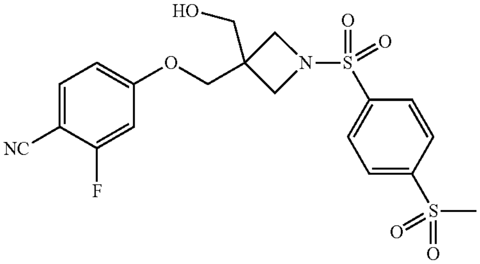

-continued
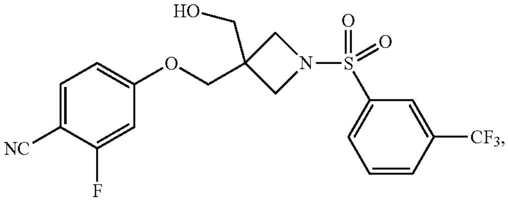
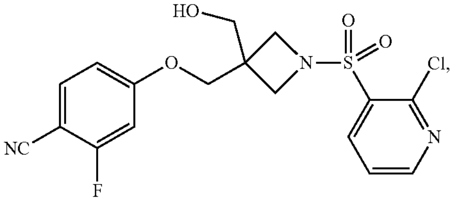
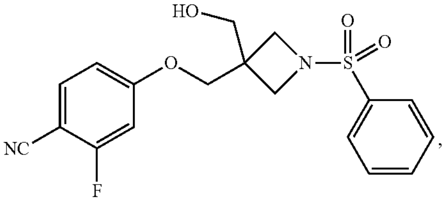
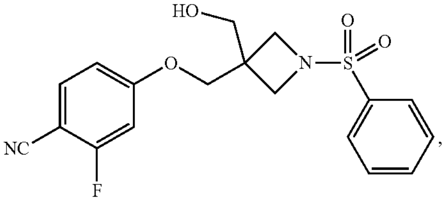
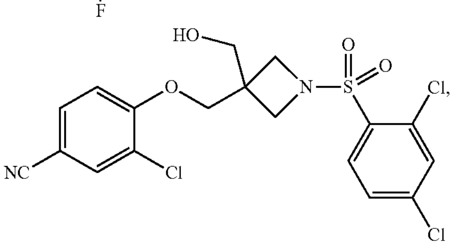
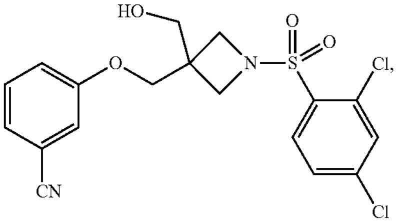
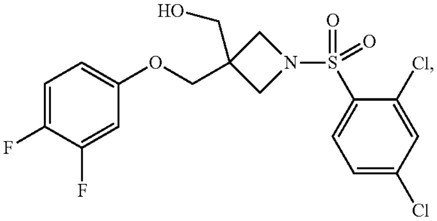
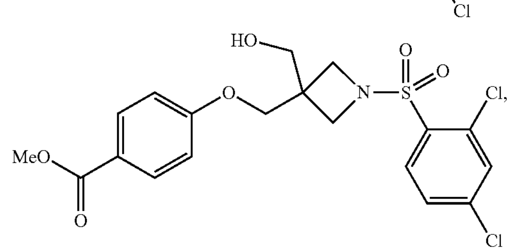
-continued
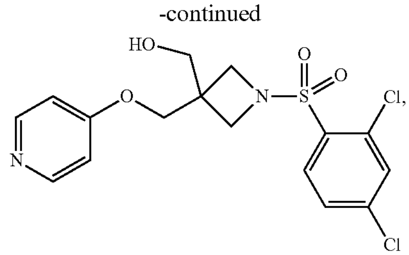
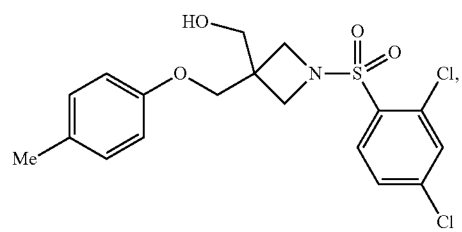
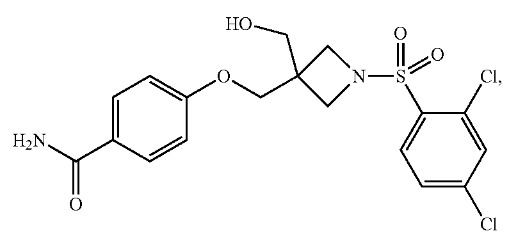
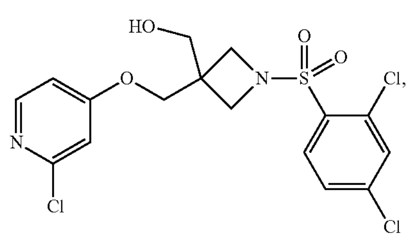
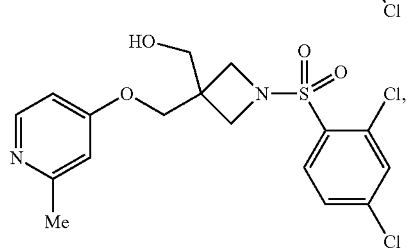
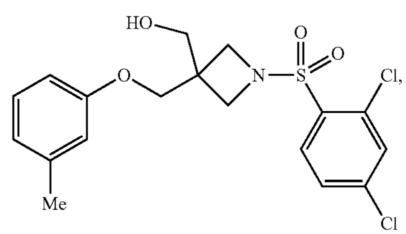
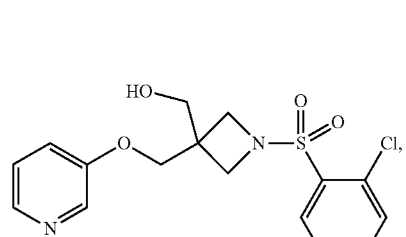

-continued
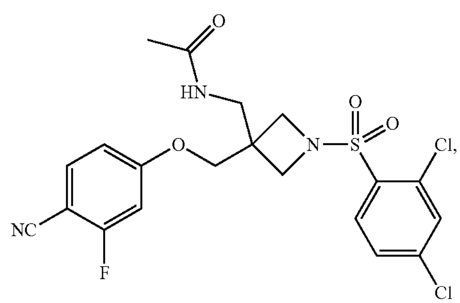
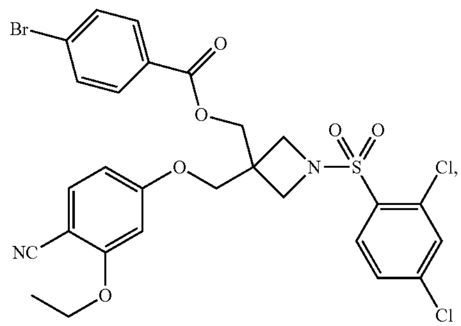
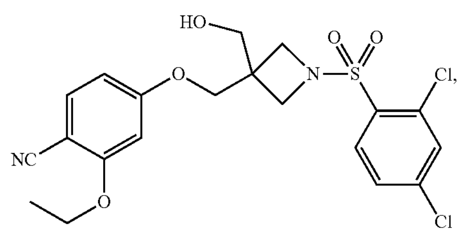
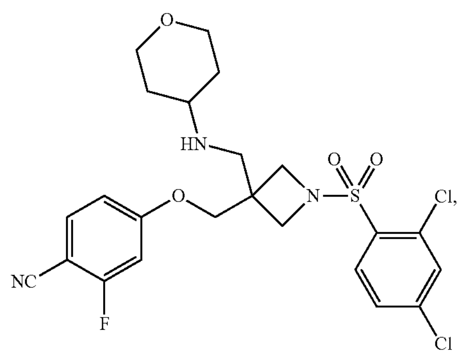
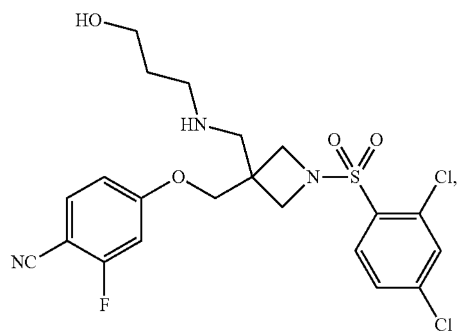
-continued
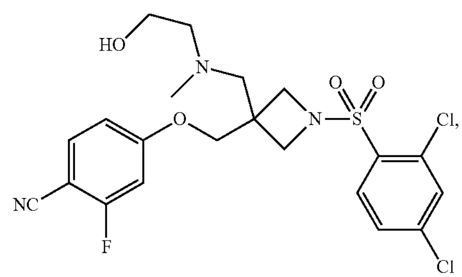
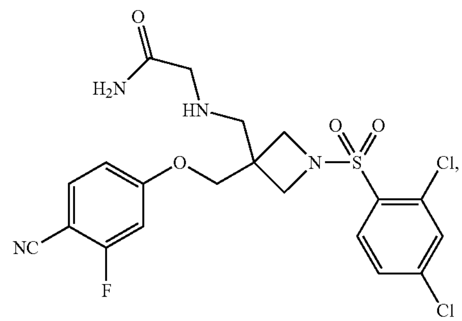
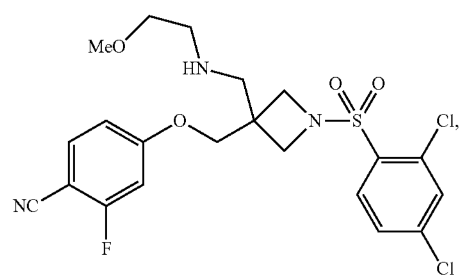
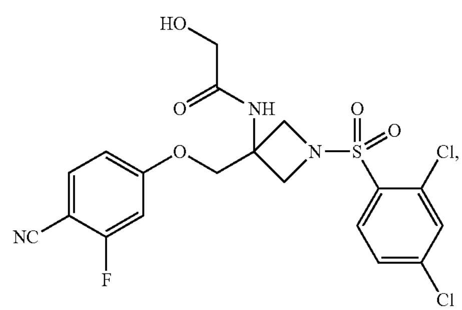
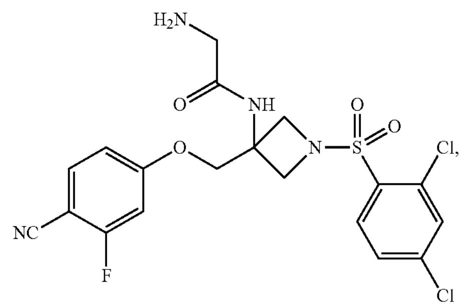

-continued
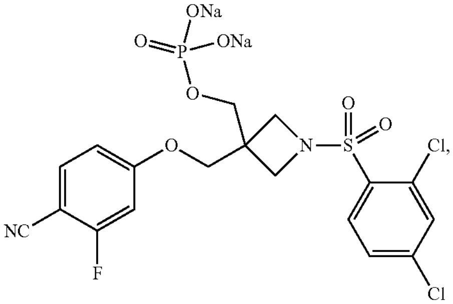
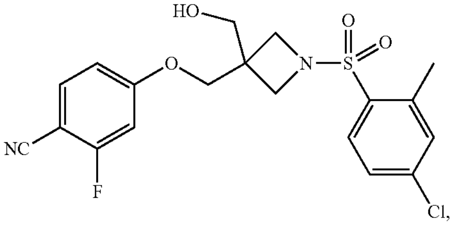
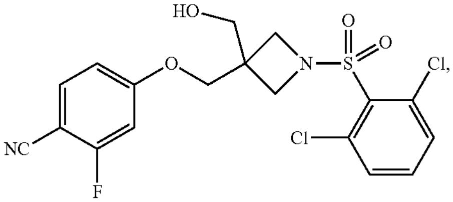
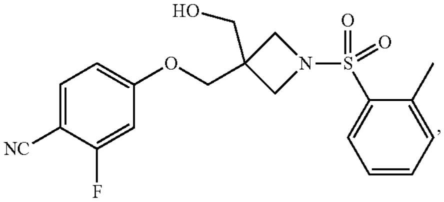
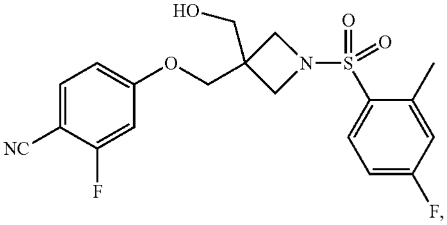
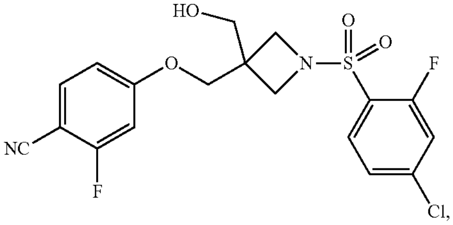
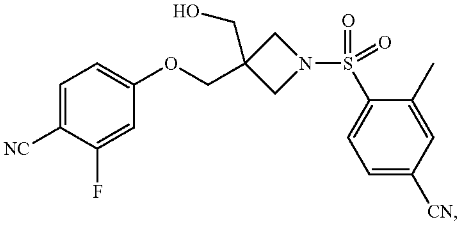
-continued
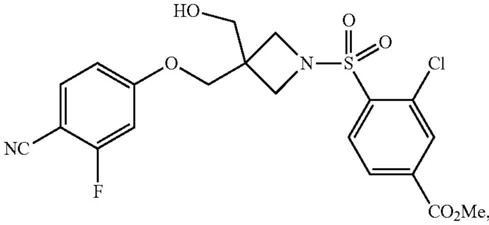
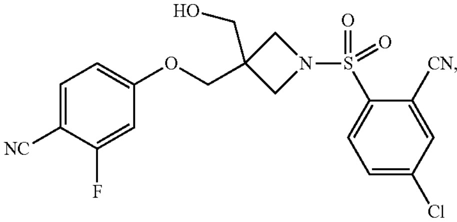
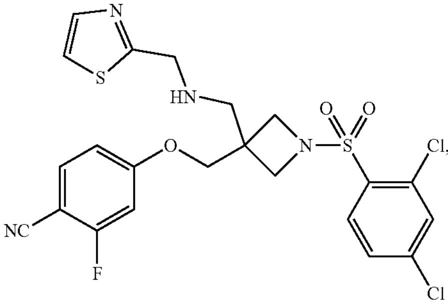
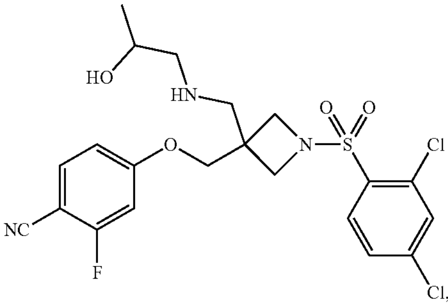
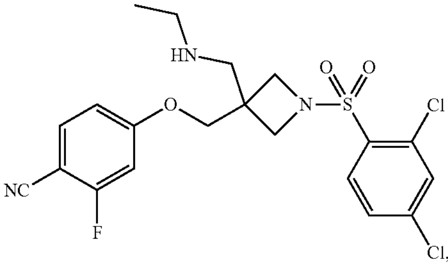
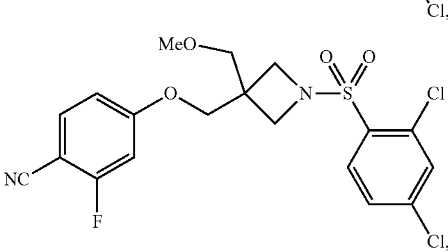

-continued
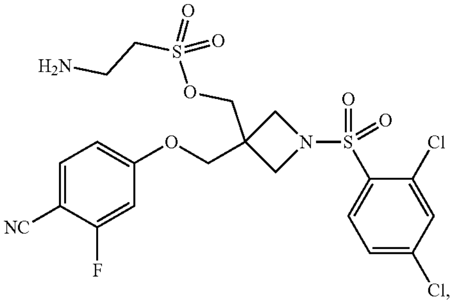
,
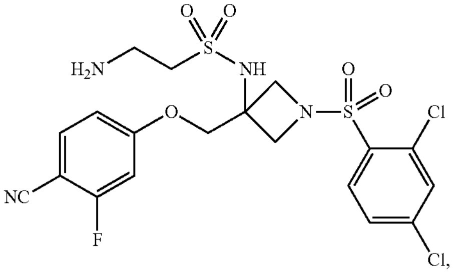
,
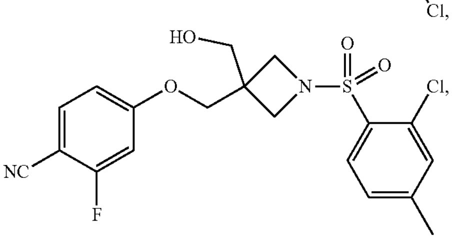
,
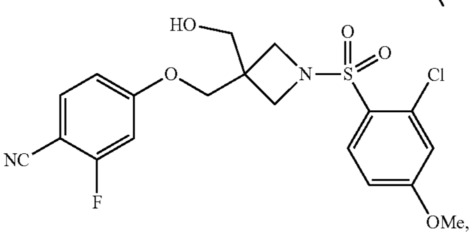
,
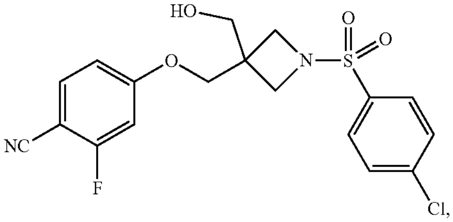 [SMILES: N#Cc1ccc(OCC2(CO)CN(S(=O)(=O)c3ccc(Cl)cc3)C2)cc1F]
,
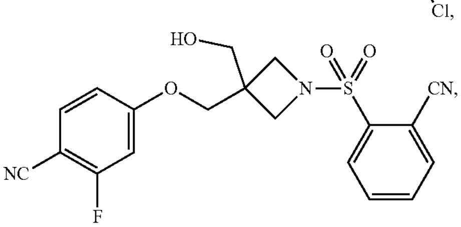
,
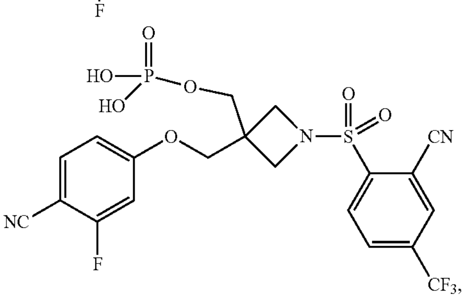
,
-continued
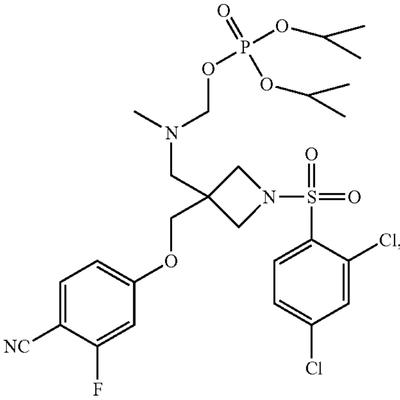
,
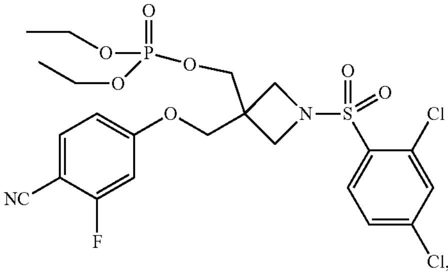
,
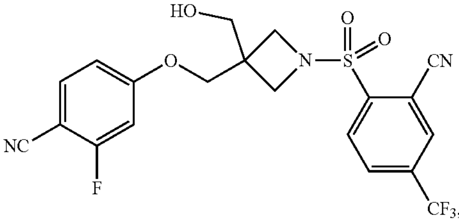
,
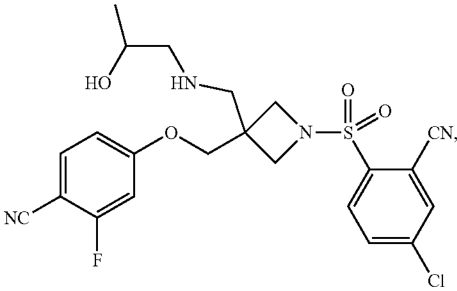
,
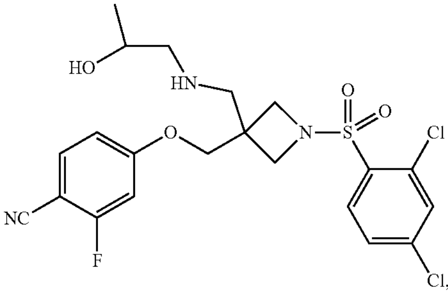
, -continued
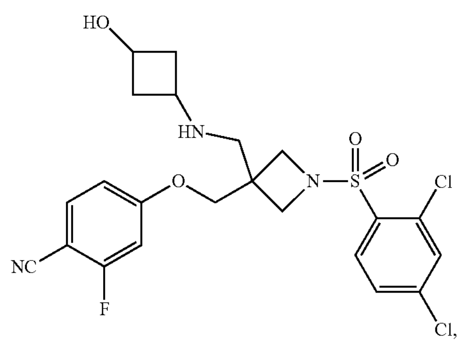
,
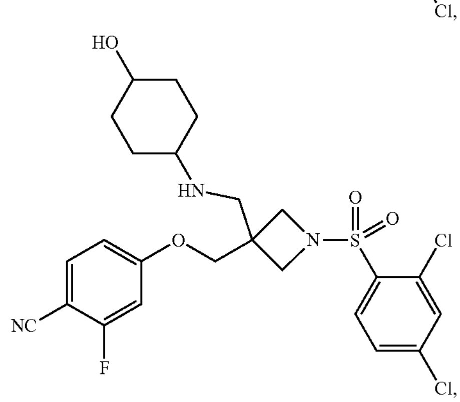
,
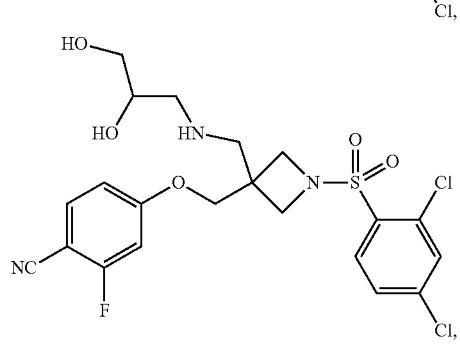
,
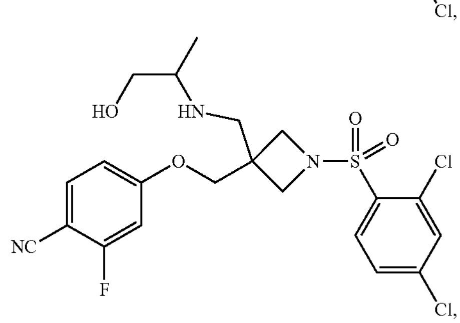
,
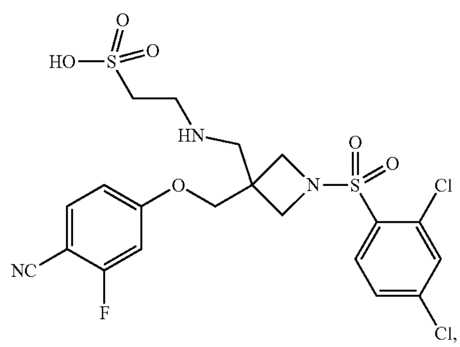
,
-continued
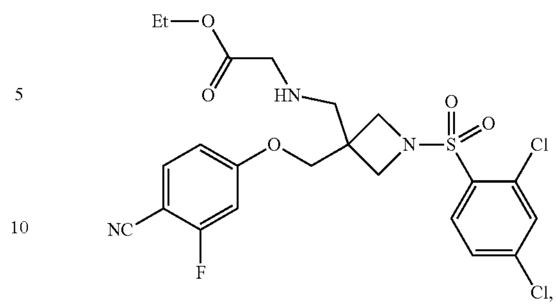
,
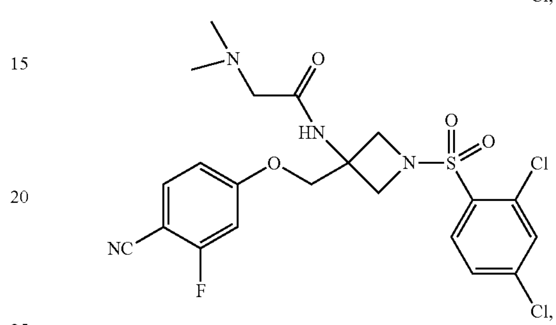
,
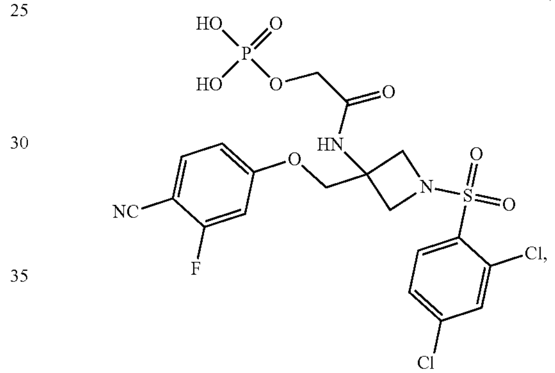
,
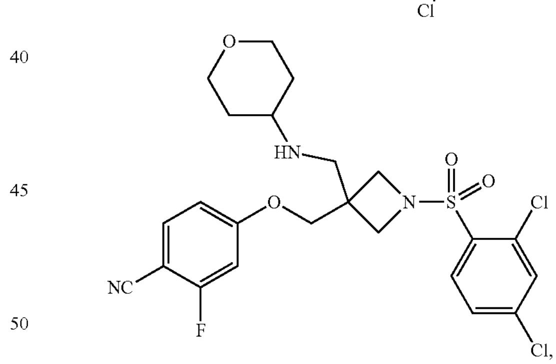
,
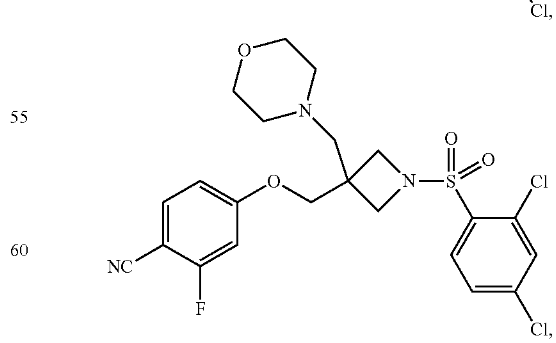
, -continued
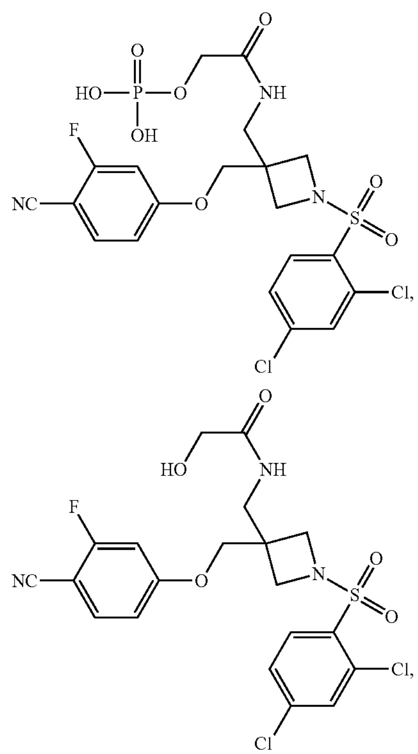
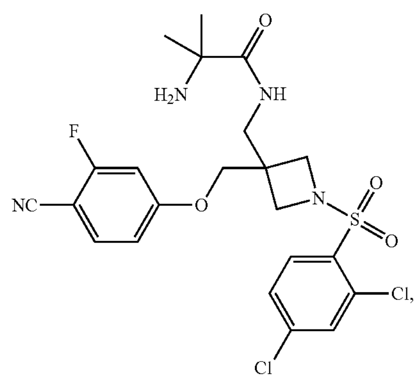
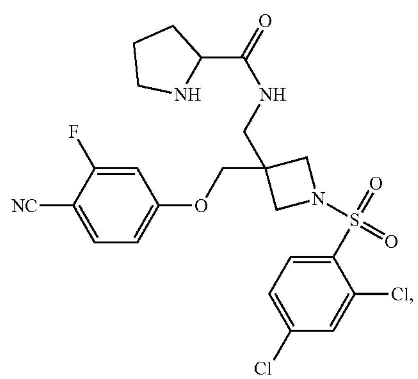
-continued
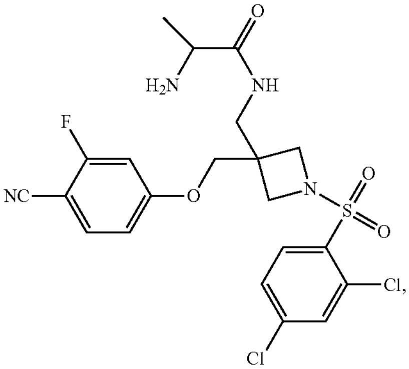
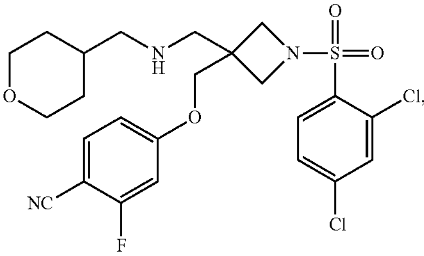
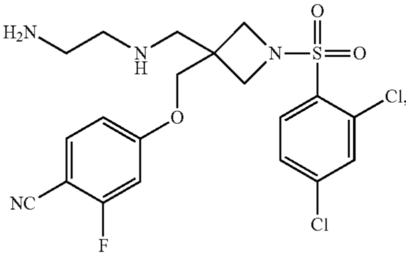
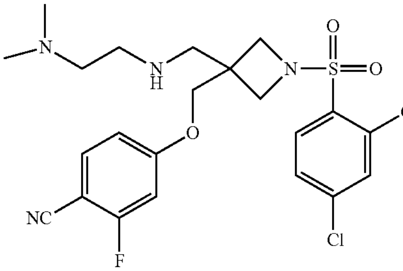
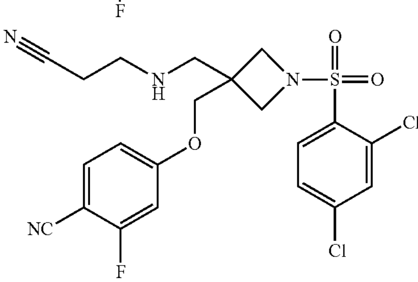
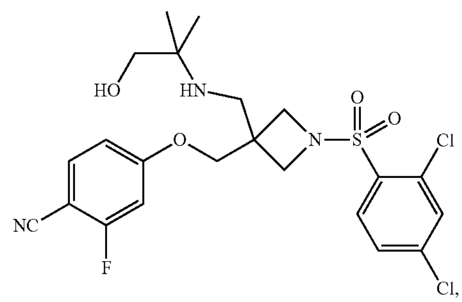

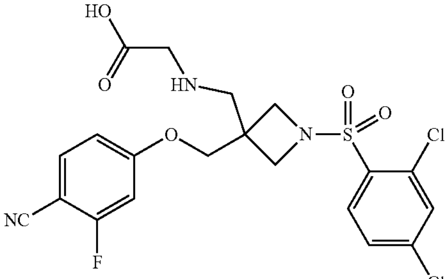
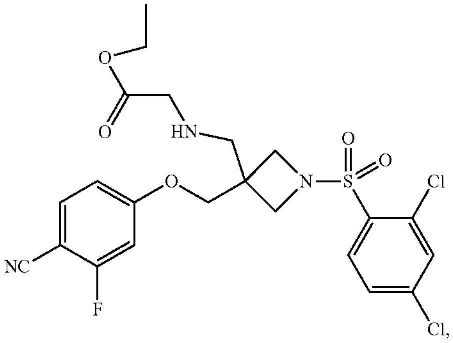
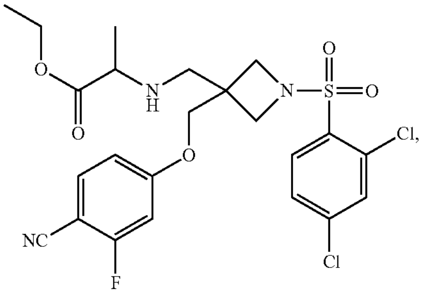
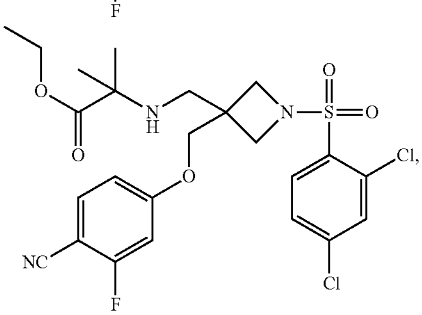
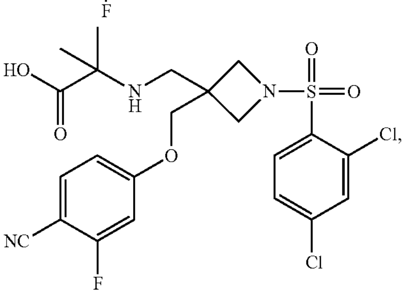
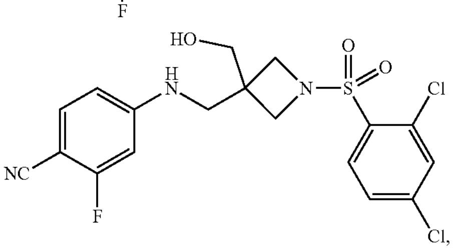
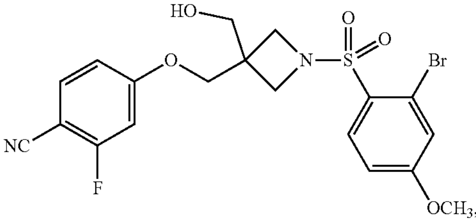
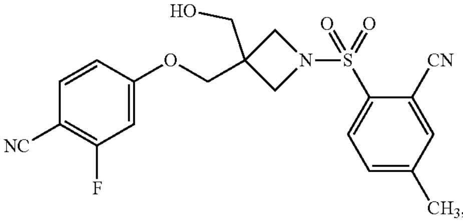
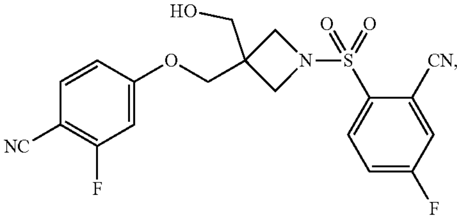
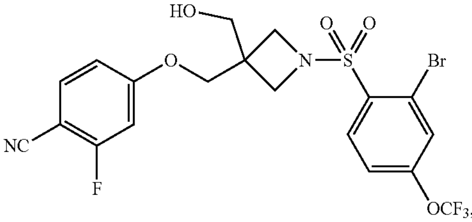
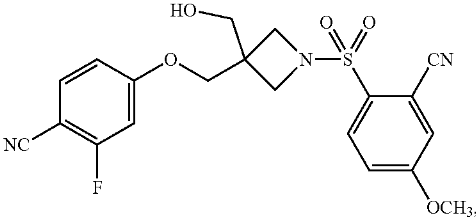
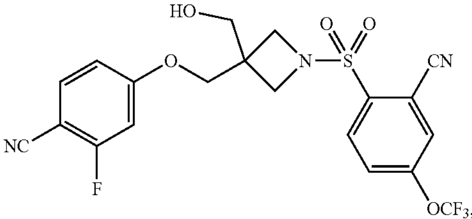
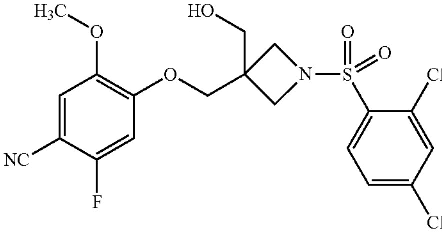

-continued

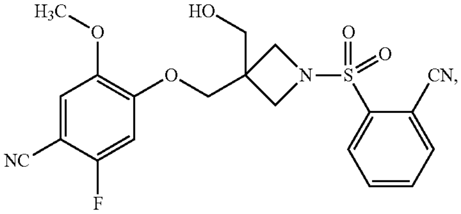

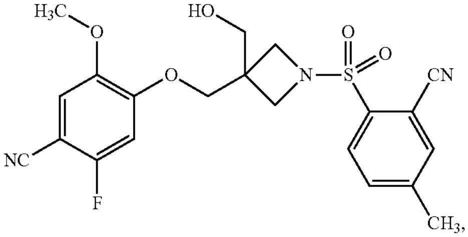

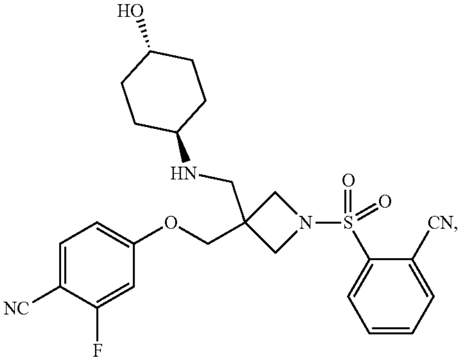

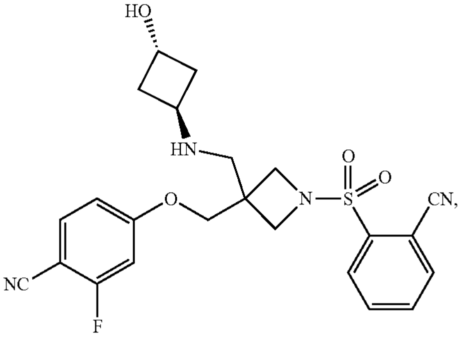

-continued

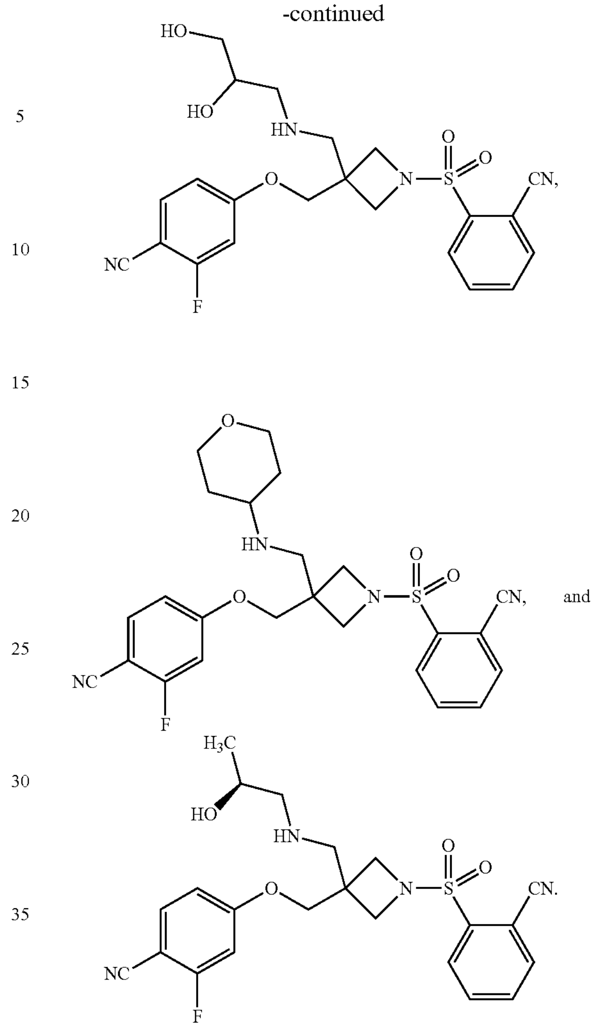

and

20. A pharmaceutical composition comprising an effective amount of at least one compound of claim 1, or pharmaceutically acceptable salt thereof, and a pharmaceutically acceptable carrier.

21. A method for the treatment of a disorder associated with Transient Receptor Potential Cation Channel Subfamily V Member 4 ("TRPV4") receptor activity in a subject, comprising administering to the subject an effective amount of the pharmaceutical composition of claim 20, and wherein the disorder is ocular hypertension.

* * * * *